(12) United States Patent
Kocis et al.

(10) Patent No.: US 11,053,192 B2
(45) Date of Patent: *Jul. 6, 2021

(54) COMPOSITIONS AND METHODS FOR TREATING AND PREVENTING NEURODEGENERATIVE DISORDERS

(71) Applicant: Alzheon, Inc., Framingham, MA (US)

(72) Inventors: Petr Kocis, Framingham, MA (US); Martin Tolar, Framingham, MA (US); John Hey, Framingham, MA (US)

(73) Assignee: Alzheon, Inc., Framingham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/807,747

(22) Filed: Mar. 3, 2020

(65) Prior Publication Data

US 2020/0347012 A1 Nov. 5, 2020

Related U.S. Application Data

(63) Continuation of application No. 15/751,547, filed as application No. PCT/US2016/046336 on Aug. 10, 2016, now Pat. No. 10,590,070.

(60) Provisional application No. 62/203,256, filed on Aug. 10, 2015.

(51) Int. Cl.
| | |
|---|---|
| *C07C 309/26* | (2006.01) |
| *C07C 309/19* | (2006.01) |
| *C07D 207/14* | (2006.01) |
| *C07D 207/16* | (2006.01) |
| *C07C 317/50* | (2006.01) |
| *C07D 401/06* | (2006.01) |
| *C07C 323/59* | (2006.01) |
| *C07D 403/12* | (2006.01) |
| *C07D 233/26* | (2006.01) |
| *C07D 403/06* | (2006.01) |
| *C07D 401/12* | (2006.01) |
| *C07D 209/20* | (2006.01) |
| *C07D 295/185* | (2006.01) |
| *C07C 323/60* | (2006.01) |
| *C07D 211/58* | (2006.01) |
| *C07C 309/27* | (2006.01) |
| *A61P 25/28* | (2006.01) |
| *C07K 5/00* | (2006.01) |
| *C07K 5/078* | (2006.01) |

(52) U.S. Cl.
CPC ............ *C07C 309/26* (2013.01); *A61P 25/28* (2018.01); *C07C 309/19* (2013.01); *C07C 309/27* (2013.01); *C07C 317/50* (2013.01); *C07C 323/59* (2013.01); *C07C 323/60* (2013.01); *C07D 207/14* (2013.01); *C07D 207/16* (2013.01); *C07D 209/20* (2013.01); *C07D 211/58* (2013.01); *C07D 233/26* (2013.01); *C07D 295/185* (2013.01); *C07D 401/06* (2013.01); *C07D 401/12* (2013.01); *C07D 403/06* (2013.01); *C07D 403/12* (2013.01); *C07K 5/00* (2013.01); *C07K 5/06165* (2013.01); *C07B 2200/07* (2013.01); *C07C 2601/08* (2017.05); *C07C 2601/14* (2017.05)

(58) Field of Classification Search
USPC .......................................................... 562/30
See application file for complete search history.

(56) References Cited

U.S. PATENT DOCUMENTS

| | | | |
|---|---|---|---|
| 10,590,070 | B2 | 3/2020 | Kocis et al. |
| 2004/0198832 | A1 | 10/2004 | Szarek et al. |
| 2005/0038117 | A1 | 2/2005 | Kong et al. |
| 2006/0135403 | A1 | 6/2006 | Gervais et al. |
| 2007/0010573 | A1 | 1/2007 | Kong et al. |
| 2008/0146642 | A1 | 6/2008 | Kong et al. |
| 2009/0004140 | A1 | 1/2009 | Qiu et al. |
| 2011/0144111 | A1 | 6/2011 | Kim et al. |

FOREIGN PATENT DOCUMENTS

| | | |
|---|---|---|
| CN | 1282316 A | 1/2001 |
| CN | 1839118 A | 9/2006 |
| CN | 103787927 A | 5/2014 |
| WO | 1999/033781 A1 | 7/1999 |
| WO | 2004/113275 A2 | 12/2004 |
| WO | 2009/019534 A2 | 2/2009 |
| WO | 2017/027582 A1 | 2/2017 |

OTHER PUBLICATIONS

Contineanu, Structure and spectral characteristics of the benzene-2,2-diazo-quinone-4-sulphonic acid. Revista de Chimie. Jul. 2001;52(7-8):365-370.

Pilichowski et al., Sultones Bicycliques Pontees Synthese et Reactivite. Tetrahedron. 1977;33(10):1113-1118.

U.S. Appl. No. 15/751,547, filed Feb. 9, 2018, U.S. Pat. No. 10,590,070.

*Primary Examiner* — Ana Z Muresan
(74) *Attorney, Agent, or Firm* — McCarter & English, LLP

(57) ABSTRACT

Compounds, pharmaceutical compositions, methods and kits are described for treating or preventing neurodegenerative diseases such as Alzheimer's disease.

5 Claims, 30 Drawing Sheets

| Compound | Structure | NMR 1H NMR (400MHz, D2O): | MS [M+H]: |
|---|---|---|---|
| 2000 | H2N-cyclopentyl-S(O)2-OH | | 166.21 |
| 2001 | H2N-cyclopentyl-S(O)2-OH | | 166.21 |
| 2002 | HOOC-CH2CH2-NH-cyclopentyl-S(O)2-OH | 1.57(sx), 1.76(o), 1.85(q), 1.91(sx), 2.21(o), 2.22(t), 2.21(q), 2.58(t), 2.93(t), 3.2(n), 3.26(t), 3.3(n), 5.18(s), 7.52(s), 11.18(s) | 238.27 |
| 2003 | HOOC-CH2CH2-NH-cyclopentyl-S(O)2-OH | 1.57(sx), 1.76(o), 1.85(q), 1.91(sx), 2.21(o), 2.22(t), 2.21(q), 2.58(t), 2.93(t), 3.2(n), 3.26(t), 3.3(n), 5.18(s), 7.52(s), 11.18(s) | 238.37 |
| 2004 | MeOOC-CH2CH2-NH-cyclopentyl-S(O)2-OH | 1.57(sx), 1.76(o), 1.85(q), 1.9(sx), 2.21(o), 2.21(q), 2.31(t), 2.67(t), 2.93(t), 3.2(n), 3.27(t), 3.29(n), 3.7(s), 4.45(s), 7.49(s) | 252.30 |
| 2005 | H2N-cyclopentyl-S(O)2-OH | 3.79-3.76 (m, 1H), 3.55-3.51 (m, 1H), 2.56-2.48 (m, 1H), 2.19-2.12 (m, 3H), 2.06-1.99 (m, 1H), 1.92 (m, 1H) | 166.00 |
| 2006 | HOOC-CH2CH2-NH-cyclopentyl-S(O)2-OH | 1.57(sx), 1.76(o), 1.85(q), 1.91(sx), 2.21(o), 2.22(t), 2.21(q), 2.58(t), 2.93(t), 3.2(n), 3.26(t), 3.3(n), 5.18(s), 7.52(s), 11.18(s) | 238.27 |
| 2007 | H2N-CH2-C(O)-NH-cyclopentyl-S(O)2-OH | 1.67(sx), 1.77(o), 1.95(q), 2.01(sx), 2.22(o), 2.31(q), 3.3(n), 3.33(s), 3.51(n), 3.66(s), 3.77(s), 6.91(s), 7.71(s) | 223.26 |
| 2008 | Ala-NH-cyclopentyl-S(O)2-OH | 7.61 (s), 6.64 (s), 4.09 (q), 3.54 (n), 3.28 (n), 3.06 (s), 2.31 (q), 2.19 (sx), 2.01 (o), 1.95 (q), 1.74 (sx), 1.67(o),1.49 (d) | 237.29 |
| 2009 | Phe-NH-cyclopentyl-S(O)2-OH | 1.63(sx), 1.72(o), 1.92(q), 1.97(sx), 2.17(o), 2.28(q), 2.92(s), 3.07(sx), 3.25(n), 3.31(sx), 3.53(m), 4.04(t), 6.5(s), 7.22(n), 7.26(m), 7.28(t), 7.3(s) | 313.38 |

Figure 2

| | | | |
|---|---|---|---|
| 2010 | | 4.31-4.27 (m, 1H), 3.63-3.50 (m, 1H), 3.48-3.46 (dd, J = 2.4 Hz, 6.4 Hz, 1H), 2.29-2.21 (m, 1H), 2.19-2.06 (m, 3H), 2.04-1.93 (m, 2H), 1.69-1.67 (m, 1H), 1.04-0.94 (m, 6H). | 265.00 |
| 2011 | | 4.28-4.26 (m, 1H), 3.70 (bs, 1H), 3.63-3.47 (m, 1H), 2.29-2.19 (m, 1H), 2.17-2.06 (m, 2H), 2.03-1.91 (m, 2H), 1.73-1.56 (m, 4H), 0.95-0.92 (m, 6H). | 279.00 |
| 2012 | | 1.65(sx), 1.73(o), 1.93(q), 1.99(sx), 2.18(o), 2.29(q), 3.26(n), 3.52(n), 3.61(s), 3.64(d), 3.71(d), 3.83(s), 3.86(t), 7.01(s), 7.53(s) | 253.29 |
| 2013 | | 1.2(d), 1.63(sx), 1.74(o), 1.91(q), 1.96(sx), 2.19(o), 2.27(q), 3.28(n), 3.52(n), 3.56(s), 3.68(d), 3.94(o), 4.77(s), 6.85(s), 7.44(s) | 267.31 |
| 2014 | | 4.20-4.16 (t, J = 8.0 Hz, 1H), 3.56 (bs, 1H), 3.49-3.41 (m, 1H), 3.23-3.19 (t, J = 8.0 Hz, 2H), 3.03 (s, 3H), 2.21-2.05 (m, 5H), 1.92-1.83 (m, 2H), 1.57 (bs, 1H). | 329.40 |
| 2015 | | 7.06 (bs, 2H), 6.81-6.80 (d, J = 4.0 Hz, 2H), 4.04 (bs, 1H), 3.93-3.92 (d, J = 4.0 Hz, 1H), 3.28-3.24 (t, J = 8.0 Hz, 1H), 3.11-3.03 (t, J = 16.0 Hz, 1H), 2.92-2.86 (t, J = 12.0 Hz, 1H), 1.94-1.75 (m, 6H). | 329.38 |
| 2016 | | 1.7(sx), 1.78(o), 1.98(q), 2.03(sx), 2.23(o), 2.34(q), 2.92(s), 3.07(q), 3.31(n), 3.33(q), 3.59(n), 4.04(t), 6.9(s), 7.02(sx), 7.11(t), 7.14(sx), 7.34(q), 7.39(s), 7.57(q), 9.59(s) | 352.41 |

Figure 2 cont'd

| | | | |
|---|---|---|---|
| 2017 | | 1.65(sx), 1.74(o), 1.94(q), 1.99(sx), 2.19(o), 2.3(q), 2.64(d), 2.75(d), 2.92(s), 3.27(n), 3.53(n), 4(t), 7.04(s), 7.53(s), 11.18(s) | 281.30 |
| 2018 | | 1.63(sx), 1.72(o), 1.92(q), 1.97(sx), 2.17(o), 2.28(q), 2.61(d), 2.79(d), 2.92(s), 3.25(n), 3.51(n), 3.89(t), 7.22(s), 7.28(s), 7.71(s) | 280.31 |
| 2019 | | 1.73(sx), 1.81(o), 2.01(q), 2.07(sx), 2.26(o), 2.38(q), 2.92(s), 3.1(q), 3.16(q), 3.35(n), 3.63(m), 4.15(t), 6.89(s), 7.1(t), 7.44(s), 8.53(s), 10.86(s) | 303.35 |
| 2020 | | 1.36(n), 1.39(s), 1.54(p), 1.55(sx), 1.59(n), 1.62(p), 1.64(sx), 1.72(o), 1.75(sx), 1.92(q), 1.98(sx), 2.17(o), 2.29(q), 2.4(t), 2.79(t), 2.92(s), 3.26(n), 3.5(n), 3.54(t), 6.46(s), 7.71(s) | 294.38 |
| 2021 | | 7.37-7.31 (m, 3H), 7.26-7.24 (d, J = 8.0 Hz, 2H), 7.03 (bs, 2H), 6.78-6.74 (m, 2H), 5.05-4.92 (m, 2H), 4.12-4.02 (m, 2H), 3.30-2.70 (m, 3H), 2.04-1.58 (m, 5H), 1.58-1.19 (m, 1H). | 463.44 |
| 2022 | | | 437.48 |
| 2023 | | | 399.47 |
| 2024 | | 7.43 (s, 6H), 5.21-5.04 (m, 3H), 4.36-4.22 (m, 1H), 4.12-3.99 (m, 2H), 3.92-3.71 (m, 1H), 3.59-3.26 (m, 2H), 2.77-1.40 (m, 18H), 0.92-0.88 (m, 10H). | 413.45 |
| 2025 | | | 387.42 |

Figure 2 cont'd

| # | Structure | NMR | MW |
|---|---|---|---|
| 2026 | 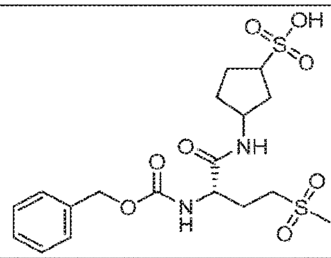 | 7.35 (bs, 5H), 5.05 (s, 2H), 4.11 (s, 2H), 3.48-3.39 (m, 1H), 3.21 (s, 2H), 3.00 (s, 3H), 2.14-2.00 (m, 5H), 1.92-1.81 (m, 2H), 1.54-1.48 (m, 1H). | 463.00 |
| 2027 | 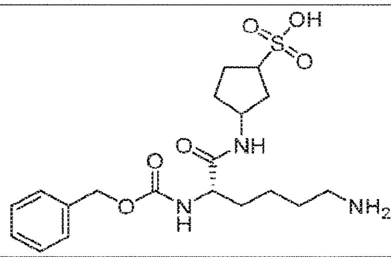 | | 428.52 |
| 2028 | 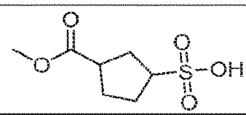 | 3.71 (s, 3H), 3.55-3.41 (m, 1H), 3.10-2.95 (m, 1H), 2.42-1.75 (m, 6H). | 207.00 |
| 2029 | 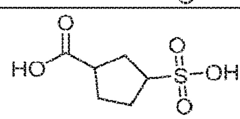 | First isomer: 3.53-3.45 (m, 1H), 2.88-2.81 (m, 1H), 2.19-2.11 (m, 3H), 2.03-2.00 (m, 1H), 1.97-1.71 (m, 2H); Second Isomer: 3.44-3.38 (m, 1H), 2.78-2.72 (m, 1H), 2.27-2.35 (m, 1H), 2.09-2.04 (m, 3H), 1.97-1.71 (m, 2H). | 193.00 |
| 2030 | 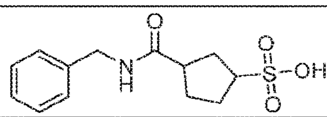 | 7.48-7.32 (m, 5H), 4.40-4.39 (d, J = 2.84 Hz, 2H), 3.60-3.40 (m, 1H), 2.99-2.87 (m, 1H), 2.36-1.77 (m, 6H). | 284.12 |
| 2031 | 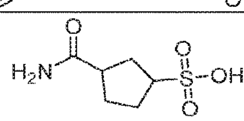 | 1.7(sx), 1.89(o), 2.03(t), 2.14(sx), 2.34(o), 2.39(t), 2.83(n), 3.42(n), 8.06(s), 9.2(s) | 194.22 |
| 2032 | 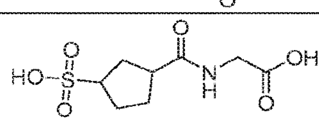 | 12.8(s), 7.89(s), 7.28(s), 3.85(s), 3.84(s), 3.44(n), 2.81(n), 2.43(t), 2.36(o), 2.17(sx), 2.06(t), 1.91(o), 1.73(sx) | 252.25 |
| 2033 | 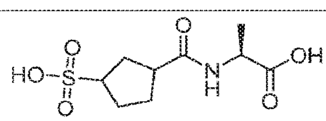 | 12(s), 7.79(s), 7.01(s), 4.32(q), 3.42(n), 2.84(n), 2.43(t), 2.34(o), 2.17(sx), 2.06(t), 1.89(o), 1.73(sx), 1.33(d) | 266.28 |

| | | | |
|---|---|---|---|
| 2034 | | δ 7.34-7.25 (m, 5 H), 4.69 (bs, 1H), 3.56-3.51 (m, 1H), 3.42-3.37 (m, 1H), 3.32-3.24 (m, 1H), 2.99-2.93 (t, J=12.0 Hz, 1H), 2.85-2.82 (t, J=8.0 Hz, 1H), 2.19-1.80 (m, 5H). | 342.01 |
| 2035 | | 11.27(s), 7.7(s), 6.9(s), 4.28(d), 3.44(n), 2.83(n), 2.4(t), 2.36(o), 2.16(m), 2.14(sx), 2.04(t), 1.91(o), 1.7(sx), 0.93(d) | 294.33 |
| 2036 | | 9.36(s), 7.69(s), 6.59(s), 4.12(t), 3.44(n), 2.81(n), 2.44(t), 2.36(o), 2.18(sx), 2.08(t), 1.91(o), 1.77(q), 1.74(sx), 1.61(m), 1.23(q), 0.86(d) | 308.36 |
| 2037 | | δ 4.49 (s, 1 H), 3.96-3.86 (m, 2H), 3.57-3.43 (m, 2H), 3.08-2.95 (m, 1H), 2.18-1.71 (m, 5H). | 281.80 |
| 2038 | | 10.21(s), 7.61(s), 7.51(s), 4.77(s), 4.03(o), 3.98(d), 3.42(n), 2.82(n), 2.38(t), 2.34(o), 2.13(sx), 2.02(t), 1.89(o), 1.69(sx), 0.99(d) | 296.31 |
| 2039 | | 9.36(s), 7.79(s), 6.8(s), 4.3(t), 3.43(n), 2.83(n), 2.55(t), 2.51(t), 2.42(t), 2.35(o), 2.17(sx), 2.06(t), 2.04(s), 2.03(sx), 1.9(o), 1.89(sx), 1.73(sx) | 326.39 |
| 2040 | | 8.19(s), 7.56(s), 7.44(s), 6.97(s), 6.94(sx), 6.66(d), 4.7(t), 3.4(n), 3.31(sx), 3.21(sx), 2.83(n), 2.39(t), 2.32(sx), 2.14(o), 2.03(t), 1.87(sx), 1.7(o) | 258.38 |
| 2041 | | 9.59(s), 7.57(q), 7.57(s), 7.54(s), 7.44(s), 7.34(q), 7.25(t), 7.14(sx), 7.02(sx), 4.7(t), 3.46(n), 3.39(q), 3.16(q), 2.89(n), 2.45(t), 2.38(o), 2.2(sx), 2.09(t), 1.93(o), 1.76(sx) | 381.42 |

Figure 2 cont'd

| # | Structure | NMR | MW |
|---|---|---|---|
| 2042 | (structure) | 11.18(s), 9.36(s), 8.62(s), 7.71(s), 4.51(t), 3.42(n), 2.93(d), 2.83(n), 2.82(d), 2.41(t), 2.33(o), 2.15(sx), 2.05(t), 1.88(o), 1.72(sx) | 310.29 |
| 2043 | (structure) | 9.36(s), 8.19(s), 7.89(s), 7.18(s), 4.44(t), 3.4(n), 2.86(d), 2.81(n), 2.64(d), 2.39(t), 2.31(o), 2.13(sx), 2.03(t), 1.86(o), 1.7(sx) | 309.31 |
| 2044 | (structure) | 10.86(s), 9.36(s), 8.53(s), 8.02(s), 7.62(s), 7(t), 4.66(t), 3.49(n), 3.34(q), 3.28(q), 2.92(n), 2.49(t), 2.41(o), 2.23(sx), 2.13(t), 1.96(o), 1.79(sx) | 332.34 |
| 2045 | (structure) | 12.4(s), 7.89(s), 6.98(s), 4.28(t), 3.4(n), 2.8(n), 2.79(t), 2.4(t), 2.4(t), 2.32(o), 2.14(sx), 2.04(t), 2.02(sx), 1.87(o), 1.7(sx), 1.61(p), 1.59(n), 1.58(sx), 1.55(p), 1.39(s), 1.36(n) | 323.38 |
| 2046 | (structure) | 0.86(s), 1.7(sx), 1.91(o), 1.93(s), 2.03(t), 2.14(sx), 2.28(s), 2.33(s), 2.36(o), 2.4(t), 2.77(n), 2.81(s), 3.2(s), 3.44(n), 5.99(s), 7.68(s) | 307.42 |
| 2047 | (structure) | 1.67(sx), 1.8(s), 1.87(o), 2(t), 2.11(sx), 2.32(o), 2.37(t), 2.58(t), 2.78(n), 2.89(t), 3.1(t), 3.4(n), 3.41(t), 3.43(t), 3.55(t), 6.2(s), 7.27(n), 7.3(m), 7.33(t), 7.65(s) | 327.41 |
| 2048 | (structure) | 1.33(n), 1.33(n), 1.64(o), 1.68(sx), 1.69(o), 1.72(p), 1.72(p), 1.9(o), 2.01(t), 2.09(sx), 2.11(sx), 2.13(sx), 2.35(o), 2.37(t), 2.5(s), 2.77(n), 2.85(o), 3.22(o), 3.43(n), 5.52(s), 7.94(s) | 291.38 |
| 2049 | (structure) | 1.41(o), 1.7(sx), 1.88(o), 1.87(sx), 2.03(t), 2.14(sx), 2.33(o), 2.39(t), 2.61(q), 2.78(n), 2.95(t), 3.15(n), 3.42(n), 4.72(s), 5.81(s), 7.94(s) | 277.35 |

Figure 2 cont'd

| # | Structure | NMR | MW |
|---|---|---|---|
| 2050 | (piperidine-4-amine with carbonyl linked to cyclopentane sulfonic acid) | 1.33(s), 1.49(o), 1.76(sx), 1.9(o), 1.95(sx), 2.09(t), 2.19(sx), 2.35(o), 2.45(t), 2.74(n), 2.76(q), 2.8(n), 3.2(t), 3.43(n), 7.94(s) | 277.35 |
| 2051 | (piperazine with carbonyl linked to cyclopentane sulfonic acid) | 1.74(sx), 1.89(o), 1.92(s), 2.07(t), 2.18(sx), 2.34(o), 2.44(t), 2.69(q), 2.87(n), 3(t), 3.34(q), 3.42(n), 3.67(t), 7.94(s) | 263.35 |
| 2052 | (4-aminocyclohexyl amide linked to cyclopentane sulfonic acid) | 1.15(s), 1.21(o), 1.26(o), 1.61(n), 1.66(sx), 1.71(sx), 1.71(sx), 1.9(o), 2.04(t), 2.15(sx), 2.35(o), 2.41(t), 2.64(n), 2.79(n), 3.43(n), 6.28(s), 7.94(s) | 291.38 |
| 2053 | (sulfo-cyclopentane carbonyl linked to 3-aminopyrrolidine) | 1.63(o), 1.72(sx), 1.89(o), 2.05(t), 2.08(o), 2.16(sx), 2.34(o), 2.42(t), 2.84(n), 2.91(t), 2.9(s), 3.02(d), 3.11(m), 3.32(t), 3.42(n), 3.41(d), 7.81(s) | 263.32 |
| 2054 | (prolinamide sulfonic acid) | 2.17(q), 2.53(q), 3.34(d), 3.56(m), 3.74(d), 4.25(q), 5.85(s), 7.07(s), 7.94(s) | 195.21 |
| 2055 | (N-benzyl prolinamide sulfonic acid) | 7.52-7.38 (m, 5H), 4.54-4.45 (d, J = 4.6 Hz, 2H), 4.43-4.38 (t, J = 8.6 Hz, 1H), 3.90-3.84 (m, 1H), 3.71-3.61 (m, 2H), 2.92-2.84 (m, 1H), 2.39-2.31 (m, 1H). | 285.33 |
| 2056 | (N-methyl prolinamide sulfonic acid) | 2.2(q), 2.57(q), 2.72(s), 3.38(d), 3.59(m), 3.77(d), 4.25(q), 5.93(s), 6.78(s), 7.85(s) | 209.23 |
| 2057 | (N,N-diethyl prolinamide sulfonic acid) | 1.14(t), 2.25(q), 2.61(q), 3.31(q), 3.36(d), 3.46(q), 3.58(m), 3.76(d), 4.26(q), 6.26(s), 7.75(s) | 251.31 |
| 2058 | (morpholine prolinamide sulfonic acid) | 2.22(q), 2.58(q), 3.35(d), 3.5(q), 3.54(q), 3.57(m), 3.68(t), 3.73(t), 3.75(d), 4.27(q), 6.34(s), 7.7(s) | 265.30 |
| 2059 | (N,N-bis(2-hydroxyethyl) prolinamide sulfonic acid) | 2.21(q), 2.57(q), 3.03(t), 3.21(t), 3.34(d), 3.56(m), 3.56(t), 3.74(d), 3.76(t), 4.06(s), 4.23(q), 6.3(s), 7.58(s) | 283.31 |

Figure 2 cont'd

| 2060 | | 2.2(q), 2.56(q), 3.36(d), 3.58(m), 3.76(d), 3.84(s), 3.85(s), 4.23(q), 6.5(s), 7.66(s), 7.77(s), 12.8(s) | 253.24 |
|---|---|---|---|
| 2061 | | 1.33(d), 2.2(q), 2.56(q), 3.34(d), 3.56(m), 3.74(d), 4.26(q), 4.32(q), 6.4(s), 7.67(s), 8.36(s), 12(s) | 267.27 |
| 2062 | | 2.16(q), 2.53(q), 3.21(sx), 3.31(sx), 3.31(d), 3.53(m), 3.71(d), 4.25(q), 4.7(t), 6.39(s), 7.22(n), 7.25(m), 7.28(t), 7.36(s), 7.44(s), 8(s) | 343.37 |
| 2063 | | 0.93(d), 2.08(m), 2.17(q), 2.53(q), 3.36(d), 3.57(m), 3.75(d), 4.12(d), 4.26(q), 6.3(s), 7.3(s), 7.58(s), 11.27(s) | 295.32 |
| 2064 | | 0.86(d), 1.23(q), 1.61(m), 1.77(q), 2.21(q), 2.57(q), 3.36(d), 3.58(m), 3.76(d), 4.12(t), 4.23(q), 6.5(s), 7.58(s), 8(s), 9.36(s) | 309.35 |
| 2065 | | 2.18(q), 2.54(q), 3.33(d), 3.55(m), 3.61(s), 3.72(d), 3.83(d), 4.02(d), 4.24(q), 4.27(t), 6.42(s), 7.59(s), 8.16(s), 10.21(s) | 283.27 |
| 2066 | | 0.99(d), 2.16(q), 2.52(q), 3.34(d), 3.56(m), 3.74(d), 3.98(d), 4.03(o), 4.24(q), 4.77(s), 6.28(s), 7.5(s), 7.89(s), 10.21(s) | 297.29 |
| 2067 | | 2.18(q), 2.3(sx), 2.43(sx), 2.54(q), 2.85(t), 3.16(t), 3.21(s), 3.33(d), 3.55(m), 3.73(d), 4.23(q), 4.3(t), 6.66(s), 7.68(s), 8(s), 9.36(s) | 359.38 |
| 2068 | | 2.17(q), 2.53(q), 3.21(sx), 3.31(sx), 3.32(d), 3.54(m), 3.71(d), 4.25(q), 4.7(t), 6.5(s), 6.66(d), 6.94(sx), 7.44(s), 7.45(s), 8(s), 8.19(s) | 359.37 |

Figure 2 cont'd

| | | | |
|---|---|---|---|
| 2069 | | 2.23(q), 2.59(q), 3.16(q), 3.38(d), 3.39(q), 3.59(m), 3.77(d), 4.24(t), 4.31(q), 6.81(s), 7.02(sx), 7.14(sx), 7.25(t), 7.34(q), 7.44(s), 7.45(s), 7.57(q), 8(s), 9.59(s) | 382.40 |
| 2070 | | 2.18(q), 2.54(q), 2.83(d), 2.94(d), 3.33(d), 3.55(m), 3.73(d), 4.25(q), 4.53(t), 6.45(s), 7.59(s), 8(s), 9.36(s), 11.18(s) | 311.28 |
| 2071 | | 2.16(q), 2.53(q), 2.64(d), 2.86(d), 3.31(d), 3.53(m), 3.71(d), 4.23(q), 4.59(t), 6.4(s), 7.18(s), 7.77(s), 8(s), 9.36(s) | 320.29 |
| 2072 | | 2.26(q), 2.62(q), 3.3(q), 3.36(q), 3.41(d), 3.63(m), 3.81(d), 4.35(q), 4.69(t), 6.68(s), 7(t), 7.5(s), 8(s), 8.53(s), 9.36(s), 10.86(s) | 333.33 |
| 2073 | | 1.36(n), 1.39(s), 1.54(p), 1.59(n), 1.59(sx), 1.62(p), 2.04(sx), 2.17(q), 2.4(t), 2.53(q), 2.79(t), 3.32(d), 3.54(m), 3.72(d), 4.22(q), 4.28(t), 6.39(s), 7.77(s), 8(s), 12.4(s) | 324.36 |
| 2074 | | 0.86(s), 1.93(s), 2.17(q), 2.28(s), 2.33(s), 2.53(q), 2.83(s), 3.23(s), 3.36(d), 3.58(m), 3.75(d), 4.19(q), 6.37(s), 6.42(s), 7.57(s) | 308.41 |
| 2075 | | 1.8(s), 2.14(q), 2.5(q), 2.58(t), 2.89(t), 3.1(t), 3.32(d), 3.41(t), 3.43(t), 3.54(m), 3.55(t), 3.71(d), 4.2(q), 6.19(s), 6.58(s), 7.27(n), 7.3(m), 7.33(t), 7.53(s) | 328.40 |
| 2076 | | 1.33(n), 1.33(n), 1.64(o), 1.69(o), 1.72(p), 1.72(p), 2.09(sx), 2.13(sx), 2.14(q), 2.51(q), 2.5(s), 2.87(o), 3.25(o), 3.35(d), 3.56(m), 3.74(d), 4.2(q), 5.9(s), 6.17(s), 7.82(s) | 292.37 |

Figure 2 cont'd

| | | | | |
|---|---|---|---|---|
| 2077 | | 1.43(o), 1.89(sx), 2.17(q), 2.53(q), 2.57(q), 2.91(t), 3.18(n), 3.33(d), 3.55(m), 3.73(d), 4.2(q), 4.72(s), 6.19(s), 6.38(s), 7.82(s) | 278.34 |
| 2078 | | 1.33(s), 1.5(o), 1.97(sx), 2.22(q), 2.58(q), 2.71(n), 2.78(q), 3.22(t), 3.35(d), 3.57(m), 3.75(d), 4.22(q), 6.53(s), 7.82(s) | 278.34 |
| 2079 | | 1.92(s), 2.21(q), 2.57(q), 2.69(q), 3(t), 3.34(q), 3.34(d), 3.55(m), 3.67(t), 3.73(d), 4.3(q), 6.54(s), 7.82(s) | 264.31 |
| 2080 | | 1.18(o), 1.15(s), 1.28(o), 1.61(n), 1.62(sx), 1.73(sx), 2.18(q), 2.54(q), 2.64(n), 3.35(d), 3.56(m), 3.74(d), 4.21(q), 6.36(s), 6.66(s), 7.82(s) | 292.37 |
| 2081 | | 1.64(o), 2.1(o), 2.19(q), 2.55(q), 2.9(s), 2.93(t), 3.04(d), 3.13(m), 3.34(d), 3.34(t), 3.44(d), 3.56(m), 3.74(d), 4.27(q), 6.41(s), 7.69(s) | 264.31 |
| 2082 | | 2.17(q), 2.53(q), 3.34(d), 3.56(m), 3.74(d), 4.25(q), 5.85(s), 7.07(s), 7.94(s) | 195.21 |
| 2083 | | 7.44-7.32 (m, 5H), 4.42 (s, 2H), 3.97-3.93 (m, 1H), 3.64-3.56 (m, 1H), 3.38-3.33 (m, 1H), 3.23-3.18 (m, 1H), 2.50-2.43 (m, 1H), 2.26-2.16 (m, 1H | 285.33 |
| 2084 | | 4.47-4.43 (t, J = 8.0 Hz, 1H), 3.93-3.85 (m, 1H), 3.77-3.66 (m, 2H), 2.90-2.83 (m, 1H), 2.80 (s, 3H), 2.39-2.31 (m, 1H). | 209.23 |
| 2085 | | 3.93-3.88 (m, 1H), 3.78-3.76 (d, J = 8.0 Hz, 2H), 3.52-3.32 (m, 4H), 3.10-2.97 (m, 2H), 2.29-2.21 (m, 1H), 1.25-1.21 (t, J = 8.0 Hz, 3H), 1.16-1.12 (t, J = 8.0 Hz, 3H). | 251.00 |

Figure 2 cont'd

| | | | |
|---|---|---|---|
| 2086 | | 2.22(q), 2.58(q), 3.35(d), 3.5(q), 3.54(q), 3.57(m), 3.68(t), 3.73(t), 3.75(d), 4.27(q), 6.34(s), 7.7(s) | 265.30 |
| 2087 | | 2.21(q), 2.57(q), 3.03(t), 3.21(t), 3.34(d), 3.56(m), 3.56(t), 3.74(d), 3.76(t), 4.06(s), 4.23(q), 6.3(s), 7.58(s) | 283.31 |
| 2088 | | 2.2(q), 2.56(q), 3.36(d), 3.58(m), 3.76(d), 3.84(s), 3.85(s), 4.23(q), 6.5(s), 7.66(s), 7.77(s), 12.8(s) | 253.24 |
| 2089 | | 1.33(d), 2.2(q), 2.56(q), 3.34(d), 3.56(m), 3.74(d), 4.26(q), 4.32(q), 6.4(s), 7.67(s), 8.36(s), 12(s) | 267.27 |
| 2090 | | 2.16(q), 2.53(q), 3.21(sx), 3.31(sx), 3.31(d), 3.53(m), 3.71(d), 4.25(q), 4.7(t), 6.39(s), 7.22(n), 7.25(m), 7.28(t), 7.36(s), 7.44(s), 8(s) | 343.37 |
| 2091 | | 0.93(d), 2.08(m), 2.17(q), 2.53(q), 3.36(d), 3.57(m), 3.75(d), 4.12(d), 4.26(q), 6.3(s), 7.3(s), 7.58(s), 11.27(s) | 295.32 |
| 2092 | | 0.86(d), 1.23(q), 1.61(m), 1.77(q), 2.21(q), 2.57(q), 3.36(d), 3.58(m), 3.76(d), 4.12(t), 4.23(q), 6.5(s), 7.58(s), 8(s), 9.36(s) | 309.35 |
| 2093 | | 2.18(q), 2.54(q), 3.33(d), 3.55(m), 3.61(s), 3.72(d), 3.83(d), 4.02(d), 4.24(q), 4.27(t), 6.42(s), 7.59(s), 8.16(s), 10.21(s) | 283.27 |
| 2094 | | 0.99(d), 2.16(q), 2.52(q), 3.34(d), 3.56(m), 3.74(d), 3.98(d), 4.03(o), 4.24(q), 4.77(s), 6.28(s), 7.5(s), 7.89(s), 10.21(s) | 297.29 |
| 2095 | | 2.18(q), 2.3(sx), 2.43(sx), 2.54(q), 2.85(t), 3.16(t), 3.21(s), 3.33(d), 3.55(m), 3.73(d), 4.23(q), 4.3(t), 6.66(s), 7.68(s), 8(s), 9.36(s) | 359.38 |

Figure 2 cont'd

| | | | |
|---|---|---|---|
| 2096 | (structure) | 2.17(q), 2.53(q), 3.21(sx), 3.31(sx), 3.32(d), 3.54(m), 3.71(d), 4.25(q), 4.7(t), 6.5(s), 6.66(d), 6.94(sx), 7.44(s), 7.45(s), 8(s), 8.19(s) | 359.37 |
| 2097 | (structure) | 2.17(q), 2.53(q), 3.21(sx), 3.31(sx), 3.32(d), 3.54(m), 3.71(d), 4.25(q), 4.7(t), 6.5(s), 6.66(d), 6.94(sx), 7.44(s), 7.45(s), 8(s), 8.19(s) | 382.40 |
| 2098 | (structure) | 2.18(q), 2.54(q), 2.83(d), 2.94(d), 3.33(d), 3.55(m), 3.73(d), 4.25(q), 4.53(t), 6.45(s), 7.59(s), 8(s), 9.36(s), 11.18(s) | 311.28 |
| 2099 | (structure) | 2.16(q), 2.53(q), 2.64(d), 2.86(d), 3.31(d), 3.53(m), 3.71(d), 4.23(q), 4.59(t), 6.4(s), 7.18(s), 7.77(s), 8(s), 9.36(s) | 310.29 |
| 2100 | (structure) | 2.26(q), 2.62(q), 3.3(q), 3.36(q), 3.41(d), 3.63(m), 3.81(d), 4.35(q), 4.69(t), 6.68(s), 7(t), 7.5(s), 8(s), 8.53(s), 9.36(s), 10.86(s) | 333.33 |
| 2101 | (structure) | 1.36(n), 1.39(s), 1.54(p), 1.59(n), 1.59(sx), 1.62(p), 2.04(sx), 2.17(q), 2.4(t), 2.53(q), 2.79(t), 3.32(d), 3.54(m), 3.72(d), 4.22(q), 4.28(t), 6.39(s), 7.77(s), 8(s), 12.4(s) | 324.36 |
| 2102 | (structure) | 0.86(s), 1.93(s), 2.17(q), 2.28(s), 2.33(s), 2.53(q), 2.83(s), 3.23(s), 3.36(d), 3.58(m), 3.75(d), 4.19(q), 6.37(s), 6.42(s), 7.57(s) | 308.41 |
| 2103 | (structure) | 1.8(s), 2.14(q), 2.5(q), 2.58(t), 2.89(t), 3.1(t), 3.32(d), 3.41(t), 3.43(t), 3.54(m), 3.55(t), 3.71(d), 4.2(q), 6.19(s), 6.58(s), 7.27(n), 7.3(m), 7.33(t), 7.53(s) | 328.40 |

Figure 2 cont'd

| | | | |
|---|---|---|---|
| 2104 | | 1.33(n), 1.33(n), 1.64(o), 1.69(o), 1.72(p), 1.72(p), 2.09(sx), 2.13(sx), 2.14(q), 2.51(q), 2.5(s), 2.87(o), 3.25(o), 3.35(d), 3.56(m), 3.74(d), 4.2(q), 5.9(s), 6.17(s), 7.82(s) | 292.37 |
| 2105 | | 1.43(o), 1.89(sx), 2.17(q), 2.53(q), 2.57(q), 2.91(t), 3.18(n), 3.33(d), 3.55(m), 3.73(d), 4.2(q), 4.72(s), 6.19(s), 6.38(s), 7.82(s) | 278.34 |
| 2106 | | 1.33(s), 1.5(o), 1.97(sx), 2.22(q), 2.58(q), 2.71(n), 2.78(q), 3.22(t), 3.35(d), 3.57(m), 3.75(d), 4.22(q), 6.53(s), 7.82(s) | 278.34 |
| 2107 | | 1.92(s), 2.21(q), 2.57(q), 2.69(q), 3(t), 3.34(q), 3.34(d), 3.55(m), 3.67(t), 3.73(d), 4.3(q), 6.54(s), 7.82(s) | 264.31 |
| 2108 | | 1.18(o), 1.15(s), 1.28(o), 1.61(n), 1.62(sx), 1.73(sx), 2.18(q), 2.54(q), 2.64(n), 3.35(d), 3.56(m), 3.74(d), 4.21(q), 6.36(s), 6.66(s), 7.82(s) | 292.37 |
| 2109 | | 1.64(o), 2.1(o), 2.19(q), 2.55(q), 2.9(s), 2.93(t), 3.04(d), 3.13(m), 3.34(d), 3.34(t), 3.44(d), 3.56(m), 3.74(d), 4.27(q), 6.41(s), 7.69(s) | 264.31 |
| 2110 | | 1.44(n), 1.66(n), 1.7(o), 1.7(sx), 1.86(sx), 1.85(sx), 2.03(t), 2.13(o), 2.31(sx), 2.39(t), 2.8(n), 2.95(t), 3.29(t), 3.4(n), 4.28(t), 4.97(s), 6(s), 7.27(s), 7.61(s), 7.89(s), 12.4(s) | 351.39 |

Figure 2 cont'd

| | | | |
|---|---|---|---|
| 2111 |  | | |
| 2112 |  | 1.7(o), 1.87(sx), 1.97(sx), 2.03(t), 2.07(t), 2.14(o), 2.14(sx), 2.32(sx), 2.39(t), 2.62(t), 2.8(n), 3.4(n), 4.28(t), 7.1(s), 7.74(s), 7.89(s), 12.4(s) | 323.33 |
| 2113 |  | 0.82(t), 0.82(d), 1.09(o), 1.38(o), 1.71(o), 1.74(m), 1.91(sx), 2.04(t), 2.15(o), 2.36(sx), 2.4(t), 2.83(n), 3.44(n), 4.02(d), 6.47(s), 7.69(s), 11.27(s) | 292.32 |
| 2114 |  | 1.67(m), 1.78(o), 1.85(m), 1.88(sx), 1.91(o), 2.11(t), 2.21(o), 2.34(o), 2.33(sx), 2.47(t), 2.92(n), 3.41(n), 3.64(t), 3.76(t), 4.68(q), 7.63(s), 10.21(s) | 292.32 |
| 2115 |  | 1.71(o), 1.88(sx), 2.05(t), 2.15(o), 2.28(sx), 2.33(sx), 2.41(sx), 2.41(t), 2.81(n), 2.88(t), 3.19(t), 3.21(s), 3.41(n), 4.3(t), 7.73(s), 7.8(s), 9.36(s) | 358.39 |

| 2116 |  | 1.44(n), 1.66(n), 1.7(sx), 1.85(sx), 2.17(q), 2.53(q), 2.95(t), 3.29(t), 3.31(d), 3.53(m), 3.71(d), 4.22(q), 4.28(t), 4.97(s), 6(s), 6.5(s), 7.61(s), 7.77(s), 8(s), 12.4(s) | 352.38 |
| --- | --- | --- | --- |
| 2117 |  | | |
| 2118 |  | 1.97(sx), 2.07(t), 2.14(sx), 2.17(q), 2.53(q), 2.62(t), 3.32(d), 3.53(m), 3.71(d), 4.22(q), 4.28(t), 6.41(s), 7.1(s), 7.77(s), 8(s), 12.4(s) | 324.32 |
| 2119 |  | 1.91(o), 1.98(m), 2.16(m), 2.24(q), 2.34(o), 2.61(q), 3.33(d), 3.55(m), 3.62(t), 3.73(d), 3.74(t), 4.35(q), 4.68(q), 6.83(s), 7.51(s), 10.21(s) | 293.31 |

| 2120 |  | 1.44(n), 1.66(n), 1.7(sx), 1.85(sx), 2.17(q), 2.53(q), 2.95(t), 3.29(t), 3.31(d), 3.53(m), 3.71(d), 4.22(q), 4.28(t), 4.97(s), 6(s), 6.5(s), 7.61(s), 7.77(s), 8(s), 12.4(s) | 352.38 |
|---|---|---|---|
| 2121 |  | | |
| 2122 |  | 1.97(sx), 2.07(t), 2.14(sx), 2.17(q), 2.53(q), 2.62(t), 3.32(d), 3.53(m), 3.71(d), 4.22(q), 4.28(t), 6.41(s), 7.1(s), 7.77(s), 8(s), 12.4(s) | 324.32 |
| 2123 |  | 0.82(t), 0.82(d), 1.09(o), 1.38(o), 1.74(m), 2.18(q), 2.54(q), 3.36(d), 3.58(m), 3.76(d), 4.02(d), 4.25(q), 6.3(s), 7.3(s), 7.58(s), 11.27(s) | 309.35 |
| 2124 |  | 1.91(o), 1.98(m), 2.16(m), 2.24(q), 2.34(o), 2.61(q), 3.33(d), 3.55(m), 3.62(t), 3.73(d), 3.74(t), 4.35(q), 4.68(q), 6.83(s), 7.51(s), 10.21(s) | 293.31 |

| | | | |
|---|---|---|---|
| 2125 |  | 1.44(n), 1.44(sx), 1.64(o), 1.67(n), 1.72(sx), 1.89(sx), 1.92(q), 1.97(o), 2.17(sx), 2.28(q), 2.92(s), 2.97(t), 3.25(n), 3.31(t), 3.5(n), 3.6(t), 4.97(s), 6.57(s), 7.61(s), 7.71(s), 8.23(s) | 322.40 |
| 2126 |  | 1.64(o), 1.72(sx), 1.73(sx), 1.84(t), 1.92(q), 1.98(o), 2.17(sx), 2.17(sx), 2.28(q), 2.39(t), 2.92(s), 3.25(n), 3.5(n), 3.7(t), 6.74(s), 7.1(s), 7.71(s) | 294.34 |
| 2127 |  | 0.79(d), 0.83(t), 1.2(o), 1.49(o), 1.65(o), 1.76(sx), 1.87(m), 1.93(q), 1.98(o), 2.21(sx), 2.29(q), 2.52(s), 3.3(n), 3.53(n), 3.54(d), 6.32(s), 7.51(s) | 279.37 |
| 2128 |  | 1.5(m), 1.64(m), 1.68(o), 1.72(sx), 1.75(o), 2(q), 2.02(o), 2.05(sx), 2.2(o), 2.36(q), 2.91(t), 3(t), 3.28(n), 3.56(n), 3.97(q), 4.15(s), 7.17(s), 7.45(s) | 263.32 |
| 2129 |  | | |

| 2130 | [structure] | 1.65(o), 1.73(sx), 1.93(q), 1.99(o), 2.1(sx), 2.18(sx), 2.24(sx), 2.3(q), 2.79(t), 2.92(s), 3.1(t), 3.21(s), 3.27(n), 3.51(n), 3.73(t), 6.74(s), 7.62(s) | 329.40 |
|---|---|---|---|
| 2131 | [structure] | 7.47-7.38 (m, 5H), 5.23-5.05 (m, 2H), 4.63-4.54 (m, 1H), 4.07-3.97 (m, 1H), 3.76 (s, 1.5H), 3.61 (s, 1.5H), 3.77-3.61 (m, 2H), 2.80-2.72 (m, 1H), 2.41-2.35 (m, 1H). | 344.03 |
| 2132 | [structure] | 7.46-7.39 (m, 5H), 5.18-5.13 (m, 2H), 4.35-4.28 (m, 1H), 4.10-3.95 (m, 1H), 3.74-3.69 (m, 1H), 3.60-3.53 (m, 1H), 2.74-2.71 (m, 1H), 2.23-2.12 (m, 1H) | 329.92 |

Figure 2 cont'd

COMPOSITIONS AND METHODS FOR TREATING AND PREVENTING NEURODEGENERATIVE DISORDERS

This application is a continuation of U.S. patent application Ser. No. 15/751,547, filed Feb. 9, 2018, which is a U.S. National Phase application, filed under 35 U.S.C. § 371(c) of International Application No. PCT/US2016/046336, filed Aug. 10, 2016, which claims priority to, and the benefit of, U.S. Provisional Application No. 62/203,256, filed Aug. 10, 2015, the disclosure of each of which is hereby incorporated by reference herein in its entirety for all purposes.

BACKGROUND

Alzheimer's disease (AD) is a progressive degenerative disease of the brain primarily associated with aging. Prevalence of AD in the United States in 2000 was close to 4.5 Million. It was estimated that about one in ten individuals over 65 and nearly half of those over 85 are affected by Alzheimer's disease. Approximately 360,000 patients will be diagnosed with AD each year in the United States alone. Clinical presentation of AD is characterized by loss of memory, cognition, reasoning, judgment, and orientation. As the disease progresses, motor, sensory, and linguistic abilities are also affected until there is global impairment of multiple cognitive functions. These cognitive losses occur gradually, but typically lead to severe impairment and eventual death in the range of four to twelve years.

Alzheimer's disease is characterized by two major pathologic observations in the brain: neurofibrillary tangles and beta amyloid plaques (neuritic plaques), comprised predominantly of an aggregate of a peptide fragment known as amyloid beta (Aß). Individuals with AD exhibit characteristic beta-amyloid deposits in the brain (beta amyloid plaques) and in cerebral blood vessels (beta amyloid angiopathy) as well as neurofibrillary tangles. Neurofibrillary tangles occur not only in Alzheimer's disease but also in other dementia-inducing disorders. Both soluble oligomeric Aβ and fibrillar Aβ are also believed to be neurotoxic and inflammatory.

ALZ-801 (3-(2-amino-3-methylbutanamido)propane-1-sulfonic acid), a prodrug of 3-amino-1-propanesulfonic acid (3APS, Tramiprosate) is a promising investigational product candidate for the treatment of Alzheimer's disease. Tramiprosate is believed to act by reducing the deposition and/or load of amyloid in the brain through its binding to soluble Aß peptide.

There remains a need for additional and improved pharmaceutical agents for preventing and treating amyloid-related diseases such as Alzheimer's disease. For improved pharmaceutical agents, it is desirable to increase the agent's bioavailability, stability and/or blood brain barrier crossing. These, and other needs, can be satisfied by the disclosure herein of new compositions and uses thereof to treat various medical disorders.

SUMMARY

The present invention relates to certain compounds and their use for treating or preventing neurodegenerative disorders such as amyloid-related diseases, including but not limited to Alzheimer's disease. Compounds of the present invention have been found to bind to Aß, and therefore may be useful for the treatment and/or prevention of neurodegenerative disorders. Without being bound by theory, it is thought that the binding of the compounds of the present invention has an amyloid-beta anti-aggregation effect, thus preventing formation of toxic amyloid oligomers, protofibrils and fibrils and eventually plagues. Also, they may promote clearance of the protein, thus reducing plaque build-up, and providing a means to treat and Alzheimer's disease. As a matter of biomolecular recognition and the complementarity of a ligand and the receptor (in general terms) the compounds are designed to express biological activity and binding based on these principles.

The invention also relates to methods of treating and/or preventing amyloid related disease in a subject comprising administering to the subject a therapeutically effective amount of a compound of the invention. The invention also relates to each of the novel compounds of the invention as described herein. Among the compounds for use in the invention are those according to the following Formulae, such that, when administered, amyloid fibril formation, organ specific dysfunction (e.g., neurodegeneration), or cellular toxicity is reduced or inhibited.

Disclosed herein are compositions for the treatment and prevention of Alzheimer's disease and methods of treating and/or preventing Alzheimer's disease to patients in need thereof. In certain embodiments of the invention, patients are homozygous or heterozygous for the ApoE4 allele.

In one aspect, the invention pertains at least in part to compounds comprising a non-aromatic carbocyclic or heterocyclic ring, wherein:
a) the non-aromatic carbocyclic or heterocyclic ring comprises from 3 to 7 ring atoms wherein from 2 to 4 ring atoms are substituted with a functional group substituent, wherein:
  (i) each functional group substituent is independently selected from the group consisting of $-NH_2$, $-NR_aR_b$, $-C(O)NH_2$, $-C(O)NR_aR_b$, $-OH$, $-CO_2H$, $-SO_3H$, and a straight chain or branched lower alkyl group substituted with a functional group selected from the group consisting of $-NH_2$, $-NR_aR_b$, $-C(O)NH_2$, $-C(O)NR_aR_b$, $-OH$, $-CO_2H$, and $-SO_3H$; wherein $R_a$ and $R_b$ are each independently selected from the group consisting of hydrogen, deuterium, halogen, alkyl, alkenyl, alkynyl, cycloalkyl, heterocycloalkyl, aryl, heteroaryl, amino acid or dipeptide; $R_a$ and $R_b$ taken together with the nitrogen optionally form a heterocycle; and
  (ii) wherein if 4 ring atoms of the non-aromatic carbocyclic or heterocyclic ring are substituted with functional group substituents, then no more than three of said functional group substituents can be identical, and
b) the non-aromatic carbocyclic or heterocyclic ring further comprises from 0 to 12 additional substituents each independently selected from the group consisting of deuterium, halogen, alkyl, alkoxy, alkenyl, alkynyl, cyano, cycloalkyl, heterocycloalkyl, aryl, and heteroaryl;
or a pharmaceutically acceptable salt thereof.

In another aspect, the invention pertains at least in part to compounds comprising a non-aromatic carbocyclic or heterocyclic ring, wherein:
a) the non-aromatic carbocyclic or heterocyclic ring comprises from 3 to 7 ring atoms wherein from 2 to 4 ring atoms are substituted with a functional group substituent, wherein:
  (i) each functional group substituent is independently selected from the group consisting of $-NH_2$, $-NR_aR_b$, $-C(O)R_z$, $-C(O)NH_2$, $-C(O)NR_aR_b$, $-OH$, $-CO_2H$, $-COOalkyl/carboxylesters$, $-SO_3H$, and a straight chain or branched lower alkyl group substituted with a functional group selected from the group consisting of —NH$_2$, —NR$_a$R$_b$, —C(O)R$_z$, —C(O)NH$_2$, —C(O)NR$_a$R$_b$, —OH, —CO$_2$H, —COOalkyl, and —SO$_3$H; wherein R$_a$ and R$_b$ are each independently selected from the group consisting of hydrogen, deuterium, halogen, alkyl, alkenyl, alkynyl, cycloalkyl, heterocycloalkyl, aryl, heteroaryl, amino acid or dipeptide; R$_a$ and R$_b$ taken together with the nitrogen optionally form a heterocycle; R$_z$ is an amino acid or a dipeptide; and (ii) wherein if 4 ring atoms of the non-aromatic carbocyclic or heterocyclic ring are substituted with functional group substituents, then no more than three of said functional group substituents can be identical, and b) the non-aromatic carbocyclic or heterocyclic ring further comprises from 0 to 12 additional substituents each independently selected from the group consisting of deuterium, halogen, alkyl, alkoxy, alkenyl, alkynyl, cyano, cycloalkyl, heterocycloalkyl, aryl, and heteroaryl;

or a pharmaceutically acceptable salt thereof.

In one embodiment, the invention pertains, at least in part to compounds of Formula I:

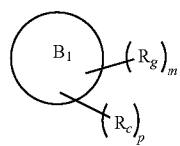

Formula I

Wherein:

B$_1$ is a 3-membered to 7-membered non-aromatic ring, wherein the ring is optionally substituted or unsubstituted, optionally carbocyclic or heterocyclic, or optionally saturated or unsaturated;

Each R$_g$ is independently —H, —NH$_2$, —NR$_a$R$_b$, —C(O)R$_z$, —C(O)NH$_2$, —C(O)NR$_a$R$_b$, —(C(R$_x$)(R$_y$))$_n$NH$_2$, —(C(R$_x$)(R$_y$))$_n$NR$_a$R$_b$, —(C(R$_a$)(R$_b$))$_n$C(O)NH$_2$, —(C(R$_a$)(R$_b$))$_n$C(O)NR$_a$R$_b$, —OH, —(C(R$_a$)(R$_b$))$_n$OH, —CO$_2$H, —COOalkyl, —(C(R$_a$)(R$_b$))$_n$CO$_2$H, —(C(R$_a$)(R$_b$))$_n$CO$_2$alkyl, —SO$_3$H, or —(C(R$_a$)(R$_b$))$_n$ SO$_3$H; provided that no more than three R$_g$ groups are identical Each R$_a$ and R$_b$ are each independently hydrogen, deuterium, halogen, alkyl, alkenyl, alkynyl, cycloalkyl, heterocycloalkyl, aryl, heteroaryl, amino acid or dipeptide; R$_a$ and R$_b$ taken together with the nitrogen optionally form a heterocycle; R$_z$ is an amino acid or a dipeptide;

Each R$_x$ and R$_y$ are each independently a hydrogen or a C1-C6 alkyl group;

Each R$_c$ is independently hydrogen, deuterium, halogen, alkyl, alkoxy, alkenyl, alkynyl, cyano, cycloalkyl, heterocycloalkyl, aryl, or heteroaryl;

m is an integer from 2 to 4;

Each n is an integer from 1 to 6;

p is an integer from 0 to 12;

or a pharmaceutically acceptable salt thereof.

In one embodiment, the invention pertains, at least in part to compounds of Formula I:

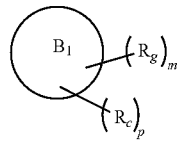

Formula I

Wherein:

B$_1$ is a 3-membered to 7-membered non-aromatic ring, wherein the ring is optionally substituted or unsubstituted, optionally carbocyclic or heterocyclic, or optionally saturated or unsaturated;

Each R$_g$ is independently —H, —NH$_2$, —NR$_a$R$_b$, —C(O)NH$_2$, —C(O)NR$_a$R$_b$, —(C(R$_x$)(R$_y$))$_n$NH$_2$, —(C(R$_x$)(R$_y$))$_n$ NR$_a$R$_b$, —(C(R$_a$)(R$_b$))$_n$C(O)NH$_2$, —(C(R$_a$)(R$_b$))$_n$ C(O)NR$_a$R$_b$, —OH, —(C(R$_a$)(R$_b$))$_n$OH, —CO$_2$H, —(C(R$_a$)(R$_b$))$_n$CO$_2$H, —SO$_3$H, or —(C(R$_a$)(R$_b$))$_n$ SO$_3$H; provided that no more than three R$_g$ groups are identical Each R$_a$ and R$_b$ are each independently hydrogen, deuterium, halogen, alkyl, alkenyl, alkynyl, cycloalkyl, heterocycloalkyl, aryl, heteroaryl, amino acid or dipeptide; R$_a$ and R$_b$ taken together with the nitrogen optionally form a heterocycle;

Each R$_x$ and R$_y$ are each independently a hydrogen or a C1-C6 alkyl group;

Each R$_c$ is independently hydrogen, deuterium, halogen, alkyl, alkoxy, alkenyl, alkynyl, cyano, cycloalkyl, heterocycloalkyl, aryl, or heteroaryl;

m is an integer from 2 to 4;

Each n is an integer from 1 to 6;

p is an integer from 0 to 12;

or a pharmaceutically acceptable salt thereof.

In one embodiment, the invention pertains, at least in part to compounds of Formula Ia:

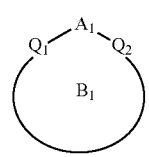

Formula Ia

Wherein:

B$_1$ is a 3-membered to 7-membered non-aromatic ring, wherein the ring is optionally substituted or unsubstituted, optionally carbocyclic or heterocyclic, or optionally saturated or unsaturated;

Q$_1$ is —C(R$_1$)(R$_2$)— or —N(R$_5$)—;

Q$_2$ is —C(R$_3$)(R$_4$)— or —N(R$_6$)—;

A$_1$ is —CH$_2$—, —C(R$_7$)(R$_8$)—, —C(O)—, —NH—, —N(R$_9$)—, —O—, —S—, —SO$_2$—, or a covalent bond;

R$_1$, R$_2$, R$_3$, R$_4$, R$_7$, and R$_8$ are each independently —H, —NH$_2$, —NR$_a$R$_b$, —C(O)R$_z$, —C(O)NH$_2$, —C(O) NR$_a$R$_b$, —(C(R$_x$)(R$_y$))$_n$NH$_2$, —(C(R$_x$)(R$_y$))$_n$NR$_a$R$_b$, —(C(R$_a$)(R$_b$))$_n$C(O)NH$_2$, —(C(R$_a$)(R$_b$))$_n$C(O)NR$_a$R$_b$, —OH, —(C(R$_a$)(R$_b$))$_n$OH, —CO$_2$H, —(C(R$_a$)(R$_b$))$_n$ CO$_2$H, —SO$_3$H, or —(C(R$_a$)(R$_b$))$_n$ SO$_3$H; deuterium, halogen, alkyl, alkoxy, alkenyl, alkynyl, cyano, cycloalkyl, heterocycloalkyl, aryl, or heteroaryl;

R$_5$, R$_6$, and each R$_9$ are each independently —H, —C(O) NH$_2$, —C(O)NR$_a$R$_b$, —(C(R$_x$)(R$_y$))$_n$NH$_2$, —(C(R$_x$)(R$_y$))$_n$ NR$_a$R$_b$, —(C(R$_a$)(R$_b$))$_n$C(O)NH$_2$, —(C(R$_a$)(R$_b$))$_n$ C(O)NR$_a$R$_b$, —(C(R$_a$)(R$_b$))$_n$OH, —CO$_2$H, —(C(R$_a$)(R$_b$))$_n$CO$_2$H, or —(C(R$_a$)(R$_b$))$_n$ SO$_3$H; deuterium, halogen, alkyl, alkoxy, alkenyl, alkynyl, cyano, cycloalkyl, heterocycloalkyl, aryl, or heteroaryl;

Each R$_a$ and R$_b$ are each independently hydrogen, deuterium, halogen, alkyl, alkenyl, alkynyl, cycloalkyl, heterocycloalkyl, aryl, heteroaryl, amino acid a dipeptide; R$_a$ and R$_b$ taken together with the nitrogen optionally form a heterocycle;

Each $R_x$ and $R_y$ are each independently a hydrogen or a C1-C6 alkyl group;

Each n is an integer from 1 to 6;

wherein at least two of $R_1$, $R_2$, $R_3$, $R_4$, $R_5$, $R_6$, $R_7$, $R_8$, and $R_9$ comprise a functional group selected from the group consisting of —$NH_2$, —$NR_aR_b$, —$C(O)R_z$, —$C(O)NH_2$, —$C(O)NR_aR_b$, —OH, —$CO_2H$, —$SO_3H$; and wherein a maximum of three of $R_1$, $R_2$, $R_3$, $R_4$, $R_5$, $R_6$, $R_7$, $R_8$, and $R_9$ comprise an identical functional group.

or a pharmaceutically acceptable salt thereof.

In a further embodiment, the invention pertains, at least in part to compounds of Formula Ia wherein:

$R_1$, $R_2$, $R_3$, $R_4$, $R_7$, and $R_8$ are each independently —H, —$NH_2$, —$NR_aR_b$, —$C(O)NH_2$, —$C(O)NR_aR_b$, —$(C(R_x)(R_y))_n NH_2$, —$(C(R_x)(R_y))_n NR_aR_b$, —$(C(R_a)(R_b))_n C(O)NH_2$, —$(C(R_a)(R_b))_n C(O)NR_aR_b$, —OH, —$(C(R_a)(R_b))_n OH$, —$CO_2H$, —$(C(R_a)(R_b))_n CO_2H$, —$SO_3H$, or —$(C(R_a)(R_b))_n SO_3H$; deuterium, halogen, alkyl, alkoxy, alkenyl, alkynyl, cyano, cycloalkyl, heterocycloalkyl, aryl, or heteroaryl.

In another embodiment, the invention pertains, at least in part to compounds of Formula Ib:

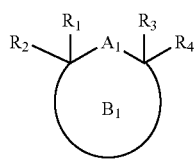

Formula Ib

Wherein:

$B_1$ is a 3-membered to 7-membered non-aromatic ring, wherein the ring is optionally substituted or unsubstituted, optionally carbocyclic or heterocyclic, or optionally saturated or unsaturated;

$R_1$ is —$SO_3H$, or —$(CH_2)_n SO_3H$;

$A_1$ is —$CH_2$—, —$C(R_7)(R_8)$—, —$C(O)$—, —NH—, —$N(R_9)$—, —O—, —S—, —$SO_2$—, or a covalent bond;

$R_2$, $R_3$, $R_4$, $R_7$, and $R_8$ are each independently —H, —$NH_2$, —$NR_aR_b$, —$C(O)R_z$, —$C(O)NH_2$, —$C(O)NR_aR_b$, —$(C(R_x)(R_y))_n NH_2$, —$(C(R_x)(R_y))_n NR_aR_b$, —$(C(R_a)(R_b))_n C(O)NH_2$, —$(C(R_a)(R_b))_n C(O)NR_aR_b$, —OH, —$(C(R_a)(R_b))_n OH$, —$CO_2H$, —$(C(R_a)(R_b))_n CO_2H$, —$SO_3H$, —$(C(R_a)(R_b))_n SO_3H$; deuterium, halogen, alkyl, alkoxy, alkenyl, alkynyl, cyano, cycloalkyl, heterocycloalkyl, aryl, or heteroaryl;

Each $R_9$ is independently —H, —$C(O)NH_2$, —$C(O)NR_aR_b$, —$(C(R_x)(R_y))_n NH_2$, —$(C(R_x)(R_y))_n NR_aR_b$, —$(C(R_a)(R_b))_n C(O)NH_2$, —$(C(R_a)(R_b))_n C(O)NR_aR_b$, —$(C(R_a)(R_b))_n OH$, —$CO_2H$, —$(C(R_a)(R_b))_n CO_2H$, or —$(C(R_a)(R_b))_n SO_3H$; deuterium, halogen, alkyl, alkoxy, alkenyl, alkynyl, cyano, cycloalkyl, heterocycloalkyl, aryl, or heteroaryl;

Each $R_a$ and $R_b$ are each independently hydrogen, deuterium, halogen, alkyl, alkenyl, alkynyl, cycloalkyl, heterocycloalkyl, aryl, heteroaryl, amino acid a dipeptide; $R_a$ and $R_b$ taken together with the nitrogen optionally form a heterocycle; $R_z$ is an amino acid or a dipeptide;

Each $R_x$ and $R_y$ are each independently a hydrogen or a C1-C6 alkyl group;

Each n is an integer from 1 to 6;

wherein at least two of $R_1$, $R_2$, $R_3$, $R_4$, $R_7$, $R_8$, and $R_9$ comprise a functional group selected from the group consisting of —$NH_2$, —$NR_aR_b$, —$C(O)R_z$, —$C(O)NH_2$, —$C(O)NR_aR_b$, —OH, —$CO_2H$, —$SO_3H$; and wherein a maximum of three of $R_1$, $R_2$, $R_3$, $R_4$, $R_7$, $R_8$, and $R_9$ comprise an identical functional group;

or a pharmaceutically acceptable salt thereof.

In a further embodiment, the invention pertains, at least in part to compounds of Formula Ib wherein:

$R_2$, $R_3$, $R_4$, $R_7$, and $R_8$ are each independently —H, —$NH_2$, —$NR_aR_b$, —$C(O)NH_2$, —$C(O)NR_aR_b$, —$(C(R_x)(R_y))_n NH_2$, —$(C(R_x)(R_y))_n NR_aR_b$, —$(C(R_a)(R_b))_n C(O)NH_2$, —$(C(R_a)(R_b))_n C(O)NR_aR_b$, —OH, —$(C(R_a)(R_b))_n OH$, —$CO_2H$, —$(C(R_a)(R_b))_n CO_2H$, —$SO_3H$, or —$(C(R_a)(R_b))_n SO_3H$; deuterium, halogen, alkyl, alkoxy, alkenyl, alkynyl, cyano, cycloalkyl, heterocycloalkyl, aryl, or heteroaryl In another embodiment, the invention pertains, at least in part to non-aromatic compounds of Formula II:

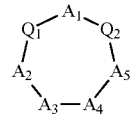

Formula II wherein:

$Q_1$ is —$C(R_1)(R_2)$— or —$N(R_5)$—;

$Q_2$ is —$C(R_3)(R_4)$— or —$N(R_6)$—;

$A_1$ is —$CH_2$—, —$C(R_7)(R_8)$—, —$C(O)$—, —NH—, —$N(R_9)$—, —O—, —S—, —$SO_2$—, or a covalent bond;

$A_2$, $A_3$, $A_4$, and $A_5$ are each independently —$CH_2$—, —$C(R_7)(R_8)$—, —$C(O)$—, —NH—, —$N(R_9)$—, —O—, —S—, —$SO_2$—; or $A_2$ and $A_3$ taken together are —$C(R_7)=C(R_8)$—, —$C(R_7)=N$—, or —$N=C(R_7)$—, or $A_3$ and $A_4$ taken together are —$C(R_7)=C(R_8)$—, —$C(R_7)=N$—, or —$N=C(R_7)$—; or $A_4$, and $A_5$ taken together are —$C(R_7)=C(R_8)$—, —$C(R_7)=N$—, or —$N=C(R_7)$—;

$R_1$, $R_2$, $R_3$, $R_4$, $R_7$, and $R_8$ are each independently —H, —$NH_2$, —$NR_aR_b$, —$C(O)R_z$, —$C(O)NH_2$, —$C(O)NR_aR_b$, —$(C(R_x)(R_y))_n NH_2$, —$(C(R_x)(R_y))_n NR_aR_b$, —$(C(R_a)(R_b))_n C(O)NH_2$, —$(C(R_a)(R_b))_n C(O)NR_aR_b$, —OH, —$(C(R_a)(R_b))_n OH$, —$CO_2H$, —$(C(R_a)(R_b))_n CO_2H$, —$SO_3H$, or —$(C(R_a)(R_b))_n SO_3H$; deuterium, halogen, alkyl, alkoxy, alkenyl, alkynyl, cyano, cycloalkyl, heterocycloalkyl, aryl, or heteroaryl;

$R_5$, $R_6$, and each $R_9$ are each independently —H, —$C(O)NH_2$, —$C(O)NR_aR_b$, —$(C(R_x)(R_y))_n NH_2$, —$(C(R_x)(R_y))_n NR_aR_b$, —$(C(R_a)(R_b))_n C(O)NH_2$, —$(C(R_a)(R_b))_n C(O)NR_aR_b$, —$(C(R_a)(R_b))_n OH$, —$CO_2H$, —$(C(R_a)(R_b))_n CO_2H$, or —$(C(R_a)(R_b))_n SO_3H$; deuterium, halogen, alkyl, alkoxy, alkenyl, alkynyl, cyano, cycloalkyl, heterocycloalkyl, aryl, or heteroaryl;

Each $R_a$ and $R_b$ are each independently hydrogen, deuterium, halogen, alkyl, alkenyl, alkynyl, cycloalkyl, heterocycloalkyl, aryl, heteroaryl, amino acid a dipeptide; $R_a$ and $R_b$ taken together with the nitrogen optionally form a heterocycle; $R_z$ is an amino acid or a dipeptide;

Each $R_x$ and $R_y$ are each independently a hydrogen or a C1-C6 alkyl group;

Each n is an integer from 1 to 6;

wherein at least two of $R_1$, $R_2$, $R_3$, $R_4$, $R_5$, $R_6$, $R_7$, $R_8$, and $R_9$ comprise a functional group selected from the group consisting of —$NH_2$, —$NR_aR_b$, —$C(O)R_z$, —$C(O)NH_2$, —$C(O)NR_aR_b$, —OH, —$CO_2H$, —$SO_3H$; and wherein a maximum of three of $R_1$, $R_2$, $R_3$, $R_4$, $R_5$, $R_6$, $R_7$, $R_8$, and $R_9$ comprise an identical functional group;

or a pharmaceutically acceptable salt thereof.

In a further embodiment, the invention pertains, at least in part to compounds of Formula II wherein:

$R_1$, $R_2$, $R_3$, $R_4$, $R_7$, and $R_8$ are each independently —H, —$NH_2$, —$NR_aR_b$, —C(O)$NH_2$, —C(O)$NR_aR_b$, —(C($R_x$)($R_y$))$_n$$NH_2$, —(C($R_x$)($R_y$))$_n$ $NR_aR_b$, —(C($R_a$)($R_b$))$_n$C(O)$NH_2$, —(C($R_a$)($R_b$))$_n$C(O)$NR_aR_b$, —OH, —(C($R_a$)($R_b$))$_n$OH, —$CO_2H$, —(C($R_a$)($R_b$))$_n$$CO_2H$, —$SO_3H$, or —(C($R_a$)($R_b$))$_n$$SO_3H$; deuterium, halogen, alkyl, alkoxy, alkenyl, alkynyl, cyano, cycloalkyl, heterocycloalkyl, aryl, or heteroaryl In another embodiment, the invention pertains, at least in part to non-aromatic compounds of Formula III:

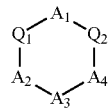

Formula III wherein:
$Q_1$ is —C($R_1$)($R_2$)— or —N($R_5$)—;
$Q_2$ is —C($R_3$)($R_4$)— or —N($R_6$)—;
$A_1$ is —$CH_2$—, —C($R_7$)($R_8$)—, —C(O)—, —NH—, —N($R_9$)—, —O—, —S—, —$SO_2$—, or a covalent bond;
$A_2$, $A_3$, and $A_4$ are each independently —$CH_2$—, —C($R_7$)($R_8$)—, —C(O)—, —NH—, —N($R_9$)—, —O—, —S—, —$SO_2$—; or $A_2$ and $A_3$ taken together are —C($R_7$)=C($R_8$)—, —C($R_7$)=N—, or —N=C($R_7$)—, or $A_3$ and $A_4$ taken together are —C($R_7$)=C($R_8$)—, —C($R_7$)=N—, or —N=C($R_7$)—;
$R_1$, $R_2$, $R_3$, $R_4$, $R_7$, and $R_8$ are each independently —H, —$NH_2$, —$NR_aR_b$, —C(O)$R_z$, —C(O)$NH_2$, —C(O)$NR_aR_b$, —(C($R_x$)($R_y$))$_n$$NH_2$, —(C($R_x$)($R_y$))$_n$$NR_aR_b$, —(C($R_a$)($R_b$))$_n$C(O)$NH_2$, —(C($R_a$)($R_b$))$_n$C(O)$NR_aR_b$, —OH, —(C($R_a$)($R_b$))$_n$OH, —$CO_2H$, —(C($R_a$)($R_b$))$_n$$CO_2H$, —$SO_3H$, or —(C($R_a$)($R_b$))$_n$$SO_3H$; deuterium, halogen, alkyl, alkoxy, alkenyl, alkynyl, cyano, cycloalkyl, heterocycloalkyl, aryl, or heteroaryl;
$R_5$, $R_6$, and each $R_9$ are each independently —H, —C(O)$NH_2$, —C(O)$NR_aR_b$, —(C($R_x$)($R_y$))$_n$$NH_2$, —(C($R_x$)($R_y$))$_n$ $NR_aR_b$, —(C($R_a$)($R_b$))$_n$C(O)$NH_2$, —(C($R_a$)($R_b$))$_n$C(O)$NR_aR_b$, —(C($R_a$)($R_b$))$_n$OH, —$CO_2H$, —(C($R_a$)($R_b$))$_n$$CO_2H$, or —(C($R_a$)($R_b$))$_n$ $SO_3H$; deuterium, halogen, alkyl, alkoxy, alkenyl, alkynyl, cyano, cycloalkyl, heterocycloalkyl, aryl, or heteroaryl;
Each $R_a$ and $R_b$ are each independently hydrogen, deuterium, halogen, alkyl, alkenyl, alkynyl, cycloalkyl, heterocycloalkyl, aryl, heteroaryl, amino acid a dipeptide; $R_a$ and $R_b$ taken together with the nitrogen optionally form a heterocycle; $R_z$ is an amino acid or a dipeptide;
Each $R_x$ and $R_y$ are each independently a hydrogen or a C1-C6 alkyl group
Each n is an integer from 1 to 6;
wherein at least two of $R_1$, $R_2$, $R_3$, $R_4$, $R_5$, $R_6$, $R_7$, $R_8$, and $R_9$ comprise a functional group selected from the group consisting of —$NH_2$, —$NR_aR_b$, —C(O)$R_z$, —C(O)$NH_2$, —C(O)$NR_aR_b$, —OH, —$CO_2H$, —$SO_3H$; and wherein a maximum of three of $R_1$, $R_2$, $R_3$, $R_4$, $R_5$, $R_6$, $R_7$, $R_8$, and $R_9$ comprise an identical functional group;
or a pharmaceutically acceptable salt thereof.

In a further embodiment, the invention pertains, at least in part to compounds of Formula III wherein:
$R_1$, $R_2$, $R_3$, $R_4$, $R_7$, and $R_8$ are each independently —H, —$NH_2$, —$NR_aR_b$, —C(O)$NH_2$, —C(O)$NR_aR_b$, —(C($R_x$)($R_y$))$_n$$NH_2$, —(C($R_x$)($R_y$))$_n$$NR_aR_b$, —(C($R_a$)($R_b$))$_n$C(O)$NH_2$, —(C($R_a$)($R_b$))$_n$C(O)$NR_aR_b$, —OH, —(C($R_a$)($R_b$))$_n$ OH, —$CO_2H$, —(C($R_a$)($R_b$))$_n$$CO_2H$, —$SO_3H$, or —(C($R_a$)($R_b$))$_n$$SO_3H$; deuterium, halogen, alkyl, alkoxy, alkenyl, alkynyl, cyano, cycloalkyl, heterocycloalkyl, aryl, or heteroaryl.

In another embodiment, the invention pertains, at least in part to non-aromatic compounds of Formula IV:

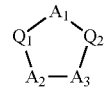

Formula IV wherein:
$Q_1$ is —C($R_1$)($R_2$)— or —N($R_5$)—;
$Q_2$ is —C($R_3$)($R_4$)— or —N($R_6$)—;
$A_1$ is —$CH_2$—, —C($R_7$)($R_8$)—, —C(O)—, —NH—, —N($R_9$)—, —O—, —S—, —$SO_2$—, or a covalent bond;
$A_2$, and $A_3$ are each independently —$CH_2$—, —C($R_7$)($R_8$)—, —C(O)—, —NH—, —N($R_9$)—, —O—, —S—, —$SO_2$—; or $A_2$ and $A_3$ taken together are —C($R_7$)=C($R_8$)—, —C($R_7$)=N—, or —N=C($R_7$)—;
$R_1$, $R_2$, $R_3$, $R_4$, $R_7$, and $R_8$ are each independently —H, —$NH_2$, —$NR_aR_b$, —C(O)$R_z$, —C(O)$NH_2$, —C(O)$NR_aR_b$, —(C($R_x$)($R_y$))$_n$$NH_2$, —(C($R_x$)($R_y$))$_n$$NR_aR_b$, —(C($R_a$)($R_b$))$_n$C(O)$NH_2$, —(C($R_a$)($R_b$))$_n$C(O)$NR_aR_b$, —OH, —(C($R_a$)($R_b$))$_n$OH, —$CO_2H$, —(C($R_a$)($R_b$))$_n$$CO_2H$, —$SO_3H$, or —(C($R_a$)($R_b$))$_n$$SO_3H$; deuterium, halogen, alkyl, alkoxy, alkenyl, alkynyl, cyano, cycloalkyl, heterocycloalkyl, aryl, or heteroaryl;
$R_5$, $R_6$, and each $R_9$ are each independently —H, —C(O)$NH_2$, —C(O)$NR_aR_b$, —(C($R_x$)($R_y$))$_n$$NH_2$, —(C($R_x$)($R_y$))$_n$ $NR_aR_b$, —(C($R_a$)($R_b$))$_n$C(O)$NH_2$, —(C($R_a$)($R_b$))$_n$C(O)$NR_aR_b$, —(C($R_a$)($R_b$))$_n$OH, —$CO_2H$, —(C($R_a$)($R_b$))$_n$$CO_2H$, or —(C($R_a$)($R_b$))$_n$ $SO_3H$; deuterium, halogen, alkyl, alkoxy, alkenyl, alkynyl, cyano, cycloalkyl, heterocycloalkyl, aryl, or heteroaryl;
Each $R_a$ and $R_b$ are each independently hydrogen, deuterium, halogen, alkyl, alkenyl, alkynyl, cycloalkyl, heterocycloalkyl, aryl, heteroaryl, amino acid a dipeptide; $R_a$ and $R_b$ taken together with the nitrogen optionally form a heterocycle; $R_z$ is an amino acid or a dipeptide;
Each $R_x$ and $R_y$ are each independently a hydrogen or a C1-C6 alkyl group
Each n is an integer from 1 to 6;
wherein at least two of $R_1$, $R_2$, $R_3$, $R_4$, $R_5$, $R_6$, $R_7$, $R_8$, and $R_9$ comprise a functional group selected from the group consisting of —$NH_2$, —$NR_aR_b$, —C(O)$R_z$, —C(O)$NH_2$, —C(O)$NR_aR_b$, —OH, —$CO_2H$, —$SO_3H$; and wherein a maximum of three of $R_1$, $R_2$, $R_3$, $R_4$, $R_5$, $R_6$, $R_7$, $R_8$, and $R_9$ comprise an identical functional group;
or a pharmaceutically acceptable salt thereof.

In a further embodiment, the invention pertains, at least in part to compounds of Formula IV wherein:
$R_1$, $R_2$, $R_3$, $R_4$, $R_7$, and $R_8$ are each independently —H, —$NH_2$, —$NR_aR_b$, —C(O)$NH_2$, —C(O)$NR_aR_b$, —(C($R_x$)($R_y$))$_n$$NH_2$, —(C($R_x$)($R_y$))$_n$$NR_aR_b$, —(C($R_a$)($R_b$))$_n$C(O)$NH_2$, —(C($R_a$)($R_b$))$_n$C(O)$NR_aR_b$, —OH, —(C($R_a$)($R_b$))$_n$ OH, —$CO_2H$, —(C($R_a$)($R_b$))$_n$$CO_2H$, —$SO_3H$, or —(C($R_a$)($R_b$))$_n$$SO_3H$; deuterium, halogen, alkyl, alkoxy, alkenyl, alkynyl, cyano, cycloalkyl, heterocycloalkyl, aryl, or heteroaryl.

In another embodiment, the invention pertains, at least in part to non-aromatic compounds of Formula V:

Formula V $$Q_1 \overset{A_1}{\underset{A_2}{\diamond}} Q_2$$

wherein:

$Q_1$ is —C($R_1$)($R_2$)— or —N($R_5$)—;

$Q_2$ is —C($R_3$)($R_4$)— or —N($R_6$)—;

$A_1$ is —$CH_2$—, —C($R_7$)($R_8$)—, —C(O)—, —NH—, —N($R_9$)—, —O—, —S—, —$SO_2$—, or a covalent bond;

$A_2$ is —$CH_2$—, —C($R_7$)($R_8$)—, —C(O)—, —NH—, —N($R_9$)—, —O—, —S—, —$SO_2$—;

$R_1$, $R_2$, $R_3$, $R_4$, $R_7$, and $R_8$ are each independently —H, —$NH_2$, —$NR_aR_b$, —C(O)$R_z$, —C(O)$NH_2$, —C(O)$NR_aR_b$, —(C($R_x$)($R_y$))$_n$$NH_2$, —(C($R_x$)($R_y$))$_n$ $NR_aR_b$, —(C($R_a$)($R_b$))$_n$C(O)$NH_2$, —(C($R_a$)($R_b$))$_n$C(O)$NR_aR_b$, —OH, —(C($R_a$)($R_b$))$_n$OH, —$CO_2H$, —(C($R_a$)($R_b$))$_n$ $CO_2H$, —$SO_3H$, or —(C($R_a$)($R_b$))$_n$ $SO_3H$; deuterium, halogen, alkyl, alkoxy, alkenyl, alkynyl, cyano, cycloalkyl, heterocycloalkyl, aryl, or heteroaryl;

$R_5$, $R_6$, and each $R_9$ are each independently —H, —C(O)$NH_2$, —C(O)$NR_aR_b$, —(C($R_x$)($R_y$))$_n$$NH_2$, —(C($R_x$)($R_y$))$_n$ $NR_aR_b$, —(C($R_a$)($R_b$))$_n$C(O)$NH_2$, —(C($R_a$)($R_b$))$_n$ C(O)$NR_aR_b$, —(C($R_a$)($R_b$))$_n$OH, —$CO_2H$, —(C($R_a$) ($R_b$))$_n$$CO_2H$, or —(C($R_a$)($R_b$))$_n$ $SO_3H$; deuterium, halogen, alkyl, alkoxy, alkenyl, alkynyl, cyano, cycloalkyl, heterocycloalkyl, aryl, or heteroaryl;

Each $R_a$ and $R_b$ are each independently hydrogen, deuterium, halogen, alkyl, alkenyl, alkynyl, cycloalkyl, heterocycloalkyl, aryl, heteroaryl, amino acid a dipeptide; $R_a$ and $R_b$ taken together with the nitrogen optionally form a heterocycle; $R_z$ is an amino acid or a dipeptide;

Each $R_x$ and $R_y$ are each independently a hydrogen or a C1-C6 alkyl group;

Each n is an integer from 1 to 6;

wherein at least two of $R_1$, $R_2$, $R_3$, $R_4$, $R_5$, $R_6$, $R_7$, $R_8$, and $R_9$ comprise a functional group selected from the group consisting of —$NH_2$, —$NR_aR_b$, —C(O)$R_z$, —C(O)$NH_2$, —C(O)$NR_aR_b$, —OH, —$CO_2H$, —$SO_3H$; and wherein a maximum of three of $R_1$, $R_2$, $R_3$, $R_4$, $R_5$, $R_6$, $R_7$, $R_8$, and $R_9$ comprise an identical functional group;

or a pharmaceutically acceptable salt thereof.

In a further embodiment, the invention pertains, at least in part to compounds of Formula V wherein:

$R_1$, $R_2$, $R_3$, $R_4$, $R_7$, and $R_8$ are each independently —H, —$NH_2$, —$NR_aR_b$, —C(O)$NH_2$, —C(O)$NR_aR_b$, —(C($R_x$) ($R_y$))$_n$$NH_2$, —(C($R_x$)($R_y$))$_n$$NR_aR_b$, —(C($R_a$)($R_b$))$_n$C(O) $NH_2$, —(C($R_a$)($R_b$))$_n$C(O)$NR_aR_b$, —OH, —(C($R_a$)($R_b$))$_n$ OH, —$CO_2H$, —(C($R_a$)($R_b$))$_n$$CO_2H$, —$SO_3H$, or —(C($R_a$) ($R_b$))$_n$$SO_3H$; deuterium, halogen, alkyl, alkoxy, alkenyl, alkynyl, cyano, cycloalkyl, heterocycloalkyl, aryl, or heteroaryl. In another embodiment, the invention pertains, at least in part to compounds of Formula III$_a$ or III$_b$:

Formula III$_a$ $$R_2 \overset{R_1}{\underset{A_2}{\overset{A_1}{\diagup\diagdown}}} \overset{R_3}{\underset{A_3}{\overset{A_4}{\diagup\diagdown}}} R_4$$

-continued

Formula III$_b$ $$R_1 \overset{R_2}{\underset{A_2}{\overset{A_1}{\diagup\diagdown}}} \overset{R_3}{\underset{A_3}{\overset{A_4}{\diagup\diagdown}}} R_4$$

wherein:

$A_1$ is —$CH_2$—, —C($R_7$)($R_8$)—, —C(O)—, —NH—, —N($R_9$)—, —O—, —S—, —$SO_2$—, or a covalent bond;

$A_2$, $A_3$, and $A_4$, are each independently —$CH_2$—, —C($R_7$) ($R_8$)—, —C(O)—, —NH—, —N($R_9$)—, —O—, —S—, —$SO_2$—; or $A_2$ and $A_3$ taken together are —C($R_7$)=C ($R_8$)—, —C($R_7$)=N—, or —N=C($R_7$)—, or $A_3$ and $A_4$ taken together are —C($R_7$)=C($R_8$)—, —C($R_7$)=N—, or —N=C($R_7$)—;

$R_1$, $R_2$, $R_3$, $R_4$, $R_7$, and $R_8$ are each independently —H, —$NH_2$, —$NR_aR_b$, —C(O)$R_z$, —C(O)$NH_2$, —C(O) $NR_aR_b$, —(C($R_x$)($R_y$))$_n$$NH_2$, —(C($R_x$)($R_y$))$_n$ $NR_aR_b$, —(C($R_a$)($R_b$))$_n$C(O)$NH_2$, —(C($R_a$)($R_b$))$_n$C(O)$NR_aR_b$, —OH, —(C($R_a$)($R_b$))$_n$OH, —$CO_2H$, —(C($R_a$)($R_b$))$_n$ $CO_2H$, —$SO_3H$, or —(C($R_a$)($R_b$))$_n$ $SO_3H$; deuterium, halogen, alkyl, alkoxy, alkenyl, alkynyl, cyano, cycloalkyl, heterocycloalkyl, aryl, or heteroaryl;

Each $R_9$ is independently —H, —C(O)$NH_2$, —C(O)$NR_aR_b$, —(C($R_x$)($R_y$))$_n$$NH_2$, —(C($R_x$)($R_y$))$_n$ $NR_aR_b$, —(C($R_a$) ($R_b$))$_n$C(O)$NH_2$, —(C($R_a$)($R_b$))$_n$C(O)$NR_aR_b$, —(C($R_a$) ($R_b$))$_n$OH, —$CO_2H$, —(C($R_a$)($R_b$))$_n$$CO_2H$, or —(C($R_a$) ($R_b$))$_n$ $SO_3H$; deuterium, halogen, alkyl, alkoxy, alkenyl, alkynyl, cyano, cycloalkyl, heterocycloalkyl, aryl, or heteroaryl;

Each $R_a$ and $R_b$ are each independently hydrogen, deuterium, halogen, alkyl, alkenyl, alkynyl, cycloalkyl, heterocycloalkyl, aryl, heteroaryl, amino acid a dipeptide; $R_a$ and $R_b$ taken together with the nitrogen optionally form a heterocycle; $R_z$ is an amino acid or a dipeptide;

Each $R_x$ and $R_y$ are each independently a hydrogen or a C1-C6 alkyl group;

Each n is an integer from 1 to 6;

wherein at least two of $R_1$, $R_2$, $R_3$, $R_4$, $R_7$, $R_8$, and $R_9$ comprise a functional group selected from the group consisting of —$NH_2$, —$NR_aR_b$, —C(O)Rz, —C(O)$NH_2$, —C(O)$NR_aR_b$, —OH, —$CO_2H$, —$SO_3H$; and wherein a maximum of three of $R_1$, $R_2$, $R_3$, $R_4$, $R_7$, $R_8$, and $R_9$ comprise an identical functional group;

or a pharmaceutically acceptable salt thereof.

In a further embodiment, the invention pertains, at least in part to compounds of Formula III$_a$ or III$_b$ wherein:

$R_1$, $R_2$, $R_3$, $R_4$, $R_7$, and $R_8$ are each independently —H, —$NH_2$, —$NR_aR_b$, —C(O)$NH_2$, —C(O)$NR_aR_b$, —(C($R_x$) ($R_y$))$_n$$NH_2$, —(C($R_x$)($R_y$))$_n$$NR_aR_b$, —(C($R_a$)($R_b$))$_n$C(O) $NH_2$, —(C($R_a$)($R_b$))$_n$C(O)$NR_aR_b$, —OH, —(C($R_a$)($R_b$))$_n$ OH, —$CO_2H$, —(C($R_a$)($R_b$))$_n$$CO_2H$, —$SO_3H$, or —(C($R_a$) ($R_b$))$_n$$SO_3H$; deuterium, halogen, alkyl, alkoxy, alkenyl, alkynyl, cyano, cycloalkyl, heterocycloalkyl, aryl, or heteroaryl. In one particular embodiment the variables of Formula III$_a$ or III$_b$ are:

$R_1$ is —$SO_3H$, or —$(CH_2)_n$$SO_3H$;

$R_2$ is —H, —$CH_3$, —$(CH_2)_n$ OH, —$(CH_2)_n$$NH_2$, —C(O) $NH_2$, or —$(CH_2)_n$C(O)$NH_2$;

$R_3$ is —H, —$CH_3$, —$(CH_2)_n$ OH, —$(CH_2)_n$$NH_2$, —C(O) $NH_2$, or —$(CH_2)_n$C(O)$NH_2$;

$R_4$ is —H, —$CH_3$, —$(CH_2)_n$ OH, —$(CH_2)_n$$NH_2$, —C(O) $NH_2$, or —$(CH_2)_n$C(O)$NH_2$;

n is 1 or 2;

A₁ is —CH₂— or —NH—;
A₂ is —CH₂— or —NH—;
A₃ is —CH₂— or —NH—;
A₄ is —CH₂— or —NH—;
or a pharmaceutically acceptable salt thereof.

In another embodiment, the invention pertains, at least in part to compounds of Formula IV$_a$, IV$_b$, IV$_c$, or IV$_d$:

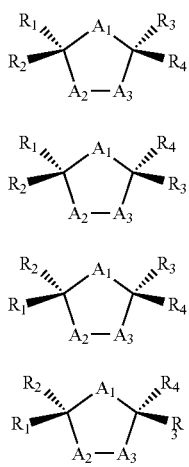

Formula IV$_a$

Formula IV$_a$

Formula IV$_a$

Formula IV$_a$ wherein:
A₁ is —CH₂—, —C(R₇)(R₈)—, —C(O)—, —NH—, —N(R₉)—, —O—, —S—, —SO₂—, or a covalent bond;
A₂ and A₃ are each independently —CH₂—, —C(R₇)(R₈)—, —C(O)—, —NH—, —N(R₉)—, —O—, —S—, —SO₂—; or A₂ and A₃ taken together are —C(R₇)═C(R₈)—, —C(R₇)═N—, or —N═C(R₇)—;
R₁, R₂, R₃, R₄, R₇, and R₈ are each independently —H, —NH₂, —NR$_a$R$_b$, —C(O)Rz, —C(O)NH₂, —C(O)NR$_a$R$_b$, —(C(R$_x$)(R$_y$))$_n$NH₂, —(C(R$_x$)(R$_y$))$_n$ NR$_a$R$_b$, —(C(R$_a$)(R$_b$))$_n$C(O)NH₂, —(C(R$_a$)(R$_b$))$_n$C(O)NR$_a$R$_b$, —OH, —(C(R$_a$)(R$_b$))$_n$OH, —CO₂H, —COOalkyl, —(C(R$_a$)(R$_b$))$_n$CO₂H, —SO₃H, or —(C(R$_a$)(R$_b$))$_n$ SO₃H; deuterium, halogen, alkyl, alkoxy, alkenyl, alkynyl, cyano, cycloalkyl, heterocycloalkyl, aryl, or heteroaryl;
Each R₉ is independently —H, —C(O)NH₂, —C(O)NR$_a$R$_b$, —(C(R$_x$)(R$_y$))$_n$NH₂, —(C(R$_x$)(R$_y$))$_n$ NR$_a$R$_b$, —(C(R$_a$)(R$_b$))$_n$C(O)NH₂, —(C(R$_a$)(R$_b$))$_n$C(O)NR$_a$R$_b$, —(C(R$_a$)(R$_b$))$_n$OH, —CO₂H, —(C(R$_a$)(R$_b$))$_n$CO₂H, or —(C(R$_a$)(R$_b$))$_n$ SO₃H; deuterium, halogen, alkyl, alkoxy, alkenyl, alkynyl, cyano, cycloalkyl, heterocycloalkyl, aryl, or heteroaryl;
Each R$_a$ and R$_b$ are each independently hydrogen, deuterium, halogen, alkyl, alkenyl, alkynyl, cycloalkyl, heterocycloalkyl, aryl, heteroaryl, amino acid, a dipeptide; or R$_a$ and R$_b$ are taken together with the nitrogen to which they are commonly bound to form a heterocycle; R$_z$ is an amino acid or a dipeptide;
Each R$_x$ and R$_y$ are each independently a hydrogen or a C1-C6 alkyl group;
Each n is an integer from 1 to 6;
wherein at least two of R₁, R₂, R₃, R₄, R₇, R₈, and R₉ comprise a functional group selected from the group consisting of —NH₂, —NR$_a$R$_b$, —C(O)R$_z$, —C(O)NH₂, —C(O)NR$_a$R$_b$, —OH, —CO₂H, —SO₃H; and wherein a maximum of three of R₁, R₂, R₃, R₄, R₇, R₈, and R₉ comprise an identical functional group;

a racemic mixture thereof, or a pharmaceutically acceptable salt of the foregoing.

In a particular embodiment, the invention pertains, at least in part, to compounds of Formula IV$_a$, IV$_b$, IV$_c$ or IV$_d$ wherein:
R₁, R₂, R₃, R₄, R₇, and R₈ are each independently —H, —NH₂, —NR$_a$R$_b$, —C(O)NH₂, —C(O)NR$_a$R$_b$, —(C(R$_x$)(R$_y$))$_n$NH₂, —(C(R$_x$)(R$_y$))$_n$ NR$_a$R$_b$, —(C(R$_a$)(R$_b$))$_n$ C(O)NH₂, —(C(R$_a$)(R$_b$))$_n$C(O)NR$_a$R$_b$, —OH, —(C(R$_a$)(R$_b$))$_n$OH, —CO₂H, —(C(R$_a$)(R$_b$))$_n$CO₂H, —SO₃H, or —(C(R$_a$)(R$_b$))$_n$ SO₃H; deuterium, halogen, alkyl, alkoxy, alkenyl, alkynyl, cyano, cycloalkyl, heterocycloalkyl, aryl, or heteroaryl.

In one particular embodiment the variables of Formula IV$_a$, IV$_b$, IV$_c$ or IV$_d$ are:
R₁ is —SO₃H or —(CH₂)$_n$SO₃H;
R₂ is —H, —CH₃, —(CH₂)$_n$ OH, —(CH₂)$_n$NH₂, —C(O)NH₂, or —(CH₂)$_n$C(O)NH₂;
R₃ is —H, —CH₃, —(CH₂)$_n$ OH, —(CH₂)$_n$NH₂, —C(O)NH₂, or —(CH₂)$_n$C(O)NH₂;
R₄ is —H, —CH₃, —(CH₂)$_n$ OH, —(CH₂)$_n$NH₂, —C(O)NH₂, or —(CH₂)$_n$C(O)NH₂;
n is 1 or 2;
A₁ is —CH₂—, —NH—, or —C(O)—;
A₂ is —CH₂—, —NH—, or —C(O)—;
A₃ is —CH₂—, —NH—, or —C(O)—;

In another particular embodiment the variables of Formula IV$_a$, IV$_b$, IV$_c$ or IV$_d$ are:
R₁ is —SO₃H or —(CH₂)$_n$SO₃H;
R₂ is —H;
R₃ is —H, —CH₃, —(CH₂)$_n$ OH, —(CH₂)$_n$NH₂, —C(O)NH₂, or —(CH₂)$_n$C(O)NH₂;
R₄ is —H, —CH₃, —(CH₂)$_n$ OH, —(CH₂)$_n$NH₂, —C(O)NH₂, or —(CH₂)$_n$C(O)NH₂;
n is 1 or 2;
A₁ is —CH₂—, —NH—, or —C(O)—;
A₂ is —CH₂—, —NH—, or —C(O)—;
A₃ is —CH₂—, —NH—, or —C(O)—;

In one particular embodiment the variables of Formula IV$_a$, IV$_b$, IV$_c$ or IV$_d$ are:
R₁ is —SO₃H, or —(CH₂)$_n$SO₃H;
R₂ is —H, —CH₃, —(CH₂)$_n$ OH, —(CH₂)$_n$NH₂, —C(O)NH₂, or —(CH₂)$_n$C(O)NH₂;
R₃ is —H, —CH₃, —(CH₂)$_n$ OH, —NH₂, —(CH₂)$_n$NH₂, —C(O)NH₂, or —(CH₂)$_n$C(O)NH₂;
R₄ is —H, —CH₃, —(CH₂)$_n$ OH, —NH₂, —(CH₂)$_n$NH₂, —C(O)NH₂, or —(CH₂)$_n$C(O)NH₂;
n is 1 or 2;
A₁ is —CH₂—, —NH—, or —C(O)—;
A₂ is —CH₂—, —NH—, or —C(O)—;
A₃ is —CH₂—, —NH—, or —C(O)—;

In another particular embodiment the variables of Formula IV$_a$, IV$_b$, IV$_c$ or IV$_d$ are:
R₁ is —SO₃H, or —(CH₂)$_n$SO₃H;
R₂ is —H;
R₃ is —H, —CH₃, —(CH₂)$_n$ OH, —NH₂, —(CH₂)$_n$NH₂, —C(O)NH₂, or —(CH₂)$_n$C(O)NH₂;
R₄ is —H, —CH₃, —(CH₂)$_n$ OH, —NH₂, —(CH₂)$_n$NH₂, —C(O)NH₂, or —(CH₂)$_n$C(O)NH₂;
n is 1 or 2;
A₁ is —CH₂—, —NH—, or —C(O)—;
A₂ is —CH₂—, —NH—, or —C(O)—;
A₃ is —CH₂—, —NH—, or —C(O)—;

In still another particular embodiment the variables of Formula IV$_a$, IV$_b$, IV$_c$ or IV$_d$ are:
R$_1$ is —SO$_3$H, or —(CH$_2$)$_n$SO$_3$H;
R$_2$ is —H, —CH$_3$, —(CH$_2$)$_n$OH, —(CH$_2$)$_n$NH$_2$, —C(O)NH$_2$, or —(CH$_2$)$_n$C(O)NH$_2$;
R$_3$ is —NR$_a$R$_b$;
R$_4$ is —H, —CH$_3$, —(CH$_2$)$_n$ OH, —NH$_2$, —(CH$_2$)$_n$NH$_2$, —C(O)NH$_2$, or —(CH$_2$)$_n$C(O)NH$_2$;
R$_a$ is —H or optionally substituted alkyl;
R$_b$ is selected from hydrogen, alkyl substituted with a carboxyl or a carboxylate, an amino acid or a dipeptide, wherein the amino acid or the dipeptide is bound to the nitrogen atom in R$_3$ through a carboxy group;
n is 1 or 2;
A$_1$ is —CH$_2$—, —NH—, or —C(O)—;
A$_2$ is —CH$_2$—, —NH—, or —C(O)—;
A$_3$ is —CH$_2$—, —NH—, or —C(O)—;
In some aspects of this particular embodiment R$_1$ is —SO$_3$H. In some aspects of this particular embodiment, R$_2$ is —H. In some aspects of this particular embodiment, R$_4$ is —H. In some aspects of this particular embodiment, R$_a$ is —H. In some aspects of this particular embodiment, R$_b$ is selected from hydrogen, alkyl terminally substituted with —COOH or —COOCH$_3$ or —COOalkyl, and an α-amino acid bound to the nitrogen atom in R$_3$ through a carboxy group. In some aspects of this particular embodiment, each of A$_1$, A$_2$ and A$_3$ is —CH$_2$—.

In still another particular embodiment the variables of Formula IV$_a$, IV$_b$, IV$_c$ or IV$_d$ are:
R$_1$ is —SO$_3$H, —(CH$_2$)$_n$SO$_3$H;
R$_2$ is —H, —CH$_3$, —(CH$_2$)$_n$OH, —(CH$_2$)$_n$NH$_2$, —C(O)NH$_2$, or —(CH$_2$)$_n$C(O)NH$_2$;
R$_3$ is —C(O)—NR$_a$R$_b$;
R$_4$ is —H, —CH$_3$, —(CH$_2$)$_n$ OH, —NH$_2$, —(CH$_2$)$_n$NH$_2$, —C(O)NH$_2$, or —(CH$_2$)$_n$C(O)NH$_2$;
R$_a$ is —H or optionally substituted alkyl;
R$_b$ is selected from hydrogen, optionally substituted cycloalkyl, optionally substituted heterocycloalkyl, and optionally substituted alkyl, or;
R$_a$ and R$_b$ are taken together to form an optionally substituted heterocyclyl;
n is 1 or 2;
A$_1$ is —CH$_2$—, —NH—, or —C(O)—;
A$_2$ is —CH$_2$—, —NH—, or —C(O)—;
A$_3$ is —CH$_2$—, —NH—, or —C(O)—;
In some aspects of this particular embodiment, R$_1$ is —SO$_3$H. In some aspects of this particular embodiment, R$_2$ is —H. In some aspects of this particular embodiment, R$_4$ is —H. In some aspects of this particular embodiment, R$_a$ is —H. In some aspects of this particular embodiment, R$_a$ is unsubstituted or hydroxy-substituted alkyl. In some particular aspects of this particular embodiment, R$_b$ is selected from hydrogen; alkyl substituted with one or more substituents independently selected from carboxy, amino, optionally substituted heteroaryl, optionally substituted aryl, alkylthio, aminocarbonyl, hydroxy, and optionally substituted alkylamino or dialkylamino; cycloalkyl optionally substituted with amino, and heterocyclyl optionally substituted with amino. In some particular aspects of this particular embodiment, R$_a$ and R$_b$ are taken together to form optionally substituted pyrrolidinyl, piperidinyl, morpholinyl, or piperazinyl. In some aspects of this particular embodiment, each of A$_1$, A$_2$ and A$_3$ is —CH$_2$—. In alternate aspects of this particular embodiment A$_1$, and A$_2$ are —CH$_2$—, and A$_3$ is —NH—.

In yet another embodiment of the invention, the variables of Formula IV$_a$, IV$_b$, IV$_c$ or IV$_d$ are:

R$_1$ is —SO$_3$H, or —(CH$_2$)$_n$SO$_3$H;
R$_2$ is —H, —CH$_3$, —(CH$_2$)$_n$OH, —(CH$_2$)$_n$NH$_2$, —C(O)NH$_2$, or —(CH$_2$)$_n$C(O)NH$_2$;
R$_3$ is —C(O)R$_z$, wherein:
R$_z$ is selected from an amino acid or a dipeptide, wherein the amino acid or the dipeptide is bound to the carbon atom through an amino group; or optionally substituted alkyl;
R$_4$ is —H, —CH$_3$, —(CH$_2$)$_n$ OH, —NH$_2$, —(CH$_2$)$_n$NH$_2$, —C(O)NH$_2$, or —(CH$_2$)$_n$C(O)NH$_2$;
n is 1 or 2;
A$_1$ is —CH$_2$—, —NH—, or —C(O)—;
A$_2$ is —CH$_2$—, —NH—, or —C(O)—; and
A$_3$ is —CH$_2$—, —NH—, or —C(O)—.
In some aspects of this particular embodiment R$_1$ is —SO$_3$H. In some aspects of this particular embodiment, R$_2$ is —H. In some aspects of this particular embodiment, R$_4$ is —H. In some aspects of this particular embodiment, R$_z$ is a naturally occurring amino acid. In some aspects of this particular embodiment, R$_z$ is a dipeptide comprising one or two naturally occurring amino acids. In some aspects of this particular embodiment R$_z$ is Alanine, Arginine, Asparagine, Aspartic acid, Cystein, Glutamine, Glutamic acid, Glycine, Valine, Leucine, Isoleucine, Phenylalanine, Tyrosine, Proline, Serine, Threonine, Methionine, Histidine, Tryptophan, Lysine. In some aspects of this particular embodiment, each of A$_1$, A$_2$ and A$_3$ is —CH$_2$—.

In another embodiment, the invention pertains, at least in part, to a compound of Formula IV-1:

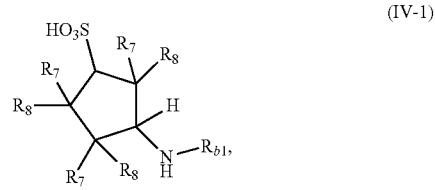

(IV-1)

or an enantiomer, diastereoisomer or stereoisomer thereof, or a pharmaceutically acceptable salt of any of the foregoing, wherein R$_{b1}$ is selected from hydrogen, —(CH$_2$)$_{1-3}$—C(O)OH, —(CH$_2$)$_{1-3}$—C(O)O(C$_1$-C$_3$ alkyl), —C(O)—[CH(R$^A$)]$_{1-2}$—NH—R$^B$, or —C(O)—[CH(R$^A$)]$_{1-2}$—NH—C(O)—[CH(R$^A$)]$_{1-2}$—NH—R$^B$, wherein:

each R$_7$ and each R$_8$ is independently selected from —H, —NH$_2$, —NR$_a$R$_b$, —C(O)NH$_2$, —C(O)NR$_a$R$_b$, —(C(R$_x$)(R$_y$))$_n$NH$_2$, —(C(R$_x$)(R$_y$))$_n$ NR$_a$R$_b$, —(C(R$_a$)(R$_b$))$_n$C(O)NH$_2$, —(C(R$_a$)(R$_b$))$_n$C(O)NR$_a$R$_b$, —OH, —(C(R$_a$)(R$_b$))$_n$ OH, —CO$_2$H, —(C(R$_a$)(R$_b$))$_n$CO$_2$H, —SO$_3$H, or —(C(R$_a$)(R$_b$))$_n$ SO$_3$H; deuterium, halogen, alkyl, alkoxy, alkenyl, alkynyl, cyano, cycloalkyl, heterocycloalkyl, aryl, or heteroaryl;

each R$^A$ is independently selected from hydrogen or a side group of a natural amino acid (e.g., the side group of Ala, Arg, Asn, Asp, Cys, Glu, Gln, Gly, His, Ile, Leu, Lys, Met, Phe, Pro, Ser, Thr, Trp, Tyr, or Val) or a side group of an unnatural amino acid (e.g., the side group of diaminobutyric acid, diaminopropionic acid, aminobutanoic acid, selenocysteine, pyrrolysine, hydroxyproline, hydroxylysine, norvaline, 2-aminoisobutyric acid); and R$^B$ is selected from hydrogen or a protecting group (e.g, Cbz, p-methoxybenzylcarbonyl, BOC, FMOC, acetyl, benzoyl, tosyl, methyl esters, benzyl esters, t-butyl esters, silyl esters).

In certain embodiments of Formula IV-1, each $R^7$ and each $R^8$ is hydrogen.

In certain embodiments of Formula IV-1, $R_{a1}$ is selected from hydrogen, —(CH$_2$)$_2$—C(O)OH, —(CH$_2$)$_2$—C(O)O—CH$_3$ and —C(O)—[CH(R$^A$)]$_{1-2}$—NH—R$^B$.

In certain embodiments of Formula IV-1, each $R^A$, if present, is selected from —CH$_3$, —CH$_2$OH, —(CH$_2$)$_4$—NH$_2$, —CH$_2$—CH(CH$_3$)$_2$, —(CH$_2$)$_2$—S(O)$_2$—CH$_3$, —(CH$_2$)$_2$—S—CH$_3$, —CH$_2$—C(O)—NH$_2$, —CH$_2$—C(O) OH, —CH(CH$_3$)OH, —CH(CH$_3$)$_2$, benzyl, 1H-imidazol-4-yl-methyl, 4-hydroxybenzyl, and 1H-indolyl-3-ylmethyl, In certain embodiments of Formula IV-1, $R^B$ is selected from hydrogen and Cbz.

In certain embodiments of Formula IV-1, the compound is selected from:

In another embodiment, the invention pertains, at least in part, to a compound of Formula IV-2a:

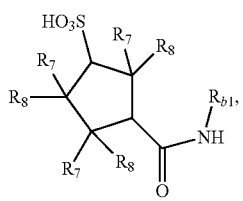

(IV-2a)

or
Formula IV-2b:

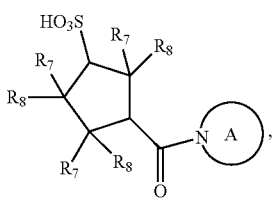

(IV-2b)

or an enantiomer or stereoisomer thereof, or a pharmaceutically acceptable salt of any of the foregoing, wherein:

$R_{b1}$ is selected from hydrogen; C1-C5 alkyl substituted with one or more substituents independently selected from carboxy, amino, optionally substituted heteroaryl, optionally substituted aryl, alkylthio, aminocarbonyl, hydroxy, dialkylamino, alkylamino, and arylalkylamino; cycloalkyl optionally substituted with amino, and heterocyclyl optionally substituted with amino, aralkyl, alkylaryl, heteroalkyl, natural or unnatural desamino-amino acid;

each $R_7$ and each $R_8$ is independently selected from —H, —NH$_2$, —NR$_a$R$_b$, —C(O)NH$_2$, —C(O)NR$_a$R$_b$, —(C(R$_x$)(R$_y$))$_n$NH$_2$, —(C(R$_x$)(R$_y$))$_n$ NR$_a$R$_b$, —(C(R$_a$)(R$_b$))$_n$C(O) NH$_2$, —(C(R$_a$)(R$_b$))$_n$C(O)NR$_a$R$_b$, —OH, —(C(R$_a$)(R$_b$))$_n$ OH, —CO$_2$H, —(C(R$_a$)(R$_b$))$_n$CO$_2$H, —SO$_3$H, or —(C(R$_a$)(R$_b$))$_n$ SO$_3$H; deuterium, halogen, alkyl, alkoxy, alkenyl, alkynyl, cyano, cycloalkyl, heterocycloalkyl, aryl, or heteroaryl; and ring A is selected from optionally substituted morpholinyl, prolyl, pyrrolidinyl, piperidinyl or piperazinyl.

In certain embodiments of Formula IV-2a and IV-2b, each $R^7$ and each $R^8$ is hydrogen.

In certain embodiments of Formula IV-2a, $R_{b1}$ is selected from hydrogen, natural or unnatural desamino-amino acid, 4-amino cyclohexyl, 2-aminocyclohexyl, piperidin-4-yl, 2-(benzylamino)ethyl, 3-(dimethylamino)-2,2-dimethylpropyl, 5-amino-1-(hydroxycarbonyl)pentyl, 2-(1H-imidazol-4-yl)-1-hydroxycarbonylethyl, 2-carbamyl-1-hydroxycarbonylethyl, 1,2-bishydroxycarbonylethyl, 2-(1H-indol-3-yl)-1-hydroxycarbonylethyl, 2-(4-hydroxyphenyl)-1-hydroxycarbonylethyl, 3-(methylthio)-1-hydroxycarbonylpropyl, 2-hydroxy-1-hydroxycarbonylpropyl, 2-hydroxy-1-hydroxycarbonylethyl, 3-methyl-1-hydroxycarbonylbutyl, 2-methyl-1-hydroxycarbonylpropyl, 2-phenyl-1-hydroxycarbonylethyl, 1-hydroxycarbonylethyl, hydroxycarbonylmethyl, and benzyl.

In certain embodiments of Formula IV-2b, ring A is selected from substituted or unsubstituted cycloamino, 3-aminopyrrolidin-1-yl, piperazin-1-yl, 4-aminopiperidin-1-yl, and 2-aminopiperidin-1-yl, morpholinyl, prolyl.

In another embodiment, the invention pertains, at least in part, to a compound of Formula IV-3a:

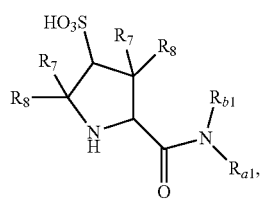

(IV-3a)

or
Formula IV-3b:

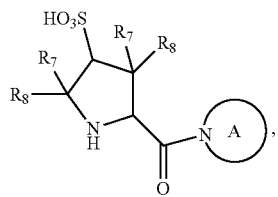

(IV-3b)

or an enantiomer or stereoisomer thereof, or a pharmaceutically acceptable salt of any of the foregoing, wherein:

$R_{a1}$ is selected from hydrogen, and C1-C3 alkyl optionally substituted with one or more hydroxy $R_{b1}$ is selected from hydrogen; natural or unnatural desamino-amino acid, C1-C5 alkyl substituted with one or more substituents independently selected from carboxy, amino, optionally substituted heteroaryl, optionally substituted aryl, alkylthio, aminocarbonyl, hydroxy, dialkylamino, alkylamino, and arylalkylamino; cycloalkyl optionally substituted with amino, and heterocyclyl optionally substituted with amino;

each $R_7$ and each $R_8$ is independently selected from —H, —NH$_2$, —NR$_a$R$_b$, —C(O)NH$_2$, —C(O)NR$_a$R$_b$, —(C(R$_x$)(R$_y$))$_n$NH$_2$, —(C(R$_x$)(R$_y$))$_n$ NR$_a$R$_b$, —(C(R$_a$)(R$_b$))$_n$C(O) NH$_2$, —(C(R$_a$)(R$_b$))$_n$C(O)NR$_a$R$_b$, —OH, —(C(R$_a$)(R$_b$))$_n$ OH, —CO$_2$H, —(C(R$_a$)(R$_b$))$_n$CO$_2$H, —SO$_3$H, or —(C(R$_a$)(R$_b$))$_n$ SO$_3$H; deuterium, halogen, alkyl, alkoxy, alkenyl, alkynyl, cyano, cycloalkyl, heterocycloalkyl, aryl, or heteroaryl; and ring A is selected from optionally substituted or unsubstituted cycloamino, pyrrolidinyl, piperidinyl, prolyl, morpholinyl, or piperazinyl.

In certain embodiments of Formula IV-3a and IV-3b, each $R^7$ and each $R^8$ is hydrogen.

In certain embodiments of Formula IV-3a, $R_{a1}$ is selected from hydrogen, methyl, ethyl, hydroxymethyl, and 2-hydroxyethyl In certain embodiments of Formula IV-3a, $R_{b1}$ is selected from hydrogen, methyl, ethyl, 2-hydroxyethyl, 4-amino cyclohexyl, 2-aminocyclohexyl, piperidin-4-yl, 2-(benzylamino)ethyl, 3-(dimethylamino)-2,2-dimethylpropyl, 5-amino-1-(hydroxycarbonyl)pentyl, 2-(1H-imidazol-4-yl)-1-hydroxycarbonylethyl, 2-carbamyl-1-hydroxycarbonylethyl, 1,2-bishydroxycarbonylethyl, 2-(1H-indol-3-yl)-1-hydroxycarbonylethyl, 2-(4-hydroxyphenyl)-1-hydroxycarbonylethyl, 3-(methylthio)-1-hydroxycarbonylpropyl, 2-hydroxy-1-hydroxycarbonylpropyl, 2-hydroxy-1-hydroxycarbonylethyl, 3-methyl-1-hydroxycarbonylbutyl, 2-methyl-1-hydroxycarbonylpropyl, 2-phenyl-1-hydroxycarbonylethyl, 1-hydroxycarbonylethyl, hydroxycarbonylmethyl, and benzyl.

In certain embodiments of Formula IV-3b, ring A is selected from 3-aminopyrrolidin-1-yl, piperazin-1-yl, 4-aminopiperidin-1-yl, and 2-aminopiperidin-1-yl.

Representative examples of compounds of Formula IVa, IVb, IV-1, IV-2a, IV-2b, IV-3a, and IV-3b are shown in FIG. 2.

In another embodiment, the invention pertains, at least in part to compounds of Formula $VI_a$, $VI_b$, $VI_c$ or $VI_d$:

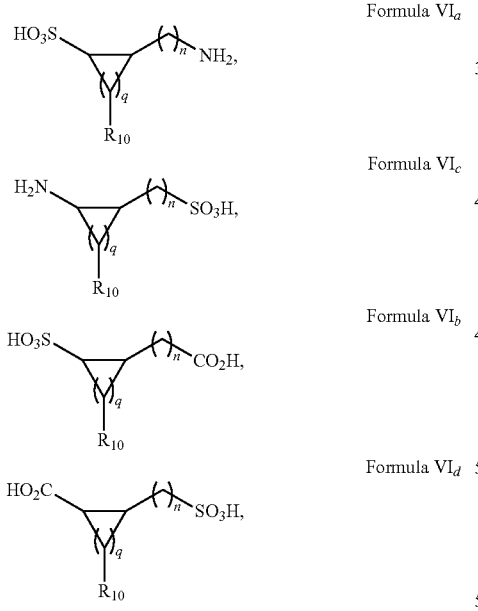

wherein:
n is 1, 2, 3, 4, 5 or 6;
q is 1, 2, 3, 4, or 5;
Each $R_{10}$ is independently hydrogen, deuterium, halogen, alkyl, alkoxy, alkenyl, alkynyl, cyano, cycloalkyl, heterocycloalkyl, aryl, or heteroaryl;
or a pharmaceutically acceptable salt thereof.

In another embodiment, the invention pertains, at least in part to compounds of Formula VIIa:

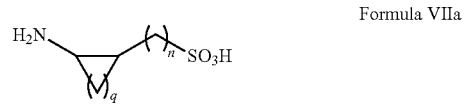

wherein:
n is 1, 2, 3, 4, 5 or 6;
q is 1, 2, 3, 4, or 5;
or a pharmaceutically acceptable salt thereof.

In another embodiment, the invention pertains, at least in part to compounds of Formula VIIb:

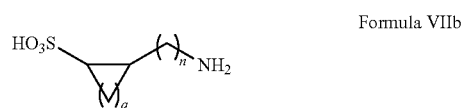

wherein:
n is 1, 2, 3, 4, 5 or 6;
m is 1, 2, 3, 4, or 5;
or a pharmaceutically acceptable salt thereof.

In another embodiment, the invention pertains, at least in part to compounds of Formula VIIIa-VIIIo:

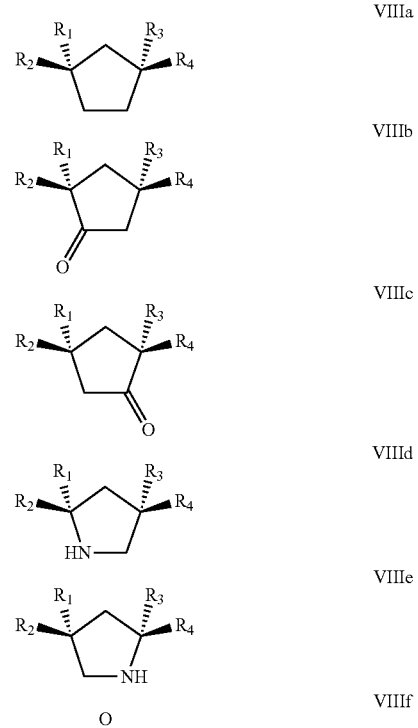
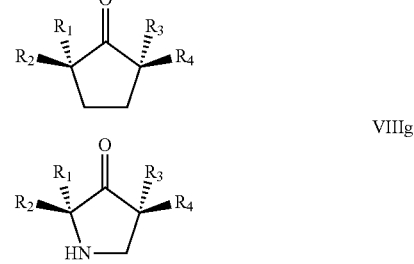

-continued

VIIIh 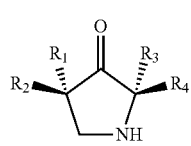

VIIIi 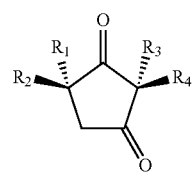

VIIIj 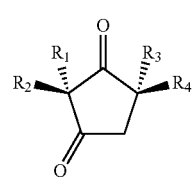

VIIIk 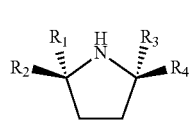

VIIIl 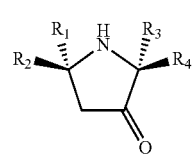

VIIIm 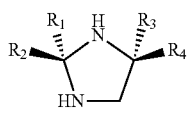

VIIIn 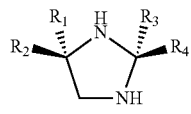

VIIIo 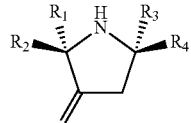

wherein:
$R_1$ is —SO$_3$H, or —(CH$_2$)$_n$SO$_3$H;
$R_2$ is —H
$R_3$ is —H, —CH$_3$, —C(O)NH$_2$, or —(CH$_2$)$_n$SO$_3$H;
$R_4$ is —H, —CH$_3$, —C(O)NH$_2$, or —(CH$_2$)$_n$SO$_3$H;
Each n is 1 or 2;
or a pharmaceutically acceptable salt thereof.

In another embodiment, the invention pertains, at least in part to compounds of Formula VIIIaa-VIIIoo:

VIIIaa 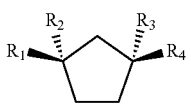

-continued

VIIIbb 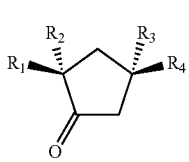

VIIIcc 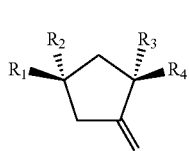

VIIIdd 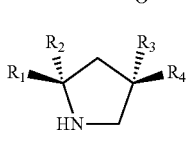

VIIIee 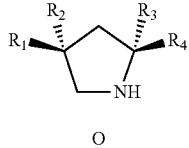

VIIIff 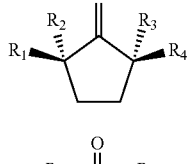

VIIIgg 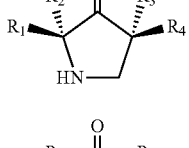

VIIIhh 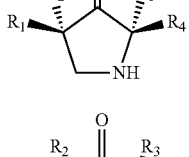

VIIIii 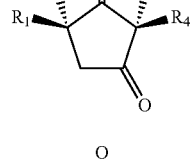

VIIIjj 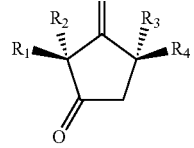

VIIIkk 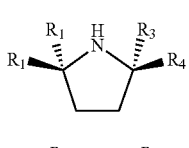

VIIIll 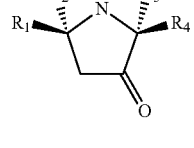

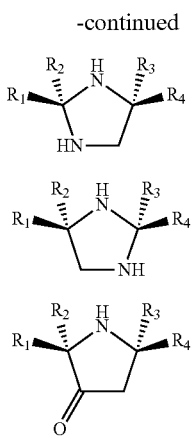

Wherein:
R$_1$ is —SO$_3$H, or —(CH$_2$)$_n$SO$_3$H;
R$_2$ is —H
R$_3$ is —H, —CH$_3$, —C(O)NH$_2$, or —(CH$_2$)$_n$SO$_3$H;
R$_4$ is —H, —CH$_3$, —C(O)NH$_2$, or —(CH$_2$)$_n$SO$_3$H;
Each n is 1 or 2;

Although, as indicated above, various embodiments and aspects thereof for a variable in Formula I, Ia, Ib, II, III, IIIa, IIIb, IV, IVa, IVb, IV-1, IV-2a, IV-2b, V, VIa, VIb, VIc, VId, VIIa, VIIb, VIIIa-VIIIo, and VIIIaa-VIIIoo, may be selected from a group of chemical moieties, the invention also encompasses as further embodiments and aspects thereof situations where such variable is: a) selected from any subset of chemical moieties in such a group; and b) any single member of such a group.

Although various embodiments and aspects thereof are set forth (or implied, as discussed in the preceding paragraph) individually for each variable in Formula I, Ia, Ib, II, III, IIIa, IIIb, IV, IVa, IVb, IV-1, IV-2a, IV-2b, V, VIa, VIb, VIc, VId, VIIa, VIIb, VIIIa-VIIIo, and VIIIaa-VIIIoo, the invention encompasses all possible combinations of the different embodiments and aspects for each of the variables in Formula I, Ia, Ib, II, III, IIIa, IIIb, IV, IVa, IVb, IV-1, IV-2a, IV-2b, V, VIa, VIb, VIc, VId, VIIa, VIIb, VIIIa-VIIIo, and VIIIaa-VIIIoo.

DETAILED DESCRIPTION OF THE INVENTION

Figure 1:
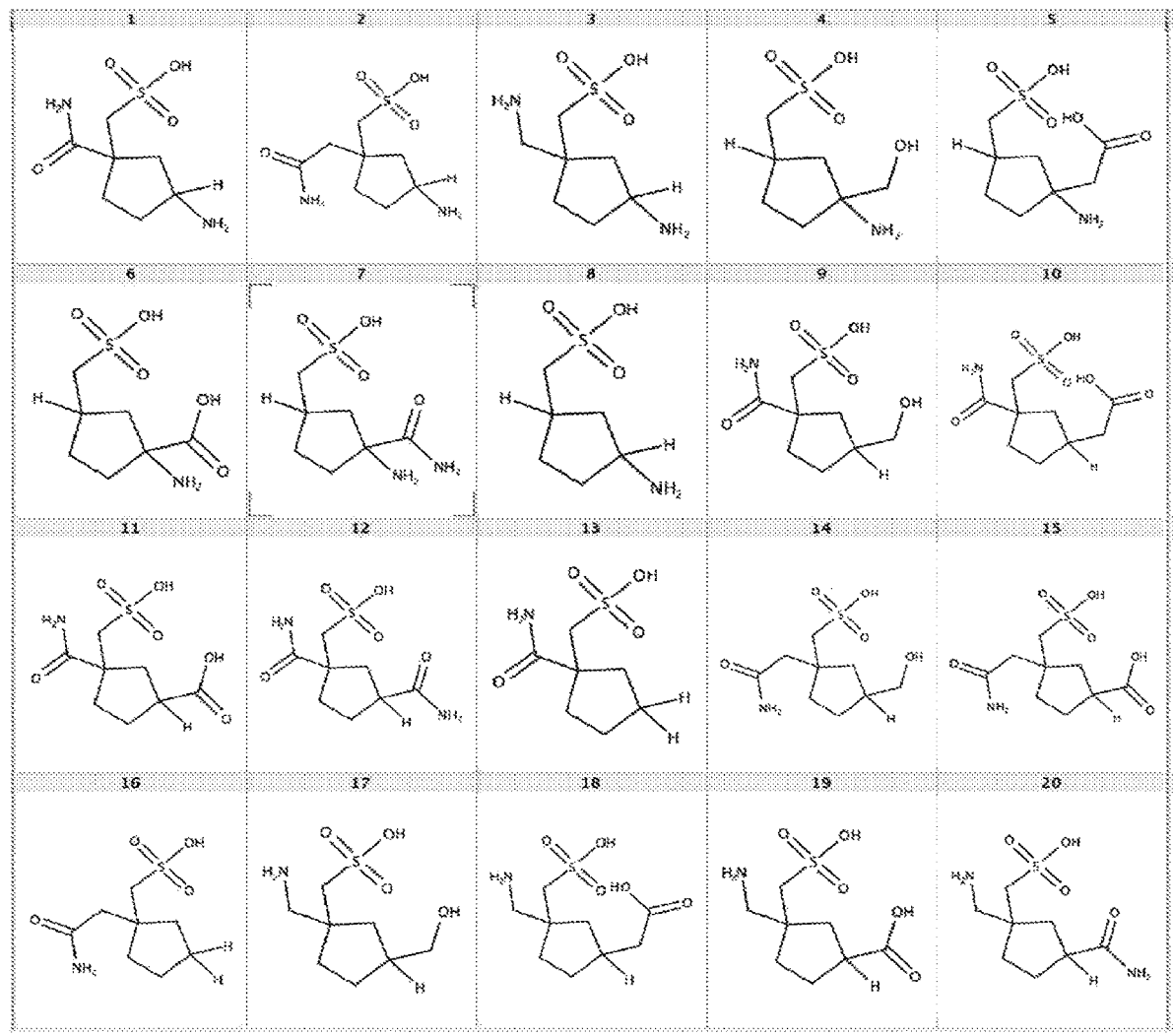
FIG. 1 is a table illustrating exemplary compounds of the present invention.
Figure 1:
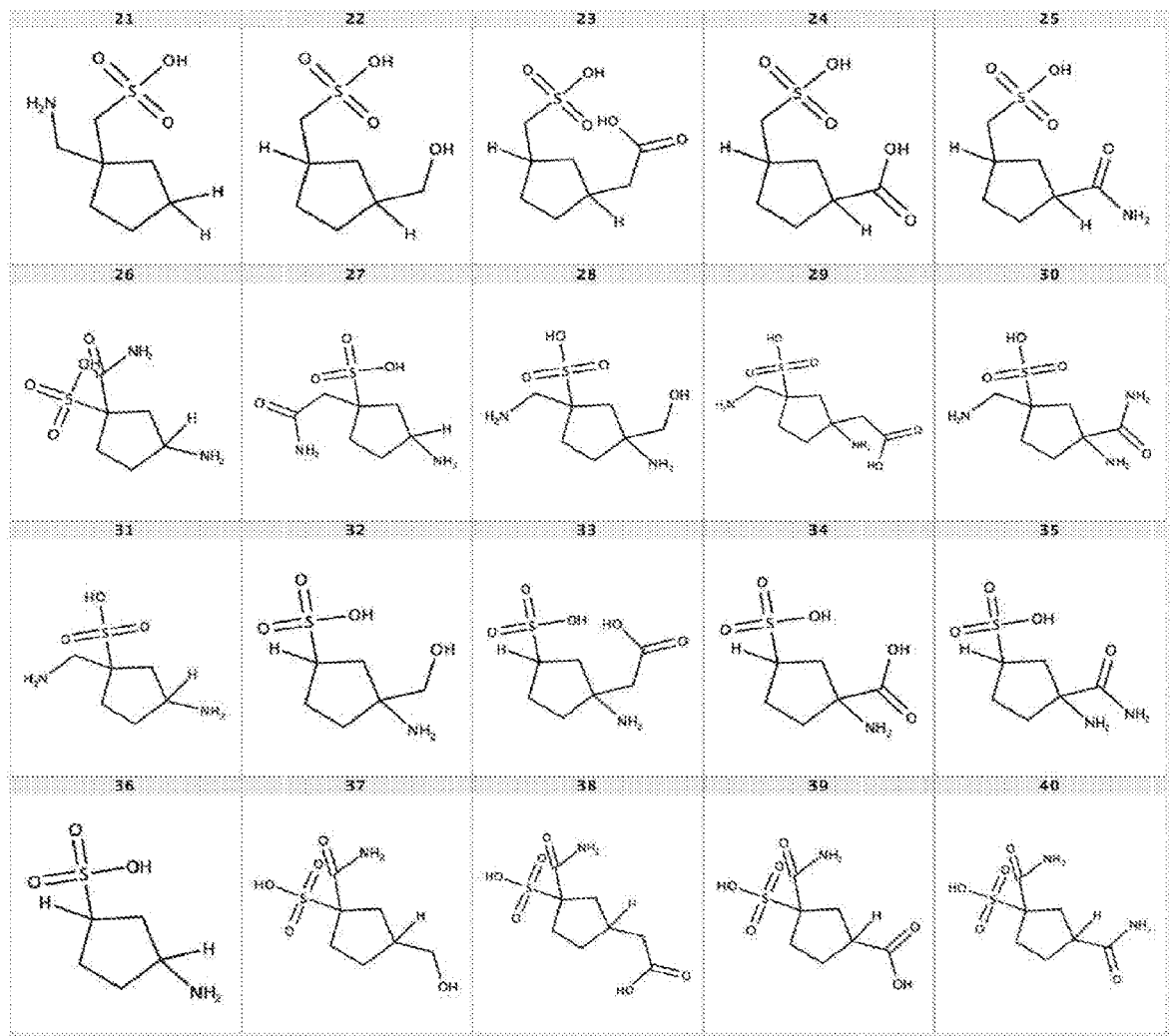
Figure 1:
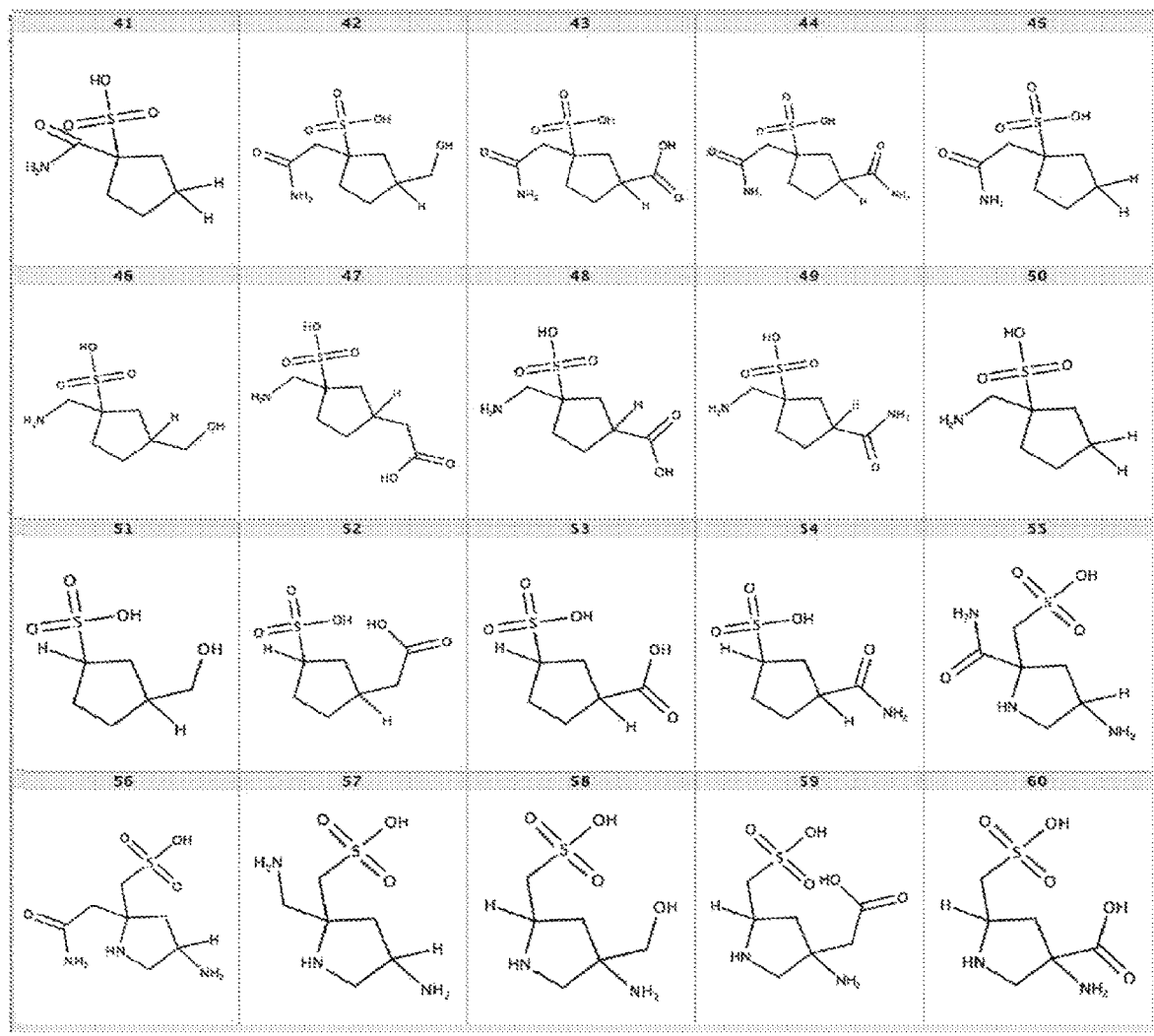
Figure 1:
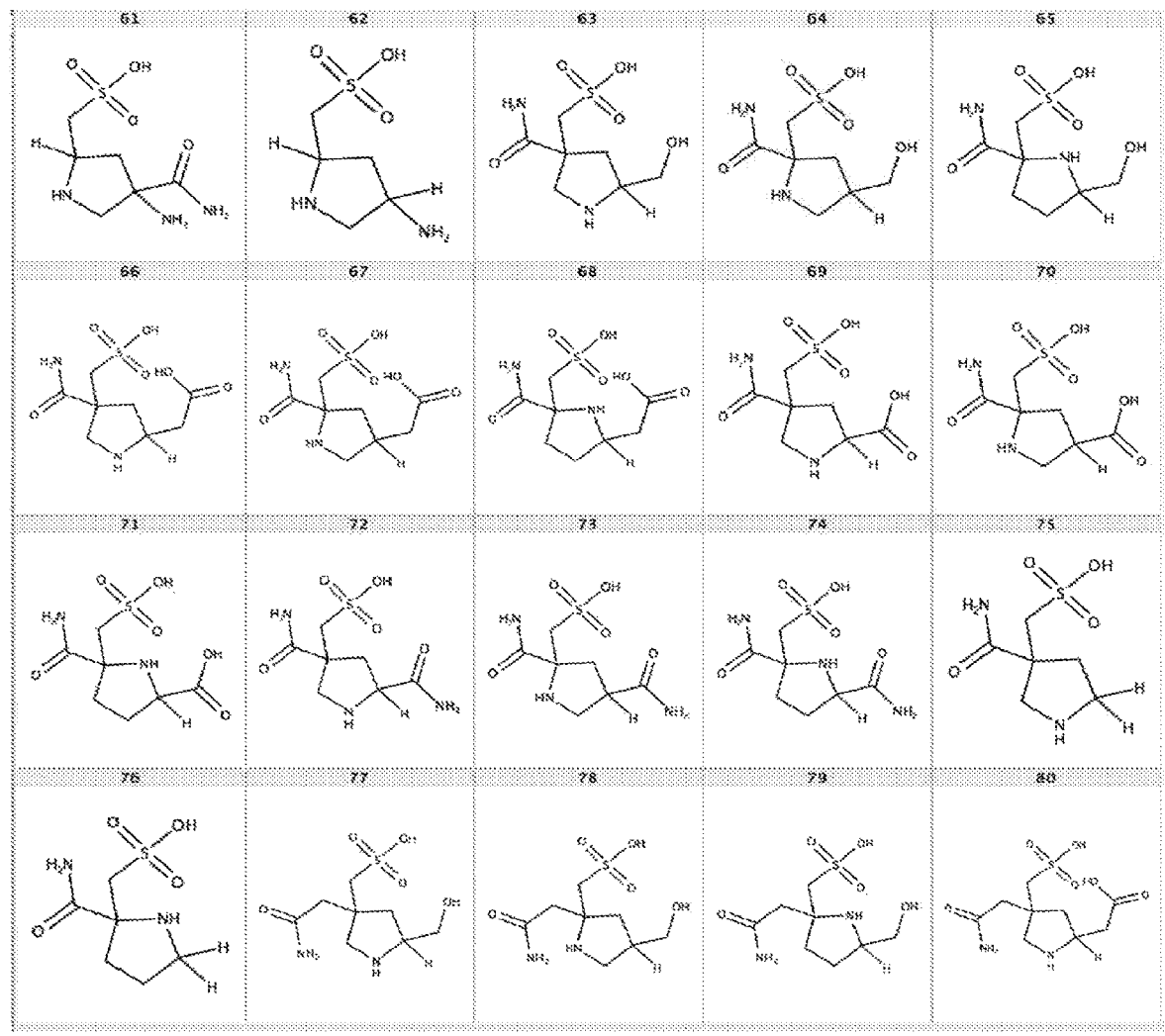
Figure 1:
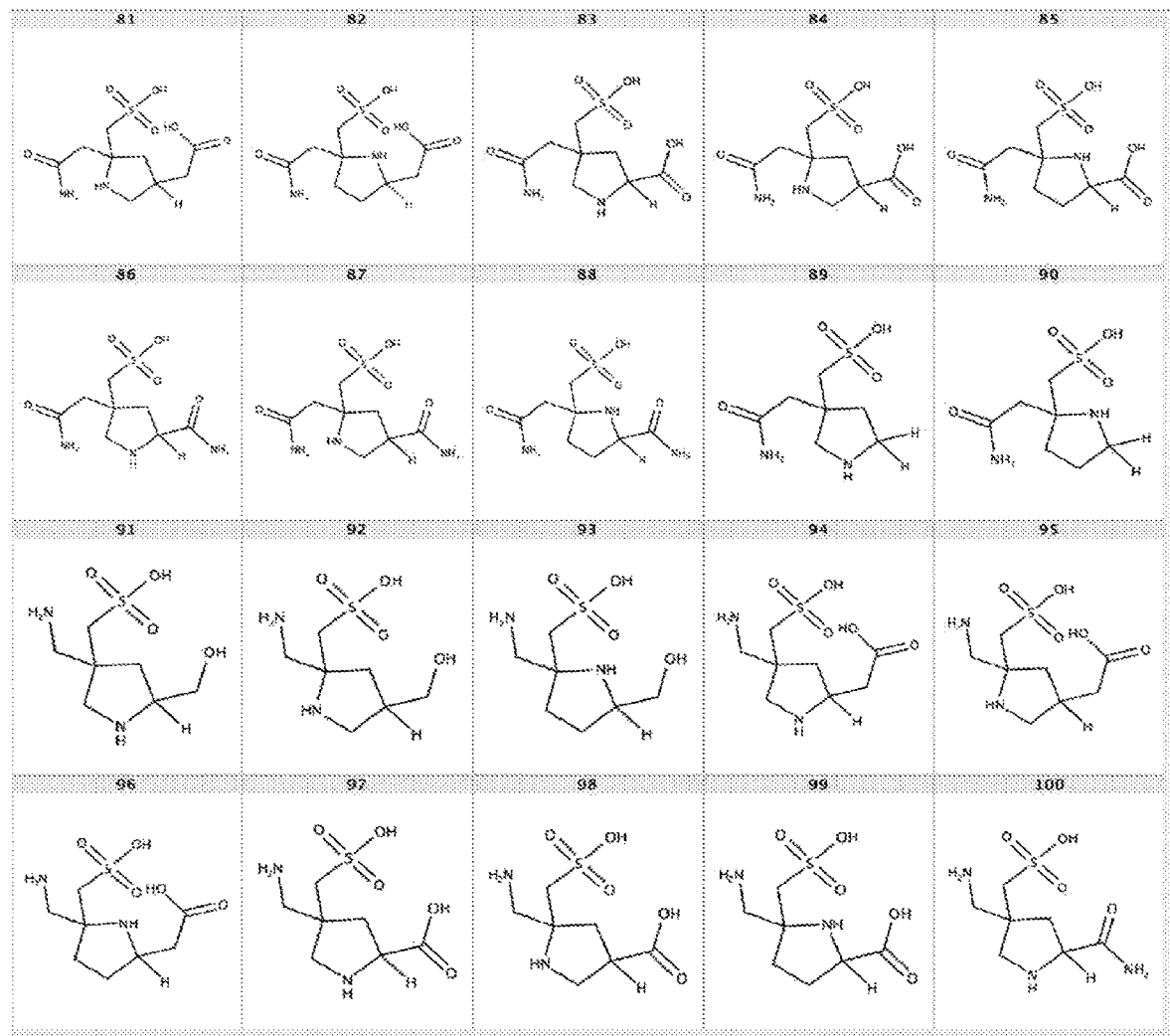
Figure 1:
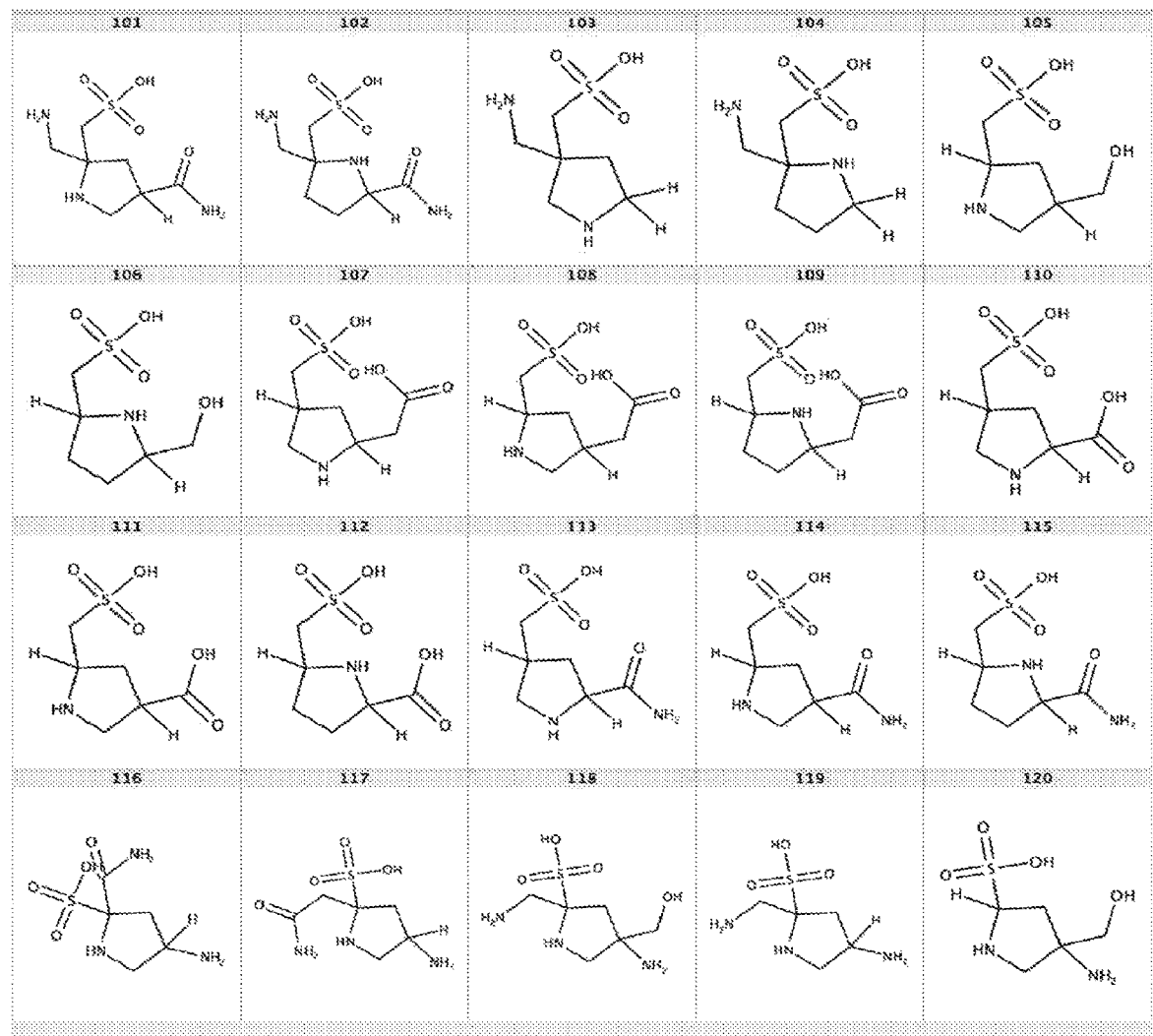
Figure 1:
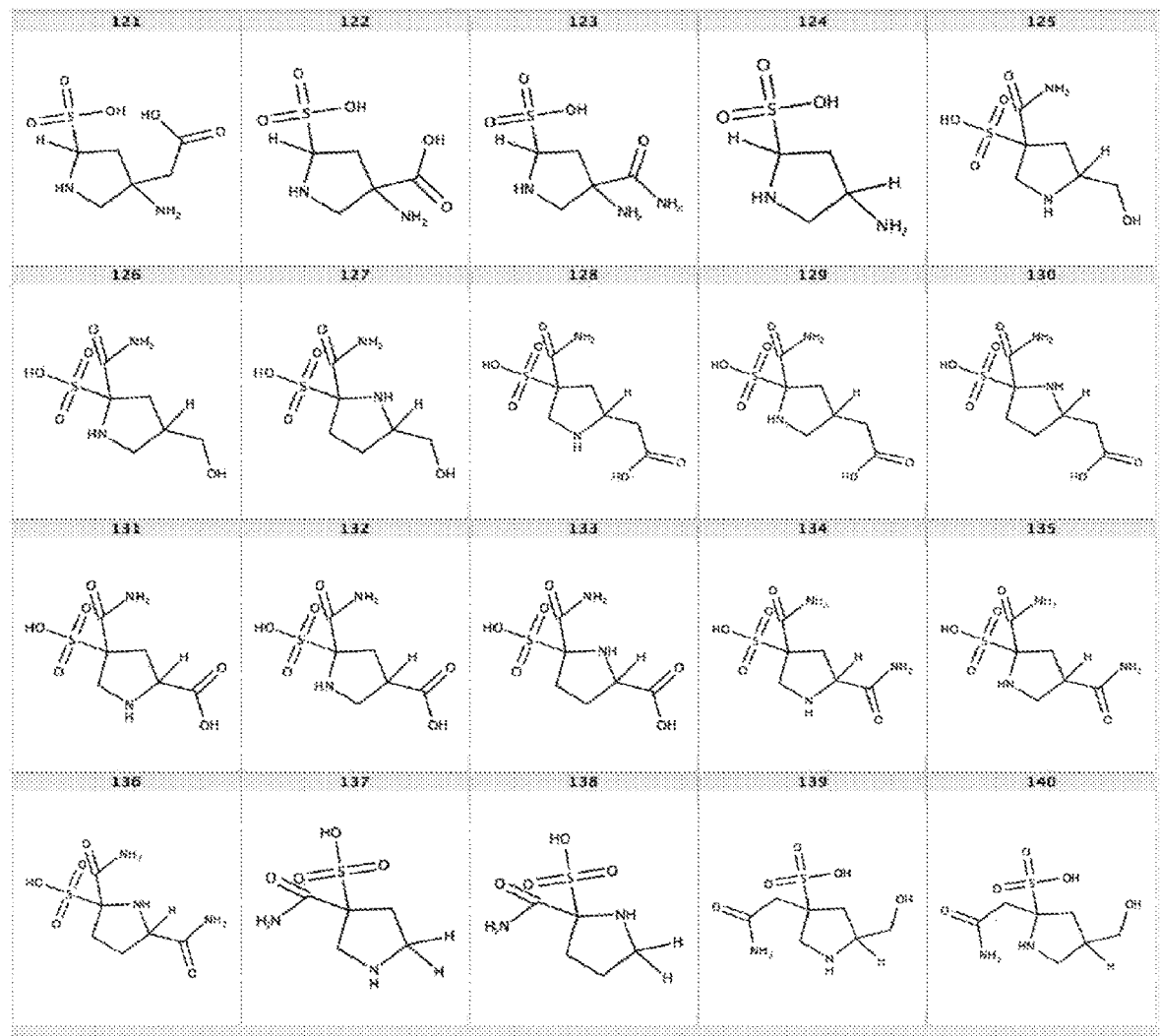
Figure 1:
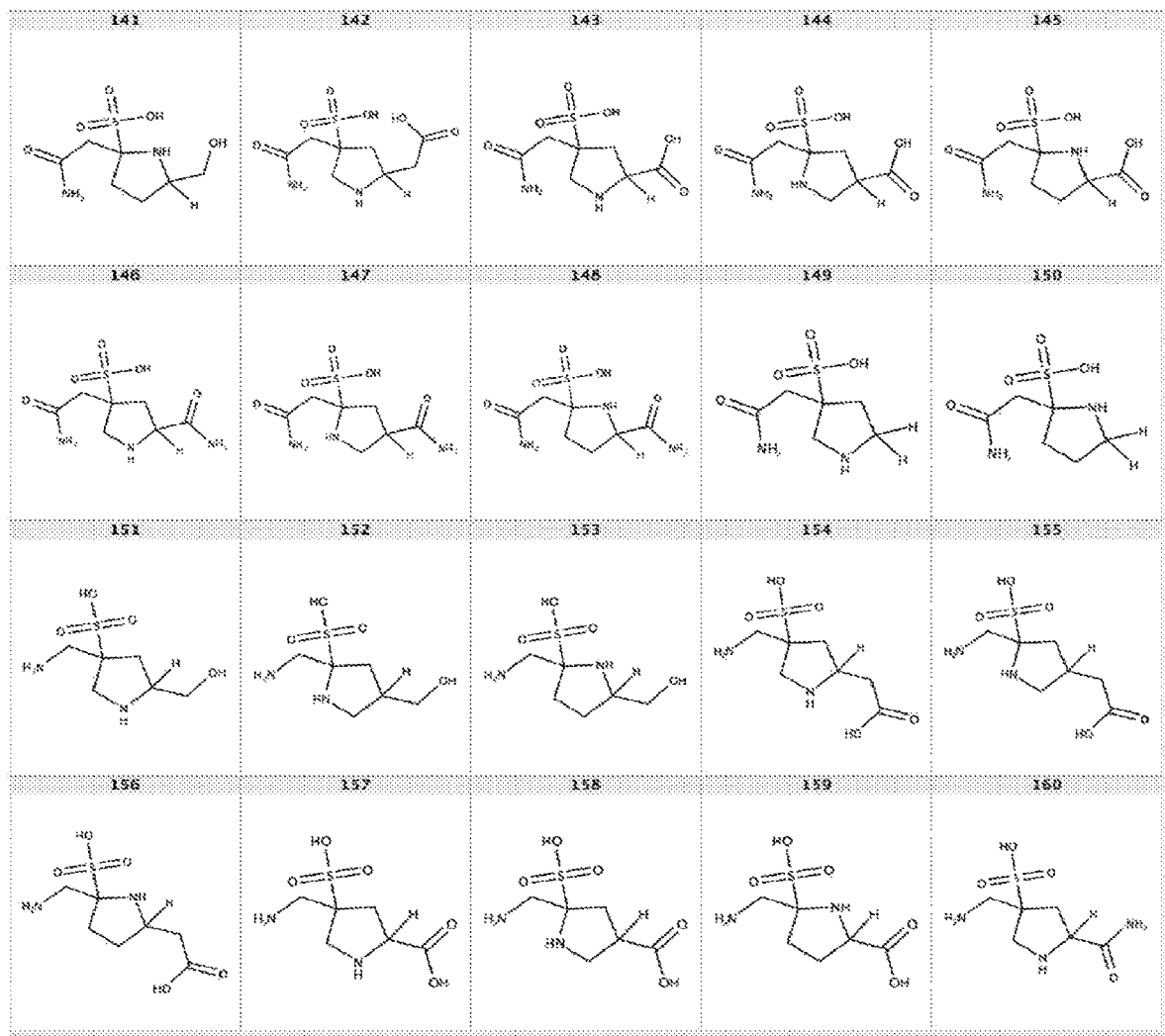
Figure 1:
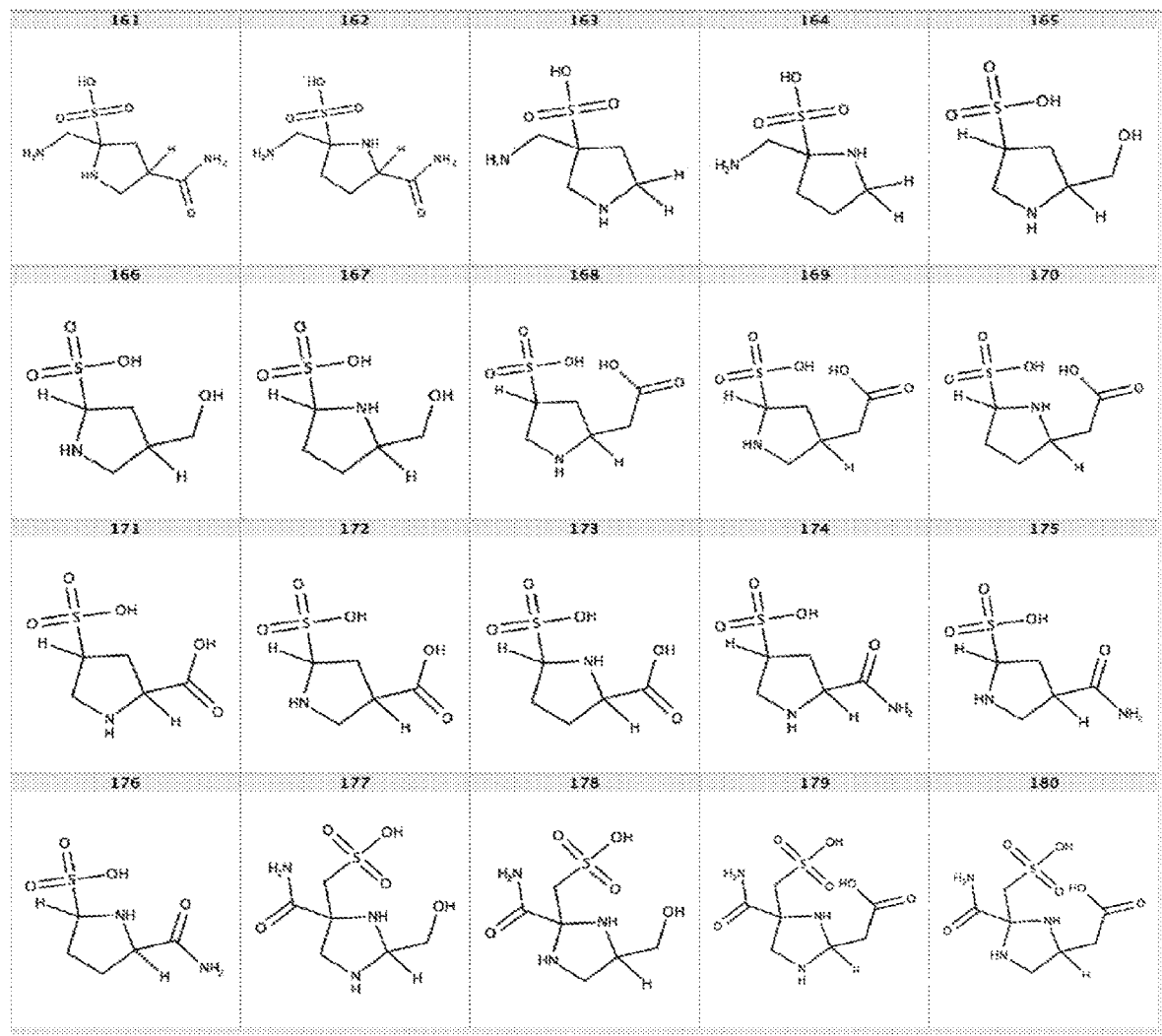
Figure 1:
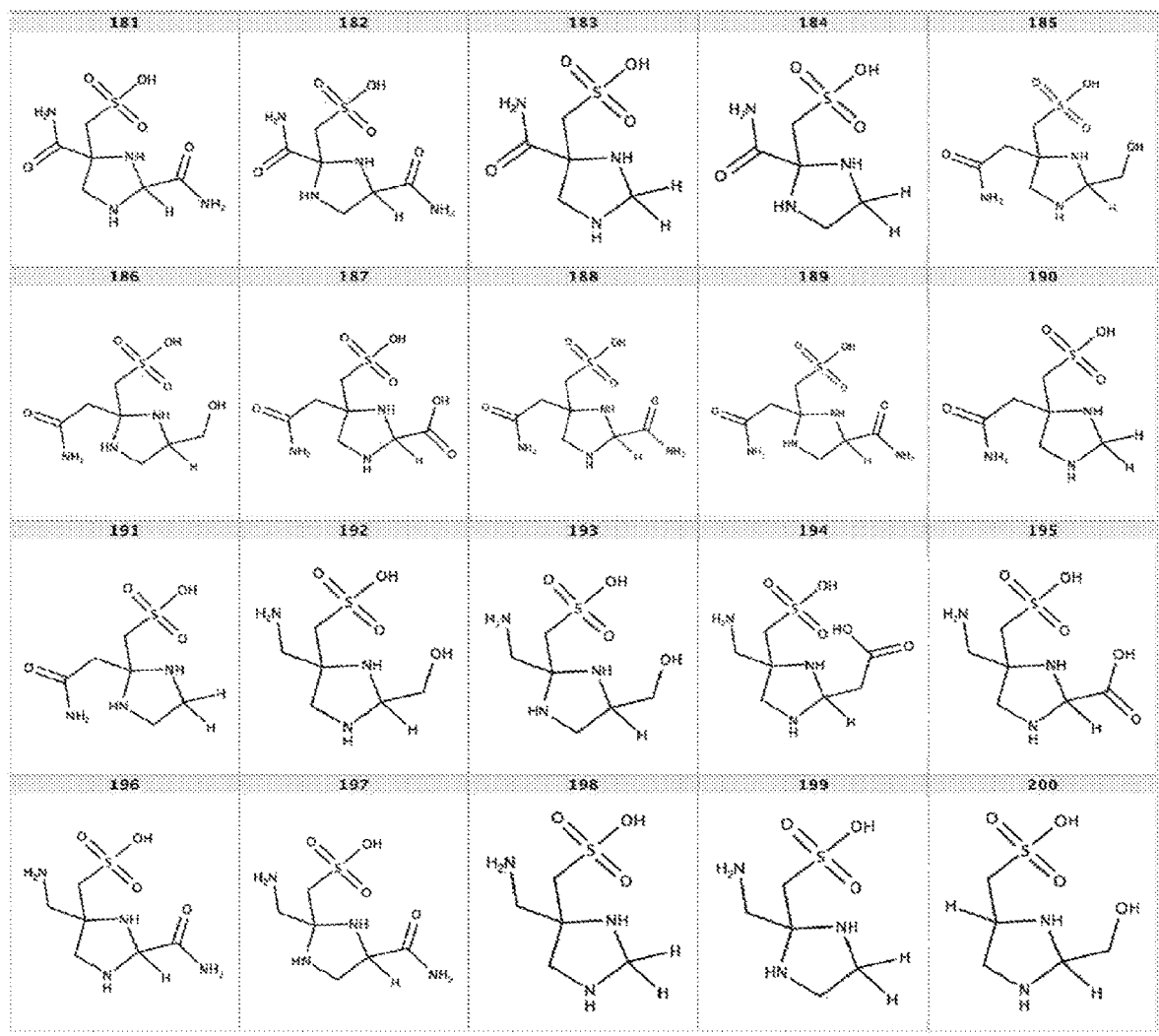
Figure 1:
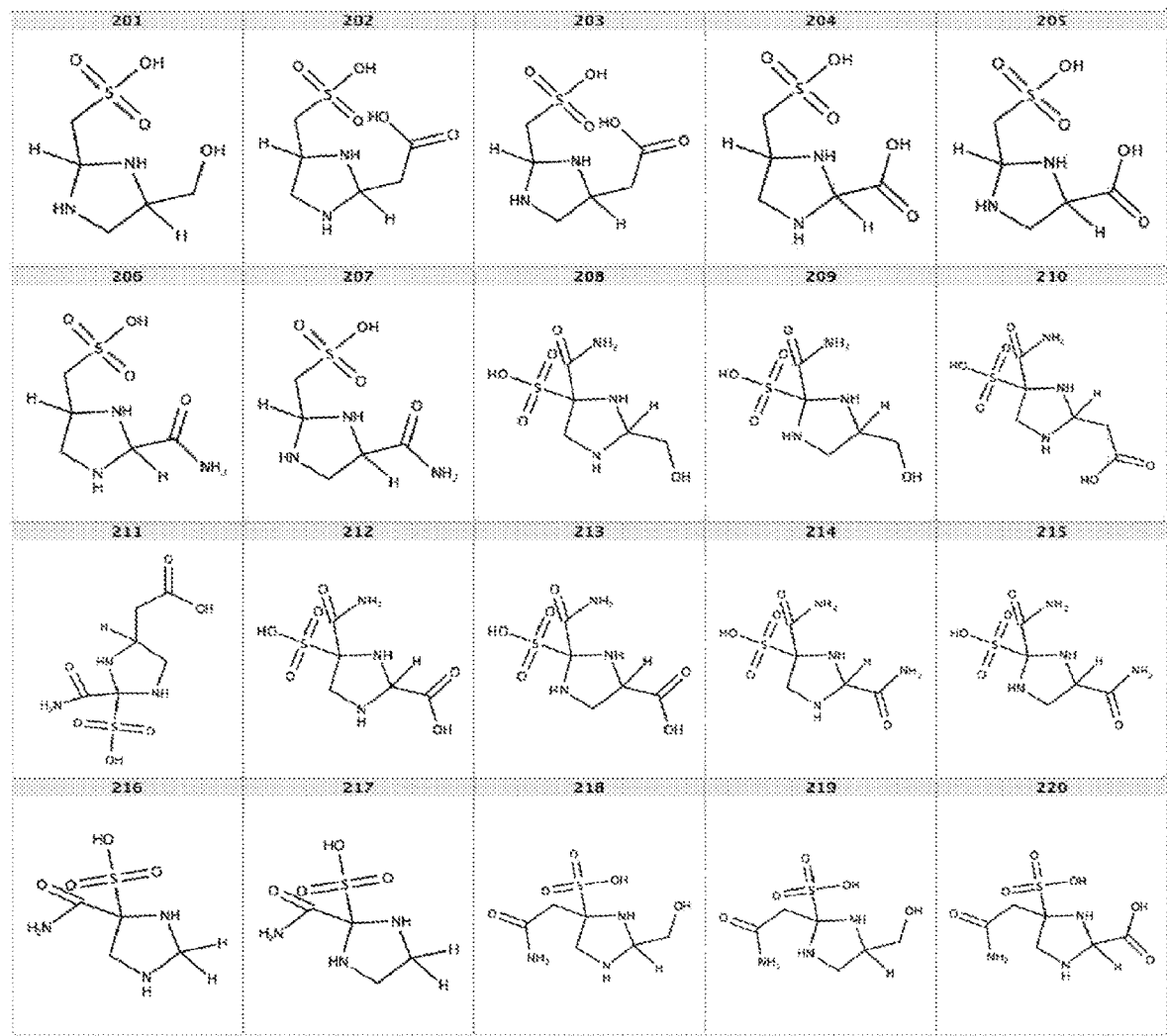
Figure 1:
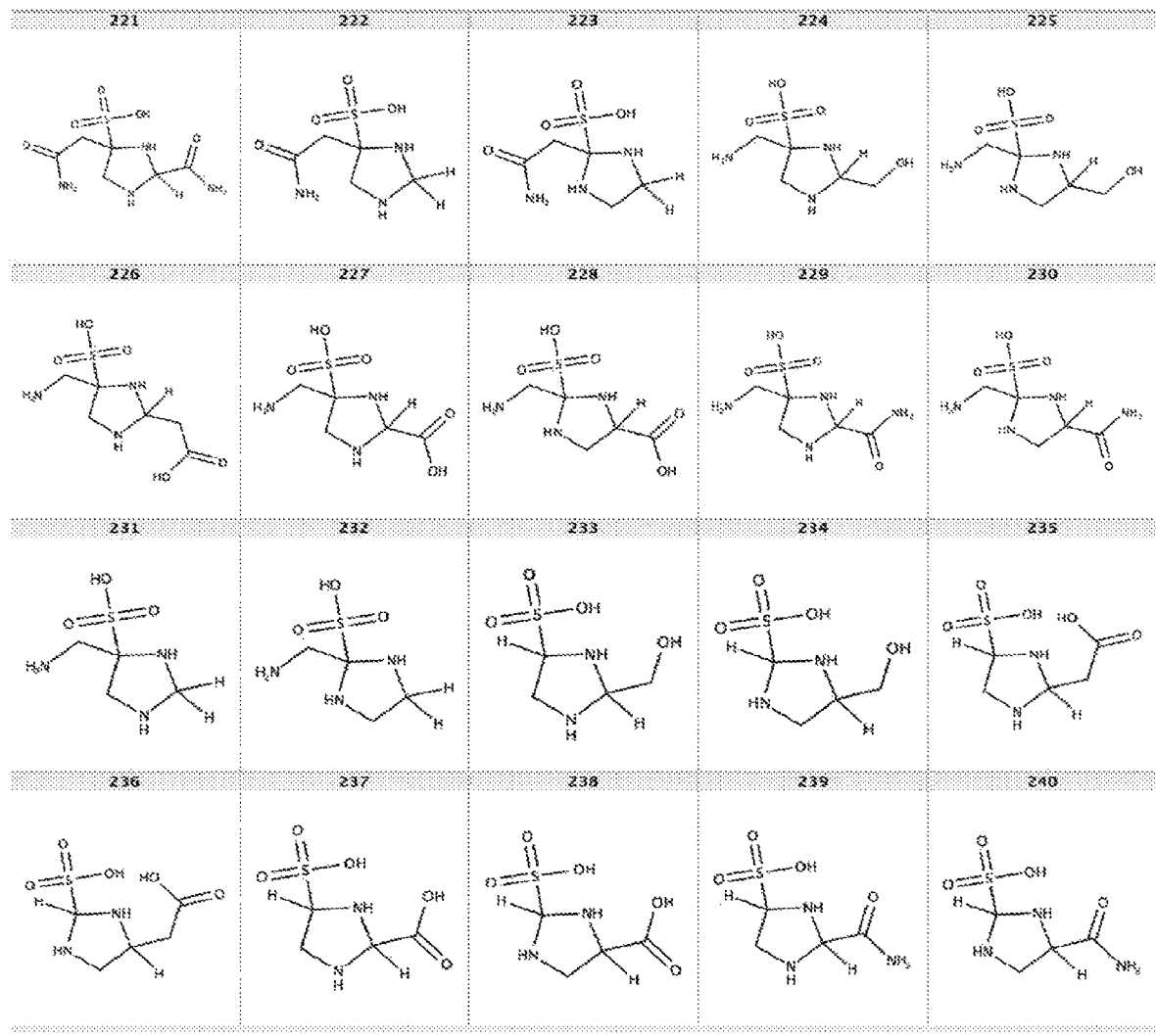

The contents of each cited patent, patent application and journal article are incorporated by reference as if set forth fully herein.

All technical and scientific terms used herein have the same meaning as commonly understood by one ordinary skilled in the art to which the invention pertains. For convenience, the meaning of certain terms and phrases used herein are provided below.

To the extent the definitions of terms in the publications, patents, and patent applications incorporated herein by reference are contrary to the definitions set forth in this specification, the definitions in this specification control. The section headings used herein are for organizational purposes only, and are not to be construed as limiting the subject matter disclosed.

It should be noted that, the singular forms "a", "an", and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

The chemical structures herein are drawn according to the conventional standards known in the art. Thus, where an atom, such as a carbon atom, as drawn appears to have an unsatisfied valency, then that valency is assumed to be satisfied by a hydrogen atom even though that hydrogen atom is not necessarily explicitly drawn. Hydrogen atoms should be inferred to be part of the compound.

The symbol "—" in general represents a bond between two atoms in the chain. Thus CH$_3$—O—CH$_2$—CH(R$_i$)—CH$_3$ represents a 2-substituted-1-methoxypropane compound. In addition, the symbol "-" represents the point of attachment of the substituent to a compound. Thus for example aryl(C1-C6)-alkyl indicates an arylalkyl group, such as benzyl, attached to the compound at the alkyl moiety.

Where multiple substituents are indicated as being attached to a structure, it is to be understood that the substituents can be the same or different. Thus for example "Rm optionally substituted with 1, 2 or 3 Rq groups" indicates that Rm is substituted with 1, 2, or 3 Rq groups where the Rq groups can be the same or different.

The compounds of the invention may contain one or more chiral centers and/or double bonds and, therefore, may exist as stereoisomers, such as double-bond isomers (i.e., geometric isomers), enantiomers, or diastereomers. When compounds of the invention are depicted or named without indicating the stereochemistry, it is to be understood that both stereomerically pure forms (e.g., geometrically pure, enantiomerically pure, or diastereomerically pure) and stereoisomeric mixtures are encompassed.

When the stereochemistry of the disclosed compounds is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

As used herein, a racemic mixture means about 50% of one enantiomer and about 50% of is corresponding enantiomer relative to all chiral centers in the molecule. The invention encompasses all enantiomerically-pure, enantiomerically-enriched, diastereomerically pure, diastereomerically enriched, and racemic mixtures of the compounds of the invention.

Enantiomeric and diastereomeric mixtures can be resolved into their component enantiomers or stereoisomers by well-known methods, such as chiral-phase gas chromatography, chiral-phase high performance liquid chromatography, crystallizing the compound as a chiral salt complex or crystallizing the compound in a chiral solvent. Enantiomers and diastereomers can also be obtained from diastereomerically- or enantiomerically-pure intermediates, reagents, and catalysts by well-known asymmetric synthetic methods.

Definitions

The following definitions are used in connection with the disclosure:

As used herein, the term "Compounds of the present invention" and equivalent expressions refers to compounds mentioned herein as being useful for at least one purpose of the invention, e.g., those encompassed by structural Formulae such as (I) through (VII), and includes specific compounds mentioned herein, as well as their pharmaceutically acceptable salts and solvates. Embodiments herein may exclude one or more of the compounds of the invention. Compounds may be identified either by their chemical structure and/or chemical name. If a chemical structure and chemical name conflict, then the chemical structure determines the identity of the compound. The compounds described herein may contain one or more chiral centers and/or double bonds and therefore, may exist as stereoisomers, such as double-bond isomers (i.e., geometric isomers), enantiomers, or diastereomers. Accordingly, the chemical structures disclosed herein encompass all possible enantiomers and stereoisomers of the illustrated compounds including the stereoisomerically pure form (e.g., geometrically pure, enantiomeric ally pure, or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan, e.g., chiral chromatography (such as chiral HPLC), immunoassay techniques, or the use of covalently (such as Mosher's esters) and non-covalently (such as chiral salts) bound chiral reagents to respectively form a diastereomeric mixture which can be separated by conventional methods, such as chromatography, distillation, crystallization or sublimation, the chiral salt or ester is then exchanged or cleaved by conventional means, to recover the desired isomers. The compounds may also exist in several tautomeric forms including the enol form, the keto form, and mixtures thereof. Accordingly, the chemical structures depicted herein encompass all possible tautomeric forms of the illustrated compounds. The disclosed compounds also include isotopically labeled compounds where one or more atoms have an atomic mass different from the atomic mass most abundantly found in nature. Examples of isotopes that may be incorporated into the compounds of the present invention include, but are not limited to, $^2H$ (D), $^3H$ (T), $^{11}C$, $^{13}C$, $^{14}C$, $^{15}N$, $^{18}O$, $^{17}O$, etc. Compounds may exist in unsolvated forms as well as solvated forms, including hydrated forms. In general, compounds may be hydrated or solvated. Certain compounds may exist in multiple crystalline or amorphous forms. In general, all physical forms are equivalent for the uses contemplated herein and are intended to be within the scope of the present invention. Further, when partial structures of the compounds are illustrated, brackets or equivalents indicate the point of attachment of the partial structure to the rest of the molecule.

The term "prodrug" and equivalent expressions refer to agents which can be converted in vitro or in vivo directly or indirectly to an active form (see, e.g., R. B. Silverman, 1992, "The Organic Chemistry of Drug Design and Drug Action," Academic Press, Chap. 8; Bundgaard, Hans; Editor. Neth. (1985), "Design of Prodrugs". 360 pp. Elsevier, Amsterdam; Stella, V.; Borchardt, R.; Hageman, M.; Oliyai, R.; Maag, H.; Tilley, J. (Eds.) (2007), "Prodrugs: Challenges and Rewards, XVIII, 1470 p. Springer). Prodrugs can be used to alter the biodistribution (e.g., to allow agents which would not typically enter the reactive site of the protease) or the pharmacokinetics for a particular agent. A wide variety of groups have been used to modify compounds to form prodrugs, for example, amides, esters, ethers, phosphates, etc. When the prodrug is administered to a subject, the group is cleaved, enzymatically or non-enzymatically, reductively, oxidatively, or hydrolytically, or otherwise to reveal the active form. As used herein, "prodrug" includes pharmaceutically acceptable salts thereof, or pharmaceutically acceptable solvates as well as crystalline forms of any of the foregoing. Prodrugs are frequently, although not necessarily, pharmacologically inactive until converted to the parent drug.

As used herein, the term "acyclic" refers to an organic moiety without ring system.

The term "aliphatic group" includes organic moieties characterized by straight or branched chains, typically having between 1 and 12 carbon atoms. Aliphatic groups include non-cyclic alkyl groups, alkenyl groups, and alkynyl groups.

As used herein, the term "alkyl" refers to a saturated hydrocarbon. In one embodiment, an alkyl group is a C1-C12 alkyl group, referring to a saturated hydrocarbon having from one to twelve carbon atoms, including linear, branched, and cyclic alkyl groups. Examples of alkyl groups include, without limitation, methyl, ethyl, propyl, butyl, pentyl, hexyl, heptyl, octyl, nonyl, decyl, isopropyl, tert-butyl, sec-butyl, isobutyl, cyclopropyl, cyclopentyl, cyclohexyl, cycloheptyl, cyclooctyl, and the like. The term alkyl includes both unsubstituted alkyl groups and substituted alkyl groups. In one embodiment, an alkyl group is a C1-C6 alkyl group, wherein the alkyl group comprises from one to six carbon atoms. In another embodiment, an alkyl group is a C1-C3 alkyl group, wherein the alkyl group comprises from one to six carbon atoms.

The term "alkyl" used alone or as part of a larger moiety, such as "alkoxy", "haloalkyl", "arylalkyl", "alkylamine", "cycloalkyl", "dialkyamine", "alkylamino", "dialkyamino" "alkylcarbonyl", "alkoxycarbonyl" and the like, includes as used herein means saturated straight-chain, cyclic or branched aliphatic group.

Unless the number of carbons is otherwise specified, "lower" as in "lower aliphatic," as used herein means that the moiety has at least one (two for alkenyl and alkynyl) and equal or less than 6 carbon atoms. Similarly, the terms "lower alkoxy", "lower haloalkyl", "lower arylalkyl", "lower alkylamine", "lower cycloalkylalkyl", "lower dialkyamine", "lower alkylamino", "lower dialkyamino" "lower alkylcarbonyl", "lower alkoxycarbonyl" include straight and branched saturated chains containing one to six carbon atoms.

As used herein, the term "alkenyl" refers to unsaturated hydrocarbons having from two to twelve carbon atoms, including linear, branched, and cyclic non aromatic alkenyl groups, and comprising at least one carbon-carbon double bond. Examples of alkenyl groups include, without limitation, vinyl, allyl, 1-propen-2-yl, 1-buten-3-yl, 1-buten-4-yl, 2-buten-4-yl, 1-penten-5-yl, 1,3-pentadien-5-yl, cyclopentenyl, cyclohexenyl, ethylcyclopentenyl, ethylcylohexenyl, and the like. The term alkenyl includes both unsubstituted alkenyl groups and substituted alkenyl groups. The term "C2-Cnalkenyl", wherein n is an integer from 3 to 12, refers to an alkenyl group having from 2 to the indicated "n" number of carbon atoms.

As used herein, the term "alkynyl" refers to unsaturated hydrocarbons having from two to twelve carbon atoms, including linear, branched, and cyclic non aromatic alkynyl groups, and comprising at least one carbon-carbon triple bond. Examples of alkynyl groups include, without limitation, ethynyl, 1-propyn-3-yl, 1-butyn-4-yl, 2-butyn-4-yl, 1-pentyn-5-yl, 1,3-pentadiyn-5-yl, and the like. The term alkynyl includes both unsubstituted alkynyl groups and substituted alkynyl groups. The term "C2-Cnalkynyl", wherein n is an integer from 3 to 12, refers to an alkynyl group having from 2 to the indicated "n" number of carbon atoms.

The term "alkoxy" means —O-alkyl; "hydroxyalkyl" means alkyl substituted with hydroxy; "aralkyl" means alkyl substituted with an aryl group; "alkoxyalkyl" mean alkyl substituted with an alkoxy group; "alkylamine" means amine substituted with an alkyl group; "cycloalkylalkyl" means alkyl substituted with cycloalkyl; "dialkylamine" means amine substituted with two alkyl groups; "alkylcarbonyl" means C(O)R, wherein R is alkyl; "alkoxycarbonyl" means C(O)OR, wherein R is alkyl; and where alkyl is as defined herein.

The term "amino acid" means a moiety containing both an amino group and a carboxyl group. In some embodiments, the amino acids are α, β-, or γ-amino acids, including their stereoisomers and racemates (e.g., either D- or L-amino acids). The free amino or carboxyl group of an amino acid may be protected or unprotected. The orientation of the amino acid moiety in a compound of this invention will determine whether there is a free amino group, e.g., —C(O)—[CH($R^A$)]$_{1-3}$—NH—$R^B$, or a free carboxyl, e.g., —NH—[CH($R^A$)]$_{1-3}$—C(O)O$R^B$, wherein $R^A$ is any amino acid side chain and $R^B$ is hydrogen (i.e., unprotected), or a protecting group (i.e., protected). The orientation of the amino acid moiety in a compound of this invention is, in part, determined by the atom in the compound to which it is bound. When an amino acid moiety is bound to a nitrogen atom, it will have a free amino group, e.g., —C(O)—[CH($R^A$)]$_{1-3}$—NH—$R^B$. When an amino acid moiety is bound to a carbon atom, it will typically, but not always, have a free carboxyl group, e.g., —NH—[CH($R^A$)]$_{1-3}$—C(O)O$R^B$ The term "protected" as used to describe a moiety means that a reactive hydrogen has been replaced with a nonreactive (protecting) group. Amino protecting groups are well known in the art and include but are not limited to Boc (t-butoxycarbonyl), Cbz (benzyloxycarbonyl), and the like. Carboxy protecting groups are well known in the art and include but are not limited to alkyl, benzyl and the like.

The term "cycloalkyl" means a saturated carbocyclic ring, with from three to eight carbons.

The term "dipeptide" means two amino acids bound to one another in the same orientation, e.g., —C(O)—[CH($R^A$)]$_{1-3}$—NH—C(O)—CH($R^A$)—NH—$R^B$; or —C(O)—CH($R^A$)—NH—C(O)—[CH($R^A$)]$_{1-3}$—NH—$R^B$.

The terms "haloalkyl" and "haloalkoxy" respectively mean alkyl or alkoxy substituted with one or more halogen atoms.

Carbocyclic aromatic rings have only carbon ring atoms (typically six to fourteen) and include monocyclic aromatic rings such as phenyl and fused polycyclic aromatic ring systems in which two or more carbocyclic aromatic rings are fused to one another. Examples include 1-naphthyl, 2-naphthyl, 1-anthracyl.

Also included are solvates, hydrates or polymorphs of the disclosed compounds herein. Thus, it is to be understood that when any compound is referred to herein by name and structure, solvates, hydrates and polymorphs thereof are included.

The term "solvate" refers to a physical association of a compound of this invention with one or more solvent molecules, whether organic or inorganic. This physical association includes hydrogen bonding. In certain instances, the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, hemiethanolates, and the like.

The terms "cycloalkyl", "alicyclic", "carbocyclic" and equivalent expressions refer to a group comprising a saturated or partially unsaturated carbocyclic ring in a single, spiro (sharing one atom), or fused (sharing at least one bond) carbocyclic ring system having from three to fifteen ring members. Examples of cycloalkyl groups include, without limitation, cyclopropyl, cyclobutyl, cyclopentyl, cyclopenten-1-yl, cyclopenten-2-yl, cyclopenten-3-yl, cyclohexyl, cyclohexen-1-yl, cyclohexen-2-yl, cyclohexen-3-yl, cycloheptyl, bicyclo[4,3,0]nonanyl, norbornyl, and the like. The term cycloalkyl includes both unsubstituted cycloalkyl groups and substituted cycloalkyl groups. The term "C3-Cn cycloalkyl", wherein n is an integer from 4 to 15, refers to a cycloalkyl group having from 3 to the indicated "n" number of carbon atoms in the ring structure. Unless the number of carbons is otherwise specified, "lower cycloalkyl" groups as herein used, have at least 3 and equal or less than 8 carbon atoms in their ring structure.

The term "heterocycloalkyl" and equivalent expressions refer to a group comprising a saturated or partially unsaturated carbocyclic ring in a single, spiro (sharing one atom), or fused (sharing at least one bond) carbocyclic ring system having from three to fifteen ring members, including one to six heteroatoms (e.g. N, O, S, P) or groups containing such heteroatoms (e.g. NH, N$R_x$ ($R_x$ is alkyl, acyl, aryl, heteroaryl or cycloalkyl), PO$_2$, SO, SO$_2$, and the like). Heterocycloalkyl groups may be C-attached or heteroatom-attached (e.g. via a nitrogen atom) where such is possible. Examples of heterocycloalkyl groups include, without limitation, pyrrolidino, tetrahydrofuranyl, tetrahydrodithienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3,1,0]hexanyl, 3-azabicyclo[4,1,0]heptanyl, 3H-indolyl, quinolizinyl, and sugars, and the like. The term heterocycloalkyl includes both unsubstituted heterocycloalkyl groups and substituted heterocycloalkyl groups. The term "C$_3$-C$_n$ heterocycloalkyl", wherein n is an integer from 4 to 15, refers to a heterocycloalkyl group having from 3 to the indicated "n" number of atoms in the ring structure, including at least one hetero group or atom as defined above. Unless the number of carbons is otherwise specified, "lower heterocycloalkyl" groups as herein used, have at least 3 and equal or less than 8 carbon atoms in their ring structure.

The terms "aryl" and "aryl ring" refer to aromatic groups having "4n+2"π(pi) electrons, wherein n is an integer from 1 to 3, in a conjugated monocyclic or polycyclic system (fused or not) and having six to fourteen ring atoms. A "substituted aryl group" is an aryl group substituted at any one or more substitutable ring atom. The terms "heteroaryl," "heteroaromatic", and "heteroaryl ring" refer to an aromatic groups having "4n+2"π(pi) electrons, wherein n is an integer from 1 to 3, in a conjugated monocyclic or polycyclic system (fused or not) and having five to fourteen ring members, including one to six heteroatoms (e.g. N, O, S) or groups containing such heteroatoms (e.g. NH, NR$_x$ (R$_x$ is alkyl, acyl, aryl, heteroaryl or cycloalkyl), SO, and the like). Examples of heteroaryl groups include, without limitation, pyridyl, imidazolyl, pyrimidinyl, pyrazolyl, triazolyl, tetrazolyl, furyl, thienyl; isoxazolyl, thiazolyl, oxazolyl, isothiazolyl, pyrrolyl, quinolinyl, isoquinolinyl, indolyl, isoindolyl, chromenyl, isochromenyl, benzimidazolyl, benzofuranyl, cinnolinyl, indazolyl, indolizinyl, phthalazinyl, pyridazinyl, pyrazinyl, triazinyl, isoindolyl, pteridinyl, purinyl, oxadiazolyl, thiadiazolyl, furazanyl, benzofurazanyl, benzothiophenyl, benzothienyl, benzothiazolyl, benzoxazolyl, quinazolinyl, quinolizinyl, quinolinyl, isoquinolinyl, quinoxalinyl, naphthyridinyl, furopyridinyl, carbazolyl, phenanthridinyl, acridinyl, perimidinyl, phenanthrolinyl, phenazinyl, phenothiazinyl, phenoxazinyl, dibenzofuranyl, and the like. The term heteroaryl includes both unsubstituted heteroaryl groups and substituted heteroaryl groups. The term "C5-Cn-heteroaryl", wherein n is an integer from 6 to 15, refers to an heteroaryl group having from 5 to the indicated "n" number of atoms in the ring structure, including at least one hetero group or atom as defined above.

A "substituted aryl group" is an aryl group substituted at any one or more substitutable ring atom.

The terms "heterocycle" or "heterocyclic" include heterocycloalkyl and heteroaryl groups. Examples of heterocycles include, without limitation, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4☐H carbazolyl, carbolinyl, chromanyl, chromenyl, cinnolinyl, decahydroquinolinyl, 2H,6H 1,5,2 dithiazinyl, dihydrofuro[2,3 b]tetrahydrofuran, furanyl, furazanyl, imidazolidinyl, imidazolinyl, imidazolyl, 1H indazolyl, indolenyl, indolinyl, indolizinyl, indolyl, 3H indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3 oxadiazolyl, 1,2,4 oxadiazolyl, 1,2,5 oxadiazolyl, 1,3,4 oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4 piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H pyrrolyl, pyrrolyl, quinazolinyl, quinolinyl, 4H quinolizinyl, quinoxalinyl, quinuclidinyl, tetrahydrofuranyl, tetrahydroisoquinolinyl, tetrahydroquinolinyl, tetrazolyl, 6H 1,2,5 thiadiazinyl, 1,2,3 thiadiazolyl, 1,2,4 thiadiazolyl, 1,2,5 thiadiazolyl, 1,3,4 thiadiazolyl, thianthrenyl, thiazolyl, thienyl, thienothiazolyl, thienooxazolyl, thienoimidazolyl, thiophenyl, triazinyl, 1,2,3 triazolyl, 1,2,4 triazolyl, 1,2,5 triazolyl, 1,3,4 triazolyl, xanthenyl, and the like. The term heterocycle includes both unsubstituted heterocyclic groups and substituted heterocyclic groups.

The term "nitro" means —NO$_2$;

The terms "halo" and "halogen" refer to bromine, chlorine, fluorine or iodine substituents;

The term "thiol", "thio", or "mercapto" means —SH; and the term "hydroxyl" or "hydroxy" means —OH.

The term "alkylthio" refers to an alkyl group, having a sulfhydryl group attached thereto. Suitable alkylthio groups include groups having 1 to about 12 carbon atoms, preferably from 1 to about 6 carbon atoms. "Alkylthioalkyl" mean alkyl substituted with an alkylthio group. An example of an "alkylthioalkyl" group is —CH$_2$SCH$_3$.

The term "alkylcarboxyl" as used herein means an alkyl group having a carboxyl group attached thereto.

The term "alkoxy" or "lower alkoxy" as used herein means an alkyl group having an oxygen atom attached thereto. Representative alkoxy groups include groups having 1 to about 6 carbon atoms, e.g., methoxy, ethoxy, propoxy, tert butoxy and the like. Examples of alkoxy groups include methoxy, ethoxy, isopropyloxy, propoxy, butoxy, pentoxy, fluoromethoxy, difluoromethoxy, trifluoromethoxy, chloromethoxy, dichloromethoxy, trichloromethoxy groups and the like. The term alkoxy includes both unsubstituted or substituted alkoxy groups, etc., as well as perhalogenated alkyloxy groups.

The term "carbonyl" or "carboxy" includes compounds and moieties which contain a carbon connected with a double bond to an oxygen atom. Examples of moieties which contain a carbonyl include aldehydes, ketones, carboxylic acids, amides, esters, anhydrides, etc.

The term "acyl" refers to a carbonyl group that is attached through its carbon atom to a hydrogen (i.e., formyl), an aliphatic group (C1-C6alkyl, C1-C6alkenyl, C1-C6alkynyl, e.g. acetyl), a cycloalkyl group (C3-C8cycloalkyl), a heterocyclic group (C3-C8heterocycloalkyl and C5-C6heteroaryl), an aromatic group (C6aryl, e.g., benzoyl), and the like. Acyl groups may be unsubstituted or substituted acyl groups (e.g. salicyloyl).

It will be understood that "substitution" or "substituted with" includes the implicit proviso that such substitution is in accordance with the permitted valence of the substituted atom and the substituent, and that the substitution results in a stable compound, e.g., which does not spontaneously undergo transformation such as by rearrangement, cyclization, elimination, etc. As used herein, the term "substituted" is meant to include all permissible substituents of organic compounds. In a broad aspect, the permissible substituents include acyclic and cyclic, branched and unbranched, carbocyclic and heterocyclic, aromatic and nonaromatic substituents of organic compounds. The permissible substituents can be one or more. The term "substituted", when in association with any of the foregoing groups refers to a group substituted at one or more position with substituents such as acyl, amino (including simple amino, mono and dialkylamino, mono and diarylamino, and alkylarylamino), acylamino (including carbamoyl, and ureido), alkylcarbonyloxy, arylcarbonyloxy, alkoxycarbonyloxy, alkoxycarbonyl, carboxy, carboxylate, aminocarbonyl, mono and dialkylaminocarbonyl, cyano, azido, halogen, hydroxyl, nitro, trifluoromethyl, thio, alkylthio, arylthio, alkylthiocarbonyl, thiocarboxylate, lower alkyl, lower alkenyl, lower alkynyl, cycloalkyl, heterocycloalkyl, aryl, heteroaryl, lower alkoxy, aryloxy, aryloxycarbonyloxy, benzyloxy, benzyl, sulfinyl, alkylsulfinyl, sulfonyl, sulfate, sulfonate, sulfonamide, phosphate, phosphonato, phosphinato, oxo, guanidine, imino, formyl and the like. Any of the above substituents can be further substituted if permissible, e.g. if the group contains an alkyl group, an aryl group, or other.

A "functional group" is a specific group (or moiety) of atoms or bonds within molecules that are responsible for the characteristic chemical properties and/or reactions of those molecules. As used herein, examples of functional groups include, but are not limited to —NH$_2$, —NR$_5$R$_6$, —C(O) NH$_2$, —C(O)NR$_5$R$_6$, —(CH$_2$)$_n$NH$_2$, —(CH$_2$)$_n$ NR$_5$R$_6$, —(CH$_2$)$_n$C(O)NH$_2$, —(CH$_2$)$_n$C(O)NR$_5$R$_6$, —OH, —(CH$_2$)$_n$ OH, —CO$_2$H, —(CH$_2$)$_n$CO$_2$H, —SO$_3$H, or —(CH$_2$)$_n$ SO$_3$H; wherein n, R$_5$, R$_6$ are defined herein.

"Pharmaceutically acceptable" refers to drugs, medicaments, inert ingredients etc., which the term describes, suitable for use in contact with the tissues of humans and lower animals without undue toxicity, incompatibility, instability, irritation, allergic response, and the like, commensurate with a reasonable benefit/risk ratio. It preferably refers to a compound or composition that is approved or approvable by a regulatory agency of the Federal or state government or listed in the U.S. Pharmacopoeia or other generally recognized pharmacopoeia for use in animals and more particularly in humans.

"Pharmaceutically acceptable vehicle" refers to a diluent, adjuvant, excipient, or carrier with which a compound is administered.

"Pharmaceutical composition" refers to at least one compound and at least one pharmaceutically acceptable vehicle, with which the compound is administered to a patient.

"Preventing" or "prevention" is intended to refer at least the reduction of likelihood of the risk of (or susceptibility to) acquiring a disease or disorder (i.e., causing at least one of the clinical symptoms of the disease not to develop in a patient that may be exposed to or predisposed to the disease but does not yet experience or display symptoms of the disease).

"Treating" or "treatment" of any disease or disorder refers, in some embodiments, to ameliorating at least one disease or disorder (i.e., arresting or reducing the development of the disease or at least one of the clinical symptoms thereof). In certain embodiments "treating" or "treatment" refers to ameliorating at least one physical parameter, which may or may not be discernible by the patient. In certain embodiments, "treating" or "treatment" refers to inhibiting the disease or disorder, either physically, (e.g., stabilization of a discernible symptom), physiologically, (e.g., stabilization of a physical parameter), or both. In certain embodiments, "treating" or "treatment" refers to delaying the onset of the disease or disorder. The term "treating" refers to any indicia of success in the treatment or amelioration of an injury, pathology or condition, including any objective or subjective parameter such as abatement; remission; diminishing of symptoms or making the injury, pathology or condition more tolerable to the subject; slowing in the rate of degeneration or decline; making the final point of degeneration less debilitating; improving a subject's physical or mental well-being; or, in some situations, preventing the onset of dementia. The treatment or amelioration of symptoms can be based on objective or subjective parameters; including the results of a physical examination, a psychiatric evaluation, or a cognition test such as CDR, MMSE, DAD, ADAS-Cog, or another test known in the art. For example, the methods of the invention successfully treat a subject's dementia by slowing the rate of or lessening the extent of cognitive decline.

A "pharmaceutically acceptable salt" of a compound means a salt of a compound that is pharmaceutically acceptable. Desirable are salts of a compound that retain or improve the biological effectiveness and properties of the free acids and bases of the parent compound as defined herein or that takes advantage of an intrinsically basic, acidic or charged functionality on the molecule and that is not biologically or otherwise undesirable. Example of pharmaceutically acceptable salts are also described, for example, in Berge et al., "Pharmaceutical Salts", J. Pharm. Sci. 66, 1 19 (1977).

Such salts include:

(1) acid addition salts, formed on a basic or positively charged functionality, by the addition of inorganic acids such as hydrochloric acid, hydrobromic acid, hydroiodic acid, sulfuric acid, sulfamic acid, nitric acid, phosphoric acid, carbonate forming agents, and the like; or formed with organic acids such as acetic acid, propionic acid, lactic acid, oxalic, glycolic acid, pivalic acid, t-butylacetic acid, β-hydroxybutyric acid, valeric acid, hexanoic acid, cyclopentanepropionic acid, pyruvic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2 hydroxyethanesulfonic acid, cyclohexylaminosulfonic acid, benzenesulfonic acid, sulfanilic acid, 4-chlorobenzenesulfonic acid, 2 napthalenesulfonic acid, 4 toluenesulfonic acid, camphorsulfonic acid, 3-phenyl propionic acid, lauryl sulphonic acid, lauryl sulfuric acid, oleic acid, palmitic acid, stearic acid, lauric acid, embonic (pamoic) acid, palmoic acid, pantothenic acid, lactobionic acid, alginic acid, galactaric acid, galacturonic acid, gluconic acid, glucoheptonic acid, glutamic acid, naphthoic acid, hydroxynapthoic acid, salicylic acid, ascorbic acid, stearic acid, muconic acid, and the like;

(2) base addition salts, formed when an acidic proton present in the parent compound either is replaced by a metal ion, including, an alkali metal ion (e.g. lithium, sodium, potassium), an alkaline earth ion (e.g. magnesium, calcium, barium), or other metal ions such as aluminum, zinc, iron and the like; or coordinates with an organic base such as ammonia, ethylamine, diethylamine, ethylenediamine, N,N'-dibenzylethylenediamine, ethanolamine, diethanolamine, triethanolamine, tromethamine, N-methylglucamine, piperazine, chloroprocain, procain, choline, lysine and the like.

Pharmaceutically acceptable salts may be synthesized from the parent agent that contains a basic or acidic moiety, by conventional chemical methods. Generally, such salts are prepared by reacting the free acid or base forms of these agents with a stoichiometric amount of the appropriate base or acid in water or in an organic solvent, or in a mixture of the two. Salts may be prepared in situ, during the final isolation or purification of the agent or by separately reacting a purified compound of the invention in its free acid or base form with the desired corresponding base or acid, and isolating the salt thus formed. The term "pharmaceutically acceptable salts" also include zwitterionic compounds containing a cationic group covalently bonded to an anionic group, as they are "internal salts".

All acid, salt, base, and other ionic and non-ionic forms of the compounds described are included as compounds of the invention. For example, if a compound is shown as an acid herein, the salt forms of the compound are also included. Likewise, if a compound is shown as a salt, the acid and/or basic forms are also included.

The term "subject," as used herein, unless otherwise defined, is a mammal, e.g., a human, mouse, rat, guinea pig, dog, cat, horse, cow, pig, or non-human primate, such as a monkey, chimpanzee, or baboon. In one embodiment, the subject is a human.

The term "pharmaceutically acceptable salt," as used herein unless otherwise defined, is a salt of a basic group, such as an amino group, or of an acidic group, such as a carboxyl group, on the compounds disclosed herein. Illustrative salts of a basic group include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, and pamoate (i.e., 1,1'-methylene-bis-(2-hydroxy-3-naphthoate)) salts. Illustrative salts of an acidic group include, but are not limited, to lithium, sodium, potassium, calcium, magnesium, aluminum, chromium, iron, copper, zinc, cadmium, ammonium, guanidinium, pyridinium, and organic ammonium salts.

The terms "hydrate" and "solvate" as used herein and unless otherwise defined, describe a compound or salts thereof, which further include a stoichiometric or non-stoichiometric amount of water or other solvent bound by non-covalent intermolecular forces.

"Effective amount" or "Therapeutically effective amount" means the amount of compound that, when administered to a patient for treating or preventing a disease, is sufficient to effect such treatment or prevention of the disease. The "therapeutically effective amount" will vary depending on the compound, the disease and its severity, and the age, weight, etc., of the patient having the disease to be treated or prevented.

The term "about" when used in connection with a referenced numeric indication means the referenced numeric indication plus or minus up to 10% of that referenced numeric indication. For example, the language "about 50" covers the range of 45 to 55.

"Neurodegeneration" refers to a gradual or progressive loss or alteration of neural tissue or neuron structure or function, including demyelination or death of neurons. Accordingly, a "neurodegenerative disorder" or "neurodegenerative disease" or is any disorder that involves neurodegeneration. Neurodegenerative diseases or disorders typically result in reduced central nervous system (CNS) function as a result of a gradual and progressive loss of neural tissue.

Examples of neurodegenerative disorders include, but are not limited to, Alzheimer's disease (AD), dementias related to Alzheimer's disease (e.g., Pick's disease), Parkinson's disease (PD), Lewy diffuse body diseases, Lewy body dementia (Dementia with Lewy Bodies, DLB), senile dementia, Huntington's disease (HD), encephalitis, multiple sclerosis (MS), amyotrophic lateral sclerosis (ALS), progressive supranuclear palsy, epilepsy, prion diseases, Gilles de la Tourette's syndrome, Creutzfeldt-Jakob disease (CJD), stroke, Traumatic Brain Injury, Fragile X syndrome, bovine spongiform encephalopathy (BSE), and scrapie. Further neurodegenerative disorders include, for example, those listed by the National Institutes of Health.

Further Examples of neurodegenerative disorders include, but are not limited to, fatal familial insomnia (FFI); fatal sporadic insomnia (FSI); Gerstmann-Straussler Syndrome (GSS); Kuru; Iatrogenic Creutzfeld-Jakob disease (iCJD); variant Creutzfeldt-Jakob disease (vCJD); Familial Creutzfeldt-Jakob disease (fCJD), Sporadic Creutzfeldt-Jakob disease (sCJD), Gerstmann-Straussler-Scheinker syndrome (GSS), Fatal familial insomnia (FFI), Sporadic Fatal Insomnia (sFI); bovine spongiform encephalopathy (BSE); scrapie; chronic wasting disease (CWD); and tauopathies, such as Progressive supranuclear palsy, Dementia, Dementia pugilistica (chronic traumatic encephalopathy), Frontotemporal dementia and parkinsonism linked to chromosome 17, Lytico-Bodig disease, Ganglioglioma and gangliocytoma, Meningioangiomatosis, Subacute sclerosing panencephalitis, lead encephalopathy, tuberous sclerosis, Hallervorden-Spatz disease, lipofuscinosis, Pick's disease, Pick's complex, argyrophilic grain disease (AGD), corticalbasal degeneration, frontotemporal dementia and frontotemporal lobar degeneration Further Examples of neurodegenerative disorders include neurodegenerative disorders that are associated with inflammation of the brain and spinal cord, e.g., encephalomyelitis acute disseminated encephalomyelitis (or postinfectious encephalomyelitis); encephalomyelitis disseminate, i.e., multiple sclerosis; equine encephalomyelitis; myalgic encephalomyelitis; and autoimmune encephalomyelitis (EAE).

Further Examples of neurodegenerative disorders include demyelination associated disorders wherein the myelin sheath of neurons is damaged. Demyelination is associated with many diseases in both the CNS and the peripheral nervous system, such as multiple sclerosis, Vitamin B12 deficiency, central pontine myelinolysis, Tabes Dorsalis, transverse myelitis, Devic's disease, progressive multifocal leukoencephalopathy, optic neuritis, leukodystrophies, Guillain-Barre syndrome, chronic inflammatory demyelinating polyneuropathy, anti-MAG peripheral neuropathy, Charcot-Marie-Tooth disease, and copper deficiency.

"Amyloid-related" diseases are diseases associated with amyloid (e.g., AL amyloid protein ($\lambda$ or $\kappa$-chain related, e.g., amyloid $\lambda$, amyloid $\kappa$, amyloid $\kappa$IV, amyloid $\lambda$VI, amyloid $\gamma$, amyloid $\gamma$1), A$\beta$, IAPP, $\beta_2$M, AA, or AH amyloid protein) fibril formation, aggregation or deposition.

"Amyloidosis" refers to a pathological condition characterized by the presence of amyloid fibrils. Amyloid is a generic term referring to a group of diverse but specific protein deposits (intracellular or extracellular) which are seen in a number of different diseases.

"Abeta", "Aß", or "ß-amyloid", is defined as any peptide resulting from beta-secretase mediated cleavage of Beta Amyloid Precursor Protein (APP), including for examples peptides of 37, 38, 39, 40, 41, 42, and 43 amino acids, and extending from the beta-secretase cleavage site to amino acids 37, 38, 39, 40, 41, 42, or 43. It also includes It also includes N-terminal truncated species of above peptides, such as the pyroglutamic forms pE3-40, pE3-42, pE3-43, pE11-42, pE11-43 and the like. For convenience of nomenclature, "Aß1-42", may be referred to herein as "Aß(1-42)" or simply as "Aß42" (and likewise for any other amyloid peptides discussed herein). As used herein, the terms "Abeta", "Aß", "ß-amyloid", "amyloid-ß" are synonymous referring collectively to truncated and non-truncated peptide species of the sequence between β- and γ-cleavage sites of APP.

The term "amyloid-β disease" or "amyloid-β related disease" may be used for mild cognitive impairment; vascular dementia; early Alzheimer's disease; Alzheimer's disease, including sporadic (non-hereditary) Alzheimer's disease and familial (hereditary) Alzheimer's disease; age-related cognitive decline; cerebral amyloid angiopathy ("CAA"); hereditary cerebral hemorrhage; senile dementia; Down's syndrome; inclusion body myositis ("IBM"); or age-related macular degeneration ("ARMD"), Mild cognitive impairment ("MCI"), Cerebral amyloid angiopathy ("CAA"), age-related macular degeneration (ARMD).

Pharmaceutical Compositions

For the purposes of administration, in certain embodiments, the compounds described herein are administered as a raw chemical or are formulated as pharmaceutical compositions. Pharmaceutical compositions of the present disclosure comprise the compounds disclosed herein or pharmaceutically acceptable salts thereof, and one or more pharmaceutically acceptable carriers. A compound of the present invention is present in the composition in an amount which is effective to treat a particular disease or condition of interest.

The compounds and compositions thereof can be administered orally. The compounds and compositions thereof can also be administered by any other convenient route, for example, by intravenous infusion or bolus injection, by absorption through epithelial or mucocutaneous linings (e.g., oral mucosa, rectal and intestinal mucosa, etc.) and can be administered together with another biologically active agent. Administration can be systemic or local. Various delivery systems are known, e.g., encapsulation in liposomes, microparticles, microcapsules, capsules, etc., and can be used to administer a compound. In certain embodiments, more than one compound is administered to a subject. Methods of administration include but are not limited to intradermal, intramuscular (including depot), intraperitoneal, intravenous, subcutaneous (including depot), intranasal, epidural, oral, sublingual (including rapid dissolving tablet, gum or equivalent), intranasal, intracerebral, intravaginal, transdermal, rectally, Intrapulmonary (aerosol or equivalent, including by inhalation), or topically, particularly to the ears, nose, eyes, or skin.

The present compositions comprise a therapeutically effective amount of a compound of the disclosure, optionally more than one compound, together with a suitable amount of a pharmaceutically acceptable vehicle so as to provide a form for administration to the subject.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155). Other examples of suitable pharmaceutical vehicles are described in "Remington's Pharmaceutical Sciences" by E. W. Martin, incorporated by reference in its entirety for teachings of pharmaceutical compositions and methods of administering the same.

In certain embodiments of the invention a compound of the invention or pharmaceutical salt thereof may be coated on to a medical device suitable for implantation or impregnated into such a medical device. In further embodiments of the invention, such a coated or impregnated device would provide for the controlled release of said compound of the invention or pharmaceutical salt thereof. In particular embodiments of the invention, the medical device is a disc.

In some embodiments, the compounds and compositions are formulated in accordance with routine procedures as a pharmaceutical composition adapted for intravenous administration to humans. Compounds and compositions of the compounds for intravenous administration can be solutions in sterile isotonic aqueous buffer. The compositions can also include a solubilizing agent. The ingredients can be supplied either separately or mixed together in unit dosage form, for example, as a dry lyophilized powder or water free concentrate in a hermetically sealed container such as an ampoule or sachette.

Compounds and compositions of the compounds for oral delivery can be in the form of tablets, lozenges, aqueous or oily suspensions, granules, powders, emulsions, capsules, syrups, or elixirs. Compounds and compositions of the compounds for oral delivery can also be formulated in foods and food mixes. Orally administered compositions can comprise one or more optional agents, for example, sweetening agents such as fructose, aspartame or saccharin; flavoring agents such as peppermint, oil of wintergreen, or cherry; coloring agents; and preserving agents, to provide a pharmaceutically-palatable preparation. The compositions can be coated to delay disintegration and absorption in the gastrointestinal tract thereby providing a sustained action over an extended period of time. Selectively permeable membranes surrounding an osmotically active driving compound are also suitable for orally administered compounds and compositions of the compounds. A time delay material such as glycerol monostearate or glycerol stearate can also be used. Oral compositions can include standard vehicles such as mannitol, lactose, starch, magnesium stearate, sodium saccharine, cellulose, and magnesium carbonate.

In certain embodiments, the compounds or compositions may be in the form of beads or minitabs. Minitabs, also described in the literature as microtabs or minitablets, are small tablets typically having a diameter (or length) of about 0.5 mm to about 10 mm. Minitabs are generally prepared by techniques known in the art, such as wet or dry granulation followed by compression of the granules; direct compression of blended materials, or any other tableting techniques known in the art.

In further embodiments, compounds and compositions of the compounds may be formulated in multi-dose forms, i.e., in the form of multi-particulate dosage forms (e.g., hard gelatin capsules or conventional tablets prepared using a rotary tablet press) comprising one or more bead or minitab populations for oral administration. The conventional tablets rapidly disperse on entry into the stomach. The one or more coated bead or minitab populations may be compressed together with appropriate excipients into tablets (for example, a binder, a diluent/filler, and a disintegrant for conventional tablets.

The tablets, pills, beads, or minitabs of the compounds and compositions of the compounds may be coated or otherwise compounded to provide a dosage form affording the advantage of controlled release, including delayed or extended release, or to protect from the acid conditions of the stomach. For example, the tablet or pill can include an inner dosage and an outer dosage component, the latter being in the form of a coating over the former. The two components can be separated by a polymer layer that controls the release of the inner dosage.

In certain embodiments, the layer may comprise at least one enteric polymer. In further embodiments, the layer may comprise at least one enteric polymer in combination with at least one water-insoluble polymer. In still further embodiments, the layer may comprise at least one enteric polymer in combination with at least one water-soluble polymer. In yet further embodiments, the layer may comprise at least one enteric polymer in combination with a pore-former.

In certain embodiments, the layer may comprise at least one water-insoluble polymer. In still further embodiments, the layer may comprise at least one water-insoluble polymer in combination with at least one water-soluble polymer. In yet further embodiments, the layer may comprise at least one water-insoluble polymer in combination with a pore-former.

Representative examples of water-soluble polymers include polyvinylpyrrolidone (PVP), hydroxypropylmethylcellulose (HPMC), hydroxypropylcellulose (HPC), polyethylene glycol, and the like.

Representative examples of enteric polymers include esters of cellulose and its derivatives (cellulose acetate phthalate, hydroxypropyl methylcellulose phthalate, hydroxypropyl methylcellulose acetate succinate), polyvinyl acetate phthalate, pH-sensitive methacrylic acid-methylmethacrylate copolymers and shellac. These polymers may be used as a dry powder or an aqueous dispersion. Some commercially available materials that may be used are methacrylic acid copolymers sold under the trademark Eudragit (L100, S100, L30D) manufactured by Rohm Pharma, Cellacefate (cellulose acetate phthalate) from Eastman Chemical Co., Aquateric (cellulose acetate phthalate aqueous dispersion) from FMC Corp. and Aqoat (hydroxypropyl methylcellulose acetate succinate aqueous dispersion) from Shin Etsu K.K.

Representative examples of useful water-insoluble polymers include ethylcellulose, polyvinyl acetate (for example, Kollicoat SR #30D from BASF), cellulose acetate, cellulose acetate butyrate, neutral copolymers based on ethyl acrylate and methylmethacrylate, copolymers of acrylic and methacrylic acid esters with quaternary ammonium groups such as Eudragit NE, RS and RS30D, RL or RL30D and the like.

Any of the above polymers may be further plasticized with one or more pharmaceutically acceptable plasticizers. Representative examples of plasticizers include triacetin, tributyl citrate, triethyl citrate, acetyl tri-n-butyl citrate diethyl phthalate, castor oil, dibutyl sebacate, acetylated monoglycerides and the like or mixtures thereof. The plasticizer, when used, may comprise about 3 to 30 wt. % and more typically about 10 to 25 wt. % based on the polymer. The type of plasticizer and its content depends on the polymer or polymers and nature of the coating system (e.g., aqueous or solvent based, solution or dispersion based and the total solids).

The term "carrier" refers to diluents or fillers, disintegrants, precipitation inhibitors, surfactants, glidants, binders, lubricants, anti-oxidants, and other excipients and vehicles with which the compound is administered. Carriers are generally described herein and also in "Remington's Pharmaceutical Sciences" by E. W. Martin. Examples of carriers include, but are not limited to, aluminum monostearate, aluminum stearate, carboxymethylcellulose, carboxymethylcellulose sodium, crospovidone, glyceryl isostearate, glyceryl monostearate, hydroxyethyl cellulose, hydroxyethyl cellulose, hydroxymethyl cellulose, hydroxyoctacosanyl hydroxystearate, hydroxypropyl cellulose, hydroxypropyl cellulose, hydroxypropyl methylcellulose, lactose, lactose monohydrate, magnesium stearate, mannitol, microcrystalline cellulose, poloxamer 124, poloxamer 181, poloxamer 182, poloxamer 188, poloxamer 237, poloxamer 407, povidone, silicon dioxide, colloidal silicon dioxide, silicone, silicone adhesive 4102, and silicone emulsion. It should be understood, however, that the carriers selected for the pharmaceutical compositions provided in the present disclosure, and the amounts of such carriers in the composition, may vary depending on the method of formulation (e.g., dry granulation formulation, solid dispersion formulation).

The term "diluent" or "filler" generally refers to a substance that is used to dilute the compound of interest prior to delivery. Diluents can also serve to stabilize compounds. Examples of diluents may include starch, saccharides, disaccharides, sucrose, lactose, polysaccharides, cellulose, cellulose ethers, hydroxypropyl cellulose, sugar alcohols, xylitol, sorbitol, maltitol, microcrystalline cellulose, calcium or sodium carbonate, lactose, lactose monohydrate, dicalcium phosphate, cellulose, compressible sugars, dibasic calcium phosphate dehydrate, mannitol, microcrystalline cellulose, and tribasic calcium phosphate.

The term "disintegrant" generally refers to a substance which, upon addition to a solid preparation, facilitates its break-up or disintegration after administration and permits the release of an active ingredient as efficiently as possible to allow for its rapid dissolution. Examples of disintegrants may include maize starch, sodium starch glycolate, croscarmellose sodium, crospovidone, microcrystalline cellulose, modified corn starch, sodium carboxymethyl starch, povidone, pregelatinized starch, and alginic acid.

The term "precipitation inhibitors" generally refers to a substance that prevents or inhibits precipitation of the active agent. One example of a precipitation inhibitor includes hydroxypropylmethylcellulose.

The term "surfactants" generally refers to compounds that lower the surface tension between two liquids or between a liquid and a solid. Examples of surfactants include poloxamer and sodium lauryl sulfate.

The term "glidant" generally refers to substances used in tablet and capsule formulations to improve flow-properties during tablet compression and to produce an anti-caking effect. Examples of glidants may include colloidal silicon dioxide, talc, fumed silica, starch, starch derivatives, and bentonite.

The term "binder" generally refers to any pharmaceutically acceptable film which can be used to bind together the active and inert components of the carrier together to maintain cohesive and discrete portions. Examples of binders may include hydroxypropylcellulose, hydroxypropylmethylcellulose, povidone, copovidone, ethyl cellulose, gelatin, and polyethylene glycol.

The term "lubricant" generally refers to a substance that is added to a powder blend to prevent the compacted powder mass from sticking to the equipment during the tableting or encapsulation process. A lubricant can aid the ejection of the tablet form the dies, and can improve powder flow. Examples of lubricants may include magnesium stearate, stearic acid, silica, fats, calcium stearate, polyethylene glycol, sodium stearyl fumarate, or talc; and solubilizers such as fatty acids including lauric acid, oleic acid, and $C_8/C_{10}$ fatty acid.

Embodiments described herein also provide kits containing such compound of the present invention, optionally in a pharmaceutically acceptable carrier. In one embodiment, the kit generally comprises: (a) a first sealed container containing a compound of the present invention, and (b) a second sealed container containing a diluent.

In certain embodiments, dosage is given with respect to the weight of the compound of the present invention. In further embodiments, the dosage refers to pharmaceutically acceptable salts, hydrates, and solvates thereof. The dosage amounts described herein refer to total amounts administered; that is, if more than one compound is administered, the dosages can correspond to the total amount of the compounds administered. Oral compositions can comprise 10% to 95% active ingredient by mass.

In certain embodiments, the dosage range for oral administration is generally about 0.001 mg to about 2000 mg of a compound per kg body mass. In some embodiments, the oral dose is 0.01 mg to 100 mg per kg body mass, 0.1 mg to 50 mg per kg body mass, 0.5 mg to 20 mg per kg body mass, or 1 mg to 10 mg per kg body mass. In some embodiments, the oral dose is 5 mg of a compound per kg body mass.

In further embodiments, the dose is about 10 mg to about 1000 mg, including all ranges and subranges there between, e.g., about 10 mg to about 900 mg, about 10 mg to about 800 mg, about 10 to about 700 mg, about 10 mg to about 600 mg, about 10 mg to about 500 mg, about 10 mg to about 400 mg, about 10 mg to about 300 mg, about 10 mg to about 250 mg, about 10 mg to about 200 mg, about 10 mg to about 150 mg, about 10 mg to about 100 mg, about 10 mg to about 50 mg, about 50 mg to about 900 mg, about 50 mg to about 800 mg, about 50 to about 700 mg, about 50 mg to about 600 mg, about 50 mg to about 500 mg, about 50 mg to about 400 mg, about 50 mg to about 300 mg, about 50 mg to about 250 mg, about 50 mg to about 200 mg, about 50 mg to about 150 mg, about 50 mg to about 100 mg, about 100 mg to about 900 mg, about 100 mg to about 800 mg, about 100 to about 700 mg, about 100 mg to about 600 mg, about 100 mg to about 500 mg, about 100 mg to about 400 mg, about 100 mg to about 300 mg, about 100 mg to about 250 mg, about 100 mg to about 200 mg, about 100 mg to about 150 mg, about 150 mg to about 200 mg, about 150 mg to about 250 mg, about 150 to about 300 mg, about 150 mg to about 400 mg, about 150 mg to about 500 mg, about 200 mg to about 900 mg, about 200 mg to about 800 mg, about 200 to about 700 mg, about 200 mg to about 500 mg, about 200 mg to about 400 mg, about 200 mg to about 300 mg, about 200 mg to about 250 mg, about 300 mg to about 900 mg, about 300 mg to about 800 mg, about 300 to about 700 mg, about 300 to about 600 mg, about 300 mg to about 500 mg, about 300 mg to about 400 mg, about 400 mg to about 900 mg, about 400 mg to about 800 mg, about 400 to about 700 mg, about 400 to about 600 mg, about 400 mg to about 500 mg, about 500 mg to about 900 mg, about 500 mg to about 800 mg, about 500 to about 700 mg, about 500 to about 600 mg, about 100 mg to about 500 mg, about 100 mg to about 400 mg, about 100 mg to about 300 mg, about 100 mg to about 250 mg. In particular embodiments, the range is about 150 mg to about 400 mg.

In still further embodiments, the dose is 10 mg, 25 mg, 50 mg, 60 mg, 70 mg, 75 mg, 80 mg, 85 mg, 90 mg, 100 mg, 105 mg, 110 mg, 115 mg, 120 mg, 125 mg, 130 mg, 135 mg, 140 mg, 145 mg, 150 mg, 160 mg, 170 mg, 180 mg, 190 mg, 200 mg, 225 mg, 250 mg, 275 mg, 300 mg, 350 mg, 400 mg, 450 mg, 500 mg, 550 mg, 600 mg, 650 mg, 700 mg, 750 mg, 800 mg, 850 mg, 900 mg, 950 mg, or 1000 mg.

Methods of Treatment

The disclosure also provides the use of compounds disclosed herein for the manufacture of a medicament in the treatment of Alzheimer's patients. The disclosure also provides methods for the treatment or prevention of the aforementioned diseases comprising administration of a therapeutically effective amount of a compound or a composition comprising the same, to a subject, preferably a human subject, in need thereof. Accordingly, a related aspect of the disclosure relates to the prevention and/or treatment of Alzheimer's disease in humans by administering an effective amount of a compound or composition of the present disclosure to a human subject in need thereof.

The disclosure also provides for methods for the treatment or prevention of the aforementioned disease comprising administration of a therapeutically effective amount of a compound or a composition comprising the same, to a subject, preferably a human subject, in need thereof where the patient is heterozygous or homozygous for the ApoE4 (or F4) allele (i.e. ApoE4-positive patients).

Identifying ApoE4-positive patients may be performed by any particular approach capable of determining that a patient as one or two copies of the ApoE4 (or F4) allele. In particular aspects, sequencing technology is used to genotype the patient prior to administration of a compound.

In certain embodiments, the efficacy of a compound may be determined through the ADAS-cog (Alzheimer's Disease Assessment Scale-cognitive subscale). ADAS was designed to measure the severity of the most important symptoms of Alzheimer's disease (AD). Its subscale ADAS-cog is the most popular cognitive testing instrument used in clinical trials of nootropics. It consists of 11 tasks measuring the disturbances of memory, language, praxis, attention and other cognitive abilities which are often referred to as the core symptoms of AD. The ADAS-Cog helps evaluate cognition and differentiates between normal cognitive functioning and impaired cognitive functioning. It is especially useful for determining the extent of cognitive decline and can help evaluate which stage of Alzheimer's disease a person is in, based on his answers and score. The ADAS-Cog can be used in clinical trials in order to determine incremental improvements or declines in cognitive functioning. An increased ADAS-Cog score compared to placebo demonstrates improved cognitive functioning.

The compounds or a composition comprising a compound may be administered once, twice, three, or four times daily, using any suitable mode described above. Also, in certain embodiments, administration or treatment with the compounds according to any of the formulae described herein may be continued for a number of weeks; for example, commonly treatment would continue for at least 2 weeks, 4 weeks, 8 weeks, 12 weeks, 16 weeks, 20 weeks, 24 weeks, 28 weeks, 32 weeks, 36 weeks, 40 weeks, 44 weeks, 48 weeks, 52 weeks, 56 weeks, 60 weeks, 64 weeks, 68 weeks, 72 weeks, 76 weeks, 80 weeks, 84 weeks, 88 weeks, 92 weeks, 96 weeks, 100 weeks, or 104 weeks. In yet further embodiments, administration or treatment with the compounds according to any of the formulae described herein may be continued for a number of months; for example, commonly treatment would continue for at least 2 months, 4 months, 6 months, 8 months, 10 months, 12 months, 15 months, 18 months, 20 months, or 24 months. In still further embodiments, administration or treatment with the compounds according to any of the formulae described herein may be continued indefinitely. In still further embodiments, administration or treatment with the compounds according to any of the formulae described herein may be continued until the ADAS-Cog score improves by about 1.5-fold to about 4.5-fold. In some aspects, the improvement in score is about 1.5-fold, about 2.0-fold, about 3.5-fold, about 4.0-fold, about 4.5-fold, about 5.0-fold, about 7.5-fold, about 10.0-fold, about 15.0-fold. In particular aspects, the improvement is about 1.5-fold to about 10.0-fold.

In yet further embodiments, administration or treatment with the compounds according to any of the formulae described herein may be continued until metabolite 3-sulfo-propanoic acid is present in plasma. Metabolite appearance may be detected and quantified by LC/MS/MS bioanalysis methods.

In a particular embodiment, a compound or a pharmaceutically acceptable salt thereof is administered orally in a loose-filled capsule and provides for an extended half-life. For example, the 3-sulfo-propanoic acid or a pharmaceutically acceptable salt thereof supplied in the loose-filled capsule provides a half-life of about 10 to about 18 hours.

EXAMPLES

Example 1. Molecular Modeling

The binding of compounds of the present invention was modeled using Schrodinger Maestro version 10.1.013. The resulting model shows that the compounds bind to the same binding site(s) on Aβ42 as does 3-APS (Tramiprosate). Binding site surface interactions interact with similar energy as shown in the electrostatic potential scheme. Additionally, the compounds interact with Lys16, which plays a central role in neurotoxicity, aggregation and distribution of Aβ42 conformers.

Example 2. Binding Assay

Compounds of the invention were screened by mass spectrometry ("MS") binding assays to assess the ability of compounds to bind to the protein.

Sample Preparation

Approximately 1 mg of the compound was reconstituted in 1 mL of MilliQ water and vortexed vigorously for 2 minutes until completely in solution. The sample was then diluted to create an approximately 2200 pmol/µL solution.

One mg of recombinant Human β-Amyloid Peptide (1-42) from BioLegend (99% purity, cat: 843801) was reconstituted in 200 µL of MilliQ water and vortexed vigorously for 2 minutes to solubilize the peptide creating a 5 mg/mL solution. Samples were then diluted to a final concentration 44 pmol/µL prior to mix with drug solution.

Samples were then mixed together for a final concentration of 22 pmol/µL (x) for peptide and 1100 pmol/µL for individual compounds (50x).

Samples were infused directly in mass specs after adding 50 µL of 10% formic acid in final solution to increase the ionization.

Instrumentation

The data acquisition was performed using a Waters time of flight mass spectrometer (Q-TOF Micro). The data was acquired using the scanning mode to allow for the detection of the peptide. Samples were infused at room temperature.

The mass spectrometer conditions were maintained throughout the study to ensure consistency of the data. The Waters Qtof conditions were as follows:

Positive Polarity in sensitivity mode
Capillary=3.5 kV
Desolvation gas flow=500 L/Hr
Cone gas flow=50 L/Hr
Source Temperature=150° C.
Desolvation Temperature=60° C.
Sample cone setting=35 V
Extraction cone setting=3 V
Mass Range=1475 to 2000 m/z Samples were directly infused into the mass spectrometer at a flow rate of 20 µL/min using in-build Syringe Pump and Hamilton 1 mL Syringe and the acquisition time was kept 2 minutes.

Sample Analysis

Once acquisition of the samples was completed, the raw data was then analyzed using the Water MassLynx 4.1, SCN744. Stoichiometry of the binding was determined and the semiquantitative evaluation of the binding was compared to a blank.

The results of the above assay for those compounds tested are presented in Table 1:

TABLE 1

Binding Data for Compounds of the Invention

| Compound Number | Exact Mass | Number of molecules bound to Aβ42 | Semiquantitative Estimation |
|---|---|---|---|
| 2005 | 165.05 | [+1] | [+] |
| 2010 | 264.11 | [+2] | [++] |
| 2011 | 278.13 | [+1] | [+] |
| 2012 | 252.08 | [+4] | [++++] |
| 2014 | 328.08 | [+3] | [+++] |
| 2015 | 328.11 | [+3] | [+++] |
| 2021 | 462.15 | No Binding Observed | — |
| 2024 | 412.17 | No Binding Observed | — |
| 2026 | 462.11 | [+2] | [++] |
| 2028 | 208.04 | [+3] | [+++] |
| 2029 | 194.02 | [+3] | [+++] |
| 2030 | 283.09 | [+1] | [+] |
| 2034 | 341.09 | No Binding | — |

TABLE 1-continued

Binding Data for Compounds of the Invention

| Compound Number | Exact Mass | Number of molecules bound to Aβ42 | Semiquantitative Estimation |
|---|---|---|---|
| | | Observed | |
| 2037 | 281.06 | [+1] | [+] |
| 2083 | 284.08 | [+2] | [++] |
| 2084 | 208.05 | [+5] | [+++++] |
| 2085 | 250.10 | [+4] | [++++] |
| 2087 | 282.09 | [+4] | [++++] |
| 2055 | 284.08 | [+4] | [++++] |
| 2059 | 282.09 | [+2] | [++] |
| 2061 | 266.06 | [+4] | [++++] |
| 2077 | 277.11 | [+4] | [++++] |

Example 3. Effects of Short Term Treatment in Adult Transgenic CRND8 Mice Overexpressing PAPP Transgenic mice, TgCRND8, expressing the human amyloid precursor protein (hAPP) develop a pathology resembling Alzheimer's disease. In particular, high levels of Aβ40 and Aβ42 have been documented in the plasma and the brain of these animals at 8-9 weeks of age, followed by early accumulation of amyloid plaques similar to the senile plaques observed in AD patients. These animals also display progressive cognitive deficits that parallel the appearance of degenerative changes. See, e.g., (Chishti, et al., J. Biol. Chem. 276, 21562-70 (2001).

The short term therapeutic effect of 19 compounds of the invention is studied. These compounds are administered over a 14 or 28 day period at the end of which the levels of Aβ peptides in the plasma and brain of TgCRND8 animals are determined.

Male and female transgenic mice from the $3^{rd}$ and $4^{th}$ B6C3F1 generations are used in this example and given daily subcutaneous or oral administrations of one of a series of compounds for 14 or 28 days. The following abbreviations are used to designate these animals from the $3^{rd}$ and $4^{th}$ generation backcross in the present protocol: TgCRND8-2.B6C3F1($N_3$); TgCRND8-2.B6C3F1($N_4$).

Baseline animals (Group 1) consist of naive TgCRND8-2.B6C3F1($N_3$) at 11±1 weeks of age. These mice are used to determine the Aβ levels in the plasma and brain of naive transgenic animals at the initiation of treatment.

Starting at 11 weeks of age (±1 week) animals received daily administration of their respective treatment for a period of 14 or 28 days (groups 2-21), at a dose of 250 mg/kg at 10 ml/kg or of vehicle only (water; group 2) or 1% methyl cellulose only (group 21). The route of administration was subcutaneous for water-soluble compounds and oral for compounds solubilized in methylcellulose 1% (MC 1%). At the end of the treatment periods, plasma and perfused brains were collected for quantification of Aβ levels.

Test System

| | |
|---|---|
| Species: | Mouse |
| Strain: | TgCRND8-2.B6C3F1($N_3$) & ($N_4$) |
| Genotype: | hAPP +/− |
| Gender: | Male and Female |
| Age at Day 1: | 11 ± 1 weeks |
| Body Weight at Day 1: | 10 to 30 g |
| Number of Animals/ | Baseline: 8 |

-continued

| Group at Day 1: | |
|---|---|
| Vehicle and Treated: | 12-15 |
| Suppliers: | TgCRND8-2 founders were obtained from the Centre for Research in Neurodegenerative Diseases, University of Toronto. The inbred B6C3F1 were obtained from Charles River (Quebec, Canada). |

The mice used in this study are derived from a breeding colony at Institut Armand Frappier, and are well-acclimated to the animal facility environment prior to initiation of the study. Animals are assigned, according to age and gender, into the following experimental groups:

Groups of Mice

| Group No. | Treatment | Daily Dose (mg/kg) | Duration of Treatment (days) |
|---|---|---|---|
| 1 | Baseline | NA | NA |
| 2 | Water | NA | 14 & 28 |
| 4 | BY | 250 | 14 & 28 |
| 6 | CV | 250 | 14 & 28 |
| 12 | CY | NA | 14 & 28 |
| 15 | BW | 250 | 14 & 28 |
| 16 | BZ | 250 | 14 & 28 |
| 18 | BX | 250 | 14 & 28 |
| 20 | DC | 250 | 14 & 28 |
| 21 | Methylcellulose 1% | 100 | 14 & 28 |
| 22 | DD | 250 | 14 & 28 |
| 23 | DH | 250 | 14 & 28 |
| 24 | DM | 250 | 14 & 28 |
| 25 | DX | 250 | 14 & 28 |
| 26 | DY | 250 | 14 & 28 |
| 27 | DZ | 250 | 14 & 28 |
| 28 | ED | 250 | 14 & 28 |
| 29 | EG | 250 | 14 & 28 |

Animal Health Monitoring

All animals were examined daily for signs of ill health when handled in the morning for their daily treatment and twice a day for mortality checks (once daily during weekends and holidays). Detailed examinations were performed on the treatment initiation, weekly during the study, and once before terminal procedures. More frequent observations were undertaken when considered appropriate. Death and all individual clinical signs were individually recorded. Individual body weights were recorded at randomization, once weekly during the study, and once before terminal procedures.

Sample Collection

At 11±1 weeks of age for the Baseline group, and at the end of the treatment period (14 or 28 days) for Groups 2 to 21, at 24 hours after the last compound administration animals are sacrificed and samples collected. An approximate blood volume of 500 µl is collected from the orbital sinus and kept on ice until centrifugation at 4° C. at a minimum speed of 3,000 rpm for 10 minutes. Plasma samples are immediately frozen and stored at −80° C. pending analysis. The brains are removed, frozen, and stored at −80° C. awaiting analysis.

Measurements of Aβ Levels

Brains are weighted frozen and homogenized with 4 volumes of ice cold 50 mM Tris-Cl pH 8.0 buffer with protease inhibitor cocktail (4 mL of buffer for 1 g of wet brain). Samples are spun at 15000 g for 20 minutes and the supernatants are transferred to fresh tubes. One hundred fifty (150) µl from each supernatant are mixed with 250 µl of 8M guanidine-HCL/50 mM Tris-HCL pH 8.0 (ratio of 0.6 vol supernatant: 1 vol 8M guanidium/Tris-HCL 50 mM pH8.0) and 400 µL 5 M guanidium/Tris-HCL 50 mM pH8.0 are added. The tubes are vortexed for 30 seconds and frozen at −80° C. In parallel, pellets are treated with 7 volumes of 5 M guanidine-HCL/50 mM Tris-HCL pH 8.0 (7 mL of guanidine for 1 g of wet brain), vortexed for 30 seconds and frozen at −80° C. Samples are thawed at room temperature, sonicated at 80° C. for 15 minutes and frozen again. This cycle is repeated 3 times to ensure homogeneity and samples were returned to −80° C. pending analysis.

Aβ levels are evaluated in plasma and brain samples by ELISA using Human Aβ40 and Aβ42 Fluorometric ELISA kits from Biosource (Cat. No. 89-344 and 89-348) according to manufacturer's recommended procedures. Samples were thawed at room temperature, sonicated for 5 minutes at 80° C. (sonication for brain homogenates; no sonication for plasma samples) and kept on ice. Aβ peptides are captured using 100 µl of the diluted samples to the plate and incubated without shaking at 4° C. overnight. The samples are aspirated and the wells are rinsed 4 times with wash buffer obtained from the Biosource ELISA kit. The anti-Aβ40 or anti-Aβ42 rabbit polyclonal antiserum (specific for the Aβ40 or Aβ42 peptide) is added (100 µl) and the plate is incubated at room temperature for 2 hours with shaking. The wells are aspirated and washed 4 times before adding 100 µL of the alkaline phosphatase labeled anti-rabbit antibody and incubating at room temperature for 2 hours with shaking. The plates are then rinsed 5 times and the fluorescent substrate (100 µL) is added to the plate. The plate is incubated for 35 minutes at room temperature and the plate is read using a titer plate reader at an excitation wavelength of 460 nm and emission at 560 nm.

Compounds are scored based on their ability to modulate levels of Aβ peptides in the plasma and the cerebral soluble/insoluble levels in the brain. Levels of Aβ observed in the plasma and brain of treated animals are normalized using values from vehicle-treated (water) or methylcellulose-treated control groups and ranked according to the strength of the pharmacological effect. Results show levels of Aβ peptides in the plasma and brain of TgCRND8 mice treated for 14 and 28 days with compounds of the invention.

Example 4. Synthesis of 3-aminocyclopentane-1-sulfonic acid (Compound 2005)

Step 1: Synthesis of 3-aminocyclopentyl methanesulfonate hydrochloride

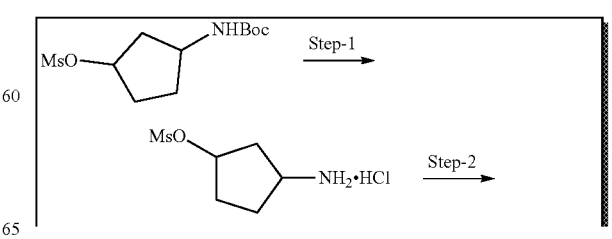

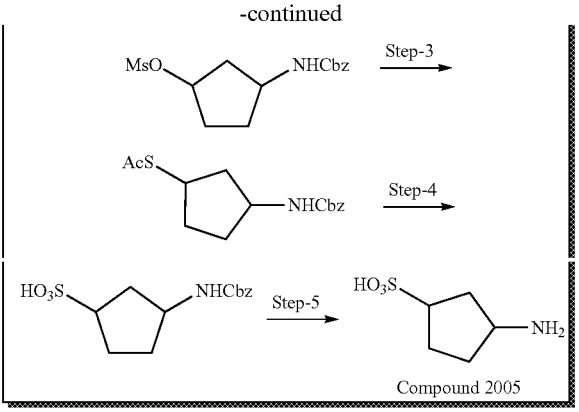
Compound 2005

3-((tert-butoxycarbonyl)amino)cyclopentyl methanesulfonate (5.0 gm, 17.9 mmol, 1.0 eq) was dissolved in 1,4-Dioxane (25 mL) and the solution was cooled to 0° C. Then 4N HCl in 1,4-dioxane (25 mL) was added and the mixture was stirred for 16 h, during which, the temperature was allowed to rise from 0° C. to ambient temperature. After complete consumption of starting material solvents evaporated from the reaction mixture under reduced pressure and the crude obtained was triturated with diethyl ether. The precipitated solid was filtered and dried under vacuum to obtain the title product as off-white solid (3.7 gm, 96.1%). LC-MS: UV Inactive. MS calculated for [M] 179.06 and found [M+H]$^+$ 179.95. $^1$H NMR (400 MHz, D$_2$O): δ 5.31-5.29 (t, J=4.0 Hz, 1H), 3.82-3.80 (d, J=8.0 Hz, 1H), 3.23 (s, 3H), 2.61-2.54 (m, 1H), 2.32-2.19 (m, 2H), 2.14-2.02 (m, 2H), 1.96-1.87 (m, 1H).

Step 2: Synthesis of 3-(((benzyloxy)carbonyl)amino)cyclopentyl methanesulfonate 3-aminocyclopentyl methanesulfonate hydrochloride (2.0 gm, 9.28 mmol, 1.0 eq) was suspended in DCM (20 mL) and the mixture was cooled to 0° C. Then triethylamine (12.9 mL, 92.8 mmol, 10.0 eq) and CbzCl (50% solution in Toluene, 3.48 mL, 10.2 mmol, 1.1 eq) were added and the mixture was stirred for 48 h. During stirring, temperature of the system gradually allowed to increase to ambient temperature. After complete consumption of the starting material, the mixture was diluted with water (20 mL), the organic extract was separated and washed with water (2×20 mL). The organic extract was then dried over anhydrous Na$_2$SO$_4$, filtered and solvents evaporated from the filtrate to obtain a crude residue, which was purified by flash chromatography on silica gel, 230-400 mesh, using 10-40% gradient of ethyl acetate in hexanes as eluent. The fractions with the desired product were concentrated to obtain the title product as a colourless viscous liquid (0.85 g, 30.1%). LCMS: Purity 31.33%. MS calculated for [M] 313.10 and found [M−H]$^−$ 312.05. $^1$H NMR (400 MHz, CDCl$_3$): δ 7.37-7.28 (m, 5H), 5.09 (s, 2H), 4.71-4.70 (d, J=4.0 Hz, 3H), 4.45-4.33 (m, 2H), 2.40-2.12 (m, 2H), 1.97-1.96 (d, J=4.0 Hz, 2H), 1.64-1.59 (m, 2H).

Step 3: Synthesis of S-(3-(((benzyloxy)carbonyl)amino)cyclopentyl)ethanethioate 3-(((benzyloxy)carbonyl)amino)cyclopentyl methanesulfonate (0.85 gm, 2.71 mmol, 1.0 eq) was dissolved in DMF (10 mL). Potassium thioacetate (0.46 gm, 4.07 mmol, 1.5 eq) was added and the mixture was heated at 80° C. for 16 h. After complete consumption of starting material, reaction mixture was cooled to ambient temperature and diluted with chilled water (10 mL). The mixture was then extracted with ethyl acetate (2×20 mL). The organic extract was again washed with cold water (1×20 mL) followed by cold brine (1×20 mL), dried over anhydrous Na$_2$SO$_4$, filtered and solvents evaporated from the filtrate under reduced pressure. The crude residue obtained was purified by column chromatography on silica gel, 100-200 mesh, using 0-12% gradient of EtOAc in hexanes as eluent. The fractions containing the desired product were concentrated to obtain the title product as brown solid (0.4 gm, 50.0%). LC-MS: Purity 91.94%. MS calculated for [M] 293.11 and found [M+H]$^+$ 294.13. $^1$H NMR (400 MHz, CDCl$_3$): δ 7.36-7.30 (m, 5H), 5.09 (s, 2H), 4.87 (s, 1H), 4.14-4.09 (m, 1H), 3.74-3.66 (m, 1H), 2.58-2.50 (m, 1H), 2.29 (s, 3H), 2.16-1.99 (m, 2H), 1.73-1.66 (m, 1H), 1.63-1.54 (m, 1H), 1.49-1.43 (m, 1H).

Step 4: Synthesis of 3-(((benzyloxy)carbonyl)amino)cyclopentane-1-sulfonic acid

S-(3-(((benzyloxy)carbonyl)amino)cyclopentyl) ethanethioate (0.4 gm, 1.4 mmol, 1.0 eq) was dissolved in AcOH (4 mL). Sodium acetate trihydrate (0.19 gm, 1.4 mmol, 1.0 eq) and 33% H$_2$O$_2$ (1.4 ml, 12.3 mmol, 9.0 eq) were added and the mixture was heated at 80° C. for 16 h. After complete consumption of starting material, reaction mixture was cooled to ambient temperature and solvents evaporated under reduced pressure. The resulting residue was dissolved in water (4 mL) and washed with DCM (2×4 mL). The aqueous layer was concentrated under vacuum and triturated with diethyl ether to obtain the title product as yellow solid (0.32 gm, 80.0%). LC-MS: Purity 94.53%. MS calculated for [M] 299.08 and found [M+H]$^+$ 299.98. $^1$H NMR (400 MHz, D$_2$O): δ 7.45-7.34 (m, 5H), 5.11 (s, 2H), 3.97-3.94 (d, J=12.0 Hz, 1H), 3.45-3.41 (t, J=6.0 Hz, 1H), 2.44-2.36 (m, 1H), 2.01-1.92 (m, 3H), 1.78-1.60 (m, 2H).

Step 5: Synthesis of 3-aminocyclopentane-1-sulfonic acid 3-(((benzyloxy)carbonyl)amino)cyclopentane-1-sulfonic acid (0.32 gm, 1.07 mmol, 1.0 eq) was dissolved in methanol (5.0 mL) under nitrogen atmosphere. Pd/C (10% w/w, 50% moisture, 0.32 g) was added and the mixture was stirred under hydrogen atmosphere (hydrogen balloon) at room temperature for 16 h. After complete consumption of starting material, reaction mixture was diluted with ethyl acetate (10 mL) and filtered through a celite bed. Then celite bed was thoroughly washed with ethyl acetate (2×10 mL). Mixture of filtrate and washings was concentrated under reduced pressure and the crude obtained was purified by prep HPLC on Atlantis HILIC prep column. The fractions with desired product were concentrated and lyophilized to obtain Compound 2005 as brown solid (0.065 gm, 37.0%). ELSD-MS: Purity 98.74%.

Example 5. Synthesis of 3-((S)-2-amino-3-methylbutanamido)cyclopentane-1-sulfonic acid (Compound 2010)

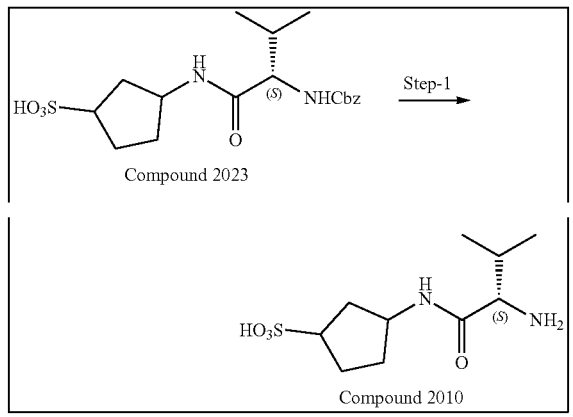

Compound 2023 (14 g_4) (0.3 gm, 0.75 mmol, 1.0 eq) was dissolved in methanol (6.0 mL) under nitrogen atmosphere. Pd/C (10% w/w, 50% moisture, 0.3 gm) was added and the mixture was stirred under hydrogen atmosphere (hydrogen balloon) at room temperature for 16 h. After complete consumption of starting material, reaction mixture was diluted with methanol (30 mL) and filtered through a celite bed. Then celite bed was thoroughly washed with methanol (3×20 mL). Mixture of filtrate and washings was concentrated under reduced pressure. The crude compound was dissolved in water (6.0 mL) and filtered through 0.2 micron syringe filter. The filtrate was concentrated and lyophilized to obtain Compound 2010 as white solid (0.115 gm, 57.8%). ELSD-MS: Purity 98.94%.

Example 6. Synthesis of 3-((S)-2-(((benzyloxy)carbonyl)amino)-3-(4-hydroxyphenyl)propanamido)cyclopentane-1-sulfonic acid (Compound 2021)

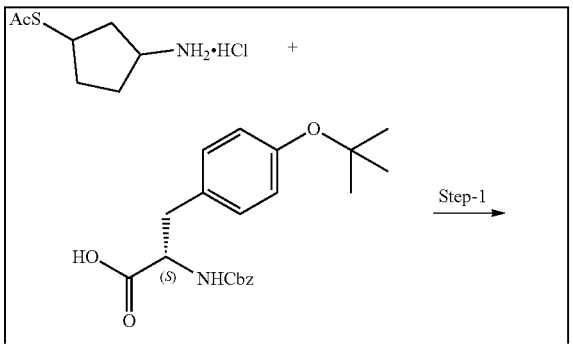

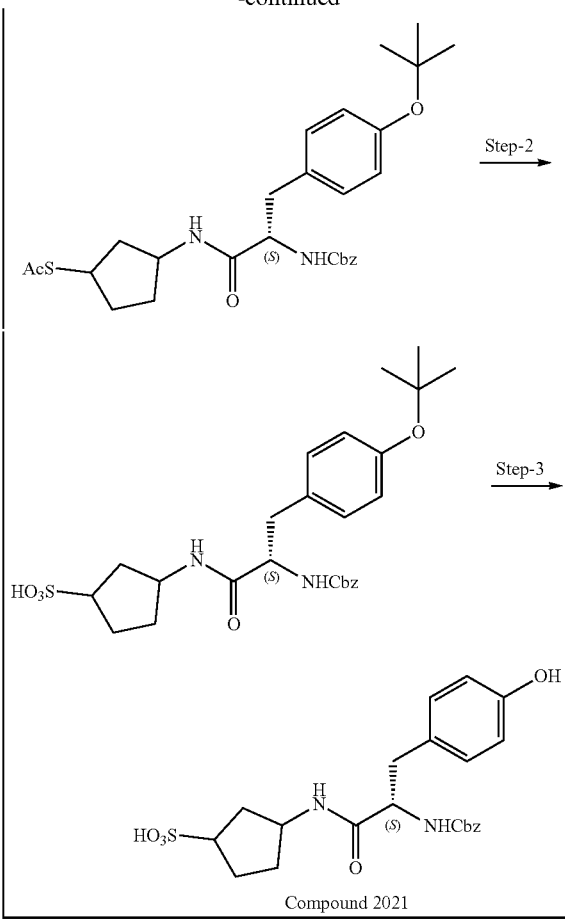

Step 1: Synthesis of S-(3-((S)-2-(((benzyloxy)carbonyl)amino)-3-(4-(tert-butoxy)phenyl)propanamido)cyclopentyl)ethanethioate (S)-2-(((benzyloxy)carbonyl)amino)-3-(4-(tert-butoxy)phenyl)propanoic acid (0.95 gm, 2.55 mmol, 1.0 eq) was dissolved in DCM (5.0 mL) and the mixture was cooled to 0° C. DIPEA (1.32 mL, 7.66 mmol, 3.0 eq) and HATU (1.46 gm, 3.83 mmol, 1.5 eq) were added and the reaction mixture was stirred at 0° C. for 0.5 h. Then S-(3-aminocyclopentyl)ethanethioate hydrochloride 10g (0.5 gm, 2.55 mmol, 1.0 eq) was added and the reaction mixture was stirred for 16 h, allowing temperature to gradually rise to ambient temperature. After complete consumption of starting material, reaction mixture was quenched with water (5 mL). The mixture was then extracted with DCM (3×10 mL). The organic extract was again washed with water (3×10 mL) followed by saturated aq. NaHCO$_3$ (1×10 mL), dried over anhydrous Na$_2$SO$_4$, filtered and solvents evaporated from the filtrate under reduced pressure. The crude residue obtained was purified by flash chromatography on silica gel, 230-400 mesh, using 0-30% gradient of EtOAc in hexanes as eluent. The fractions containing the desired product were concentrated to obtain the title product as white solid (0.49 gm, 37.4%). LC-MS: Purity 94.17%. MS calculated for [M] 512.23 and found [M+H]$^+$ 513.30. $^1$H NMR (400 MHz, CDCl$_3$): δ 7.33 (s, 5H), 7.08-7.06 (d, J=8.0 Hz, 2H), 6.92-6.90 (d, J=8.0 Hz, 2H), 5.09 (s, 2H), 4.24-4.19 (m, 2H), 3.70-3.66 (t, J=8.0 Hz, 1H), 3.10-3.05 (m, 1H), 2.93-2.87

(m, 1H), 2.28-2.27 (d, J=4.0 Hz, 3H), 2.08-1.99 (m, 2H), 1.88-1.82 (m, 2H), 1.53-1.46 (m, 1H), 1.32 (s, 9H), 1.16-1.11 (m, 1H).

Step 2: Synthesis of 3-((S)-2-(((benzyloxy)carbonyl)amino)-3-(4-(tert-butoxy)phenyl)propanemido)cyclopentane-1-sulfonic acid S-(3-((S)-2-(((benzyloxy)carbonyl)amino)-3-(4-(tert-butoxy)phenyl)propanamio)cyclopentyl) ethanethioate, (0.49 gm, 0.96 mmol, 1.0 eq) was dissolved in AcOH (5 mL). Sodium acetate trihydrate (0.13 gm, 0.96 mmol, 1.0 eq) and 33% $H_2O_2$ (0.98 ml, 8.61 mmol, 9.0 eq) were added and the mixture was heated at 60° C. for 3 h. After complete consumption of starting material, reaction mixture was cooled to ambient temperature and solvents evaporated under reduced pressure. The resulting residue was dissolved in water (5 mL) and washed with DCM (3×10 mL). The aqueous layer was concentrated under vacuum and triturated with ether. The resulting residue was lyophilized to obtain the title product as colorless semi-solid (0.45 gm, 88.9%). LC-MS: Purity 71.96%. MS calculated for [M] 518.21 and found $[M+H]^+$ 519.34. $^1H$ NMR (400 MHz, $D_2O$): δ 7.31-7.24 (m, 5H), 7.06-7.04 (d, J=8.0 Hz, 2H), 6.90-6.88 (d, J=8.0 Hz, 2H), 5.01-4.91 (m, 2H), 4.09-3.88 (m, 2H), 3.27-2.47 (m, 3H), 2.16-1.36 (m, 6H), 1.20 (s, 9H).

Step 3: Synthesis of 3-((S)-2-(((benzyloxy)carbonyl)amino)-3-(4-hydroxyphenyl)propanamido)cyclopentane-1-sulfonic acid (Compound 2021)

3-((S)-2-(((benzyloxy)carbonyl)amino)-3-(4-(tert-butoxy)phenyl)propanemido)cyclopentane-1-sulfonic acid (0.3 gm, 0.59 mmol, 1.0 eq) was dissolved in the mixture of THF and DCM (1:9, 10 mL) and the solution was cooled to 0° C. Then TFA (5 mL) was added and the mixture was stirred for 4 h, during which, the temperature was allowed to rise from 0° C. to ambient temperature. After complete consumption of starting material, solvents evaporated from the reaction mixture under reduced pressure and the crude obtained was triturated with diethyl ether to provide 0.25 gm of crude compound. 0.05 gm of crude compound was purified by prep HPLC on Waters Sunfire C18 OBD column. The fractions with desired product were concentrated and lyophilized to obtain Compound 2021 as white solid (0.025 gm, 46.0%). LC-MS: Purity 90.74%.

Example 7. Synthesis of 3-((S)-2-amino-3-(4-hydroxyphenyl)propanamido)cyclopentane-1-sulfonic acid (Compound 2015)

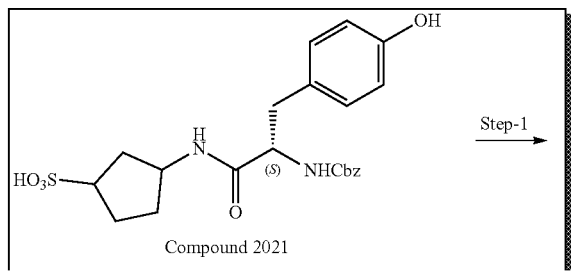

Compound 2021

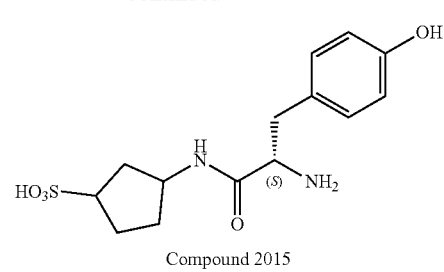

Compound 2015

Compound 2021 (0.2 gm, 0.43 mmol, 1.0 eq) was dissolved in methanol (6.0 mL) under nitrogen atmosphere. Pd/C (10% w/w, 50% moisture, 0.2 gm) was added and the mixture was stirred under hydrogen atmosphere (hydrogen balloon) at room temperature for 6 h. After complete consumption of starting material, reaction mixture was diluted with methanol (30 mL) and filtered through a celite bed. Then celite bed was thoroughly washed with methanol (3×20 mL). Mixture of filtrate and washings was concentrated under reduced pressure. The crude compound was dissolved in water (6.0 mL) and filtered through 0.2 micron syringe filter. The filtrate was concentrated and the crude obtained was purified by prep HPLC on Atlantis HILIC Prep column. The fractions with desired product were concentrated and lyophilized to obtain Compound 2015 as brown semi-solid (0.04 gm, 28.3%). ELSD-MS: Purity 92.67%.

Example 8. Synthesis of 3-((S)-2-(((benzyloxy)carbonyl)amino)-4-methylpentanamido)cyclopentane-1-sulfonic acid (Compound 2024)

Step 1: Synthesis of 3-((tert-butoxycarbonyl)amino)cyclopentyl methanesulfonate

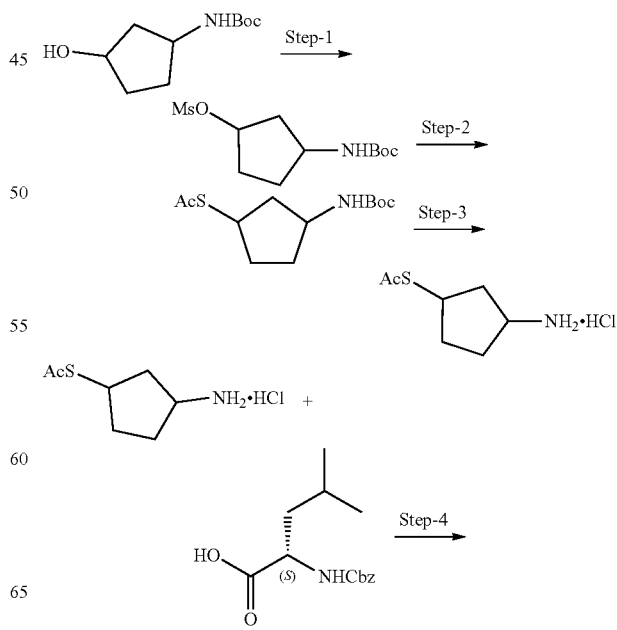

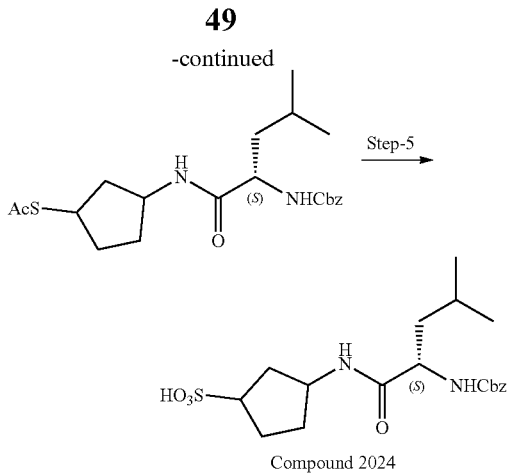

Compound 2024

Tert-butyl (3-hydroxycyclopentyl)carbamate (40.0 gm, 198.7 mmol, 1.0 eq) was dissolved in DCM (400 mL) and the solution was cooled to 0° C. Then methanesulfonyl chloride (23.2 mL, 298.1 mmol, 1.5 eq) and triethyl amine (55.3 mL, 397.5 mmol, 2.0 eq) were added and the mixture was stirred at 0° C. for 2 h. After complete consumption of starting material, reaction mixture was diluted with water (400 mL), separated the DCM layer and washed it again washed with water (2×400 mL). The organic extract was separated, dried over anhydrous $Na_2SO_4$, filtered and solvents evaporated from the filtrate under reduced pressure to obtain the title product as light yellow colour solid (54.0 gm, 97.0%). LC-MS: Low UV Response. MS calculated for [M] 279.11 and found [M+H]$^+$ 280.09. $^1$H NMR (400 MHz, $CDCl_3$): δ 5.13 (s, 1H), 4.72 (s, 1H), 4.11 (s, 1H), 3.00 (s, 3H), 2.38-2.31 (m, 1H), 2.11-2.09 (s, 2H), 1.95-1.85 (m, 2H), 1.71-1.63 (m, 1H), 1.44 (s, 9H).

Step 2: Synthesis of S-(3-((tert-butoxycarbonyl)amino)cyclopentyl) ethanethioate 3-((tert-butoxycarbonyl)amino)cyclopentyl methanesulfonate (30.0 gm, 107.4 mmol, 1.0 eq) was dissolved in DMF (300 mL). Potassium thioacetate (18.4 gm, 161.1 mmol, 1.5 eq) was added and the mixture was heated at 60° C. for 2 h. After complete consumption of starting material, reaction mixture was cooled to ambient temperature and diluted with chilled water (300 mL). The mixture was then extracted with ethyl acetate (2×600 mL). The organic extract was again washed with cold water (1×600 mL) followed by cold brine (1×600 mL), dried over anhydrous $Na_2SO_4$, filtered and solvents evaporated from the filtrate under reduced pressure. The crude residue obtained was purified by column chromatography on silica gel, 100-200 mesh, using 0-6% gradient of EtOAc in hexanes as eluent. The fractions containing the desired product were concentrated to obtain the title product as brown liquid (20.5 gm, 74.0%). LC-MS: Purity 94.96%. MS calculated for [M] 259.12 and found [M+H]$^+$ 260.05. $^1$H NMR (400 MHz, $CDCl_3$): δ 4.51 (s, 1H), 4.07 (s, 1H), 3.83-3.79 (t, J=8.0 Hz, 1H), 2.29 (s, 3H), 2.26-2.10 (m, 2H), 1.99-1.90 (m, 2H), 1.57-1.47 (m, 2H), 1.43 (s, 9H).

Step 3: Synthesis of S-(3-aminocyclopentyl) ethanethioate hydrochloride

S-(3-((tert-butoxycarbonyl)amino)cyclopentyl) ethanethioate (20.5 gm, 79.04 mmol, 1.0 eq) was dissolved in 1,4-Dioxane (200 mL) and the solution was cooled to 0° C. Then 4N HCl in 1,4-dioxane (200 mL) was added and the mixture was stirred for 3 h, during which, the temperature was allowed to rise from 0° C. to ambient temperature. After complete consumption of starting material solvents evaporated from the reaction mixture under reduced pressure and the crude obtained was triturated with diethyl ether. The precipitated solid was filtered and dried under vacuum to obtain the title product as light brown solid (14.0 gm, 91.0%). LC-MS: Purity 97.79%. MS calculated for [M] 159.07 and found [M+H]$^+$ 160.03. $^1$H NMR (400 MHz, $D_2O$): δ 3.94-3.76 (m, 2H), 2.36 (s, 3H), 2.31-2.21 (m, 3H), 2.15-2.08 (m, 1H), 1.76-1.70 (m, 2H).

Step 4: Synthesis of S-(3-((S)-2-(((benzyloxy)carbonyl)amino)-4-methylpentanamido)cyclopentyl) ethanethioate ((Benzyloxy)carbonyl)-L-leucine (0.78 gm, 3.06 mmol, 1.2 eq) was dissolved in DCM (5.0 mL) and the mixture was cooled to 0° C. DIPEA (1.32 mL, 7.66 mmol, 3.0 eq) and HATU (1.55 gm, 4.08 mmol, 1.6 eq) were added and the reaction mixture was stirred at 0° C. for 0.5 h. Then S-(3-aminocyclopentyl) ethanethioate hydrochloride (0.5 gm, 2.55 mmol, 1.0 eq) was added and the reaction mixture was stirred for 16 h, allowing temperature to gradually rise to ambient temperature. After complete consumption of starting material, reaction mixture was quenched with water (5 mL). The mixture was then extracted with DCM (3×10 mL). The organic extract was again washed with water (3×10 mL) followed by brine (1×10 mL), dried over anhydrous $Na_2SO_4$, filtered and solvents evaporated from the filtrate under reduced pressure. The crude residue obtained was purified by flash chromatography on silica gel, 230-400 mesh, using 0-10% gradient of EtOAc in hexanes as eluent. The fractions containing the desired product were concentrated to obtain the title product as white solid (0.65 gm, 62.1%). LCMS: Purity 82.67%. MS calculated for [M] 406.19 and found [M+H]$^+$ 407.24. $^1$H NMR (400 MHz, $D_2O$): δ 7.34 (s, 5H), 5.10 (m, 3H), 4.29 (bs, 1H), 4.08 (bs, 1H), 3.80 (bs, 1H), 2.29 (s, 3H), 2.20-2.12 (m, 2H), 1.95-1.94 (d, J=4.0 Hz, 2H), 1.59-1.44 (m, 4H), 0.93-0.92 (d, J=4.0 Hz, 6H).

Step 5: Synthesis of 3-((S)-2-(((benzyloxy)carbonyl)amino)-4-methylpentanamido)cyclopentane-1-sulfonic acid (Compound 2024)

S-(3-((S)-2-(((benzyloxy)carbonyl)amino)-4-methylpentanamido)cyclopentyl) ethanethioate (0.15 gm, 0.37 mmol, 1.0 eq) was dissolved in AcOH (2 mL). Sodium acetate trihydrate (0.05 gm, 0.37 mmol, 1.0 eq) and 33% $H_2O_2$ (0.37 ml, 3.32 mmol, 9.0 eq) were added and the mixture was heated at 80° C. for 16 h. After complete consumption of starting material, reaction mixture was cooled to ambient temperature and solvents evaporated under reduced pressure. The resulting residue was dissolved in water (6 mL) and washed with DCM (2×10 mL). The aqueous layer was concentrated under vacuum and triturated with ether. The resulting residue was lyophilized to obtain Compound 2024 as colourless semi-solid (0.13 gm, 85.52%). LCMS: Purity [(38.52%+53.84%), mixture of cis-isomer and trans-isomer].

Example 9. Synthesis of 3-((S)-2-(((benzyloxy)carbonyl)amino)-4-(methylsulfonyl)butanamido)cyclopentane-1-sulfonic acid (Compound 2026)

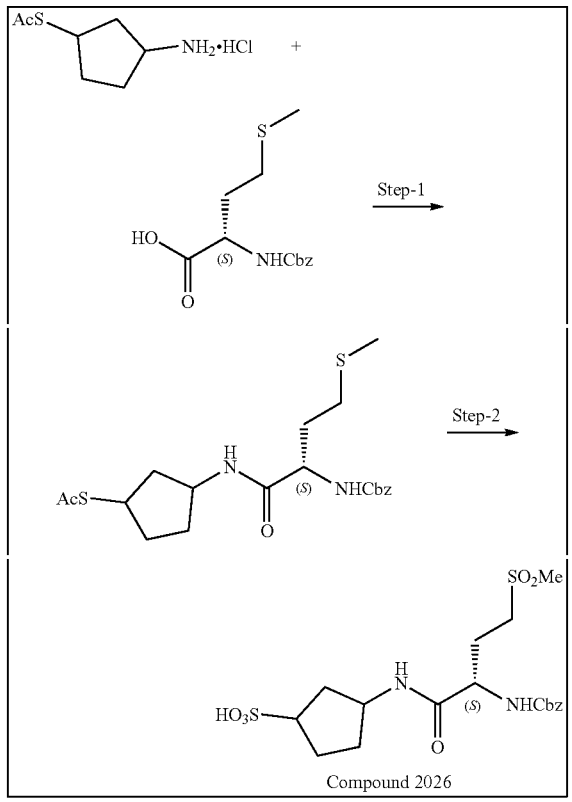

Compound 2026

Step 1: Synthesis of S-(3-((S)-2-(((benzyloxy)carbonyl)amino)-4-(methylthio)butanamido)cyclopentyl) ethanethioate ((Benzyloxy)carbonyl)-L-methionine (0.72 gm, 2.55 mmol, 1.0 eq) was dissolved in DCM (5.0 mL) and the mixture was cooled to 0° C. DIPEA (1.32 mL, 7.66 mmol, 3.0 eq) and HATU (1.46 gm, 3.83 mmol, 1.5 eq) were added and the reaction mixture was stirred at 0° C. for 0.5 h. Then S-(3-aminocyclopentyl) ethanethioate hydrochloride (0.5 gm, 2.55 mmol, 1.0 eq) was added and the reaction mixture was stirred for 16 h, allowing temperature to gradually rise to ambient temperature. After complete consumption of starting material, reaction mixture was quenched with water (5 mL). The mixture was then extracted with DCM (3×10 mL). The organic extract was again washed with water (3×10 mL) followed by saturated aq. NaHCO$_3$ (1×10 mL), dried over anhydrous Na$_2$SO$_4$, filtered and solvents evaporated from the filtrate under reduced pressure. The crude residue obtained was purified by flash chromatography on silica gel, 230-400 mesh, using 10-30% gradient of EtOAc in hexanes as eluent. The fractions containing the desired product were concentrated to obtain the title product as white solid (0.8 gm, 73.8%). LCMS: Purity 82.13%. MS calculated for [M] 424.15 and found [M+H]$^+$ 425.25. $^1$H NMR (400 MHz, CDCl$_3$): δ 7.35 (s, 5H), 5.11 (s, 2H), 4.33-4.26 (m, 2H), 3.82-3.78 (m, 1H), 2.58-2.45 (m, 2H), 2.30 (s, 3H), 2.22-2.02 (m, 3H), 1.96 (m, 3H), 1.58-1.43 (m, 5H).

Step 2: Synthesis of 3-((S)-2-(((benzyloxy)carbonyl)amino)-4-(methylsulfonyl)butanamido)cyclopentane-1-sulfonic acid (Compound 2026)

S-(3-((S)-2-(((benzyloxy)carbonyl)amino)-4-(methylthio)butanamido)cyclopentyl) ethanethioate (0.5 gm, 1.18 mmol, 1.0 eq) was dissolved in AcOH (5 mL). Sodium acetate trihydrate (0.16 gm, 1.18 mmol, 1.0 eq) and 33% H$_2$O$_2$ (1.2 ml, 10.61 mmol, 9.0 eq) were added and the mixture was heated at 60° C. for 3 h. After complete consumption of starting material, reaction mixture was cooled to ambient temperature and solvents evaporated under reduced pressure. The resulting residue was dissolved in water (5 mL) and washed with DCM (2×10 mL). The aqueous layer was concentrated under vacuum and triturated with ether. The resulting residue was lyophilized to obtain Compound 2026 as white solid (0.45 gm, 83.0%). ELSD-MS: Purity 97.18%.

Example 10. Synthesis of 3-((S)-2-amino-4-methylpentanamido)cyclopentane-1-sulfonic acid (Compound 2011)

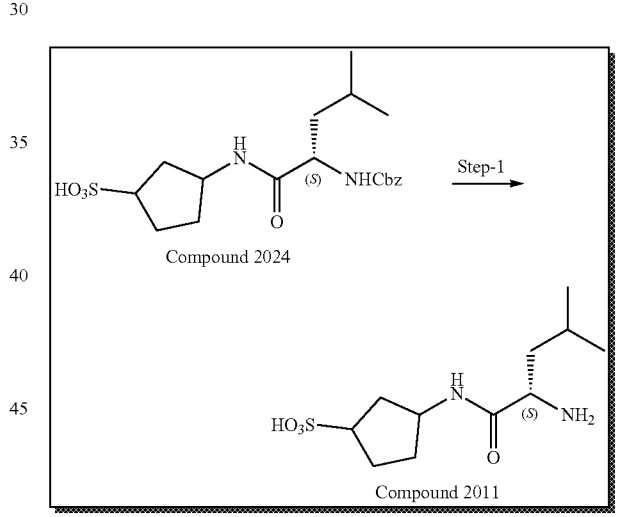

Compound 2024 (0.35 gm, 0.85 mmol, 1.0 eq) was dissolved in methanol (6.0 mL) under nitrogen atmosphere. Pd/C (10% w/w, 50% moisture, 0.35 gm) was added and the mixture was stirred under hydrogen atmosphere (hydrogen balloon) at room temperature for 16 h. After complete consumption of starting material, reaction mixture was diluted with methanol (30 mL) and filtered through a celite bed. Then celite bed was thoroughly washed with methanol (3×20 mL). Mixture of filtrate and washings was concentrated under reduced pressure. The crude compound was dissolved in water (6.0 mL) and filtered through 0.2 micron syringe filter. The filtrate was concentrated and lyophilized to obtain Compound 2011 as off-white solid (0.030 gm, 12.3%). ELSD-MS: Purity 98.76%.

Example 11. Synthesis of 3-((S)-2-amino-4-(methylsulfonyl)butanamido)cyclopentane-1-sulfonic acid (Compound 2014)

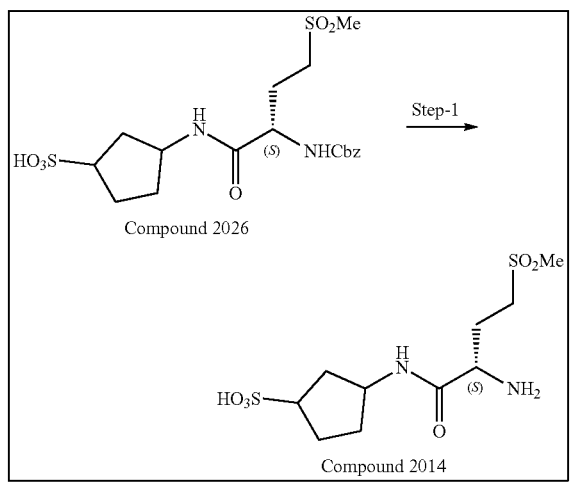

Compound 2026 (0.45 gm, 0.97 mmol, 1.0 eq) was dissolved in methanol (9.0 mL) under nitrogen atmosphere. Pd/C (10% w/w, 50% moisture, 0.45 gm) was added and the mixture was stirred under hydrogen atmosphere (hydrogen balloon) at room temperature for 6 h. After complete consumption of starting material, reaction mixture was diluted with methanol (45 mL) and filtered through a celite bed. Then celite bed was thoroughly washed with methanol (3×20 mL). Mixture of filtrate and washings was concentrated under reduced pressure. The crude compound was dissolved in water (9.0 mL) and filtered through 0.2 micron syringe filter. The filtrate was concentrated and lyophilized to obtain Compound 2014 as brown solid (0.15 gm, 47.0%). ELSD-MS: Purity 96.76%. MS calculated for [M] 328.08 and found [M+H]$^+$ 329.00. $^1$H NMR (400 MHz, D$_2$O): δ 4.20-4.16 (t, J=8.0 Hz, 1H), 3.56 (bs, 1H), 3.49-3.41 (m, 1H), 3.23-3.19 (t, J=8.0 Hz, 2H), 3.03 (s, 3H), 2.21-2.05 (m, 5H), 1.92-1.83 (m, 2H), 1.57 (bs, 1H).

Example 12. Synthesis of 3-(Methoxycarbonyl)cyclopentane-1-sulfonic acid (Compound 2028)

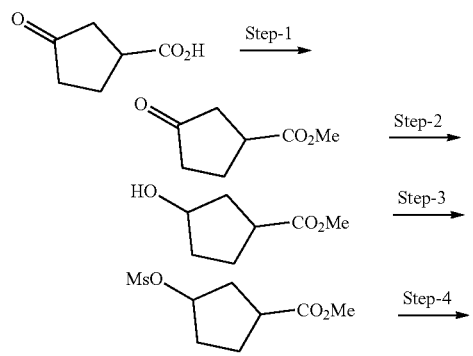

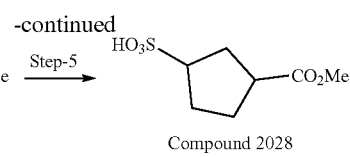

Compound 2028

Step 1: Synthesis of Methyl 3-oxocyclopentane-1-carboxylate 3-oxocyclopentane-1-carboxylic acid (10.0 gm, 78.13 mmol, 1.0 eq) was dissolved in methanol (100 mL) and the solution was cooled to 0° C. Then sulfuric acid (2 mL) was added and the mixture was heated at 80° C. for 6 h. After complete consumption of starting material, solvents evaporated from the reaction mixture under reduced pressure and the crude obtained was quenched with water (100 mL). The mixture was then extracted with ethyl acetate (2×100 mL) and combined filtrate was again washed with aq. sodium bicarbonate (1×100 mL) followed by water (1×100 mL). The organic extract was then dried over anhydrous Na$_2$SO$_4$, filtered and solvents evaporated from the filtrate under reduced pressure to obtain the title product as colorless liquid (10.0 gm, 91.0%). LC-MS: UV inactive compound. MS calculated for [M] 142.06 and found [M+H$_2$O]$^+$ 159.96. $^1$H NMR (400 MHz, CDCl$_3$): δ 3.73 (s, 3H), 3.17-3.09 (m, 1H), 2.55-2.24 (m, 4H), 2.21-2.04 (m, 2H).

Step 2: Synthesis of Methyl 3-hydroxycyclopentane-1-carboxylate

Methyl 3-oxocyclopentane-1-carboxylate (1.0 gm, 7.04 mmol, 1.0 eq) was dissolved in THF (10 mL) and the mixture was cooled to 0° C. Then sodium borohydride (0.32 gm, 8.45 mmol, 1.2 eq) was added and the mixture was stirred for 12 h. During stirring, temperature of the system gradually allowed to increase to ambient temperature. After completion consumption of the starting material, the mixture was quenched with saturated aq. ammonium chloride (10 mL). The mixture was then extracted with ethyl acetate (2×10 mL). The organic extract was separated, dried over anhydrous Na$_2$SO$_4$, filtered and solvents evaporated from the filtrate to obtain a crude residue. The crude residue obtained was purified by column chromatography on silica gel, 100-200 mesh, using 0-25% gradient of ethyl acetate in hexane as eluent. The fractions with the desired product were concentrated to obtain the title product as a colourless liquid (0.7 gm, 70.0%). ELSD-MS: Purity 98.23%. MS calculated for [M] 144.08 and found [M+H]$^+$ 145.00. $^1$H NMR (400 MHz, CDCl$_3$): δ 4.31 (bs, 1H), 3.70-3.67 (m, 3H), 2.89-2.79 (m, 1H), 2.09-1.74 (m, 6H).

Step 3: Synthesis of Methyl 3-((methylsulfonyl)oxy)cyclopentane-1-carboxylate Methyl 3-hydroxycyclopentane-1-carboxylate (0.7 gm, 4.86 mmol, 1.0 eq) was dissolved in DCM (10 mL) and the solution was cooled to 0° C. Then methanesulfonyl chloride (0.56 mL, 7.29 mmol, 1.5 eq) and triethyl amine (2.0 mL, 14.58 mmol, 3.0 eq) were added and the mixture was stirred for 4 h, during which, the temperature was allowed to rise from 0° C. to ambient temperature. After complete consumption of starting material, reaction mixture was diluted with water (10 mL) and extracted with DCM (2×10 mL). The organic extract was separated, dried over anhydrous Na$_2$SO$_4$, filtered and solvents evaporated from the filtrate under reduced pressure. The crude residue obtained was purified by column chromatography on silica gel, 100-200 mesh, using 0-25% gradient of EtOAc in hexanes as eluent. The fractions containing the desired product were concentrated to obtain the title product as colorless liquid (0.70 gm, 70.0%). $^1$H NMR (400 MHz, CDCl$_3$): δ 5.15 (s, 1H), 3.70 (s, 3H), 3.0 (s, 3H), 2.86-2.77 (m, 1H), 2.34-1.86 (m, 6H).

Step 4: Synthesis of Methyl 3-(acetylthio)cyclopentane-1-carboxylate

Methyl 3-((methylsulfonyl)oxy)cyclopentane-1-carboxylate (6.6 gm, 29.72 mmol, 1.0 eq) was dissolved in DMF (66 mL). Potassium thioacetate (5.0 gm, 44.59 mmol, 1.5 eq) was added and the mixture was heated at 60° C. for 16 h. After complete consumption of starting material, reaction mixture was cooled to ambient temperature and diluted with chilled water (66 mL). The mixture was then extracted with diethyl ether (2×132 mL). The organic extract was again washed with cold water (1×132 mL) followed by cold brine (1×132 mL), dried over anhydrous Na$_2$SO$_4$, filtered and solvents evaporated from the filtrate under reduced pressure. The crude residue obtained was purified by column chromatography on silica gel, 100-200 mesh, using 0-12% gradient of EtOAc in hexanes as eluent. The fractions containing the desired product were concentrated to obtain the title product as colorless liquid (3.4 gm, 57.0%). LC-MS: Purity [(35.99%+62.89%), mixture of cis-isomer and trans-isomer]. MS calculated for [M] 202.07 and found [M+H]$^+$ 202.99. $^1$H NMR (400 MHz, D$_2$O): δ 3.86-3.77 (m, 1H), 3.71 (s, 3H), 3.07-2.97 (m, 1H), 2.50-2.40 (m, 1H), 2.35 (s, 3H), 2.32-1.78 (m, 4H), 1.77-1.6 (m, 1H).

Step 5: Synthesis of 3-(Methoxycarbonyl)cyclopentane-1-sulfonic acid (Compound 2028)

Methyl 3-(acetylthio)cyclopentane-1-carboxylate (3.3 gm, 16.33 mmol, 1.0 eq) was dissolved in AcOH (30 mL). Sodium acetate trihydrate (2.22 gm, 16.33 mmol, 1.0 eq) and 33% H$_2$O$_2$ (16.6 ml, 146.97 mmol, 9.0 eq) were added and the mixture was heated at 60° C. for 16 h. After complete consumption of starting material, reaction mixture was cooled to ambient temperature and solvents evaporated under reduced pressure. The resulting residue was dissolved in water (30 mL) and washed with ethyl acetate (2×30 mL). The aqueous layer was concentrated under vacuum to provide 2.9 gm of crude compound. 0.3 gm of crude compound was purified by prep HPLC on Atlantis HILIC Prep column. The fractions with desired product were concentrated and lyophilized to obtain Compound 2028 as white solid (0.03 gm, 10.0%). ELSD-MS: Purity 95.68%.

Example 13. Synthesis of 3-Sulfocyclopentane-1-carboxylic acid (Compound 2029)

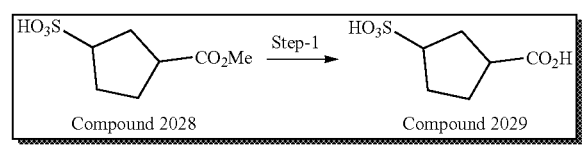

Compound 2028 (0.3 gm, 1.43 mmol, 1.0 eq) was dissolved in a mixture of THF and water (1:1, 6.0 mL) and the mixture was cooled to 0° C. Lithium hydroxide monohydrate (0.18 gm, 4.3 mmol, 3.0 eq) was added and the reaction mixture was stirred for 12 h, allowing temperature to gradually rise to ambient temperature. After complete consumption of starting material, reaction mixture was diluted with water (6 mL) and washed with ethyl acetate (2×12 mL). The resulting aqueous layer was acidified with amberlite IR 120 (H$^+$) resin up to pH=2 and filtered. The aqueous layer was concentrated under reduced pressure. The crude obtained was triturated with 10% ethanol in diethyl ether and purified by prep HPLC on Atlantis HILIC Prep column. The fractions with desired product were concentrated and lyophilized to obtain Compound 2029 as white solid (0.06 gm, 22.2%). ELSD-MS: Purity [(87.82%+10.72%), mixture of cis-isomer and trans-isomer].

Example 14. Synthesis of 3-(benzylcarbamoyl)cyclopentane-1-sulfonic acid (Compound 2030)

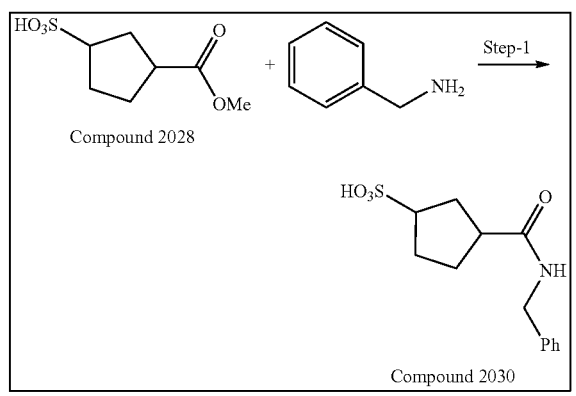

Compound 2028 (0.3 gm, 1.44 mmol, 1.0 eq) was dissolved in benzyl amine (3.0 mL) and the mixture was heated at 80° C. for 16 h. After complete consumption of starting material, reaction mixture was diluted with water (10 mL) and washed with DCM (2×10 mL) and ethyl acetate (2×10 mL). The resulting aqueous layer was concentrated under reduced pressure and the crude obtained was purified by prep HPLC on Waters Sunfire C18 OBD column. The fractions with desired product were concentrated and lyophilized to obtain Compound 2030 as white solid (0.03 gm, 7.35%). LCMS: Purity 99.60%.

Example 15. Synthesis of Compound 2055

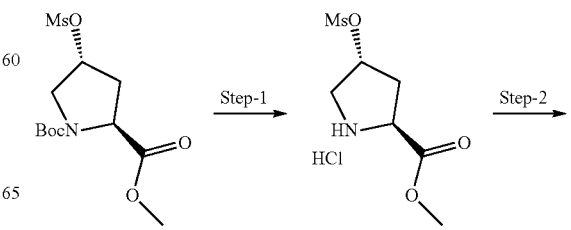

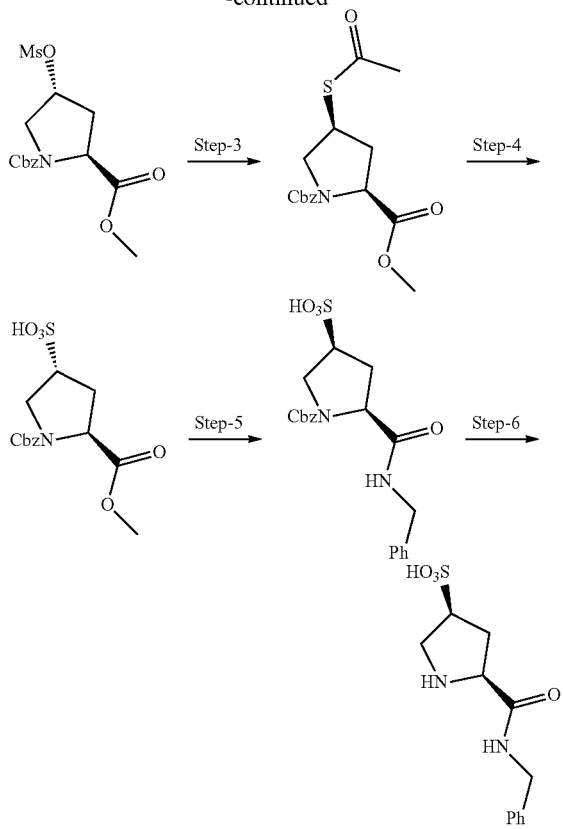

Step 1: Synthesis of methyl (2S,4R)-4-((methylsulfonyl)oxy)pyrrolidine-2-carboxylate hydrochloride 1-(tert-butyl) 2-methyl (2S,4R)-4-((methylsulfonyl)oxy) pyrrolidine-1,2-dicarboxylate (30.0 gm, 92.9 mmol, 1.0 eq) was dissolved in 1, 4-Dioxane (150 mL) and the solution was cooled to 0° C. Then 4N HCl in 1,4-dioxane (150 mL) was added and the mixture was stirred for 48 h, during which, the temperature of allowed to rise from 0° C. to ambient temperature. After complete consumption of starting material solvents evaporated from the reaction mixture under reduced pressure and the crude obtained was triturated diethyl ether and pentane. The precipitated solid was filtered and dried under vacuum to obtain the title product as white solid (23.4 gm, 98.0%). LCMS: UV inactive compound. MS calculated for [M] 223.05 and found [M+H]+ 224.16.

Step 2: Synthesis of 1-benzyl 2-methyl (2S,4R)-4-((methylsulfonyl)oxy)pyrrolidine-1,2-dicarboxylate Methyl (2S,4R)-4-((methylsulfonyl)oxy)pyrrolidine-2-carboxylate hydrochloride (23.0 gm, 88.8 mmol, 1.0 eq) was suspended in DCM (230 mL) and the mixture was cooled to 0° C. Then triethylamine (124.0 mL, 888.0 mmol, 10.0 eq) and CbzCl (50% solution in Toluene, 33.4 mL, 97.7 mmol, 1.1 eq) were added and the mixture was stirred for 72 h. During stirring, temperature of the system gradually allowed to increase to ambient temperature. After completion consumption of the starting material, the mixture was diluted with chilled water (230 mL), the organic extract was separated and washed with chilled water (2×230 mL). The organic extract was then dried over anhydrous $Na_2SO_4$, filtered and solvents evaporated from the filtrate to obtain a crude residue, which was purified by flash chromatography on silica gel, 230-400 mesh, using 0-5% gradient of methanol in DCM as eluent. The fractions with the desired product were concentrated to obtain the title product as a colourless liquid (22.3 g, 70.0%). LCMS: Purity 91.58%. MS calculated for [M] 357.09 and found [M+H]+ 358.05. $^1$H NMR (400 MHz, $CDCl_3$): δ 7.36-7.32 (m, 5H), 5.30-5.03 (m, 3H), 4.56-4.48 (m, 1H), 3.98-3.80 (m, 2H), 3.78 (s, 1.5H), 3.56 (s, 1.5H), 3.04-3.02 (d, J=8.8 Hz, 3H), 2.71-2.62 (m, 1H), 2.31-2.27 (m, 1H).

Step 3: Synthesis of 1-benzyl 2-methyl (2S,4S)-4-(acetylthio)pyrrolidine-1,2-dicarboxylate 1-Benzyl 2-methyl (2S,4R)-4-((methylsulfonyl)oxy)pyrrolidine-1,2-dicarboxylate 3b (22.3 gm, 62.5 mmol, 1.0 eq) was dissolved in DMF (220 mL). Potassium thioacetate (10.7 gm, 93.8 mmol, 1.5 eq) was added and the mixture was heated at 80° C. for 16 h. After complete consumption of starting material, reaction mixture was cooled to ambient temperature and diluted with chilled water (220 mL). The mixture was then extracted with diethyl ether (2×440 mL). The organic extract was again washed with water (1×440 mL) followed by brine (1×440 mL), dried over anhydrous $Na_2SO_4$, filtered and solvents evaporated from the filtrate under reduced pressure. The crude residue obtained was purified by flash chromatography on silica gel, 230-400 mesh, using 0-15% gradient of EtOAc in hexanes as eluent. The fractions containing the desired product were concentrated to obtain the title product as brown viscous liquid (14.5 gm, 69.0%). LCMS: Purity 85.24%. MS calculated for [M] 337.10 and found [M+H]+ 338.04. $^1$H NMR (400 MHz, $CDCl_3$): δ 7.36-7.31 (m, 5H), 5.22-5.03 (m, 2H), 4.46-4.39 (m, 1H), 4.11-3.96 (m, 2H), 3.77 (s, 1.5H), 3.58 (s, 1.5H), 3.45-3.38 (m, 1H), 2.80-2.69 (m, 1H), 2.32 (s, 3H), 2.03-1.96 (m, 1H).

Step 4: Synthesis of (3R,5S)-1-((benzyloxy)carbonyl)-5-(methoxycarbonyl)pyrrolidine-3-sulfonic acid 1-Benzyl 2-methyl (2S, 4S)-4-(acetylthio) pyrrolidine-1, 2-dicarboxylate 4b (1.5 gm, 4.45 mmol, 1.0 eq) was dissolved in AcOH (15 mL). Sodium acetate trihydrate (0.6 gm, 4.45 mmol, 1.0 eq) and 33% $H_2O_2$ (4.53 ml, 40.1 mmol, 9.0 eq) were added and the mixture was heated at 80° C. for 16 h. After complete consumption of starting material, reaction mixture was cooled to ambient temperature and solvents evaporated under reduced pressure. The resulting residue was dissolved in water (15 mL) and washed with EtOAc (2×15 mL). The aqueous layer was concentrated under vacuum to get 1.44 gm of crude compound. 0.1 gm of crude compound was purified by prep HPLC on Waters Sunfire C18 OBD column. The fractions with desired product were concentrated and lyophilized to obtain the title product as white solid (0.05 gm, 47.4%). LCMS: Purity 97.81%. MS calculated for [M] 343.35 and found [M+H]+ 344.03. $^1$H NMR (400 MHz, $D_2O$): δ 7.47-7.38 (m, 5H), 5.23-5.05 (m, 2H), 4.63-4.54 (m, 1H), 4.07-3.97 (m, 1H), 3.76 (s, 1.5H), 3.61 (s, 1.5H), 3.77-3.61 (m, 2H), 2.80-2.72 (m, 1H), 2.41-2.35 (m, 1H).

Step 5: Synthesis of (3S,5S)-5-(benzylcarbamoyl)-1-((benzyloxy)carbonyl)pyrrolidine-3-sulfonic acid (3S,5S)-1-((benzyloxy)carbonyl)-5-(methoxycarbonyl) pyrrolidine-3-sulfonic acid (0.3 gm, 0.87 mmol, 1.0 eq) was dissolved in benzyl amine (3.0 mL) and the mixture was heated at 50° C. for 16 h. After complete consumption of starting material, reaction mixture was diluted with ethyl acetate (15 mL), precipitated solid was filtered and washed with diethyl ether (2×9 mL). The residue was then dried under vacuum to get 0.3 gm of crude compound. 0.1 gm of crude compound was purified by prep HPLC on Waters Sunfire C18 OBD column. The fractions with desired product were concentrated and lyophilized to obtain the title product as white solid (0.029 gm, 23.5%). LCMS: Purity 96.91%. MS calculated for [M] 418.12 and found [M+H]$^+$ 419.10. $^1$H NMR (400 MHz, D$_2$O): δ 7.41-7.22 (m, 10H), 5.19-5.03 (m, 2H), 4.46-4.02 (m, 4H), 3.77-3.75 (m, 1H), 3.69-3.62 (m, 1H), 2.75 (bs, 1H), 2.31-2.26 (m, 1H).

Step 6: Compound 2055

The intermediate from the previous step (1.0 eq) was dissolved in methanol under nitrogen atmosphere. Pd/C (10% w/w, 50% moisture, w/w) was added and the mixture was stirred under hydrogen atmosphere (hydrogen balloon) at room temperature for 6 h. After complete consumption of starting material, reaction mixture was diluted with methanol and filtered through a celite bed. Then celite bed was thoroughly washed with methanol (3×). Mixture of filtrate and washings was concentrated under reduced pressure. The crude compound was dissolved in water and filtered through 0.2 micron syringe filter. The filtrate was concentrated and the crude obtained was purified by prep HPLC. The fractions with desired product were concentrated and lyophilized to obtain the final compound.

Example 16. Synthesis of Compound 2059

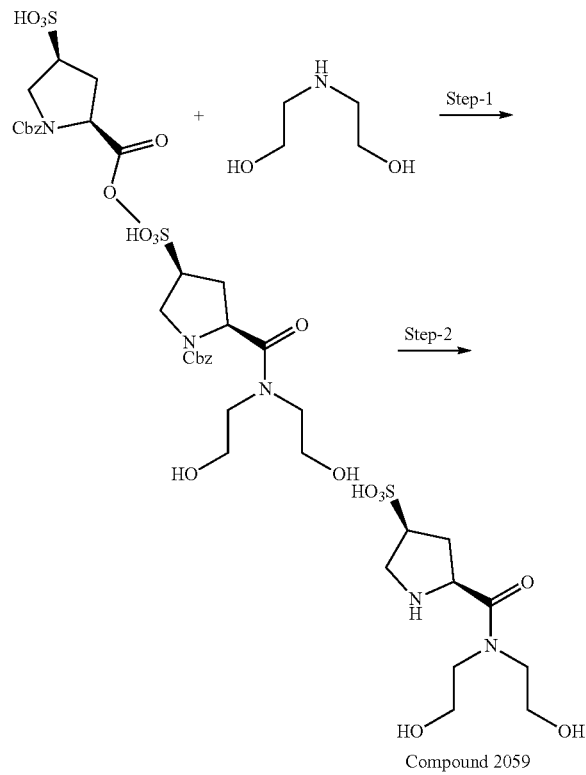

Compound 2059

Step 1: Synthesis of (3S,5S)-1-((benzyloxy)carbonyl)-5-(bis(2-hydroxyethyl)carbamoyl)pyrrolidine-3-sulfonic acid (3S,5S)-1-((Benzyloxy)carbonyl)-5-(methoxycarbonyl) pyrrolidine-3-sulfonic acid (0.45 gm, 1.3 mmol, 1.0 eq) and 2,2'-azanediylbis(ethan-1-ol) (0.41 gm, 3.9 mmol, 3.0 eq) were mixed and the mixture was heated at 80° C. for 6 h. After complete consumption of starting material, reaction mixture was diluted with water (10 mL) and washed with DCM (3×10 mL). The resulting aqueous layer was concentrated under reduced pressure to get 1.0 gm of crude compound. 0.5 gm of the crude obtained was purified by prep HPLC on Waters Sunfire C18 OBD column. The fractions with desired product were concentrated and lyophilized to obtain the title product as white solid (0.075 gm, 27.5%). LCMS: Purity 97.30%. MS calculated for [M] 416.13 and found [M+H]$^+$ 417.20. $^1$H NMR (400 MHz, D$_2$O): δ 7.48-7.38 (m, 5H), 5.16-5.06 (m, 2H), 4.89-4.84 (m, 1H), 4.04-4.02 (m, 1H), 3.80-3.22 (m, 10H), 2.73 (m, 1H), 2.16 (m, 1H).

Step 2: Compound 2059

The product from the previous step was deprotected as described in Step 6 of Example 15.

Example 17. Synthesis of Compound 2056

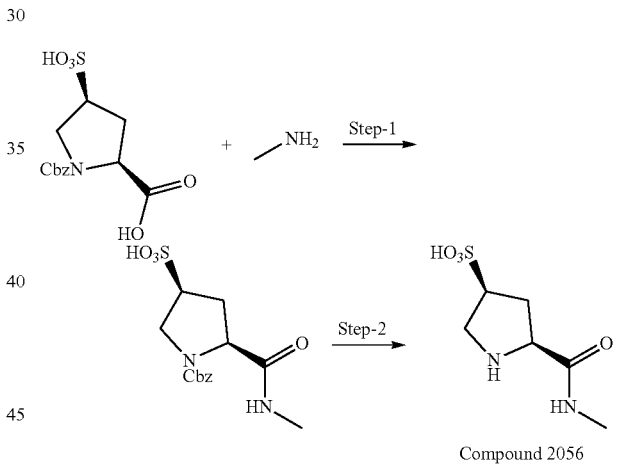

Compound 2056

Step 1: Synthesis of (3S,5S)-1-((benzyloxy)carbonyl)-5-(methylcarbamoyl)pyrrolidine-3-sulfonic acid (2S,4S)-1-((Benzyloxy)carbonyl)-4-sulfopyrrolidine-2-carboxylic acid (0.4 gm, 1.21 mmol, 1.0 eq) was dissolved in DMF (4.0 mL) and the mixture was cooled to 0° C. 1-Propanephosphonic acid cyclic anhydride (50% in ethyl acetate, 1.15 mL, 1.82 mmol, 1.5 eq) and triethyl amine (1.0 mL, 7.26 mmol, 6.0 eq) were added and the reaction mixture was stirred at 0° C. for 0.5 h. Then methyl amine hydrochloride A_5 (0.164 gm, 2.42 mmol, 2.0 eq) was added and the reaction mixture was stirred for 48 h, allowing temperature to gradually rise to ambient temperature. After complete consumption of starting material, reaction mixture was diluted with water (10 mL) and washed with DCM (3×12 mL). The resulting aqueous layer was concentrated under reduced pressure to get 2.3 gm of crude compound. 1.15 gm of the crude obtained was purified by prep HPLC on Waters Sunfire C18 OBD column. The fractions with desired product were concentrated and lyophilized to obtain the title product as off-white solid (0.037 gm, 18.1%). LCMS: Purity 96.95%. MS calculated for [M] 342.09 and found [M+H]⁺ 343.16. ¹H NMR (400 MHz, D₂O): δ 7.45-7.36 (m, 5H), 5.22-5.01 (m, 2H), 4.39-4.34 (m, 1H), 4.10-3.99 (m, 1H), 3.79-3.59 (m, 2H), 2.74 (s, 1.5H), 2.71-2.59 (m, 1H), 2.56 (s, 1.5H), 2.25-2.17 (m, 1H).

Step 2: Compound 2056

The product from the previous step was deprotected as described in Step 6 of Example 15.

Example 18. Synthesis of Compound 2057

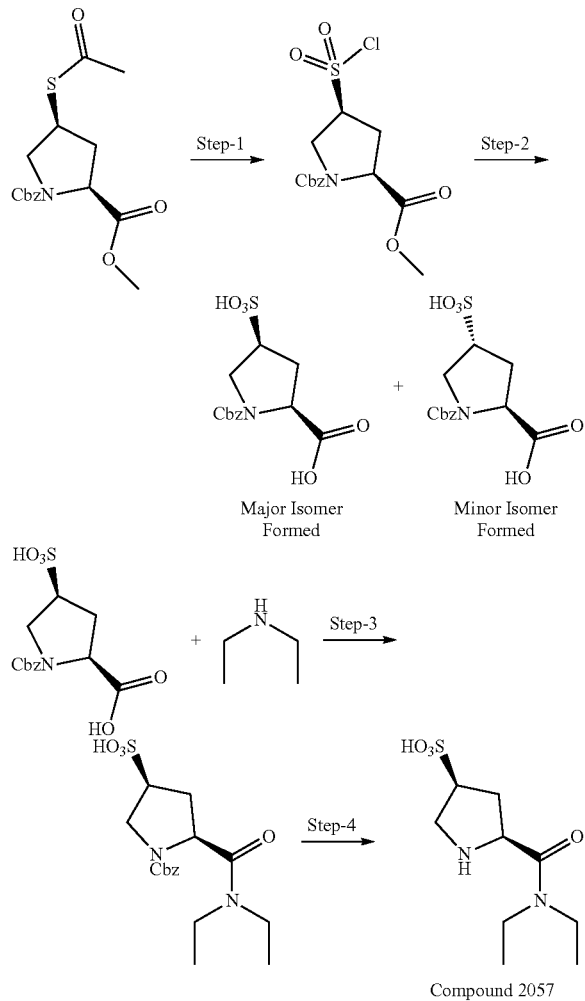

Compound 2057

Step 1: Synthesis of 1-benzyl 2-methyl (2S,4S)-4-(chlorosulfonyl)pyrrolidine-1,2-dicarboxylate 1-Benzyl 2-methyl (2S,4S)-4-(acetylthio)pyrrolidine-1,2-dicarboxylate (1.5 gm, 4.45 mmol, 1.0 eq) was dissolved in ethanol (15.0 mL) and the mixture was cooled to −10° C. Then reaction mixture was purged with chlorine gas for 15 min, allowing temperature to gradually rise to ambient temperature. After complete consumption of starting material, reaction mixture was quenched with water (15 mL). The mixture was then extracted with ethyl acetate (2×30 mL). The organic extract was again washed with water (1×30 mL), dried over anhydrous Na₂SO₄, filtered and solvents evaporated from the filtrate under reduced pressure to obtain the title product as brown liquid (2.0 gm, Crude). The crude obtained was used as such without further purification. LCMS: Purity 26.78%+26.18% (Ethyl ester analogue, which was formed due to trans-esterification during step-1). MS calculated for [M] 361.04 and found [M+H]⁺ 361.97.

Step 2: Synthesis of (2S,4S)-1-((benzyloxy)carbonyl)-4-sulfopyrrolidine-2-carboxylic acid 1-Benzyl 2-methyl (2S,4S)-4-(chlorosulfonyl)pyrrolidine-1,2-dicarboxylate (0.3 gm, Crude, 0.83 mmol, 1.0 eq) was dissolved in a mixture of THF and water (1:1, 6.0 mL) and the mixture was cooled to 0° C. Lithium hydroxide monohydrate (0.105 gm, 2.49 mmol, 3.0 eq) was added and the reaction mixture was stirred for 4 h, allowing temperature to gradually rise to ambient temperature. After complete consumption of starting material, reaction mixture was diluted with water (6 mL) and washed with DCM (2×12 mL). The resulting aqueous layer was acidified with amberlite IR 120 (H⁺) resin up to pH=2 and filtered. The aqueous layer was concentrated under reduced pressure to get 0.235 gm of crude compound. 0.1 gm of the crude obtained was purified by prep HPLC on Atlantis HILIC column. The fractions with desired product were concentrated and lyophilized to obtain mixture of the title product (cis-isomer) and a minor contaminant (trans-isomer) as white solid (0.048 gm, 41.4%). LCMS: Purity 75.49% (cis-isomer)+ 22.95% (trans-isomer). MS calculated for [M] 329.06 and found [M+H]⁺ 330.05. ¹H NMR (400 MHz, D₂O): δ 7.47-7.41 (m, 5H), 5.19-5.09 (m, 2H), 4.53-4.46 (m, 1H), 4.06-3.58 (m, 3H), 2.83-2.66 (m, 1H), 2.47-2.28 (m, 1H).

Step 3: Synthesis of (3S,5S)-1-((benzyloxy)carbonyl)-5-(diethylcarbamoyl)pyrrolidine-3-sulfonic acid (2S,4S)-1-((Benzyloxy)carbonyl)-4-sulfopyrrolidine-2-carboxylic acid (0.4 gm, 1.21 mmol, 1.0 eq) was dissolved in DMF (4.0 mL) and the mixture was cooled to 0° C. 1-Propanephosphonic acid cyclic anhydride (50% in ethyl acetate, 1.15 mL, 1.82 mmol, 1.5 eq) and triethyl amine (0.5 mL, 3.63 mmol, 3.0 eq) were added and the reaction mixture was stirred at 0° C. for 0.5 h. Then diethyl amine (0.134 gm, 1.82 mmol, 1.5 eq) was added and the reaction mixture was stirred for 48 h, allowing temperature to gradually rise to ambient temperature. After complete consumption of starting material, reaction mixture was diluted with water (10 mL) and washed with DCM (3×12 mL). The resulting aqueous layer was concentrated under reduced pressure to get 1.6 gm of crude compound. 0.8 gm of the crude obtained was purified by prep HPLC on Waters Sunfire C18 OBD column. The fractions with desired product were concentrated and lyophilized to obtain the title product as light brown solid (0.022 gm, 9.6%). LCMS: Purity 92.81%. MS calculated for [M] 384.14 and found [M+H]⁺ 385.21. ¹H NMR (400 MHz, D₂O): δ 7.46-7.36 (m, 5H), 5.12-5.01 (m, 2H), 4.03 (m, 1H), 3.75 (m, 1H), 3.63-3.60 (m, 1H), 3.45 (m, 1H), 3.32-3.20 (m, 3H), 3.09 (m, 1H), 2.75 (m, 1H), 2.10 (m, 1H), 1.29-1.24 (m, 1H), 1.14-1.10 (m, 1H), 0.97-0.90 (m, 4H).

Step 4: Compound 2057

The product from the previous step was deprotected as described in Step 6 of Example 15.

Example 19. Synthesis of Compound 2058

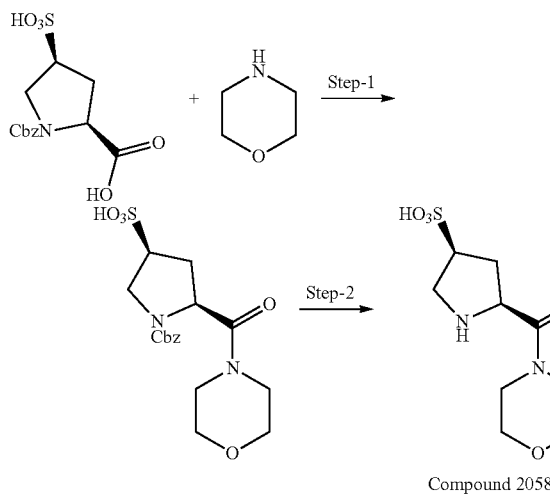

Compound 2058

Step 1: Synthesis of (3S,5S)-1-((Benzyloxy)carbonyl)-5-(morpholine-4-carbonyl)pyrrolidine-3-sulfonic acid (2S,4S)-1-((Benzyloxy)carbonyl)-4-sulfopyrrolidine-2-carboxylic acid (0.4 gm, 1.21 mmol, 1.0 eq) was dissolved in DMF (4.0 mL) and the mixture was cooled to 0° C. 1-Propanephosphonic acid cyclic anhydride (50% in ethyl acetate, 1.15 mL, 1.82 mmol, 1.5 eq) and triethyl amine (0.5 mL, 3.63 mmol, 3.0 eq) were added and the reaction mixture was stirred at 0° C. for 0.5 h. Then morpholine (0.159 gm, 1.82 mmol, 1.5 eq) was added and the reaction mixture was stirred for 48 h, allowing temperature to gradually rise to ambient temperature. After complete consumption of starting material, reaction mixture was diluted with water (10 mL) and washed with DCM (3×12 mL). The resulting aqueous layer was concentrated under reduced pressure to get 3.0 gm of crude compound. 1.5 gm of the crude obtained was purified by prep HPLC on Waters Sunfire C18 OBD column. The fractions with desired product were concentrated and lyophilized to obtain the title product as off-white solid (0.02 gm, 8.3%). LCMS: Purity 96.61%. MS calculated for [M] 398.11 and found [M+H]$^+$ 399.17. $^1$H NMR (400 MHz, D$_2$O): δ 7.46-7.40 (m, 5H), 5.17-5.02 (m, 2H), 4.96-4.89 (m, 1H), 4.08-4.04 (m, 1H), 3.81-3.29 (m, 10H), 2.76-2.70 (m, 1H), 2.14-2.09 (m, 1H).

Step 2: Compound 2058

The product from the previous step was deprotected as described in Step 6 of Example 15.

Example 20. Synthesis of Compound 2086

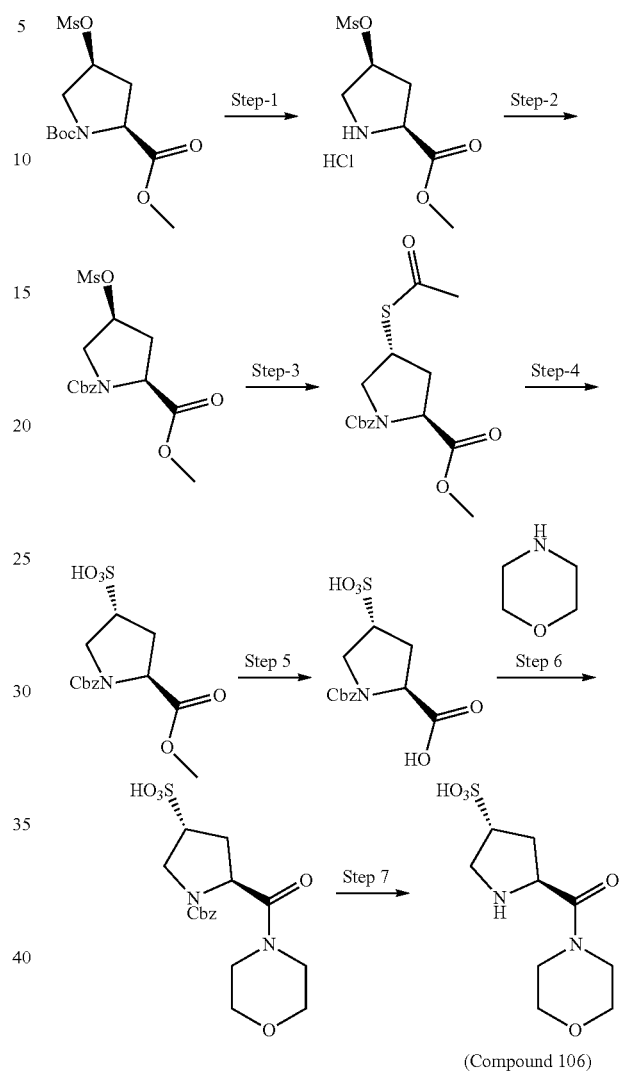

(Compound 106)

Step 1: Synthesis of methyl (2S,4S)-4-((methylsulfonyl)oxy)pyrrolidine-2-carboxylate hydrochloride 1-(tert-Butyl) 2-methyl (2S,4S)-4-((methylsulfonyl)oxy)pyrrolidine-1,2-dicarboxylate (30.0 gm, 92.9 mmol, 1.0 eq) was dissolved in 1, 4-Dioxane (150 mL) and the solution was cooled to 0° C. Then 4N HCl in 1,4-dioxane (150 mL) was added and the mixture was stirred for 16 h, during which, the temperature of allowed to rise from 0° C. to ambient temperature. After complete consumption of starting material solvents evaporated from the reaction mixture under reduced pressure and the crude obtained was triturated 10% ethanol in diethyl ether. The precipitated solid was filtered and dried under vacuum to obtain the title product as white solid (18.6 gm, 77.5%). $^1$H NMR (400 MHz, DMSO-d6): δ 10.21-10.17 (bs, 2H), 5.39 (s, 1H), 4.65-4.61 (m, 1H), 3.77 (s, 3H), 3.54 (s, 2H), 3.25 (s, 3H), 2.71-2.64 (m, 1H), 2.50 (merged with solvent peak, 1H).

Step 2: Synthesis of 1-benzyl 2-methyl (2S, 4S)-4-((methylsulfonyl)oxy)pyrrolidine-1,2-dicarboxylate Methyl (2S, 4S)-4-((methylsulfonyl) oxy) pyrrolidine-2-carboxylate hydrochloride (18.0 gm, 69.5 mmol, 1.0 eq) was suspended in DCM (180 mL) and the mixture was cooled to 0° C. Then triethylamine (97.0 mL, 695.0 mmol, 10.0 eq) and CbzCl (50% solution in Toluene, 26.0 mL, 76.5 mmol, 1.1 eq) were added and the mixture was stirred for 16 h. During stirring, temperature of the system gradually allowed to increase to ambient temperature. After completion consumption of the starting material, the mixture was diluted with chilled water (180 mL), the organic extract was separated and washed with chilled water (2×180 mL). The organic extract was then dried over anhydrous $Na_2SO_4$, filtered and solvents evaporated from the filtrate to obtain a crude residue, which was purified by flash chromatography on silica gel, 230-400 mesh, using 10-40% gradient of ethyl acetate in hexanes as eluent. The fractions with the desired product were concentrated to obtain the title product as a colourless viscous liquid (22.0 g, 88.7%). LCMS: Purity 83.38%. MS calculated for [M] 357.09 and found $[M+H]^+$ 358.07. $^1$H NMR (400 MHz, $CDCl_3$): δ 7.36-7.32 (m, 5H), 5.25-5.08 (m, 3H), 4.60-4.51 (dd, J=8.0 Hz, 28.0 Hz, 1H), 3.87-3.85 (d, J=10.4 Hz, 2H), 3.77 (s, 1.5H), 3.66 (s, 1.5H), 3.00 (s, 3H), 2.62-2.46 (m, 2H).

Step 3: Synthesis of 1-benzyl 2-methyl (2S, 4R)-4-(acetylthio) pyrrolidine-1, 2-dicarboxylate 1-Benzyl 2-methyl (2S, 4S)-4-((methylsulfonyl) oxy) pyrrolidine-1, 2-dicarboxylate (22.0 gm, 61.6 mmol, 1.0 eq) was dissolved in DMF (220 mL). Potassium thioacetate (10.5 gm, 92.4 mmol, 1.5 eq) was added and the mixture was heated at 80° C. for 24 h. After complete consumption of starting material, reaction mixture was cooled to ambient temperature and diluted with chilled water (220 mL). The mixture was then extracted with diethyl ether (2×440 mL). The organic extract was again washed with water (1×440 mL) followed by brine (1×440 mL), dried over anhydrous $Na_2SO_4$, filtered and solvents evaporated from the filtrate under reduced pressure. The crude residue obtained was purified by flash chromatography on silica gel, 230-400 mesh, using 0-15% gradient of EtOAc in hexanes as eluent. The fractions containing the desired product were concentrated to obtain the title product as brown viscous liquid (14.1 gm, 68.0%). LCMS: Purity 98.01%. MS calculated for [M] 337.10 and found $[M+H]^+$ 338.03. $^1$H NMR (400 MHz, $CDCl_3$): δ 7.36-7.28 (m, 5H), 5.21-5.02 (m, 2H), 4.49-4.40 (m, 1H), 4.06-4.02 (m, 2H), 3.76 (s, 1.5H), 3.59 (s, 1.5H), 3.51-3.41 (dd, J=5.0 Hz, 36.4 Hz, 1H), 2.43-2.41 (m, 1H), 2.33 (s, 3H), 2.27-2.23 (m, 1H).

Step 4: Synthesis of (3R, 5S)-1-((benzyloxy)carbonyl)-5-(methoxycarbonyl)pyrrolidine-3-sulfonic 1-Benzyl 2-methyl (2S, 4R)-4-(acetylthio) pyrrolidine-1, 2-dicarboxylate (1.5 gm, 4.45 mmol, 1.0 eq) was dissolved in AcOH (15 mL). Sodium acetate trihydrate (0.6 gm, 4.45 mmol, 1.0 eq) and 33% $H_2O_2$ (4.6 ml, 44.5 mmol, 10.0 eq) were added and the mixture was heated at 60° C. for 16 h. After complete consumption of starting material, reaction mixture was cooled to ambient temperature and solvents evaporated under reduced pressure. The resulting residue was dissolved in water (15 mL) and washed with EtOAc (2×15 mL). The aqueous layer was concentrated under vacuum to get 1.5 gm of crude compound. 0.25 gm of crude compound was purified by reverse phase flash chromatography on Agela Cheetah purification system, using AQ C18 column (20-35 μm, 12 gm) and 0-17% gradient of water in MeCN as eluent. The fractions with desired product were concentrated and lyophilized to obtain the title product as white solid (0.06 gm, 23.5%). LCMS: Purity 90.93%. MS calculated for [M] 343.07 and found $[M+H]^+$ 344.00. $^1$H NMR (400 MHz, $D_2O$): δ 7.45-7.36 (m, 5H), 5.24-5.04 (m, 2H), 4.67-4.58 (m, 1H), 3.92-3.85 (dd, J=6.8 Hz, 24.0 Hz, 2H), 3.77 (s, 1.5H), 3.62 (s, 1.5H), 3.75-3.72 (m, 1H), 2.73-2.64 (m, 1H), 2.47-2.40 (m, 1H).

Step 5: Synthesis of (2S, 4R)-1-((benzyloxy)carbonyl)-4-sulfopyrrolidine-2-carboxylic acid (3R,5S)-1-((Benzyloxy)carbonyl)-5-(methoxycarbonyl) pyrrolidine-3-sulfonic acid (0.3 gm, 0.87 mmol, 1.0 eq) was dissolved in a mixture of THF and water (1:1, 6.0 mL) and the mixture was cooled to 0° C. Lithium hydroxide monohydrate (0.11 gm, 2.61 mmol, 3.0 eq) was added and the reaction mixture was stirred for 16 h, allowing temperature to gradually rise to ambient temperature. After complete consumption of starting material, reaction mixture was diluted with water (6 mL) and washed with DCM (2×12 mL). The resulting aqueous layer was acidified with amberlite IR 120 ($H^+$) resin up to pH=2 and filtered. The aqueous layer was concentrated under reduced pressure and the crude obtained was purified by prep HPLC on Atlantis HILIC column. The fractions with desired product were concentrated and lyophilized to obtain the title product as white solid (0.045 gm, 15.7%). LCMS: Purity 99.23%. MS calculated for [M] 329.06 and found $[M+H]^+$ 329.92. $^1$H NMR (400 MHz, $D_2O$): δ 7.48-7.40 (m, 5H), 5.20-5.16 (m, 2H), 4.44-4.35 (m, 1H), 3.91-3.84 (m, 2H), 3.73-3.69 (m, 1H), 2.69-2.64 (m, 1H), 2.37-2.30 (m, 1H).

Step 6: Synthesis of (3R,5S)-1-((benzyloxy)carbonyl)-5-(morpholine-4-carbonyl)pyrrolidine-3-sulfonic acid (2S,4R)-1-((Benzyloxy)carbonyl)-4-sulfopyrrolidine-2-carboxylic acid (0.4 gm, 1.21 mmol, 1.0 eq) was dissolved in DMF (4.0 mL) and the mixture was cooled to 0° C. 1-Propanephosphonic acid cyclic anhydride (50% in ethyl acetate, 1.15 mL, 1.82 mmol, 1.5 eq) and triethyl amine (0.5 mL, 3.63 mmol, 3.0 eq) were added and the reaction mixture was stirred at 0° C. for 0.5 h. Then morpholine (0.159 gm, 1.82 mmol, 1.5 eq) was added and the reaction mixture was stirred for 16 h, allowing temperature to gradually rise to ambient temperature. After complete consumption of starting material, reaction mixture was diluted with water (10 mL) and washed with ethyl acetate (2×12 mL). The resulting aqueous layer was concentrated under reduced pressure to get 1.5 gm of crude compound. 0.75 gm of the crude obtained was purified by prep HPLC on Waters Sunfire C18 OBD column. The fractions with desired product were concentrated and lyophilized to obtain the title product as off-white solid (0.05 gm, 20.0%). LCMS: Purity 98.50%. MS calculated for [M] 398.11 and found $[M+H]^+$ 399.15. $^1$H NMR (400 MHz, $D_2O$): δ 7.47-7.39 (m, 5H), 5.10-5.01 (m, 2H), 4.95-4.89 (m, 1H, merged with solvent peak), 4.06-4.03 (m, 1H), 3.81-3.67 (m, 2H), 3.62-3.57 (m, 4H), 3.49-3.38 (m, 3H), 3.32-3.28 (m, 1H), 2.73 (m, 1H), 2.11-2.08 (m, 1H).

Step 7: Compound 2086

The product from the previous step was deprotected as described in Step 6 of Example 15.

Example 21. Synthesis of Compound 2084

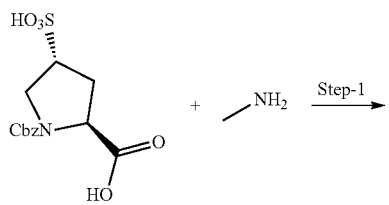

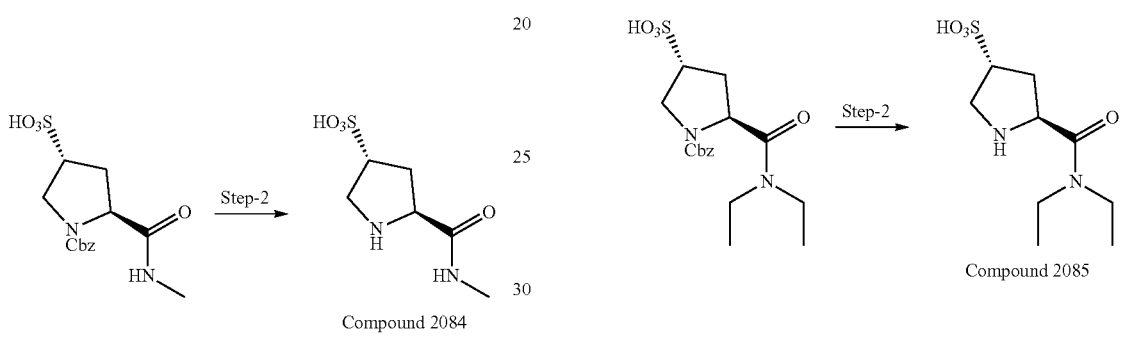

Compound 2084

Step 1: Synthesis of (3R,5S)-1-((benzyloxy)carbonyl)-5-(methylcarbamoyl)pyrrolidine-3-sulfonic acid (2S,4R)-1-((benzyloxy)carbonyl)-4-sulfopyrrolidine-2-carboxylic acid (0.4 gm, 1.21 mmol, 1.0 eq) was dissolved in DMF (4.0 mL) and the mixture was cooled to 0° C. 1-Propanephosphonic acid cyclic anhydride (50% in ethyl acetate, 1.15 mL, 1.82 mmol, 1.5 eq) and triethyl amine (0.8 mL, 6.05 mmol, 5.0 eq) were added and the reaction mixture was stirred at 0° C. for 0.5 h. Then methyl amine hydrochloride (0.164 gm, 2.42 mmol, 2.0 eq) was added and the reaction mixture was stirred for 16 h, allowing temperature to gradually rise to ambient temperature. After complete consumption of starting material, reaction mixture was diluted with water (10 mL) and washed with ethyl acetate (3×12 mL). The resulting aqueous layer was concentrated under reduced pressure and the crude obtained was purified by prep HPLC on Waters Sunfire C18 OBD column. The fractions with desired product were concentrated and lyophilized to obtain the title product as light brown solid (0.035 gm, 17.0%). LCMS: Purity 98.72%. MS calculated for [M] 342.09 and found [M+H]$^+$ 343.12. $^1$H NMR (400 MHz, D$_2$O): δ 7.46-7.36 (m, 5H), 5.19-5.02 (m, 2H), 4.39-4.35 (m, 1H), 4.10-3.99 (m, 1H), 3.77-3.59 (m, 2H), 2.75 (s, 1.5H), 2.72-2.66 (m, 1H), 2.56 (s, 1.5H), 2.25-2.19 (m, 1H).

Step 2: Compound 2084

The product from the previous step was deprotected as described in Step 6 of Example 15.

Example 22. Synthesis of Compound 2085

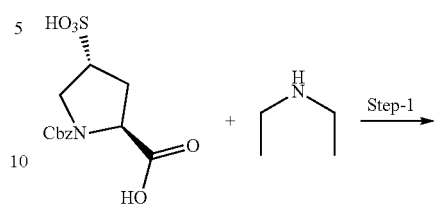

Compound 2085

Step 1: Synthesis of (3R,5S)-1-((benzyloxy)carbonyl)-5-(diethylcarbamoyl)pyrrolidine-3-sulfonic acid (2S,4R)-1-((Benzyloxy)carbonyl)-4-sulfopyrrolidine-2-carboxylic acid (0.4 gm, 1.21 mmol, 1.0 eq) was dissolved in DMF (4.0 mL) and the mixture was cooled to 0° C. 1-Propanephosphonic acid cyclic anhydride (50% in ethyl acetate, 1.15 mL, 1.82 mmol, 1.5 eq) and triethyl amine (0.5 mL, 3.63 mmol, 3.0 eq) were added and the reaction mixture was stirred at 0° C. for 0.5 h. Then diethyl amine (0.134 gm, 1.82 mmol, 1.5 eq) was added and the reaction mixture was stirred for 16 h, allowing temperature to gradually rise to ambient temperature. After complete consumption of starting material, reaction mixture was diluted with water (10 mL) and washed with DCM (2×12 mL). The resulting aqueous layer was concentrated under reduced pressure to get 0.7 gm of crude compound. 0.35 gm of the crude obtained was purified by prep HPLC on Waters Sunfire C18 OBD column. The fractions with desired product were concentrated and lyophilized to obtain the title product as light brown solid (0.042 gm, 9.0%). LCMS: Purity 97.59%. MS calculated for [M] 384.45 and found [M+H]$^+$ 385.14. $^1$H NMR (400 MHz, D$_2$O): δ 7.45-7.35 (m, 5H), 5.16-5.01 (m, 2H), 4.03-4.01 (m, 1H), 3.75 (bs, 1H), 3.63-3.58 (m, 1H), 3.45 (m, 1H), 3.32-3.22 (m, 3H), 3.11-3.07 (m, 1H), 2.74-2.71 (m, 1H), 2.12-2.09 (m, 1H), 1.26-1.22 (t, J=8.0 Hz, 1H), 1.13-1.09 (t, J=8.0 Hz, 1H), 0.97-0.90 (m, 4H).

Step 2: Compound 2085

The product from the previous step was deprotected as described in Step 6 of Example 15.

Example 23. Synthesis of Compound 2083

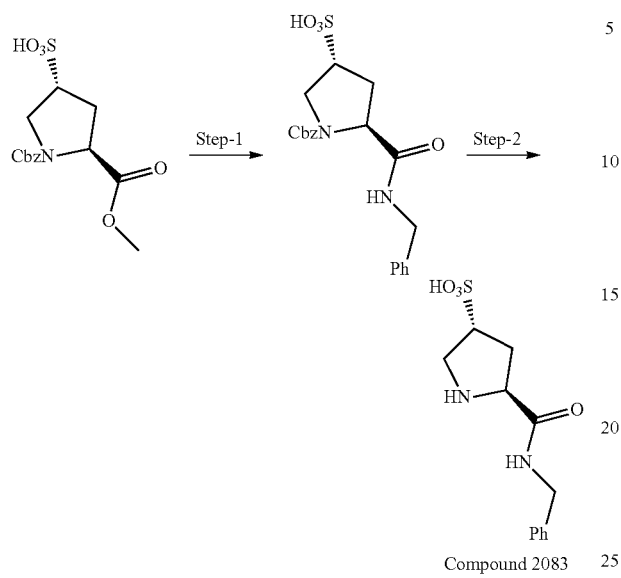

Compound 2083

Step 1: Synthesis of (3R,5S)-5-(benzylcarbamoyl)-1-((benzyloxy)carbonyl)pyrrolidine-3-sulfonic acid

(3R,5S)-1-((Benzyloxy)carbonyl)-5-(methoxycarbonyl)pyrrolidine-3-sulfonic acid (0.3 gm, 0.87 mmol, 1.0 eq) was dissolved in benzyl amine (3.0 mL) and the mixture was heated at 60° C. for 16 h. After complete consumption of starting material, reaction mixture was diluted with ethyl acetate (15 mL), precipitated solid was filtered and washed with diethyl ether (2×9 mL). The residue was then dried under vacuum and purified by prep HPLC on Waters Sunfire C18 OBD column. The fractions with desired product were concentrated and lyophilized to obtain the title product as white solid (0.055 gm, 15.1%). LCMS: Purity 99.20%. MS calculated for [M] 418.12 and found [M+H]$^+$ 419.09. $^1$H NMR (400 MHz, D$_2$O): δ 7.46-7.20 (m, 10H), 5.21-5.10 (m, 2H), 4.59-4.55 (m, 1H), 4.48-4.23 (m, 2H), 3.96-3.85 (m, 2H), 3.77-3.73 (m, 1H), 2.72-2.70 (m, 1H), 2.41-2.36 (m, 1H).

Step 2: Compound 2083

The product from the previous step was deprotected as described in Step 6 of Example 15.

Example 24. Synthesis of Compound 2087

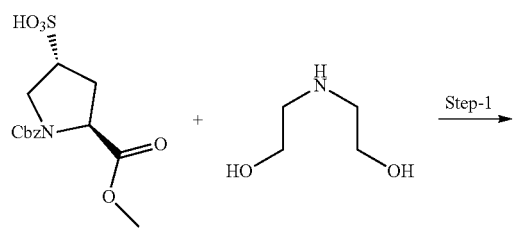

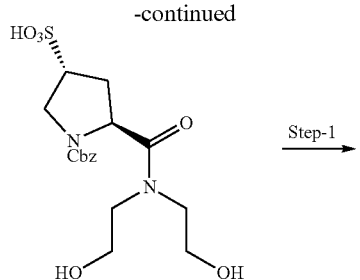

Compound 2087

Step 1: Synthesis of (3R,5S)-1-((benzyloxy)carbonyl)-5-(bis(2-hydroxyethyl)carbamoyl)pyrrolidine-3-sulfonic acid

(3R,5S)-1-((Benzyloxy)carbonyl)-5-(methoxycarbonyl)pyrrolidine-3-sulfonic acid (0.40 gm, 1.16 mmol, 1.0 eq) and 2,2'-azanediylbis(ethan-1-ol) (0.61 gm, 5.8 mmol, 5.0 eq) were mixed and the mixture was heated at 80° C. for 5 h. After complete consumption of starting material, reaction mixture was diluted with water (10 mL) and washed with DCM (3×10 mL). The resulting aqueous layer was concentrated under reduced pressure and the crude obtained was purified by prep HPLC on Waters Sunfire C18 OBD column. The fractions with desired product were concentrated and lyophilized to obtain the title product as off-white solid (0.065 gm, 13.4%). ELSD-MS: Purity 92.5%. MS calculated for [M] 416.13 and found [M+H]$^+$ 417.20. $^1$H NMR (400 MHz, D$_2$O): δ 7.45-7.38 (m, 5H), 5.16-5.03 (m, 2H), 4.89-4.87 (m, 1H), 4.04 (m, 1H), 3.81-3.74 (m, 2H), 3.68-3.58 (m, 2H), 3.54-3.22 (m, 6H), 2.76-2.73 (m, 1H), 2.16-2.13 (m, 1H).

Step 2: Compound 2087

The product from the previous step was deprotected as described in Step 6 of Example 15.

Example 25. Syntheses of Cyclopentylamine Based Library Compounds

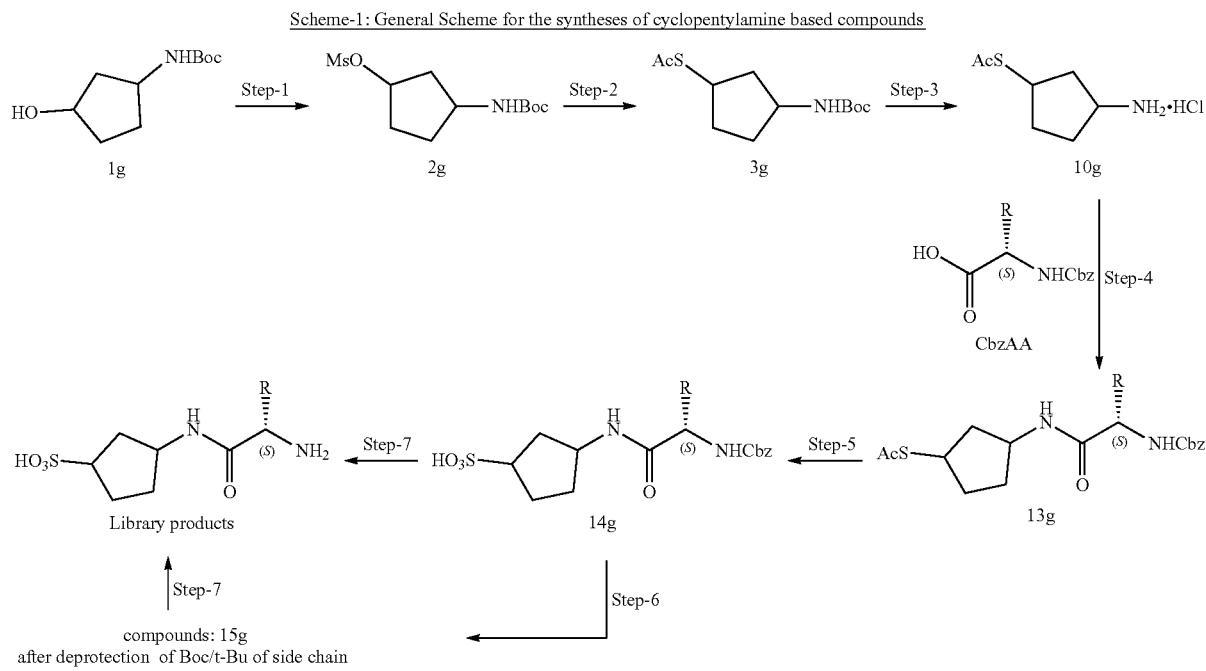

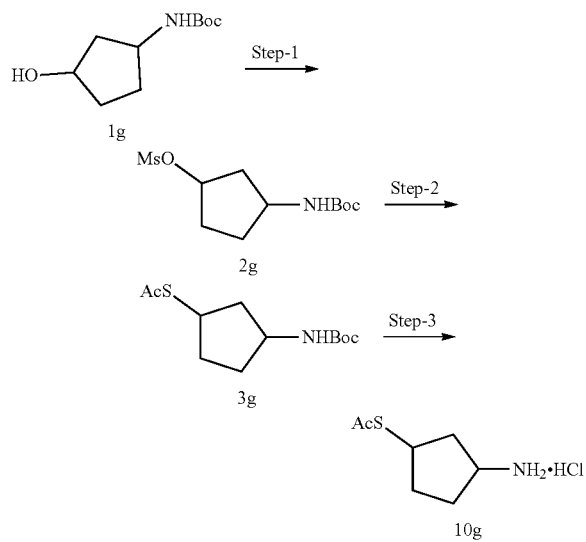

Step-1: Synthesis of 3-((tert-butoxycarbonyl)amino)cyclopentyl methanesulfonate (2g)

Tert-butyl (3-hydroxycyclopentyl)carbamate, 1g (40.0 gm, 198.7 mmol, 1.0 eq) was dissolved in DCM (400 mL) and the solution was cooled to 0° C. Then methanesulfonyl chloride (23.2 mL, 298.1 mmol, 1.5 eq) and triethyl amine (55.3 mL, 397.5 mmol, 2.0 eq) were added and the mixture was stirred at 0° C. for 2 h. After complete consumption of starting material, reaction mixture was diluted with water (400 mL), separated the DCM layer and washed it again washed with water (2×400 mL). The organic extract was separated, dried over anhydrous $Na_2SO_4$, filtered and solvents evaporated from the filtrate under reduced pressure to obtain 2g as light yellow colour solid (54.0 gm, 97.0%). LC-MS: Low UV Response. MS calculated for [M]279.11 and found [M+H]$^+$ 280.09. $^1$H NMR (400 MHz, CDCl$_3$): δ 5.13 (s, 1H), 4.72 (s, 1H), 4.11 (s, 1H), 3.00 (s, 3H), 2.38-2.31 (m, 1H), 2.11-2.09 (s, 2H), 1.95-1.85 (m, 2H), 1.71-1.63 (m, 1H), 1.44 (s, 9H).

Step-2: Synthesis of S-(3-((tert-butoxycarbonyl)amino)cyclopentyl) ethanethioate (3g)

3-((tert-butoxycarbonyl)amino)cyclopentyl methanesulfonate, 2g (30.0 gm, 107.4 mmol, 1.0 eq) was dissolved in DMF (300 mL). Potassium thioacetate (18.4 gm, 161.1 mmol, 1.5 eq) was added and the mixture was heated at 60° C. for 2 h. After complete consumption of starting material, reaction mixture was cooled to ambient temperature and diluted with chilled water (300 mL). The mixture was then extracted with ethyl acetate (2×600 mL). The organic extract was again washed with cold water (1×600 mL) followed by cold brine (1×600 mL), dried over anhydrous $Na_2SO_4$, filtered and solvents evaporated from the filtrate under reduced pressure. The crude residue obtained was purified by column chromatography on silica gel, 100-200 mesh, using 0-6% gradient of EtOAc in hexanes as eluent. The fractions containing the desired product were concentrated to obtain 3g as brown liquid (20.5 gm, 74.0%). LC-MS: Purity 94.96%. MS calculated for [M] 259.12 and found [M+H]$^+$ 260.05. $^1$H NMR (400 MHz, CDCl$_3$): δ 4.51 (s, 1H), 4.07 (s, 1H), 3.83-3.79 (t, J=8.0 Hz, 1H), 2.29 (s, 3H), 2.26-2.10 (m, 2H), 1.99-1.90 (m, 2H), 1.57-1.47 (m, 2H), 1.43 (s, 9H).

Step-3: Synthesis of S-(3-aminocyclopentyl) ethanethioate hydrochloride (10g)

S-(3-((tert-butoxycarbonyl)amino)cyclopentyl) ethanethioate, 3g (20.5 gm, 79.04 mmol, 1.0 eq) was dissolved in 1,4-Dioxane (200 mL) and the solution was cooled to 0° C. Then 4N HCl in 1,4-dioxane (200 mL) was added and the mixture was stirred for 3 h, during which, the temperature was allowed to rise from 0° C. to ambient temperature. After complete consumption of starting material solvents evaporated from the reaction mixture under reduced pressure and the crude obtained was triturated with diethyl ether. The precipitated solid was filtered and dried under vacuum to obtain 10g as light brown solid (14.0 gm, 91.0%). LC-MS: Purity 97.79%. MS calculated for [M] 159.07 and found [M+H]$^+$ 160.03. $^1$H NMR (400 MHz, D$_2$O): δ 3.94-3.76 (m, 2H), 2.36 (s, 3H), 2.31-2.21 (m, 3H), 2.15-2.08 (m, 1H), 1.76-1.70 (m, 2H).

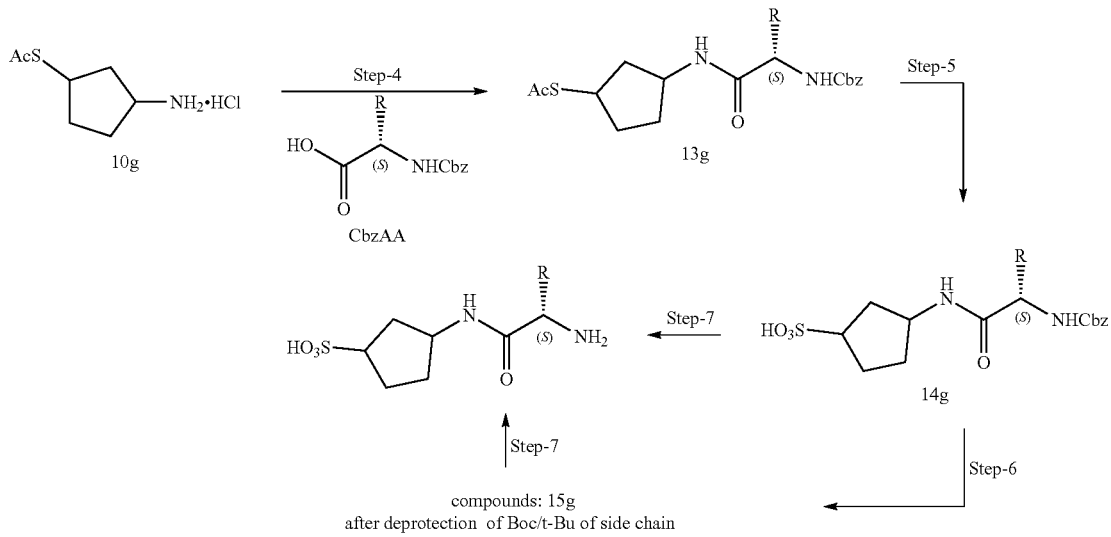

Scheme-3: General Scheme for library syntheses compounds: 15g
after deprotection of Boc/t-Bu of side chain

General Experimental Procedure for Step-4:

Cbz-protected amino acid CbzAA (1.0 eq) was dissolved in DCM and the mixture was cooled to 0° C. DIPEA (3.0 eq) and HATU (1.5 eq) were added and the reaction mixture was stirred at 0° C. for 0.5 h. Then S-(3-aminocyclopentyl) ethanethioate hydrochloride 10g (1.0 eq) was added and the reaction mixture was stirred for 16 h, allowing temperature to gradually rise to ambient temperature. After complete consumption of starting material, reaction mixture was quenched with water. The mixture was then extracted with DCM (3×). The organic extract was again washed with water (3×) followed by saturated aq. NaHCO$_3$ (1×), dried over anhydrous Na$_2$SO$_4$, filtered and solvents evaporated from the filtrate under reduced pressure. The crude residue obtained was purified by flash chromatography on silica gel, 230-400 mesh, using gradient of EtOAc in hexanes as eluent. The fractions containing the desired product were concentrated to obtain corresponding 13g_1 to 14.

| ID | Amino acid | Structure | 1H NMR | Mass |
|---|---|---|---|---|
| 13g_1 | CbzAA_1 (CbzHN-CH$_2$-COOH) | SAc-cyclopentyl-NH-C(O)-CH$_2$-NHCbz | $^1$H NMR (400 MHz, CDCl$_3$): δ 7.36 (bs, 5H), 5.97 (bs, 3H), 5.34 (bs, 1H), 5.20 (s, 2H), 4.36-4.31 (m, 1H), 3.82 (s, 2H), 2.30 (s, 3H), 2.20-2.09 (m, 2H), 1.96-1.94 (d, J = 8.0 Hz, 2H), 1.43-1.33 (m, 2H). | [M + H]: 351.17 |

-continued

| ID | Amino acid | Structure | 1H NMR | Mass |
|---|---|---|---|---|
| 13g_2 | 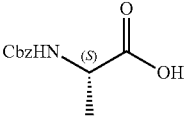<br>CbzAA_2 | 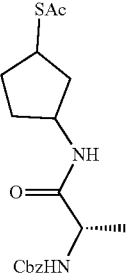 | ¹H NMR (400 MHz, CDCl₃): δ 7.35 (s, 5H), 6.07 (bs, 1H), 5.28 (bs, 1H), 5.11 (s, 2H), 4.32-4.29 (m, 1H), 4.14-4.11 (m, 1H), 3.80 (bs, 1H), 2.29 (s, 3H), 2.18-2.13 (m, 2H), 1.95-1.93 (d, J = 8.0 Hz, 2H), 1.58-1.41 (m, 2H), 1.36-1.34 (d, J = 8.0 Hz, 3H). | [M + H]: 136.17 |
| 13g_3 | <br>CbzAA_3 | 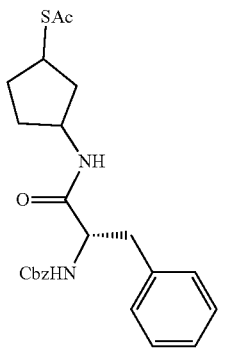 | ¹H NMR (400 MHz, CDCl₃): δ 7.35-7.28 (m, 8H), 7.19 (bs, 2H), 5.39 (bs, 2H), 5.09 (s, 2H), 4.27-4.18 (m, 2H), 3.67-3.59 (m, 1H), 3.16-3.10 (m, 1H), 2.96-2.93 (m, 1H), 2.29 (s, 3H), 2.09-2.03 (m, 2H), 1.87-1.77 (m, 2H), 1.66-1.47 (m, 2H). | [M + H]: 441.18 |
| 13g_4 | 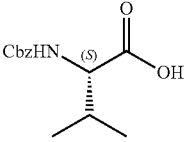<br>CbzAA_4 | 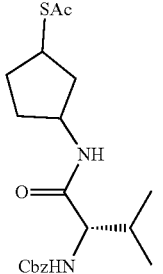 | ¹H NMR (400 MHz, CDCl₃): δ 7.35 (s, 5H), 5.88 (bs, 1H), 5.30 (bs, 1H), 5.10 (s, 2H), 4.33-4.31 (d, 1H, J = 8.0 Hz), 3.89-3.81 (m, 2H), 2.29 (s, 3H), 2.15 (bs, 3H), 1.96 (bs, 2H), 1.60-1.47 (bs, 1H), 1.44 (bs 1H), 0.95-0.90 (m, 6H). | [M + H]: 393.23 |
| 13g_5 | 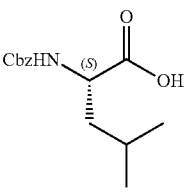<br>CbzAA_5 | 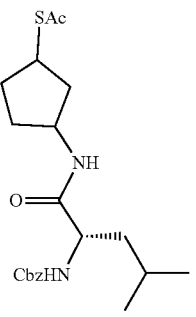 | ¹H NMR (400 MHz, D₂O): δ 7.34 (s, 5H), 5.10 (m, 3H), 4.29 (bs, 1H), 4.08 (bs, 1H), 3.80 (bs, 1H), 2.29 (s, 3H), 2.20-2.12 (m, 2H), 1.95-1.94 (d, J = 4.0 Hz, 2H), 1.59-1.44 (m, 4H), 0.9.3-0.92 (d, J = 4.0 Hz, 6H). | [M + H]: 407.24 |
| 13g_6 | 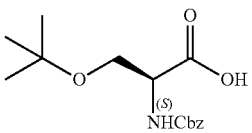<br>CbzAA_6 | 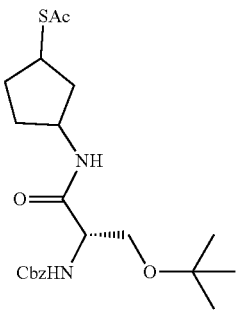 | ¹H NMR (400 MHz, CDCl₃): δ 7.36 (s, 5H), 6.65 (bs, 1H), 5.69 (bs, 1H), 5.12 (s, 2H), 4.34-4.31 (m, 1H), 4.14-4.11 (d, 1H, d, J = 12 Hz,) 3.80 (bs, 2H), 3.33 (bs, 1H) 2.29 (s, 3H), 2.23-2.16 (m, 2H), 1.96 (bs, 2H), 1.48-1.46 (d,, 1H, d, J = 8.0 Hz,), 1.25 (s 1H), 1.18 (s, 9H). | [M + H]: 437.27 |

-continued

| ID | Amino acid | Structure | 1H NMR | Mass |
|---|---|---|---|---|
| 13g_7 | CbzAA_7 | 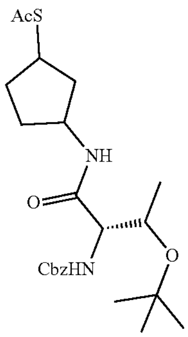 | — | — |
| 13g_8 | CbzAA_8 | 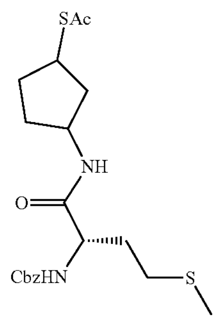 | ¹H NMR (400 MHz, CDCl₃): δ 7.35 (s, 5H), 5.11 (s, 2H), 4.33-4.26 (m, 2H), 3.82-3.78 (m, 1H), 2.58-2.45 (m, 2H), 2.30 (s, 3H), 2.22-2.02 (m, 3H), 1.96 (m, 3H), 1.58-1.43 (m, 5H). | [M + H]: 425.25 |
| 13g_9 | CbzAA_9 | 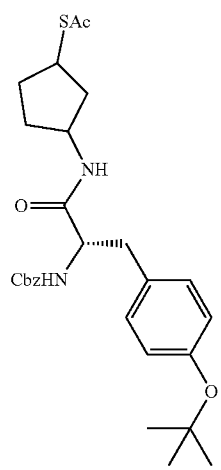 | ¹H NMR (400 MHz, CDCl₃): δ 7.33 (s, 5H), 7.08-7.06 (d, J = 8.0 Hz, 2H), 6.92-6.90 (d, J = 8.0 Hz, 2H), 5.09 (s, 2H), 4.24-4.19 (m, 2H), 3.70-3.66 (t, J = 8.0 Hz, 1H), 3.10-3.05 (m, 1H), 2.93-2.87 (m, 1H), 2.28-2.27 (d, J = 4.0 Hz, 3H), 2.08-1.99 (m, 2H), 1.88-1.82 (m, 2H), 1.53-1.46 (m, 1H), 1.32 (s, 9H), 1.16-1.11 (m, 1H). | [M + H]: 513.30 |
| 13g_10 | CbzAA_10 | 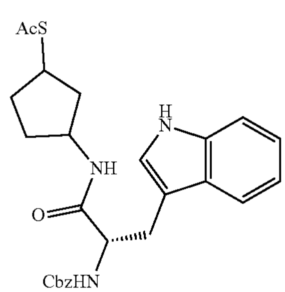 | — | — |

-continued

| ID | Amino acid | Structure | 1H NMR | Mass |
|---|---|---|---|---|
| 13g_11 | CbzAA_11 | 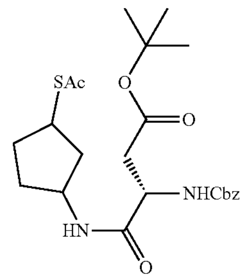 | — | [M + H]: 465.29 |
| 13g_12 | CbzAA_12 | 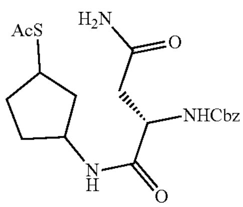 | — | — |
| 13g_13 | CbzAA_13 | 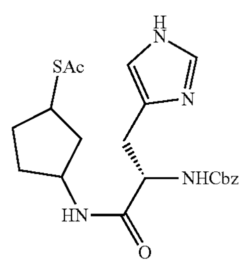 | — | [M + H]: 431.25 |
| 13g_14 | CbzAA_14 | 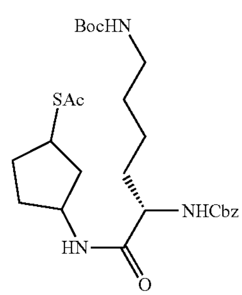 | $^1$H NMR (400 MHz, CDCl$_3$): δ 7.34 (s, 5H), 6.32 (bs, 1H), 5.50 (bs, 1H), 5.09 (s, 2H), 4.63 (bs, 1H), 4.30-4.28 (d, J = 8.0 Hz, 1H), 4.05 (s, 1H), 3.82-3.79 (t, J = 8.0 Hz, 1H), 3.09 (s, 2H), 2.29 (s, 3H), 2.20-1.12 (m, 2H), 1.96-1.92 (t, J = 8.0 Hz, 2H), 1.83-181 (d, J = 8.0 Hz, 1H), 1.64-1.37 (m, 16H). | [M + H]: 522.31 |

General Experimental Procedure for Step-5:

13g (1.0 eq) was dissolved in AcOH. Sodium acetate trihydrate (1.0 eq) and 33% H$_2$O$_2$ (9.0 eq) were added and the mixture was heated at 60° C. for 3 h. After complete consumption of starting material, reaction mixture was cooled to ambient temperature and solvents evaporated under reduced pressure. The resulting residue was dissolved in water and washed with DCM (3×). The aqueous layer was concentrated under vacuum and triturated with ether. The resulting residue was lyophilized to obtain corresponding 14g.

| ID | Structure | 1H NMR | Mass |
|---|---|---|---|
| 14g_1 | 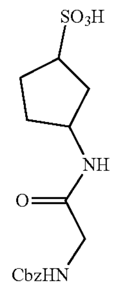 [SMILES: O=C(CNC(=O)OCc1ccccc1)NC1CCC(S(=O)(=O)O)C1] | 1H NMR (400 MHz, D2O,): δ 7.45 (s, 5H), 5.15 (s, 2H), 4.28 (s, 1H), 3.78-3.76 (d, J = 8.0 Hz, 2H), 3.50-3.47 (m, 1H), 2.27-1.90 (m, 6H). | [M + H]: 375.15 |
| 14g_2 | 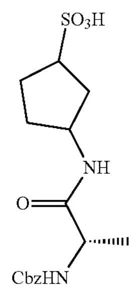 [SMILES: C[C@H](NC(=O)OCc1ccccc1)C(=O)NC1CCC(S(=O)(=O)O)C1] | 1H NMR (400 MHz, D2O,): δ 7.45-7.44 (d, J = 4.0 Hz, 5H), 5.14 (s, 2H), 4.21 (s, 1H), 4.05 (s, 1H), 3.49-3.47 (d, J = 8.0 Hz, 1H), 2.43-1.94 (m, 6H), 1.32 (s, 3H). | [M + H]: 371.09 |
| 14g_3 | 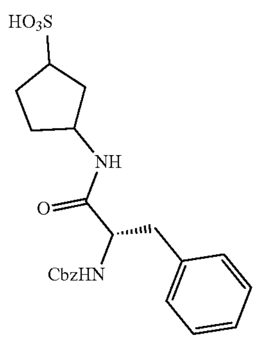 [SMILES: O=C(N[C@@H](Cc1ccccc1)C(=O)NC1CCC(S(=O)(=O)O)C1)OCc1ccccc1] | 1H NMR (400 MHz, D2O, mixture of cis-isomer and trans-isomer): δ 7.44-7.35 (s, 8H), 7.25 (s, 2H), 5.08 (s, 2H), 4.26 (s, 1H), 4.12 (s, 1H), 3.87 (s, 1H), 3.57-3.35 (m, 2H), 3.01-2.84 (m, 3H), 2.20-1.51 (m, 7H), 1.28-1.18 (m, 1H). | [M + H]: 447.18 |
| 14g_4 | 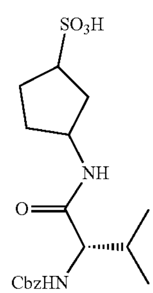 [SMILES: CC(C)[C@H](NC(=O)OCc1ccccc1)C(=O)NC1CCC(S(=O)(=O)O)C1] | — | [M + H]: 399.47 |
| 14g_5 | 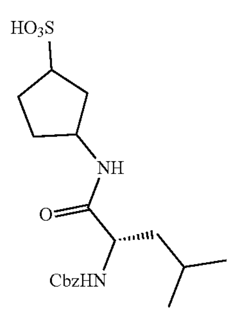 [SMILES: CC(C)C[C@H](NC(=O)OCc1ccccc1)C(=O)NC1CCC(S(=O)(=O)O)C1] | 1H NMR (400 MHz, D2O, mixture of cis-isomer and trans-isomer): δ 7.43 (s, 6H), 5.21-5.04 (m, 3H), 4.36-4.22 (m, 1H), 4.12-3.99 (m, 2H), 3.92-3.71 (m, 1H), 3.59-3.26 (m, 2H), 2.77-1.40 (m, 18H), 0.92-0.88 (m, 10H). | [M + H]: 413.45 |

| ID | Structure | 1H NMR | Mass |
|---|---|---|---|
| 14g_6 | 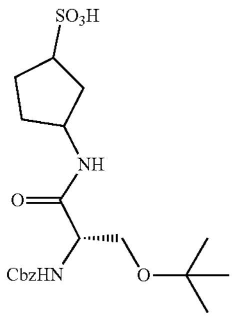 [SMILES: CC(C)(C)OC[C@H](NC(=O)OCc1ccccc1)C(=O)NC1CCC(S(=O)(=O)O)C1] | 1H NMR (400 MHz, D2O): δ 7.42 (bs, 5H), 5.18 (s, 2H), 4.22 (s, 1H), 4.13-4.12 (m, 1H), 3.63 (s, 2H), 3.56-3.54 (m, 1H), 2.02-1.90 (m, 5H), 1.72.1.53 (m, 1H), 1.16 (m, 9H). | [M + H]: 443.24 |
| 14g_7 | 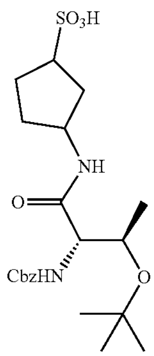 [SMILES: C[C@@H](OC(C)(C)C)[C@H](NC(=O)OCc1ccccc1)C(=O)NC1CCC(S(=O)(=O)O)C1] | — | — |
| 14g_8 | 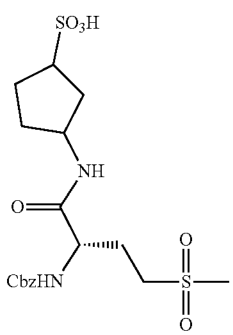 [SMILES: CS(=O)(=O)CC[C@H](NC(=O)OCc1ccccc1)C(=O)NC1CCC(S(=O)(=O)O)C1] | 1H NMR (400 MHz, D2O): δ 7.35 (bs, 5H), 5.05 (s, 2H), 4.11 (s, 2H), 3.48-3.39 (m, 1H), 3.21 (s, 2H), 3.00 (s, 3H), 2.14-2.00 (m, 5H), 1.92-1.81 (m, 2H), 1.54-1.48 (m, 1H). | [M + H]: 463.00 |
| 14g_9 | 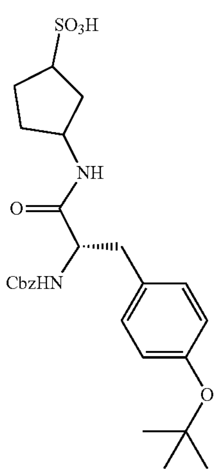 [SMILES: CC(C)(C)Oc1ccc(C[C@H](NC(=O)OCc2ccccc2)C(=O)NC2CCC(S(=O)(=O)O)C2)cc1] | 1H NMR (400 MHz, D₂O): δ 7.31-7.24 (m, 5H), 7.06-7.04 (d, J = 8.0 Hz, 2H), 6.90-6.88 (d, J = 8.0 Hz, 2H), 5.01-4.91 (m, 2H), 4.09-3.88 (m, 2H), 3.27-2.47 (m, 3H), 2.16-1.36 (m, 6H), 1.20 (s, 9H). | [M + H]: 519.34 |

-continued

| ID | Structure | 1H NMR | Mass |
|---|---|---|---|
| 14g_10 | 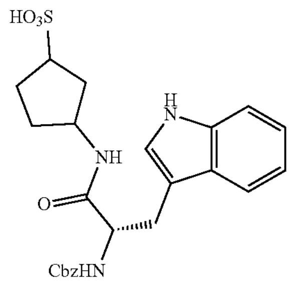 [SMILES: O=C(N[C@@H](Cc1c[nH]c2ccccc12)C(=O)NC1CCC(S(=O)(=O)O)C1)OCc1ccccc1] | — | — |
| 14g_11 | 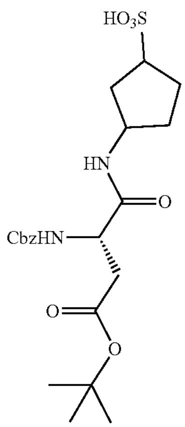 [SMILES: CC(C)(C)OC(=O)C[C@H](NC(=O)OCc1ccccc1)C(=O)NC1CCC(S(=O)(=O)O)C1] | — | [M + H]: 415.26 |
| 14g_12 | 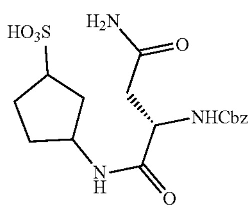 [SMILES: NC(=O)C[C@H](NC(=O)OCc1ccccc1)C(=O)NC1CCC(S(=O)(=O)O)C1] | — | — |
| 14g_13 | 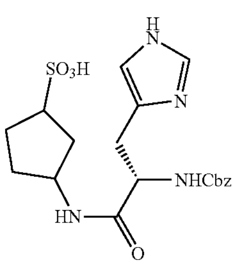 [SMILES: O=C(N[C@@H](Cc1c[nH]cn1)C(=O)NC1CCC(S(=O)(=O)O)C1)OCc1ccccc1] | — | — |
| 14g_14 | 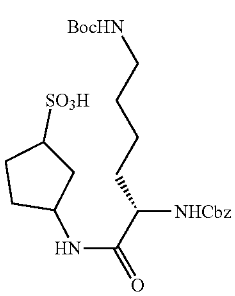 [SMILES: CC(C)(C)OC(=O)NCCCC[C@H](NC(=O)OCc1ccccc1)C(=O)NC1CCC(S(=O)(=O)O)C1] | — | [M + H]: 528.35 |

General Experimental Procedure for Step-6:

14g (1.0 eq) was dissolved in the mixture of THF and DCM (1:9) and the solution was cooled to 0° C. Then TFA (50%, v/v) was added and the mixture was stirred for 4 h, during which, the temperature was allowed to rise from 0° C. to ambient temperature. After complete consumption of starting material, solvents evaporated from the reaction mixture under reduced pressure and the crude obtained was triturated with diethyl ether to obtain corresponding 15g.

| ID | Structure | 1H NMR | Mass |
|---|---|---|---|
| 15g_6 | (structure) | — | [M + H]: 387.42 |
| 15g_7 | (structure) | — | — |
| 15g_9 | (structure) | 1H NMR (400 MHz, D2O): δ 7.37-7.31 (m, 3H), 7.26-7.24 (d, J = 8.0 Hz, 2H), 7.03 (bs, 2H), 6.78-6.74 (m, 2H), 5.05-4.92 (m, 2H), 4.12-4.02 (m, 2H), 3.30-2.70 (m, 3H), 2.04-1.58 (m, 5H), 1.58-1.19 (m, 1H). | [M + H]: 463.44 |
| 15g_11 | (structure) | — | — |
| 15g_14 | (structure) | — | [M + H]: 428.52 |

General Experimental Procedure for Step-7:

14g or 15g (1.0 eq) were dissolved in methanol under nitrogen atmosphere. Pd/C (10% w/w, 50% moisture, w/w) was added and the mixture was stirred under hydrogen atmosphere (hydrogen balloon) at room temperature for 6 h. After complete consumption of starting material, reaction mixture was diluted with methanol and filtered through a celite bed. Then celite bed was thoroughly washed with methanol (3×). Mixture of filtrate and washings was concentrated under reduced pressure. The crude compound was dissolved in water and filtered through 0.2 micron syringe filter. The filtrate was concentrated and the crude obtained was purified by prep HPLC. The fractions with desired product were concentrated and lyophilized to obtain corresponding compounds in the following table.

| ID | Structure |
|---|---|
| 2007 | (structure) |
| 2008 | (structure) |

| ID | Structure |
|---|---|
| 2009 | 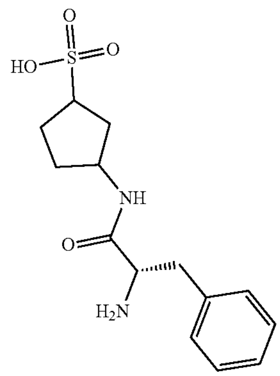 [SMILES: N[C@@H](Cc1ccccc1)C(=O)NC1CCC(S(=O)(=O)O)C1] |
| 2010 | 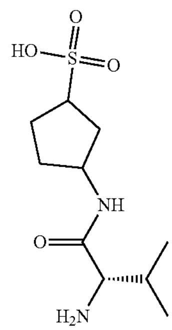 [SMILES: CC(C)[C@H](N)C(=O)NC1CCC(S(=O)(=O)O)C1] |
| 2011 | 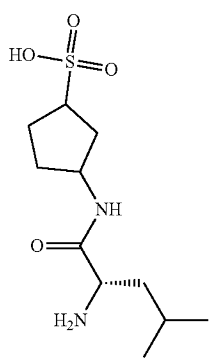 [SMILES: CC(C)C[C@H](N)C(=O)NC1CCC(S(=O)(=O)O)C1] |
| 2012 | 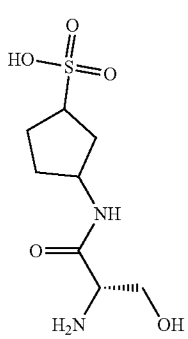 [SMILES: N[C@@H](CO)C(=O)NC1CCC(S(=O)(=O)O)C1] |

| ID | Structure |
|---|---|
| 2013 | 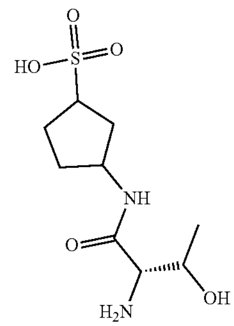 [SMILES: CC(O)[C@H](N)C(=O)NC1CCC(S(=O)(=O)O)C1] |
| 2014 | 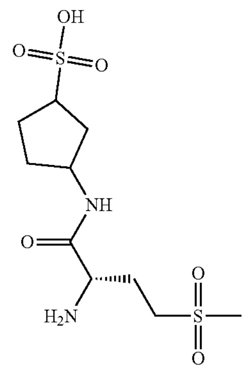 [SMILES: CS(=O)(=O)CC[C@H](N)C(=O)NC1CCC(S(=O)(=O)O)C1] |
| 2015 | 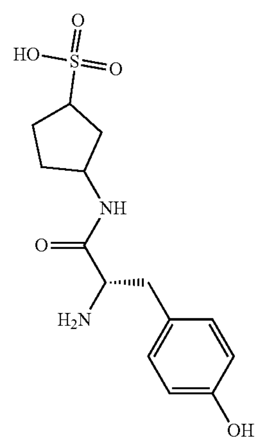 [SMILES: N[C@@H](Cc1ccc(O)cc1)C(=O)NC1CCC(S(=O)(=O)O)C1] |
| 2016 | 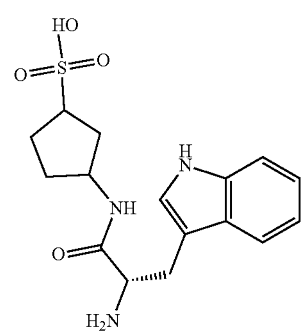 [SMILES: N[C@@H](Cc1c[nH]c2ccccc12)C(=O)NC1CCC(S(=O)(=O)O)C1] |

| ID | Structure |
|---|---|
| 2017 | |
| 2018 | |
| ID | Structure |
|---|---|
| 2019 | |
| 2020 | |
Example 26. Syntheses of Cyclopentyl Carboxylic Acid Based Compounds
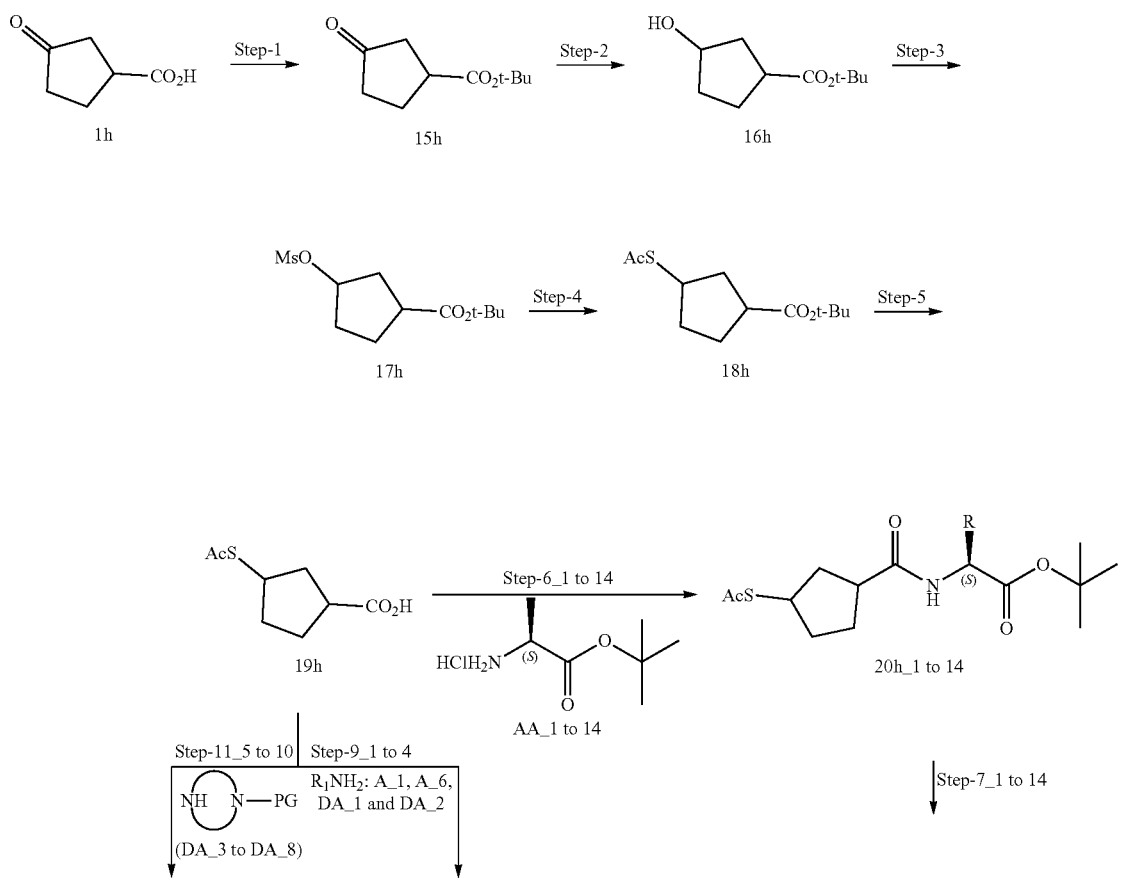
Scheme-1: General Scheme for the syntheses of cyclopentyl carboxylic acid based compounds

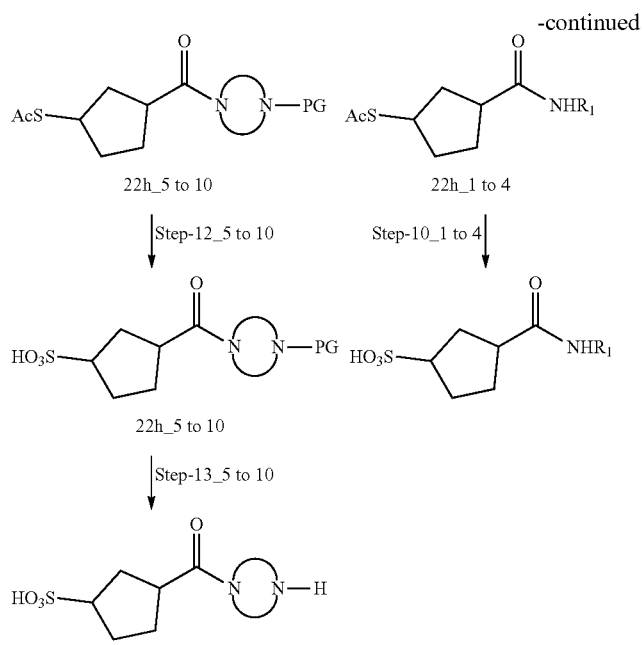

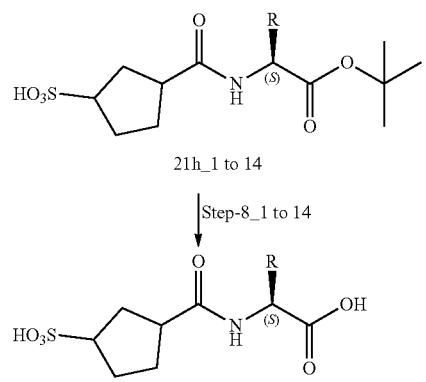

Scheme-2: Preparation of scaffold 19h (used for library synthesis)

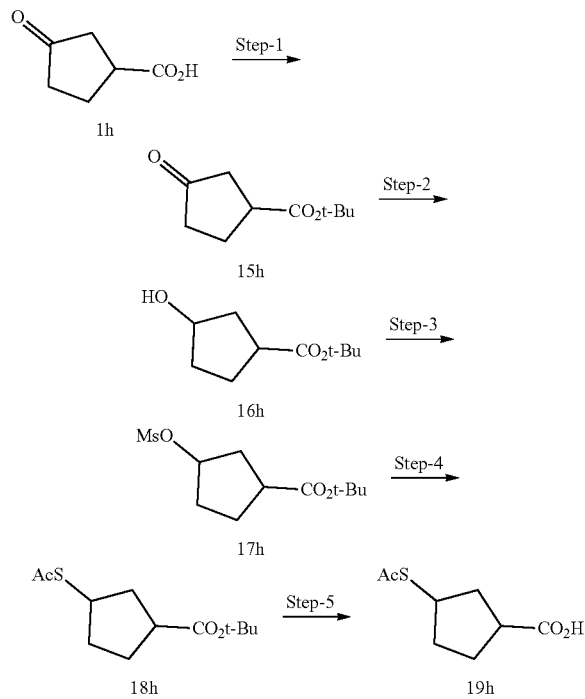

Step-1: Synthesis of tert-butyl 3-oxocyclopentane-1-carboxylate (15h)

3-oxocyclopentane-1-carboxylic acid, h (5.0 gm, 39.8 mmol, 1.0 eq) was dissolved in DCM (50 mL) and the solution was cooled to 0° C. Then DCC (12.0 g, 58.8 mmol, 1.5 eq), DMAP (0.476 g, 3.9 mmol, 0.1 eq) and t-butanol (3.46 g, 46.8 mmol, 1.2 eq) were added and the mixture was stirred from 0° C. to 5° C. for 3 h. After complete consumption of starting material, diethyl ether (50 mL) was added to reaction mixture, filtered out the precipitate and washed the precipitate with diethyl ether (3×50 mL). The combined filtrate and washings was evaporated under reduced pressure to obtain a crude product. The crude residue obtained was purified by column chromatography on silica gel, 100-200 mesh, using 30-40% gradient of EtOAc in hexanes as eluent. The fractions containing the desired product were concentrated to give 15h as yellowish liquid (4.5 gm, 61.98%). $^1$H NMR (400 MHz, CDCl$_3$): δ 3.04-2.98 (m, 1H), 2.51-2.37 (m, 3H), 2.35-2.11 (m, 3H), 1.46 (s, 9H).

Step-2: Synthesis of tert-butyl 3-hydroxycyclopentane-1-carboxylate (16h)

Tert-butyl 3-oxocyclopentane-1-carboxylate, 15h (4.5 gm, 24.45 mmol, 1.0 eq) was dissolved in THF (45 mL) and the mixture was cooled to 0° C. Then sodium borohydride (1.115 gm, 29.34 mmol, 1.2 eq) was added and the mixture was stirred for 16 h. During stirring, temperature of the reaction mixture gradually allowed to increase to ambient temperature. After completion consumption of the starting material, the mixture was quenched with saturated aq. ammonium chloride (45 mL). The mixture was then extracted with ethyl acetate (2×45 mL). The organic extract was separated, dried over anhydrous Na$_2$SO$_4$, filtered and solvents evaporated from the filtrate to obtain a crude residue. The crude residue obtained was purified by column chromatography on silica gel, 100-200 mesh, using 40-50% gradient of ethyl acetate in hexane as eluent. The fractions with the desired product were concentrated to obtain 16h as a yellow liquid (4.10 gm, 90.3%). $^1$H NMR (400 MHz, CDCl$_3$): δ 4.29 (bs, 1H), 2.86-2.78 (m, 2H), 2.01-1.92 (m, 4H), 1.83-1.72 (m, 2H), 1.43 (s, 9H).

Step-3: Synthesis of tert-butyl 3-((methylsulfonyl)oxy)cyclopentane-1-carboxylate (17h)

Tert-butyl 3-hydroxycyclopentane-1-carboxylate, 16h (4.1 gm, 22.04 mmol, 1.0 eq) was dissolved in pyridine (41 mL) and the solution was cooled to 0° C. Then methanesulfonyl chloride (6.03 gm, 52.90 mmol, 2.4 eq) was added and the mixture was stirred for 3 h, during which, the temperature was allowed to rise from 0° C. to ambient temperature. After complete consumption of starting material, reaction mixture was diluted with water (41 mL) and extracted with DCM (2×41 mL). The organic extract was separated, dried over anhydrous $Na_2SO_4$, filtered and solvents evaporated from the filtrate under reduced pressure. The crude residue obtained was purified by column chromatography on silica gel, 230-400 mesh, using 0-40% gradient of EtOAc in hexanes as eluent. The fractions containing the desired product were concentrated to obtain 17h as colorless liquid (4.0 gm, 68.84%). $^1$H NMR (400 MHz, $CDCl_3$): δ 5.12 (s, 1H), 3.00-2.95 (m, 3H), 2.75-2.71 (m, 1H), 2.28-1.85 (m, 6H), 1.44 (s, 9H).

Step-4: Synthesis of tert-butyl 3-(acetylthio)cyclopentane-1-carboxylate (18h)

Tert-butyl 3-((methylsulfonyl)oxy)cyclopentane-1-carboxylate, 17h (4.0 gm, 15.14 mmol, 1.0 eq) was dissolved in DMF (40 mL). Then Potassium thioacetate (2.59 gm, 22.71 mmol, 1.5 eq) was added and the mixture was heated at 60° C. for 16 h. After complete consumption of starting material, reaction mixture was cooled to ambient temperature and diluted with chilled water (40 mL). The mixture was then extracted with diethyl ether (2×80 mL). The organic extract was again washed with cold water (1×80 mL) followed by cold brine (1×132 mL), dried over anhydrous $Na_2SO_4$, filtered and solvents evaporated from the filtrate under reduced pressure. The crude residue obtained was purified by column chromatography on silica gel, 100-200 mesh, using 0-20% gradient of EtOAc in hexanes as eluent. The fractions containing the desired product were concentrated to obtain 18h as colorless liquid (3.5 gm, 94.85%). $^1$H NMR (400 MHz, $CDCl_3$): δ 3.87-3.84 (m, 1H), 2.83-2.79 (m, 1H), 2.32 (s, 3H), 2.29-1.80 (m, 6H), 1.43 (s, 9H).

Step-5: Synthesis of 3-(acetylthio)cyclopentane-1-carboxylic acid (19h)

Tert-butyl 3-(acetylthio)cyclopentane-1-carboxylate, 18h (3.5 gm, 14.34 mmol, 1.0 eq) was dissolved in DCM (48 mL) and the solution was cooled to 0° C. Then TFA (12 mL) was added to reaction mixture and the mixture was stirred for 2 h, during which, the temperature was allowed to rise from 0° C. to ambient temperature. After complete consumption of starting material, solvents evaporated from the reaction mixture under reduced pressure to obtain 19h as red liquid (3.5 gm, Crude). $^1$H NMR (400 MHz, $D_2O$): δ 12.15 (s, 1H), 3.11-3.08 (m, 1H), 2.84-2.80 (m, 1H), 2.29 (s, 3H), 2.25-2.20 (m, 1H), 2.12-2.07 (m, 1H), 1.96-1.90 (m, 1H), 1.78-1.70 (m, 2H), 1.55-1.48 (m, 1H).

Scheme-3: General Scheme for library syntheses

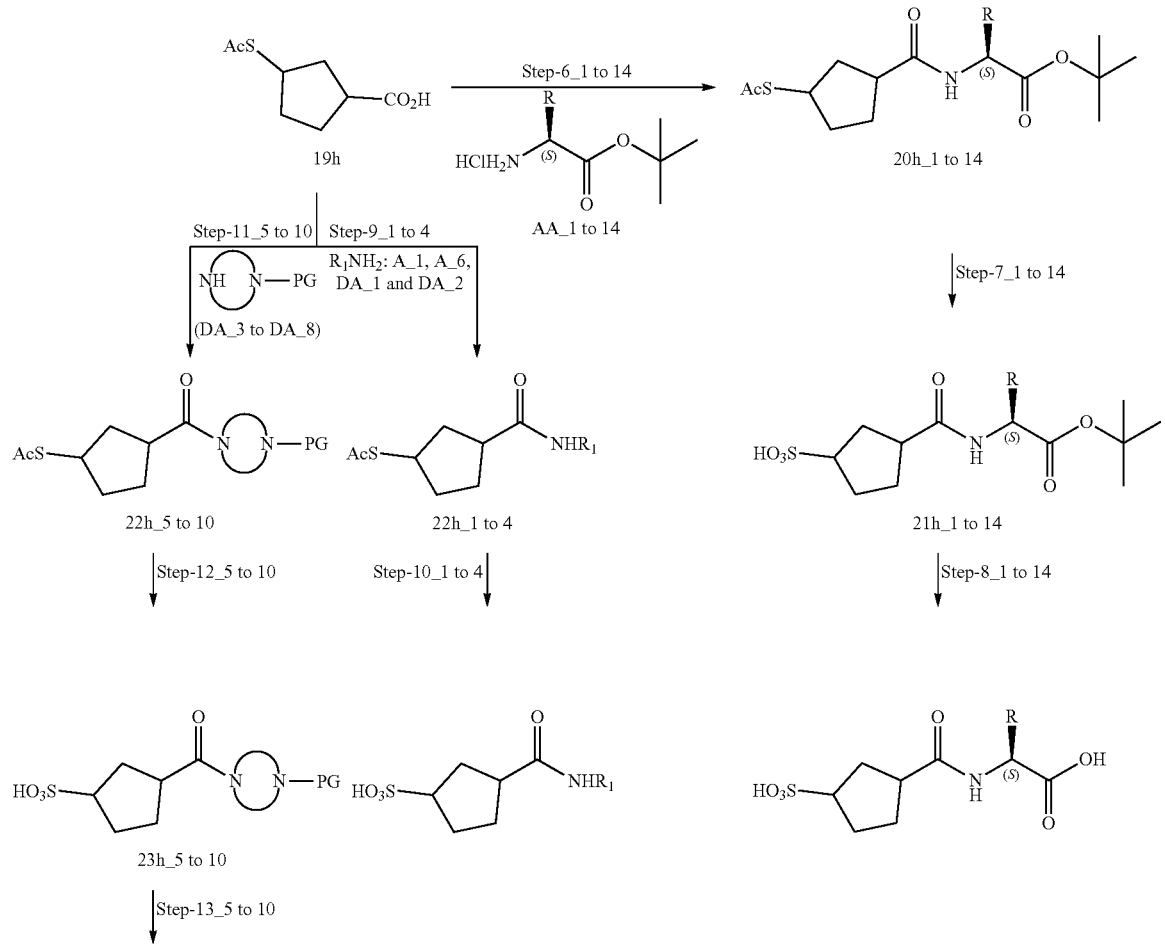

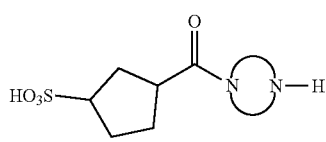

-continued

General Experimental Procedure for Step-6_1 to 14:

Scaffold 19h (1.0 eq) was dissolved in DCM and the mixture was cooled to 0° C. DIPEA (3.0 eq) and HATU (1.5 eq) were added and the reaction mixture was stirred at 0° C. for 0.5 h. Then AA_1 to 14 (1.0 eq) was added and the reaction mixture was stirred for 16 h, allowing temperature to gradually rise to ambient temperature. After complete consumption of starting material, reaction mixture was quenched with water. The mixture was then extracted with DCM (3×). The organic extract was again washed with water (3×) followed by saturated aq. NaHCO$_3$ (1×), dried over anhydrous Na$_2$SO$_4$, filtered and solvents evaporated from the filtrate under reduced pressure. The crude residue obtained was purified by flash chromatography on silica gel, 230-400 mesh, using gradient of EtOAc in hexanes as eluent. The fractions containing the desired product were concentrated to obtain corresponding 20_h1 to 14.

| ID | Amino acid | Structure | 1H NMR | Mass |
|---|---|---|---|---|
| 20h_1 | AA_1 | 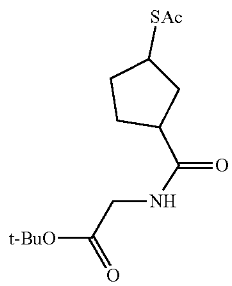 | — | — |
| 20h_2 | AA_2 | 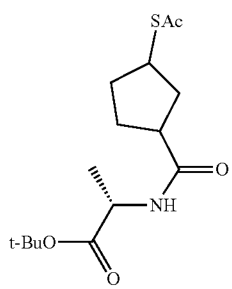 | — | — |
| 20h_3 | AA_3 | 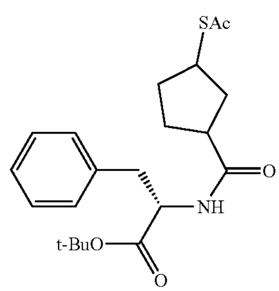 | $^1$H NMR (400 MHz, CDCl$_3$): δ 7.29-7.21 (m, 3H), 7.13-7.12 (d, J = 4.0 Hz, 2H), 5.90-5.88 (d, J = 8.0 Hz, 1H), 4.77-4.72 (m, 1H), 3.91-3.88 (t, J = 8.0 Hz, 1H), 3.10-3.07 (t, J = 8.0 Hz, 2H), 2.69-2.66 (m, 1H), 2.33-2.22 (m, 5H), 1.96-1.78 (m, 3H), 1.63-1.54 (m, 1H), 1.41 (s, 9H). | [M + H]: 392.28 |
| 20h_4 | CbzAA_4 | 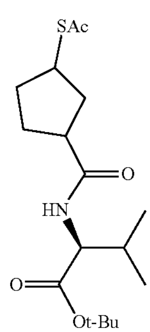 | — | — |

-continued

| ID | Amino acid | Structure | 1H NMR | Mass |
|---|---|---|---|---|
| 20h_5 | AA_5 | 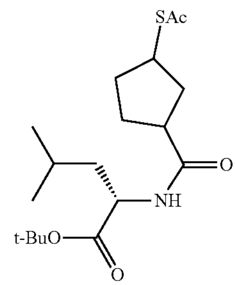 | ¹H NMR (400 MHz, CDCl₃): δ 5.81 (bs, 1H), 4.53-4.50 (t, J = 8.0 Hz, 1H), 3.93-3.89 (t, J = 8.0 Hz, 1H), 2.76-2.72 (t, J = 8.0 Hz, 1H), 2.38-2.33 (m, 1H), 2.29-2.25 (m, 4H) 1.99-1.84 (m, 3H), 1.64-1.50 (m, 4H), 1.45 (s, 9H), 0.94-0.93 (d, t, J = 4.0 Hz, 6H). | [M + H − 56]: 302.24 |
| 20h_6 | AA_6 | 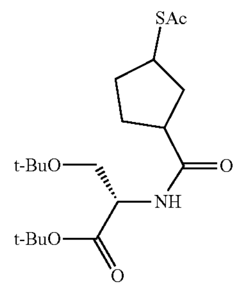 | ¹H NMR (400 MHz, CDCl₃): δ 6.27-6.25 (d, J = 8.0 Hz, 1H), 4.59-4.57 (d, J = 8.0 Hz, 1H), 3.94-3.91 (t, J = 8.0 Hz, 1H), 3.78-3.76 (d, J = 8.0 Hz, 1H), 3.52-3.50 (d, J = 8.0 Hz, 1H), 2.81-2.77 (t, J = 8.0 Hz, 1H), 2.40-2.35 (m, 1H), 2.29-2.26 (m, 4H), 2.03-1.86 (m, 3H), 1.65-1.54 (m, 1H), 1.46 (s, 9H), 1.13 (s, 9H). | [M + H]: 388.34 |
| 20h_7 | AA_7 | 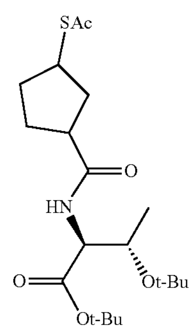 | — | — |
| 20h_8 | AA_8 | 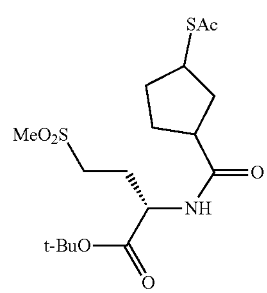 | — | — |
| 20h_9 | AA_9 | 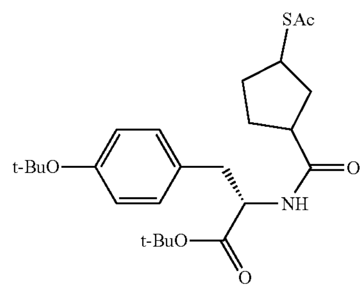 | ¹H NMR (400 MHz, CDCl₃): δ 7.03-7.01 (d, J = 8.0 Hz, 2H), 6.90-6.88 (d, J = 8.0 Hz, 2H), 5.91-5.89 (d, J = 8.0 Hz, 1H), 4.72-4.70 (d, J = 8.0 Hz, 1H), 3.91-3.88 (t, J = 8.0 Hz, 1H), 3.04-3.03 (d, J = 4.0 Hz, 2H), 2.71-2.67 (m, 1H), 2.33-2.24 (m, 5H), 1.96-1.76 (m, 3H), 1.64-1.58 (m, 1H), 1.40 (s, 9H), 1.32 (s, 9H). | [M + H]: 464.37 |

| ID | Amino acid | Structure | 1H NMR | Mass |
|---|---|---|---|---|
| 20h_10 | 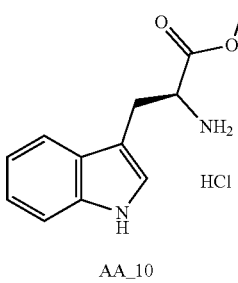 AA_10 | 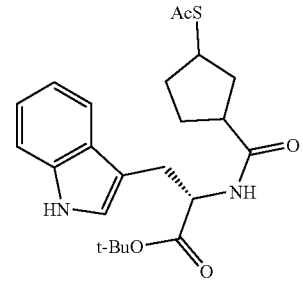 | — | — |
| 20h_11 | 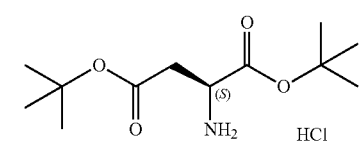 AA_11 | 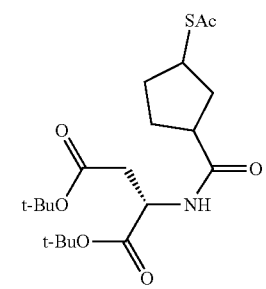 | — | — |
| 20h_12 | 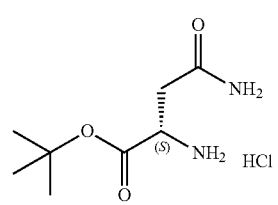 AA_12 | 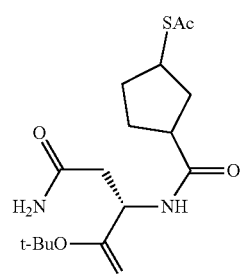 | — | — |
| 20h_13 | 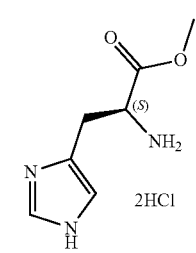 AA_13 | 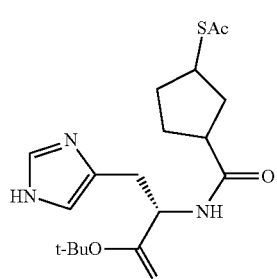 | — | — |
| 20h_14 | 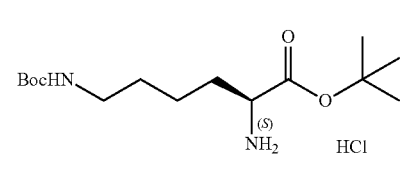 AA_14 | 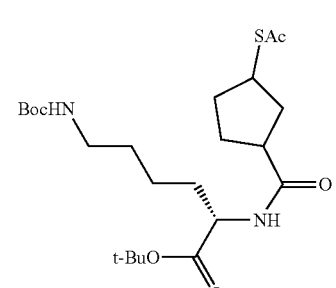 | — | — |

General Experimental Procedure for Step-7_1 to 14:

20h_1 to 14 (1.0 eq) was dissolved in AcOH. Sodium acetate trihydrate (1.0 eq) and 33% $H_2O_2$ (9.0 eq) were added and the mixture was heated at 60° C. for 3 h. After complete consumption of starting material, reaction mixture was cooled to ambient temperature and solvents evaporated under reduced pressure. The resulting residue was dissolved in water and washed with DCM (3×). The aqueous layer was concentrated under vacuum and triturated with ether to obtain corresponding 21h_1 to 14.

| ID | Structure | 1H NMR | Mass |
|---|---|---|---|
| 21h_1 | ![structure] | — | — |
| 21h_2 | ![structure] | — | — |
| 21h_3 | ![structure] | ¹H NMR (400 MHz, D₂O): δ 7.37-7.27 (m, 5H), 4.54 (bs, 2H), 3.43-3.41 (d, J = 8.0 Hz, 1H), 3.19-3.15 (d, J = 16.0 Hz, 1H), 3.00 (bs, 1H), 2.88-2.86 (d, J = 8.0 Hz, 1H), 2.10-1.93 (m, 5H), 1.40-1.33 (m, 9H). | [M + H]: 464.37 |
| 21h_4 | ![structure] | — | — |

-continued
| ID | Structure | 1H NMR | Mass |
|---|---|---|---|
| 21h_5 | 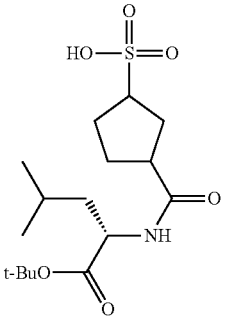 [SMILES: CC(C)C[C@H](NC(=O)C1CCC(S(=O)(=O)O)C1)C(=O)OC(C)(C)C] | — | — |
| 21h_6 | 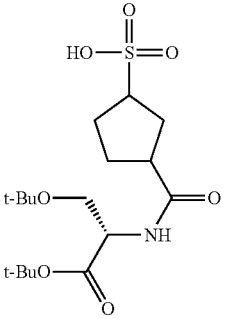 [SMILES: CC(C)(C)OC[C@H](NC(=O)C1CCC(S(=O)(=O)O)C1)C(=O)OC(C)(C)C] | — | — |
| 21h_7 | 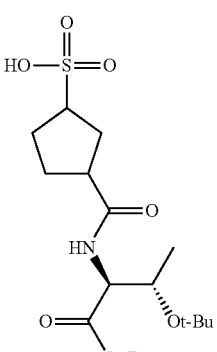 | — | — |
| 21h_8 | 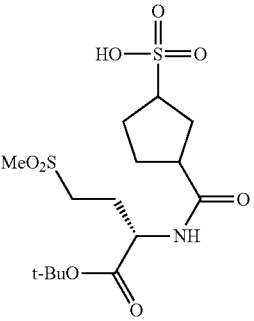 [SMILES: CC(C)(C)OC(=O)[C@H](CCS(C)(=O)=O)NC(=O)C1CCC(S(=O)(=O)O)C1] | — | — |

-continued

| ID | Structure | 1H NMR | Mass |
|---|---|---|---|
| 21h_9 | 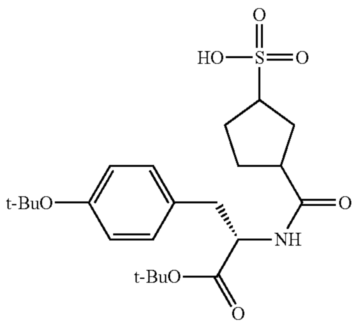 [SMILES: CC(C)(C)OC(=O)[C@H](Cc1ccc(OC(C)(C)C)cc1)NC(=O)C1CCC(S(=O)(=O)O)C1] | — | — |
| 21h_10 | 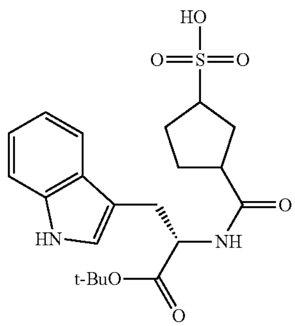 [SMILES: CC(C)(C)OC(=O)[C@H](Cc1c[nH]c2ccccc12)NC(=O)C1CCC(S(=O)(=O)O)C1] | — | — |
| 21h_11 | 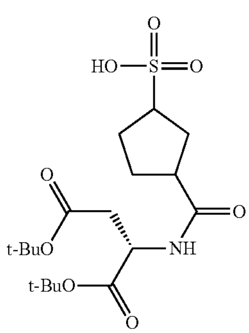 [SMILES: CC(C)(C)OC(=O)C[C@H](NC(=O)C1CCC(S(=O)(=O)O)C1)C(=O)OC(C)(C)C] | — | — |
| 21h_12 | 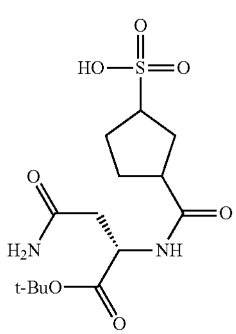 [SMILES: CC(C)(C)OC(=O)[C@H](CC(N)=O)NC(=O)C1CCC(S(=O)(=O)O)C1] | — | — |

| ID | Structure | 1H NMR | Mass |
|---|---|---|---|
| 21h_13 | 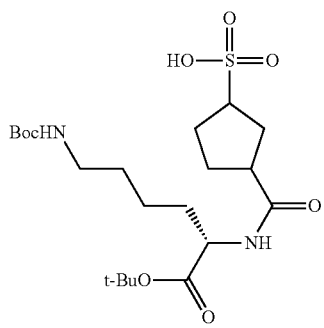 | — | — |
| 21h_14 | 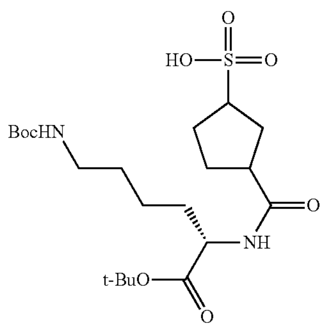 [SMILES: CC(C)(C)OC(=O)NCCCC[C@H](NC(=O)C1CCC(S(=O)(=O)O)C1)C(=O)OC(C)(C)C] | — | — |

General Experimental Procedure for Step-8_1 to 14:

21h_1 to 14 (1.0 eq) was dissolved in the mixture of DCM and the solution was cooled to 0° C. Then TFA (50%, v/v) was added and the mixture was stirred for 2 h, during which, the temperature was allowed to rise from 0° C. to ambient temperature. After complete consumption of starting material, solvents evaporated from the reaction mixture under reduced pressure and the crude obtained was triturated with diethyl ether to obtain the following compounds of the invention:

| ID | Structure |
|---|---|
| 2032 | |
| 2033 | 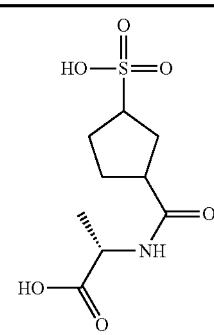 |
| 2034 | 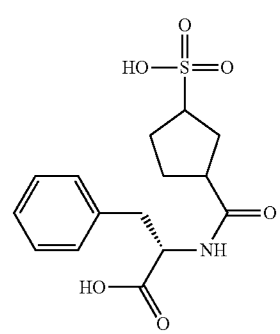 [SMILES: O=C(N[C@@H](Cc1ccccc1)C(=O)O)C1CCC(S(=O)(=O)O)C1] |

| ID | Structure |
|---|---|
| 2035 | 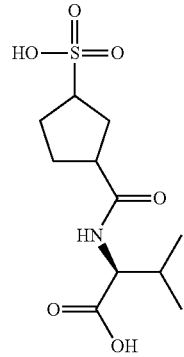 [SMILES: CC(C)[C@H](NC(=O)C1CCC(S(=O)(=O)O)C1)C(=O)O] |
| 2036 | 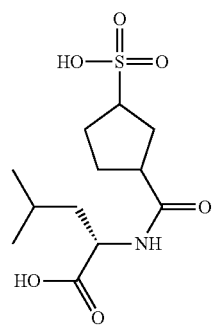 [SMILES: CC(C)C[C@H](NC(=O)C1CCC(S(=O)(=O)O)C1)C(=O)O] |
| 2037 | 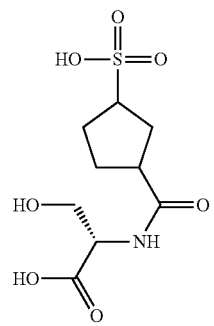 [SMILES: O=C(N[C@@H](CO)C(=O)O)C1CCC(S(=O)(=O)O)C1] |
| 2038 | 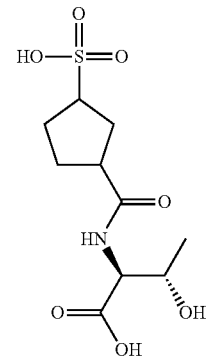 |
| ID | Structure |
|---|---|
| 2039 | 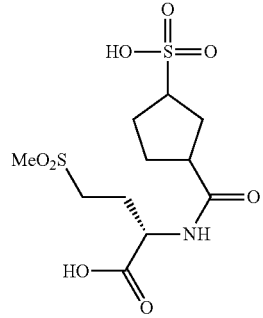 [SMILES: CS(=O)(=O)CC[C@H](NC(=O)C1CCC(S(=O)(=O)O)C1)C(=O)O] |
| 2040 | 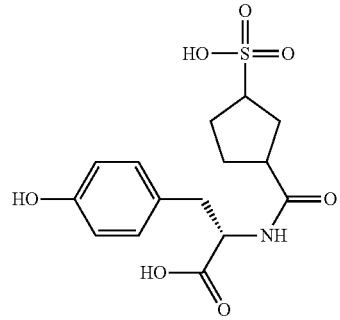 |
| 2041 | 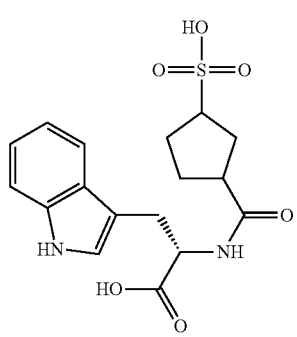 [SMILES: O=C(N[C@@H](Cc1c[nH]c2ccccc12)C(=O)O)C1CCC(S(=O)(=O)O)C1] |
| 2042 | 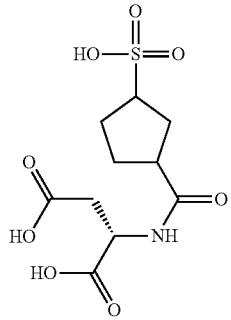 [SMILES: O=C(O)C[C@H](NC(=O)C1CCC(S(=O)(=O)O)C1)C(=O)O] |

| ID | Structure |
|---|---|
| 2043 | (structure: cyclopentane with SO3H and amide-linked asparagine) |
| 2044 | (structure: cyclopentane with SO3H and amide-linked histidine) |
| 2045 | (structure: cyclopentane with SO3H and amide-linked lysine) |

General Experimental Procedure for Step-9_1 to 4:

Scaffold 19h (1.0 eq) was dissolved in DCM and the mixture was cooled to 0° C. DIPEA (3.0 eq) and HATU (1.5 eq) were added and the reaction mixture was stirred at 0° C. for 0.5 h. Then amines A_1, A_6, DA_1 and DA_2 (1.0 eq) was added and the reaction mixture was stirred for 16 h, allowing temperature to gradually rise to ambient temperature. After complete consumption of starting material, reaction mixture was quenched with water. The mixture was then extracted with DCM (3×). The organic extract was again washed with water (3×) followed by saturated aq. NaHCO₃ (1×), dried over anhydrous Na₂SO₄, filtered and solvents evaporated from the filtrate under reduced pressure. The crude residue obtained was purified by flash chromatography on silica gel, 230-400 mesh, using gradient of EtOAc in hexanes as eluent. The fractions containing the desired product were concentrated to obtain corresponding 22h_1 to 4.

| ID | Amino acid | Structure |
|---|---|---|
| 22h_1 | benzylamine (A_1) | cyclopentane-SAc with benzyl amide |
| 22h_2 | NH₃ (A_6) | cyclopentane-SAc with primary amide |
| 22h_3 | Me₂N-C(Me)₂-CH₂NH₂ (DA_1) | cyclopentane-SAc with neopentyl-dimethylamino amide |
| 22h_4 | Bn-NH-CH₂CH₂-NH₂ (DA_2) | cyclopentane-SAc with ethylenediamine-benzyl amide |

General Experimental Procedure for Step-10_1 to 4:

22h_1 to 4 (1.0 eq) was dissolved in AcOH. Sodium acetate trihydrate (1.0 eq) and 33% H₂O₂ (9.0 eq) were added and the mixture was heated at 60° C. for 3 h. After complete consumption of starting material, reaction mixture was cooled to ambient temperature and solvents evaporated under reduced pressure. The resulting residue was dissolved in water and washed with DCM (3×). The aqueous layer was concentrated under vacuum and triturated with ether to obtain corresponding 2030, 2031, 2046, 2047.

| ID | Structure |
|---|---|
| 2030 | 3-(benzylcarbamoyl)cyclopentane-1-sulfonic acid |
| 2031 | 3-carbamoylcyclopentane-1-sulfonic acid |
| 2046 | 3-((3-(dimethylamino)-2,2-dimethylpropyl)carbamoyl)cyclopentane-1-sulfonic acid |
| 2047 | 3-((2-(benzylamino)ethyl)carbamoyl)cyclopentane-1-sulfonic acid |

General Experimental Procedure for Step-11_5 to 10:

Scaffold 19h (1.0 eq) was dissolved in DCM and the mixture was cooled to 0° C. DIPEA (3.0 eq) and HATU (1.5 eq) were added and the reaction mixture was stirred at 0° C. for 0.5 h. Then DA_3 to 8 (1.0 eq) was added and the reaction mixture was stirred for 16 h, allowing temperature to gradually rise to ambient temperature. After complete consumption of starting material, reaction mixture was quenched with water. The mixture was then extracted with DCM (3×). The organic extract was again washed with water (3×) followed by saturated aq. $NaHCO_3$ (1×), dried over anhydrous $Na_2SO_4$, filtered and solvents evaporated from the filtrate under reduced pressure. The crude residue obtained was purified by flash chromatography on silica gel, 230-400 mesh, using gradient of EtOAc in hexanes as eluent. The fractions containing the desired product were concentrated to obtain corresponding 22h_5 to 10.

| ID | Diamines | Structure |
|---|---|---|
| 22h_5 | DA_3: trans-N-Boc-1,2-diaminocyclohexane | AcS-cyclopentane-C(O)NH-cyclohexyl-NHBoc |
| 22h_6 | DA_4: 1-Boc-4-aminopiperidine | AcS-cyclopentane-C(O)NH-(1-Boc-piperidin-4-yl) |

| ID | Diamines | Structure |
|---|---|---|
| 22h_7 | DA_5 | (structure: AcS-cyclopentyl-C(O)-N-piperidine-NHBoc) |
| 22h_8 | DA_6 | (structure: AcS-cyclopentyl-C(O)-N-piperazine-NBoc) |
| 22h_9 | DA_7 | (structure: AcS-cyclopentyl-C(O)-NH-cyclohexyl-NHBoc) |
| 22h_10 | DA_8 | (structure: AcS-cyclopentyl-C(O)-N-pyrrolidine-NHCbz) |

General Experimental Procedure for Step-12_5 to 10:

22h_1 to 10 (1.0 eq) was dissolved in AcOH. Sodium acetate trihydrate (1.0 eq) and 33% $H_2O_2$ (9.0 eq) were added and the mixture was heated at 60° C. for 3 h. After complete consumption of starting material, reaction mixture was cooled to ambient temperature and solvents evaporated under reduced pressure. The resulting residue was dissolved in water and washed with DCM (3×). The aqueous layer was concentrated under vacuum and triturated with ether to obtain corresponding 23h_5 to 10.

| ID | Structure |
|---|---|
| 23h_5 | (HO3S-cyclopentyl-C(O)-NH-cyclohexyl-NHBoc) |
| 23h_6 | (HO3S-cyclopentyl-C(O)-NH-piperidine-Boc) |
| 23h_7 | (HO3S-cyclopentyl-C(O)-N-piperidine-NHBoc) |
| 23h_8 | (HO3S-cyclopentyl-C(O)-N-piperazine-NBoc) |
| 23h_9 | (HO3S-cyclopentyl-C(O)-NH-cyclohexyl-NHBoc) |
| 23h_10 | (HO3S-cyclopentyl-C(O)-N-pyrrolidine-NHCbz) |

General Experimental Procedure A for Step-13_5 to 9:

23h_5 to 9 (1.0 eq) was dissolved in the mixture of DCM and the solution was cooled to 0° C. Then TFA (50%, v/v) was added and the mixture was stirred for 2 h, during which, the temperature was allowed to rise from 0° C. to ambient temperature. After complete consumption of starting material, solvents evaporated from the reaction mixture under reduced pressure and the crude obtained was triturated with diethyl ether to obtain corresponding 2048, 2051, 2052.

General Experimental Procedure B for Step-13_10:

23h_10 (1.0 eq) was dissolved in methanol under nitrogen atmosphere. Pd/C (10% w/w, 50% moisture, w/w) was added and the mixture was stirred under hydrogen atmosphere (hydrogen balloon) at room temperature for 16 h. After complete consumption of starting material, reaction mixture was diluted with methanol and filtered through a celite bed. Then celite bed was thoroughly washed with methanol (3×). Mixture of filtrate and washings was concentrated under reduced pressure. The crude compound was dissolved in water and filtered through 0.2 micron syringe filter. The filtrate was concentrated and lyophilized to obtain the corresponding diamine products Cyclopenylcarboxy-Library Products

| Compound Number PCT | Structure | Mol Weight |
|---|---|---|
| 2110 | 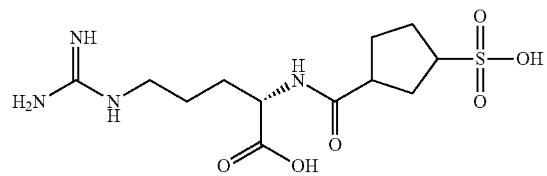 [SMILES: N=C(N)NCCC[C@H](NC(=O)C1CCC(S(=O)(=O)O)C1)C(=O)O] | 350.39 |
| 2111 | 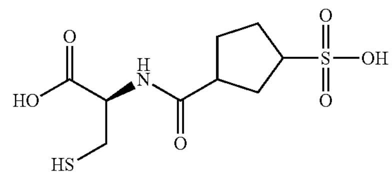 [SMILES: O=C(N[C@@H](CS)C(=O)O)C1CCC(S(=O)(=O)O)C1] | 297.34 |
| 2112 | 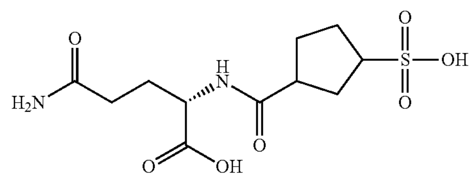 [SMILES: NC(=O)CC[C@H](NC(=O)C1CCC(S(=O)(=O)O)C1)C(=O)O] | 322.33 |
| 2113 | 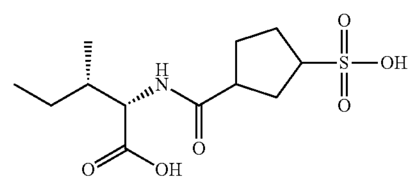 [SMILES: CC[C@H](C)[C@H](NC(=O)C1CCC(S(=O)(=O)O)C1)C(=O)O] | 307.36 |
| 2114 | 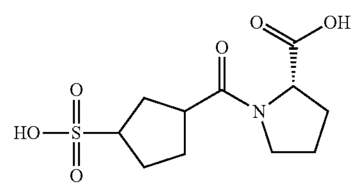 [SMILES: O=C(O)[C@@H]1CCCN1C(=O)C1CCC(S(=O)(=O)O)C1] | 291.32 |
| 2115 | 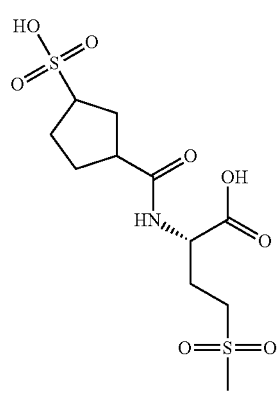 [SMILES: CS(=O)(=O)CC[C@H](NC(=O)C1CCC(S(=O)(=O)O)C1)C(=O)O] | 357.39 |

-continued

| Compound Number PCT | Structure | Mol Weight |
|---|---|---|
| 2030 | 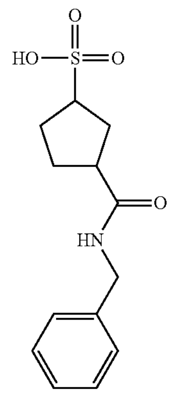 [SMILES: O=C(NCc1ccccc1)C1CCC(S(=O)(=O)O)C1] | 283.34 |
| 2031 | 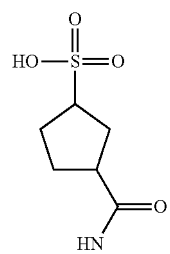 [SMILES: NC(=O)C1CCC(S(=O)(=O)O)C1] | 193.22 |
| 2032 | 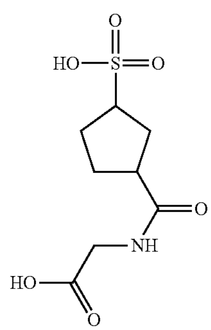 [SMILES: O=C(O)CNC(=O)C1CCC(S(=O)(=O)O)C1] | 251.25 |
| 2033 | 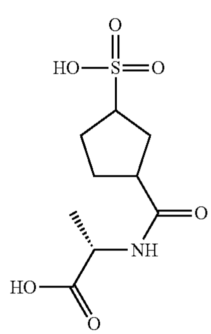 [SMILES: C[C@H](NC(=O)C1CCC(S(=O)(=O)O)C1)C(=O)O] | 265.28 |

123
-continued
| Compound Number PCT | Structure | Mol Weight |
|---|---|---|
| 2034 | 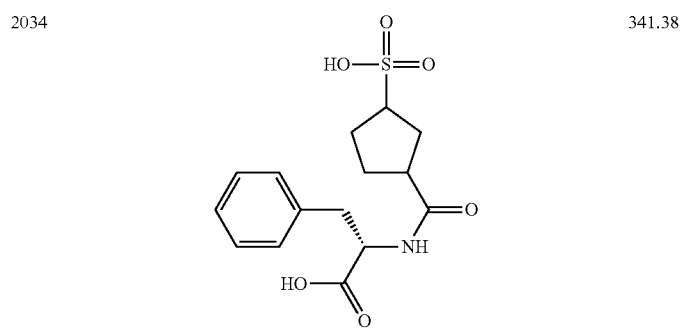 | 341.38 |
| 2035 | 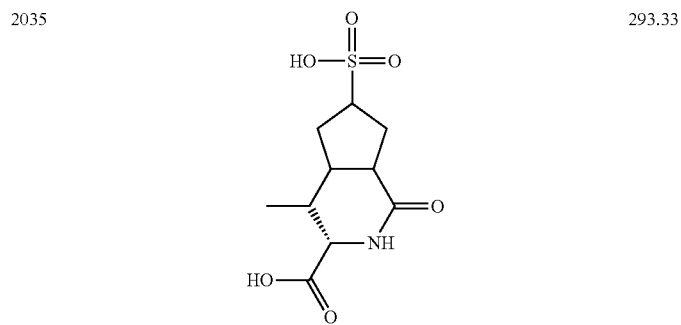 | 293.33 |
| 2036 | 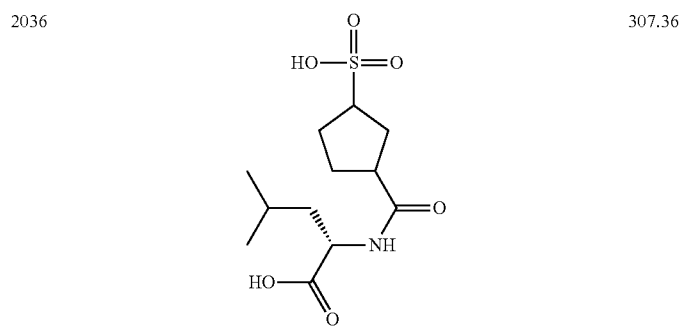 | 307.36 |
| 2037 | 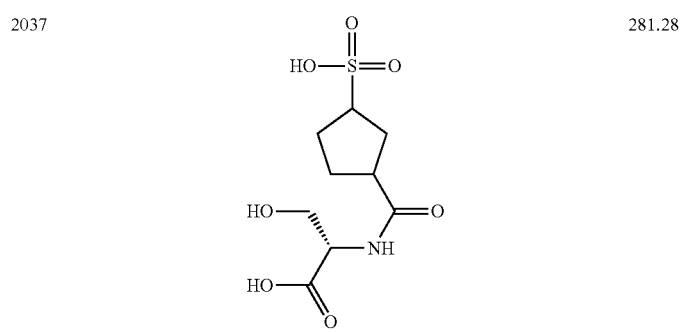 | 281.28 |
124

-continued

| Compound Number PCT | Structure | Mol Weight |
|---|---|---|
| 2038 | 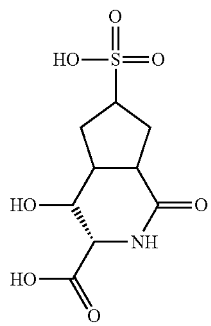 | 295.31 |
| 2039 | 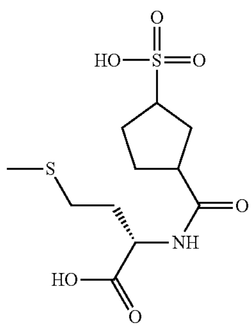 [SMILES: CSCC[C@H](NC(=O)C1CCC(S(=O)(=O)O)C1)C(=O)O] | 325.39 |
| 2040 | 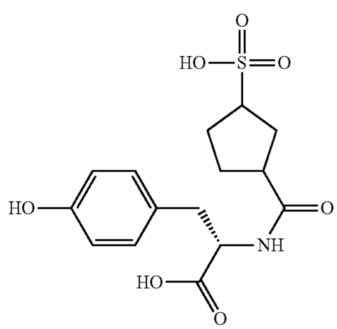 [SMILES: O=C(N[C@@H](Cc1ccc(O)cc1)C(=O)O)C1CCC(S(=O)(=O)O)C1] | 357.38 |
| 2041 | 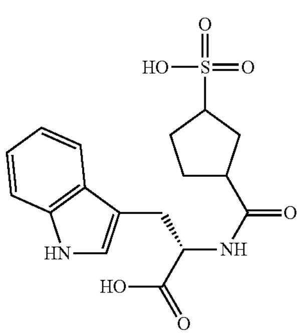 [SMILES: O=C(N[C@@H](Cc1c[nH]c2ccccc12)C(=O)O)C1CCC(S(=O)(=O)O)C1] | 380.42 |

127                                                                    128
-continued

| Compound Number PCT | Structure | Mol Weight |
|---|---|---|
| 2042 | 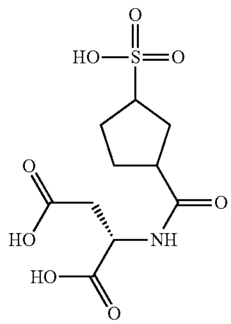 [SMILES: O=C(O)C[C@H](NC(=O)C1CCC(S(=O)(=O)O)C1)C(=O)O] | 309.29 |
| 2043 | 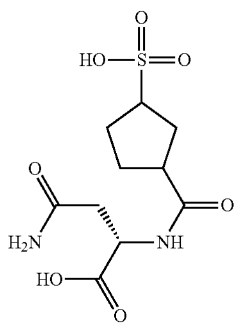 [SMILES: NC(=O)C[C@H](NC(=O)C1CCC(S(=O)(=O)O)C1)C(=O)O] | 308.31 |
| 2044 | 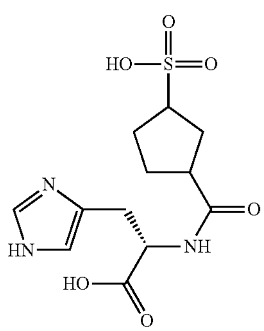 [SMILES: O=C(N[C@@H](Cc1c[nH]cn1)C(=O)O)C1CCC(S(=O)(=O)O)C1] | 331.34 |
| 2045 | 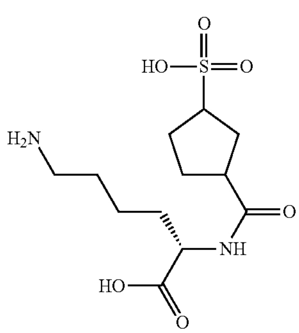 [SMILES: NCCCC[C@H](NC(=O)C1CCC(S(=O)(=O)O)C1)C(=O)O] | 322.38 |

-continued
| Compound Number PCT | Structure | Mol Weight |
|---|---|---|
| 2046 | 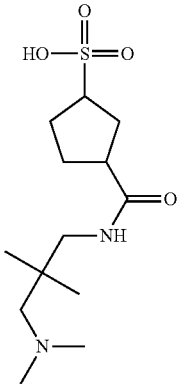 [SMILES: CN(C)CC(C)(C)CNC(=O)C1CCC(S(=O)(=O)O)C1] | 306.42 |
| 2047 | 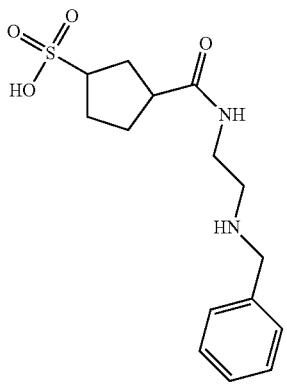 [SMILES: O=C(NCCNCc1ccccc1)C1CCC(S(=O)(=O)O)C1] | 326.41 |
| 2048 | 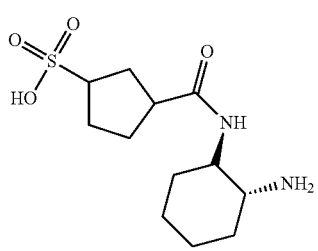 | 290.38 |
| 2049 | 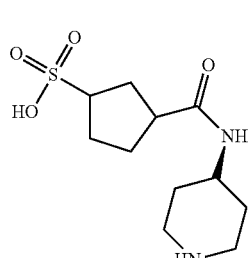 | 276.35 |
| 2050 | 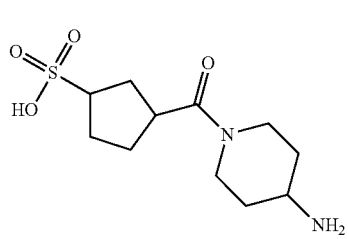 [SMILES: NC1CCN(C(=O)C2CCC(S(=O)(=O)O)C2)CC1] | 276.35 |

| Compound Number PCT | Structure | Mol Weight |
|---|---|---|
| 2051 | 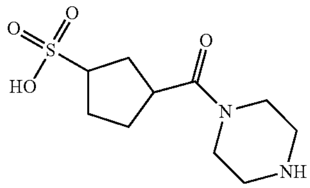 [SMILES: O=C(C1CCC(S(=O)(=O)O)C1)N1CCNCC1] | 262.32 |
| 2052 | 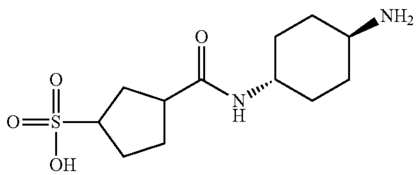 [SMILES: N[C@H]1CC[C@H](NC(=O)C2CCC(S(=O)(=O)O)C2)CC1] | 290.38 |
| 2053 | 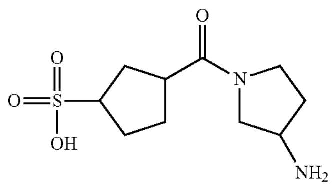 [SMILES: NC1CCN(C(=O)C2CCC(S(=O)(=O)O)C2)C1] | 262.32 |
Example 27. Syntheses of Cis-Proline Based Compounds
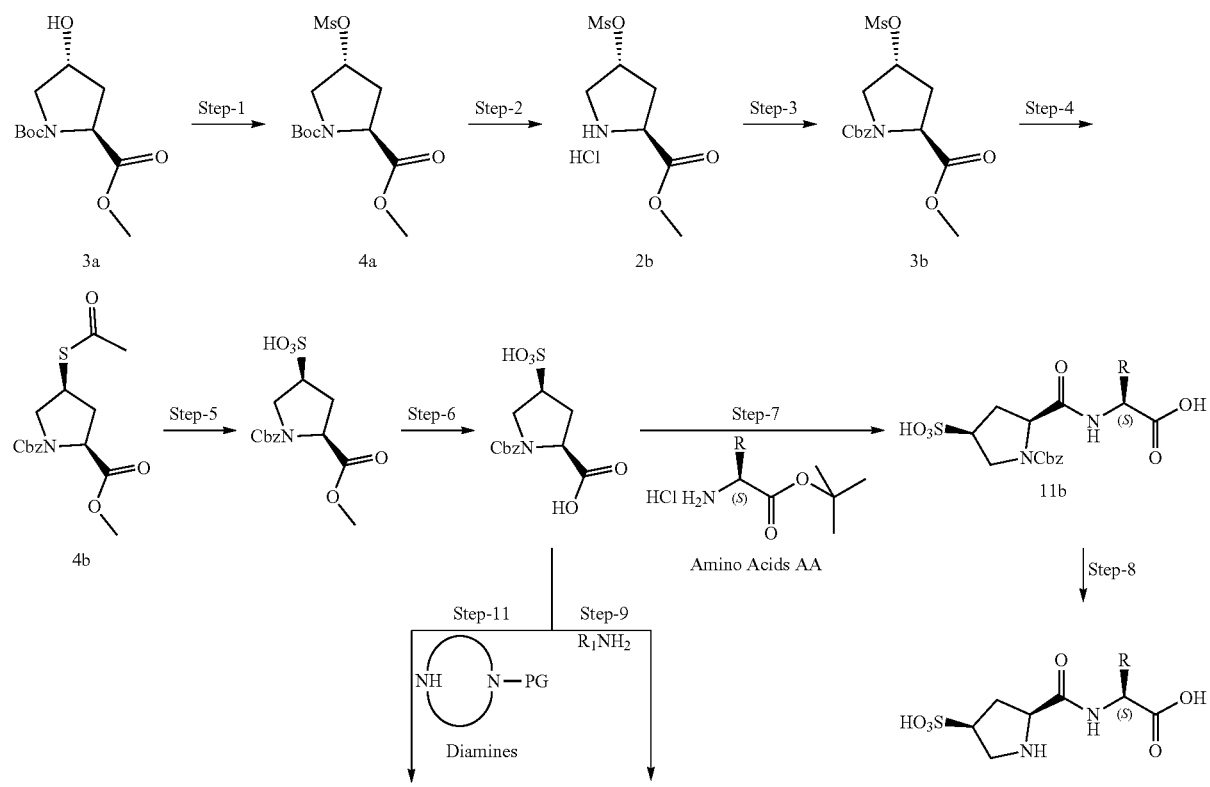
Scheme-1: General Scheme for the syntheses of cis-proline based compounds

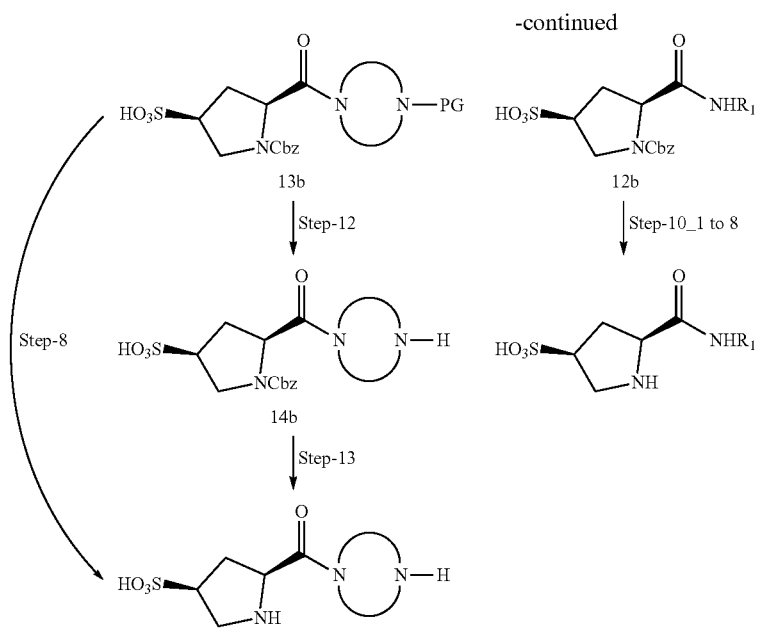

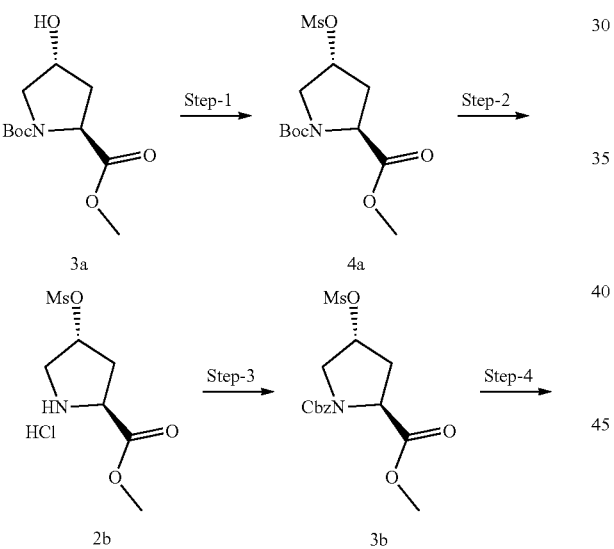

Scheme-2: Preparation of scaffold 2132 (used for library synthesis)

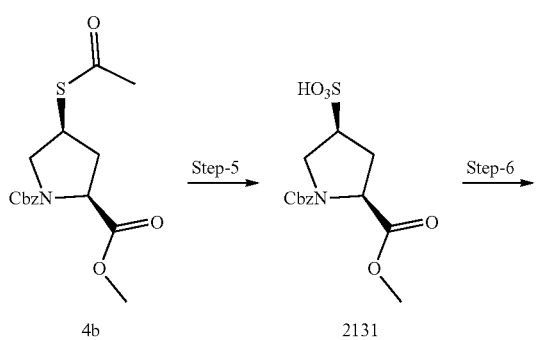

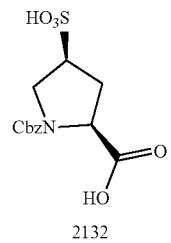

Experimental

Step-1: Synthesis of 1-(tert-butyl) 2-methyl (2S, 4R)-4-((methylsulfonyl)oxy)pyrrolidine-1,2-dicarboxylate (4a)

1-(tert-butyl) 2-methyl (2S,4R)-4-hydroxypyrrolidine-1,2-dicarboxylate 3a (20.0 gm, 81.6 mmol, 1.0 eq) was dissolved in pyridine (100 mL) and the solution was cooled to 0° C. Then methanesulfonyl chloride (15.2 mL, 195.8 mmol, 2.4 eq) was added and the mixture was stirred for 12 h, during which, the temperature was allowed to rise from 0° C. to ambient temperature. After complete consumption of starting material, reaction mixture was diluted with DCM (200 mL). The mixture was then washed with 0.1N HCl (1×200 mL), water (2×200 mL) and brine (1×200 mL), dried over anhydrous $Na_2SO_4$, filtered and solvents evaporated from the filtrate under reduced pressure. The crude residue obtained was purified by column chromatography on silica gel, 100-200 mesh, using 0-30% gradient of EtOAc in hexanes as eluent. The fractions containing the desired product were concentrated to obtain 4a as white solid (20.0 gm, 76.0%). LC-MS: Purity 98.69%. MS calculated for [M] 323.10 and found $[M+H]^+$ 324.04. $^1H$ NMR (400 MHz, $CDCl_3$): δ 5.26 (s, 1H), 4.48-4.38 (m, 1H), 3.87-3.76 (m, 2H), 3.75 (s, 3H), 3.05 (s, 3H), 2.68-2.57 (m, 1H), 2.29-2.22 (m, 1H), 1.46-1.42 (d, J=16.0 Hz, 9H).

Step-2: Synthesis of methyl (2S,4R)-4-((methylsulfonyl)oxy)pyrrolidine-2-carboxylate hydrochloride (2b)

1-(tert-butyl) 2-methyl (2S,4R)-4-((methylsulfonyl)oxy) pyrrolidine-1,2-dicarboxylate 4a (30.0 gm, 92.9 mmol, 1.0 eq) was dissolved in 1, 4-Dioxane (150 mL) and the solution was cooled to 0° C. Then 4N HCl in 1,4-dioxane (150 mL) was added and the mixture was stirred for 48 h, during which, the temperature of allowed to rise from 0° C. to ambient temperature. After complete consumption of starting material solvents evaporated from the reaction mixture under reduced pressure and the crude obtained was triturated diethyl ether and pentane. The precipitated solid was filtered and dried under vacuum to obtain 2b as white solid (23.4 gm, 98.0%). LCMS: UV inactive compound. MS calculated for [M] 223.05 and found [M+H]$^+$ 224.16.

Step-3: Synthesis of 1-benzyl 2-methyl (2S,4R)-4-((methylsulfonyl)oxy)pyrrolidine-1,2-dicarboxylate (3b)

Methyl (2S,4R)-4-((methylsulfonyl)oxy)pyrrolidine-2-carboxylate hydrochloride 2b (23.0 gm, 88.8 mmol, 1.0 eq) was suspended in DCM (230 mL) and the mixture was cooled to 0° C. Then triethylamine (124.0 mL, 888.0 mmol, 10.0 eq) and CbzCl (50% solution in Toluene, 33.4 mL, 97.7 mmol, 1.1 eq) were added and the mixture was stirred for 72 h. During stirring, temperature of the system gradually allowed to increase to ambient temperature. After completion consumption of the starting material, the mixture was diluted with chilled water (230 mL), the organic extract was separated and washed with chilled water (2×230 mL). The organic extract was then dried over anhydrous Na$_2$SO$_4$, filtered and solvents evaporated from the filtrate to obtain a crude residue, which was purified by flash chromatography on silica gel, 230-400 mesh, using 0-5% gradient of methanol in DCM as eluent. The fractions with the desired product were concentrated to obtain 3b as a colourless liquid (22.3 g, 70.0%). LCMS: Purity 91.58%. MS calculated for [M] 357.09 and found [M+H]$^+$ 358.05. $^1$H NMR (400 MHz, CDCl$_3$): δ 7.36-7.32 (m, 5H), 5.30-5.03 (m, 3H), 4.56-4.48 (m, 1H), 3.98-3.80 (m, 2H), 3.78 (s, 1.5H), 3.56 (s, 1.5H), 3.04-3.02 (d, J=8.8 Hz, 3H), 2.71-2.62 (m, 1H), 2.31-2.27 (m, 1H).

Step-4: Synthesis of 1-benzyl 2-methyl (2S,4S)-4-(acetylthio)pyrrolidine-1,2-dicarboxylate (4b)

1-Benzyl 2-methyl (2S,4R)-4-((methylsulfonyl)oxy)pyrrolidine-1,2-dicarboxylate 3b (22.3 gm, 62.5 mmol, 1.0 eq) was dissolved in DMF (220 mL). Potassium thioacetate (10.7 gm, 93.8 mmol, 1.5 eq) was added and the mixture was heated at 80° C. for 16 h. After complete consumption of starting material, reaction mixture was cooled to ambient temperature and diluted with chilled water (220 mL). The mixture was then extracted with diethyl ether (2×440 mL). The organic extract was again washed with water (1×440 mL) followed by brine (1×440 mL), dried over anhydrous Na$_2$SO$_4$, filtered and solvents evaporated from the filtrate under reduced pressure. The crude residue obtained was purified by flash chromatography on silica gel, 230-400 mesh, using 0-15% gradient of EtOAc in hexanes as eluent. The fractions containing the desired product were concentrated to obtain 4b as brown viscous liquid (14.5 gm, 69.0%). LCMS: Purity 85.24%. MS calculated for [M] 337.10 and found [M+H]$^+$ 338.04. $^1$H NMR (400 MHz, CDCl$_3$): δ 7.36-7.31 (m, 5H), 5.22-5.03 (m, 2H), 4.46-4.39 (m, 1H), 4.11-3.96 (m, 2H), 3.77 (s, 1.5H), 3.58 (s, 1.5H), 3.45-3.38 (m, 1H), 2.80-2.69 (m, 1H), 2.32 (s, 3H), 2.03-1.96 (m, 1H).

Step-5: Synthesis of (3S,5S)-1-((benzyloxy)carbonyl)-5-(methoxycarbonyl)pyrrolidine-3-sulfonic acid (2131)

1-Benzyl 2-methyl (2S, 4S)-4-(acetylthio) pyrrolidine-1,2-dicarboxylate 4b (1.5 gm, 4.45 mmol, 1.0 eq) was dissolved in AcOH (15 mL). Sodium acetate trihydrate (0.6 gm, 4.45 mmol, 1.0 eq) and 33% H$_2$O$_2$ (4.53 ml, 40.1 mmol, 9.0 eq) were added and the mixture was heated at 80° C. for 16 h. After complete consumption of starting material, reaction mixture was cooled to ambient temperature and solvents evaporated under reduced pressure. The resulting residue was dissolved in water (15 mL) and washed with EtOAc (2×15 mL). The aqueous layer was concentrated under vacuum to get 1.44 gm of crude compound. 0.1 gm of crude compound was purified by prep HPLC on Waters Sunfire C18 OBD column. The fractions with desired product were concentrated and lyophilized to obtain 2131 as white solid (0.05 gm, 47.4%). LCMS: Purity 97.81%. MS calculated for [M] 343.35 and found [M+H]$^+$ 344.03. $^1$H NMR (400 MHz, D$_2$O): δ 7.47-7.38 (m, 5H), 5.23-5.05 (m, 2H), 4.63-4.54 (m, 1H), 4.07-3.97 (m, 1H), 3.76 (s, 1.5H), 3.61 (s, 1.5H), 3.77-3.61 (m, 2H), 2.80-2.72 (m, 1H), 2.41-2.35 (m, 1H).

Step-6: Synthesis of (2S, 4S)-1-((benzyloxy)carbonyl)-4-sulfopyrrolidine-2-carboxylic acid (2132)

(3S,5S)-1-((Benzyloxy)carbonyl)-5-(methoxycarbonyl) pyrrolidine-3-sulfonic acid, 2131 (31.5 gm, 91.74 mmol, 1.0 eq) was dissolved in a mixture of THF and water (1:1, 300.0 mL) and the mixture was cooled to 0° C. Lithium hydroxide monohydrate (3.85 gm, 91.74 mmol, 1.0 eq) was added and the reaction mixture was stirred for 16 h, allowing temperature to gradually rise to ambient temperature. After complete consumption of starting material, reaction mixture was diluted with water (300 mL) and washed with DCM (2×600 mL). The resulting aqueous layer was acidified with amberlite IR 120 (H$^+$) resin up to pH=2 and filtered. The aqueous layer was concentrated under reduced pressure and the crude obtained was triturated with diethyl ether to obtain 2132 as white solid (30.0 gm, 99.3%). LCMS: Purity 99.23%. MS calculated for [M] 329.06 and found [M+H]$^+$ 329.92. $^1$H NMR (400 MHz, D$_2$O): δ 7.46-7.39 (m, 5H), 5.18-5.13 (m, 2H), 4.35-4.28 (m, 1H), 4.10-3.95 (m, 1H), 3.74-3.69 (m, 1H), 3.60-3.53 (m, 1H), 2.74-2.71 (m, 1H), 2.23-2.12 (m, 1H).

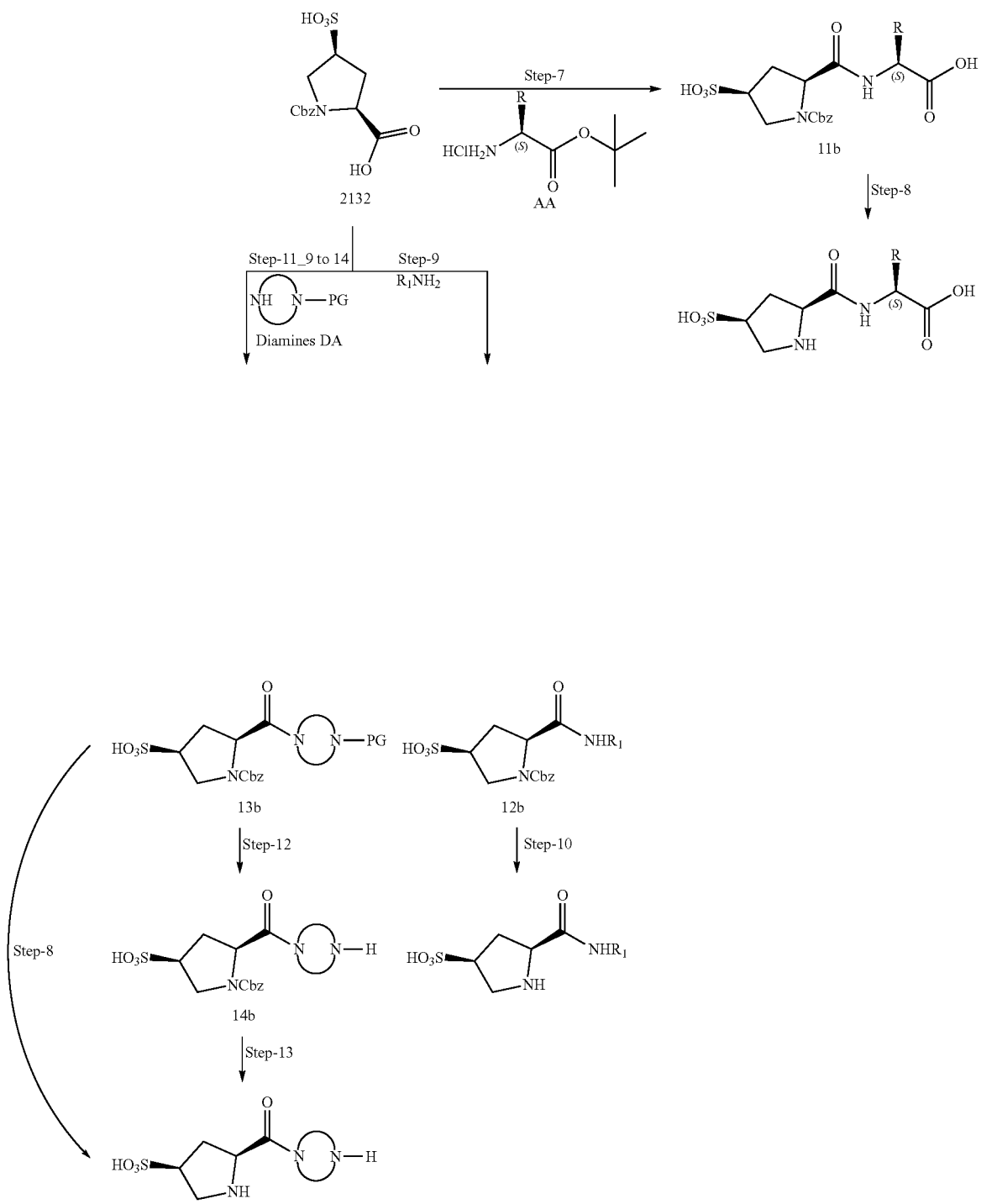

Scheme-3: General Scheme for library syntheses

General Experimental Procedure for Step-7:

Scaffold 2132 (1.0 eq) was dissolved in DMF and the mixture was cooled to 0° C. DIPEA (3.0 eq) and HATU (1.5 eq) were added and the reaction mixture was stirred at 0° C. for 0.5 h. Then amino acid AA (1.5 eq) was added and the reaction mixture was stirred for 16 h, allowing temperature to gradually rise to ambient temperature. After complete consumption of starting material, reaction mixture was poured in diethyl ether. The precipitate obtained was triturated with the mixture of ethyl acetate and DCM, filtered the solid residue and washed it thoroughly with ethyl acetate (3×). Mixture of filtrate and washings was concentrated under reduced pressure. The resulting crude was dissolved in water, acidified the aqueous layer with amberlite IR 120 ($H^+$) resin upto pH=1 and filtered the resin. The aqueous layer was concentrated under reduced pressure to obtain corresponding 11b.

| ID | Amino acid | Structure |
|---|---|---|
| 11b_1 | 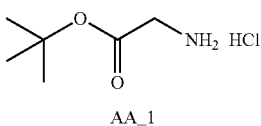<br>AA_1 | 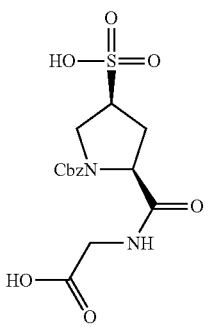 [SMILES: O=C(O)CNC(=O)[C@@H]1C[C@H](S(=O)(=O)O)CN1C(=O)OCc1ccccc1] |
| 11b_2 | 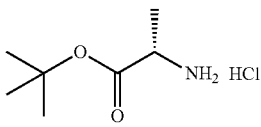<br>AA_2 | 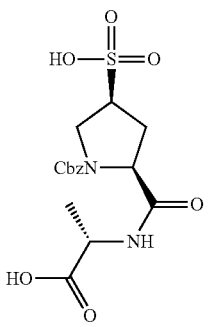 [SMILES: C[C@H](NC(=O)[C@@H]1C[C@H](S(=O)(=O)O)CN1C(=O)OCc1ccccc1)C(=O)O] |
| 11b_3 | 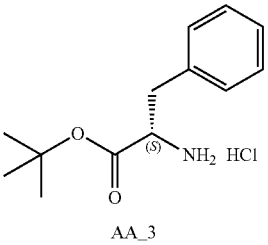<br>AA_3 | 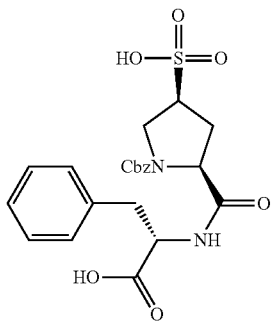 [SMILES: O=C(O)[C@H](Cc1ccccc1)NC(=O)[C@@H]1C[C@H](S(=O)(=O)O)CN1C(=O)OCc1ccccc1] |
| 11b_4 | 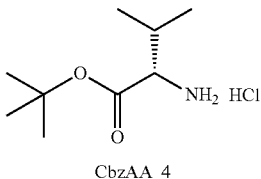<br>CbzAA_4 | 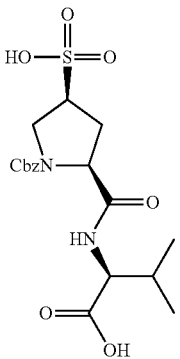 |

-continued
| ID | Amino acid | Structure |
|---|---|---|
| 11b_5 | 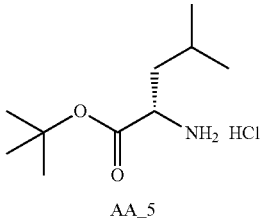<br>AA_5 | 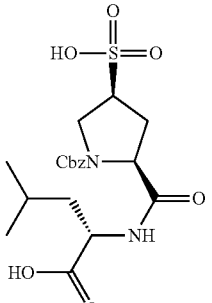 |
| 11b_6 | 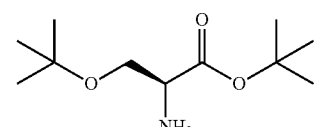<br>AA_6 | 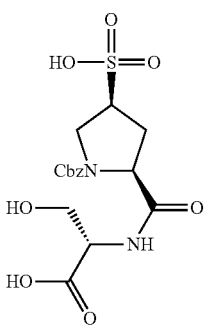 [SMILES: O=C(O)[C@H](CO)NC(=O)[C@@H]1C[C@H](S(=O)(=O)O)CN1C(=O)OCc1ccccc1] |
| 11b_7 | 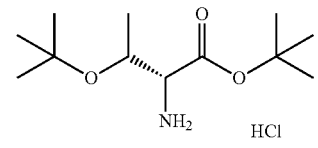<br>AA_7 | 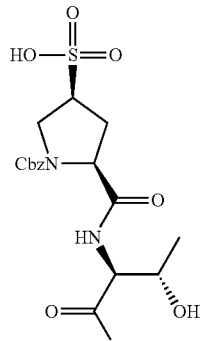 |
| 11b_8 | 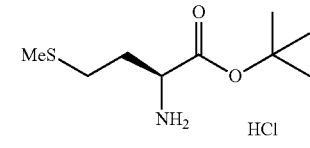<br>AA_8 | 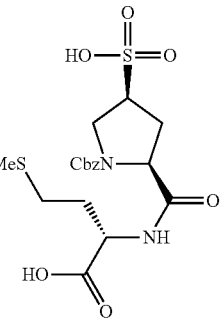 |

-continued
| ID | Amino acid | Structure |
|---|---|---|
| 11b_9 | 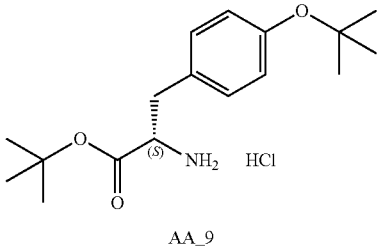 AA_9 | 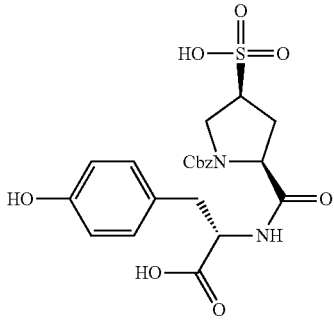 [SMILES: O=C(O)[C@H](Cc1ccc(O)cc1)NC(=O)[C@@H]1C[C@H](S(=O)(=O)O)CN1C(=O)OCc1ccccc1] |
| 11b_10 | 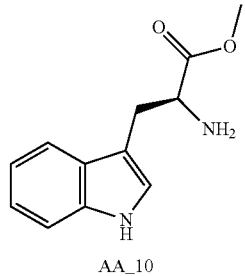 [SMILES: COC(=O)[C@@H](N)Cc1c[nH]c2ccccc12] AA_10 | 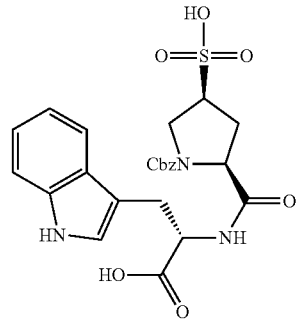 [SMILES: O=C(O)[C@H](Cc1c[nH]c2ccccc12)NC(=O)[C@@H]1C[C@H](S(=O)(=O)O)CN1C(=O)OCc1ccccc1] |
| 11b_11 | 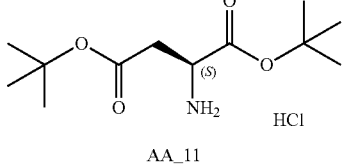 AA_11 | 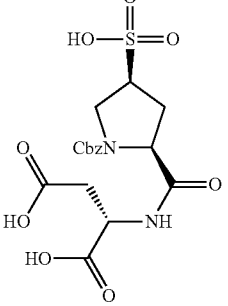 |
| 11b_12 | 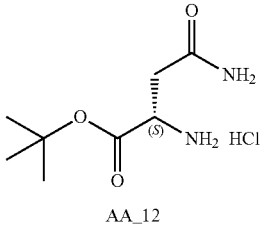 AA_12 | 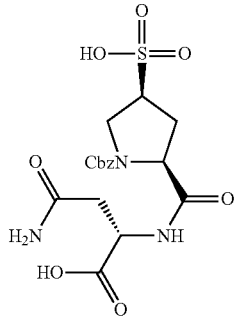 [SMILES: NC(=O)C[C@H](NC(=O)[C@@H]1C[C@H](S(=O)(=O)O)CN1C(=O)OCc1ccccc1)C(=O)O] |

| ID | Amino acid | Structure |
|---|---|---|
| 11b_13 | 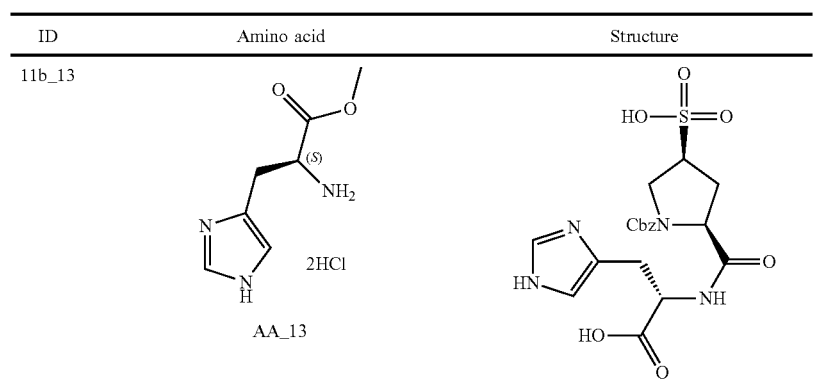 | 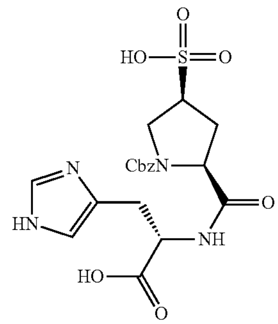 [SMILES: O=C(O)[C@H](Cc1c[nH]cn1)NC(=O)[C@@H]1C[C@H](S(=O)(=O)O)CN1C(=O)OCc1ccccc1] |
| 11b_14 | 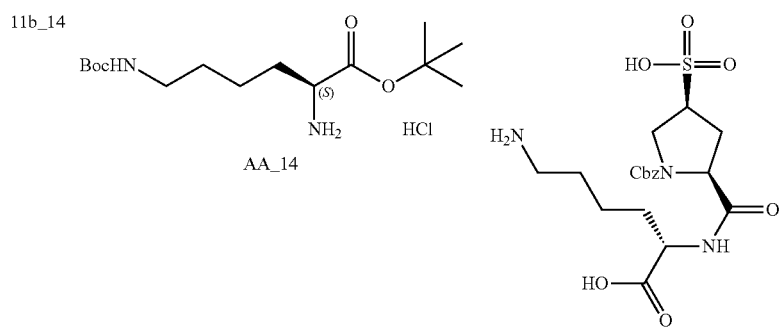 | 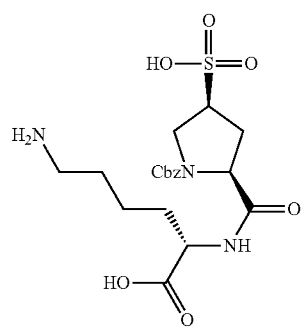 [SMILES: NCCCC[C@H](NC(=O)[C@@H]1C[C@H](S(=O)(=O)O)CN1C(=O)OCc1ccccc1)C(=O)O] |

Figure 2:
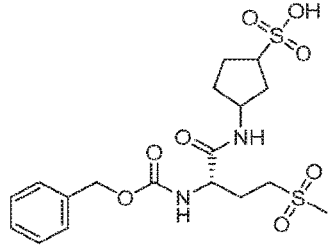
FIG. 2 is a table illustrating select exemplary compounds of the present invention and/or useful in the compositions and methods of the present invention, including NMR and mass spectrometry data where available.
Figure 2:
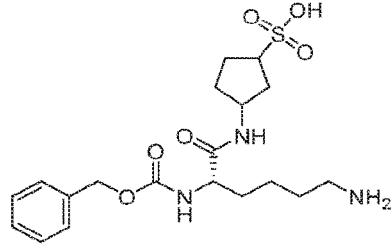
Figure 2:
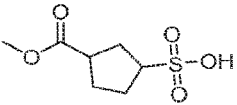
Figure 2:
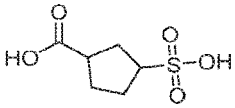
Figure 2:
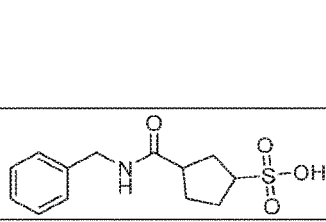
Figure 2:
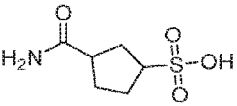
Figure 2:
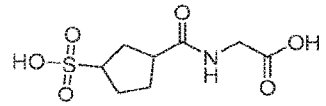
Figure 2:
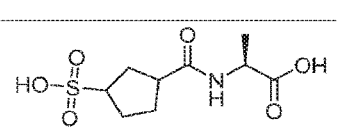
Figure 2:
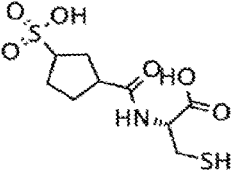
Figure 2:
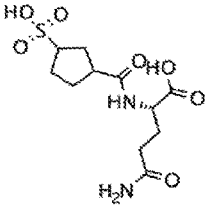
Figure 2:
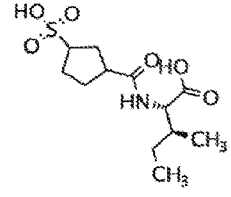
Figure 2:
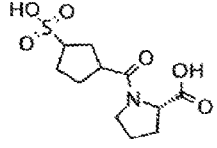
Figure 2:
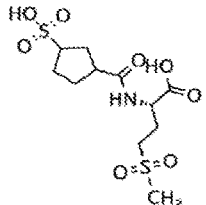
Figure 2:
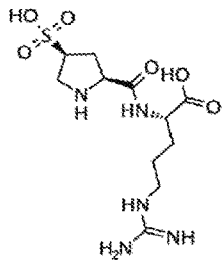
Figure 2:
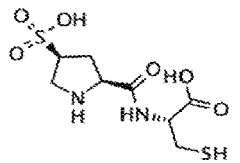
Figure 2:
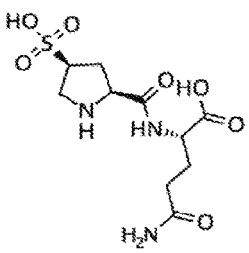
Figure 2:
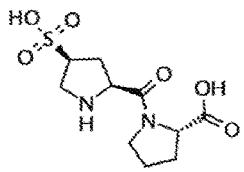
Figure 2:
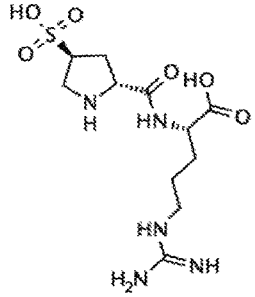
Figure 2:
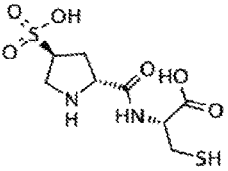
Figure 2:
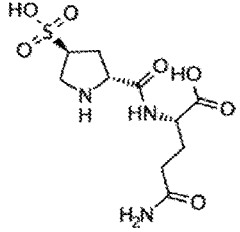
Figure 2:
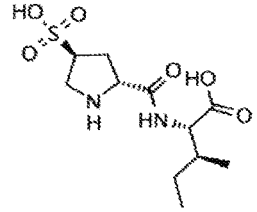
Figure 2:
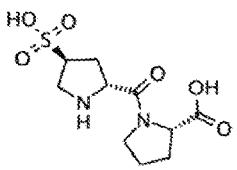
Figure 2:
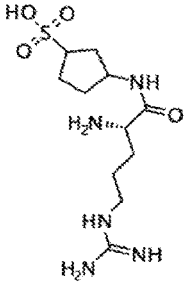
Figure 2:
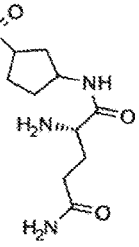
Figure 2:
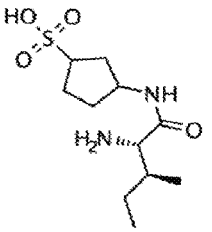
Figure 2:
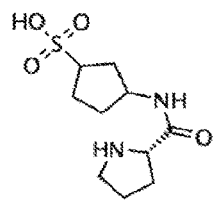

General Experimental Procedure for Step-8:

11b (1.0 eq) was dissolved in the mixture of ethyl acetate, THF and water (1:1:0.5) under nitrogen atmosphere. Pd/C (10% w/w, 50% moisture, w/w) was added and the mixture was stirred under hydrogen atmosphere (hydrogen balloon) at room temperature for 16 h. After complete consumption of starting material, reaction mixture was diluted with water and filtered through a celite bed. Then celite bed was thoroughly washed with water (3×). Mixture of filtrate and washings was concentrated under reduced pressure and the crude compound was purified by prep HPLC to obtain corresponding compounds 2060-2073 listed in FIG. 2 with NMR and MS data.

| ID | Structure |
|---|---|
| 2060 | |
| 2061 | 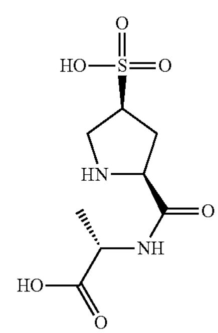 [SMILES: C[C@H](NC(=O)[C@@H]1C[C@H](S(=O)(=O)O)CN1)C(=O)O] |
| 2062 | 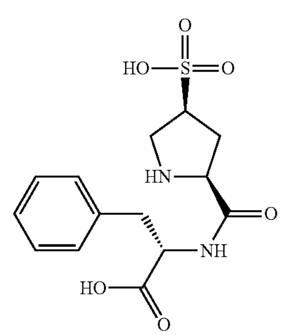 [SMILES: O=C(O)[C@H](Cc1ccccc1)NC(=O)[C@@H]1C[C@H](S(=O)(=O)O)CN1] |

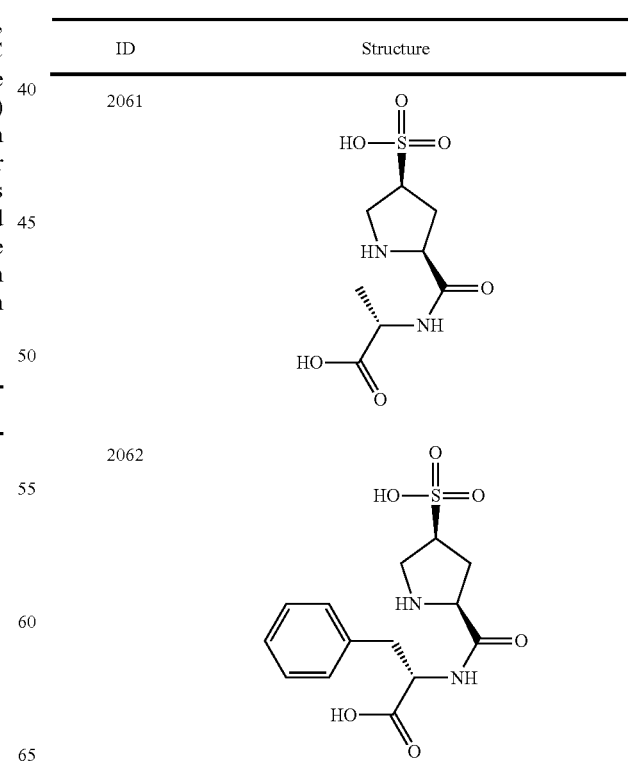

| ID | Structure |
|---|---|
| 2063 | 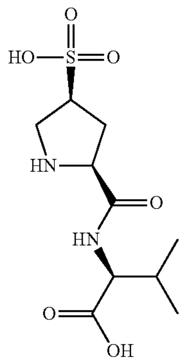 [SMILES: CC(C)[C@H](NC(=O)[C@@H]1C[C@H](S(=O)(=O)O)CN1)C(=O)O] |
| 2064 | 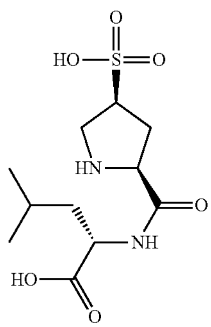 [SMILES: CC(C)C[C@H](NC(=O)[C@@H]1C[C@H](S(=O)(=O)O)CN1)C(=O)O] |
| 2065 | 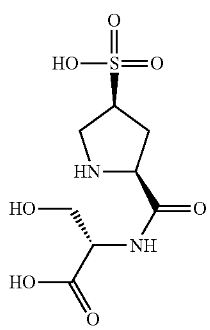 [SMILES: O=C(O)[C@H](CO)NC(=O)[C@@H]1C[C@H](S(=O)(=O)O)CN1] |
| 2066 | 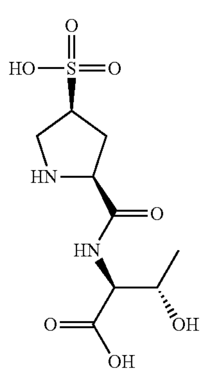 [SMILES: C[C@H](O)[C@H](NC(=O)[C@@H]1C[C@H](S(=O)(=O)O)CN1)C(=O)O] |
| 2067 | |
| 2068 | |
| 2069 | |
| 2070 | |

-continued

| ID | Structure |
|---|---|
| 2071 | (structure) |
| 2072 | (structure) |
| 2073 | (structure) |

| ID | Amines/Diamines | Structure |
|---|---|---|
| 12b_1 | A_1 | (structure) |
| 12b_2 | A_2 | (structure) |
| 12b_3 | A_3 | (structure) |
| 12b_4 | A_4 | (structure) |
| 12b_5 | A_5 | (structure) |

General Experimental Procedure for Step-9:

Scaffold 2132 (1.0 eq) was dissolved in DMF and the mixture was cooled to 0° C. DIPEA (3.0 eq) and HATU (1.5 eq) were added and the reaction mixture was stirred at 0° C. for 0.5 h. Then amines A_1 to A_6, DA_1 and DA_2 (1.5 eq) was added and the reaction mixture was stirred for 16 h, allowing temperature to gradually rise to ambient temperature. After complete consumption of starting material, reaction mixture was poured in diethyl ether. The precipitate obtained was triturated with the mixture of ethyl acetate and DCM, filtered the solid residue and washed it thoroughly with ethyl acetate (3×). Mixture of filtrate and washings was concentrated under reduced pressure. The resulting crude was dissolved in water, acidified the aqueous layer with amberlite IR 120 (H⁺) resin up to pH=1 and filtered the resin. The aqueous layer was concentrated under reduced pressure to obtain corresponding 12b.

-continued

| ID | Amines/Diamines | Structure |
|---|---|---|
| 12b_6 | NH₃ A_6 | 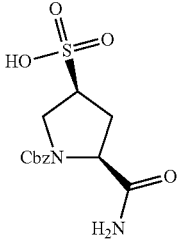 |
| 12b_7 | 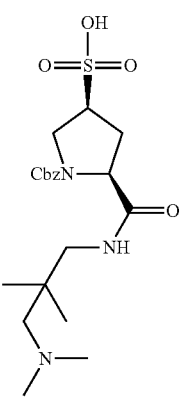 DA_1 | 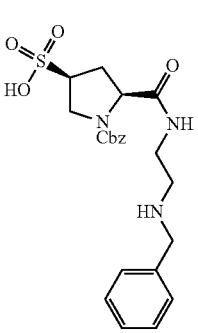 [SMILES: O=C(NCCNCc1ccccc1)[C@@H]1C[C@H](S(=O)(=O)O)CN1C(=O)OCc1ccccc1] |
| 12b_8 | 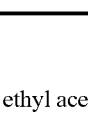 DA_2 | 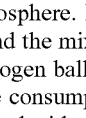 |

General Experimental Procedure for Step-10:

12b (1.0 eq) was dissolved in the mixture of ethyl acetate, THF and water (1:1:0.5) under nitrogen atmosphere. Pd/C (10% w/w, 50% moisture, w/w) was added and the mixture was stirred under hydrogen atmosphere (hydrogen balloon) at room temperature for 16 h. After complete consumption of starting material, reaction mixture was diluted with water and filtered through a celite bed. Then celite bed was thoroughly washed with water (3×). Mixture of filtrate and washings was concentrated under reduced pressure and the crude compound was purified by prep HPLC to obtain corresponding compounds in the following table, also listed in FIG. 2 with NMR and MS data.

| ID | Structure |
|---|---|
| 2055 | 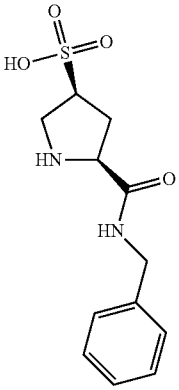 [SMILES: O=C(NCc1ccccc1)[C@@H]1C[C@H](S(=O)(=O)O)CN1] |
| 2059 | 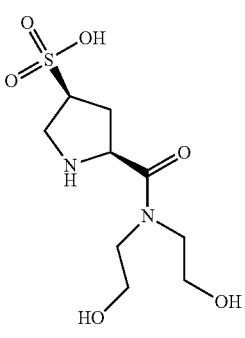 [SMILES: O=C([C@@H]1C[C@H](S(=O)(=O)O)CN1)N(CCO)CCO] |
| 2057 | 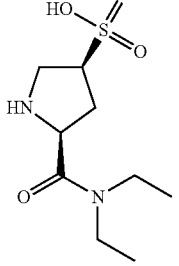 |
| 2058 | 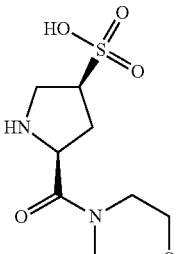 |
| 2056 | 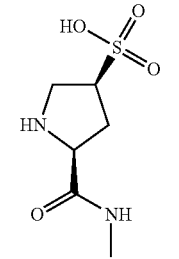 |

| ID | Structure |
|---|---|
| 2054 | (pyrrolidine with 4-sulfonic acid and 2-carboxamide, HN in ring, H₂N-C(=O)-) |
| 2074 | (pyrrolidine with 4-sulfonic acid OH and 2-carboxamide linked to -NH-CH₂-C(CH₃)₂-CH₂-N(CH₃)₂) |

| ID | Structure |
|---|---|
| 2075 | (pyrrolidine with 4-sulfonic acid and 2-carboxamide linked to -NH-CH₂CH₂-NH-CH₂-phenyl) |

General Experimental Procedure for Step-11:

Scaffold 2132 (1.0 eq) was dissolved in DMF and the mixture was cooled to 0° C. DIPEA (3.0 eq) and HATU (1.5 eq) were added and the reaction mixture was stirred at 0° C. for 0.5 h. Then DA_3 to 8 (1.5 eq) was added and the reaction mixture was stirred for 16 h, allowing temperature to gradually rise to ambient temperature. After complete consumption of starting material, reaction mixture was poured in diethyl ether. The precipitate obtained was triturated with the mixture of ethyl acetate and DCM, filtered the solid residue and washed it thoroughly with ethyl acetate (3×). Mixture of filtrate and washings was concentrated under reduced pressure. The resulting crude was dissolved in water, acidified the aqueous layer with amberlite IR 120 (H⁺) resin up to pH=1 and filtered the resin. The aqueous layer was concentrated under reduced pressure to obtain corresponding 13b.

| ID | Diamines | Structure |
|---|---|---|
| 13b_9 | DA_3: trans-cyclohexane-1,2-diamine (NH₂, NHBoc) | sulfonic acid pyrrolidine NCbz carboxamide linked to cyclohexyl-NHBoc |
| 13b_10 | DA_4: 4-amino-N-Boc-piperidine | sulfonic acid pyrrolidine NCbz carboxamide linked to 4-(N-Boc-piperidinyl) |
| 13b_11 | DA_5: 4-NHBoc-piperidine (HN ring) | sulfonic acid pyrrolidine NCbz carbonyl linked to piperidine-4-NHBoc |

| ID | Diamines | Structure |
|---|---|---|
| 13b_12 | DA_6 | 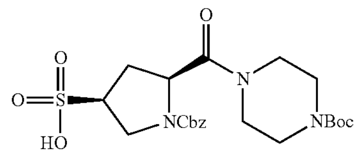 [SMILES: CC(C)(C)OC(=O)N1CCN(C(=O)[C@@H]2C[C@H](S(=O)(=O)O)CN2C(=O)OCc2ccccc2)CC1] |
| 13b_13 | DA_7 | 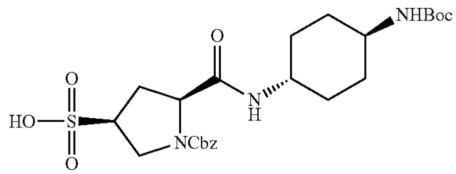 [SMILES: CC(C)(C)OC(=O)N[C@H]1CC[C@H](NC(=O)[C@@H]2C[C@H](S(=O)(=O)O)CN2C(=O)OCc2ccccc2)CC1] |
| 13b_14 | DA_8 | 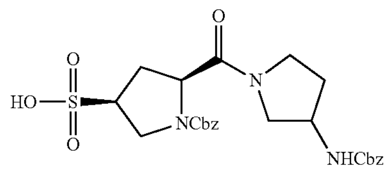 [SMILES: O=C(NC1CCN(C(=O)[C@@H]2C[C@H](S(=O)(=O)O)CN2C(=O)OCc2ccccc2)C1)OCc1ccccc1] |

General Experimental Procedure for Step-12:

13b (1.0 eq) was dissolved in dioxane and the solution was cooled to 0° C. Then 4M HCl in dioxane (50%, v/v) was added and the mixture was stirred for 3 h, during which, the temperature was allowed to rise from 0° C. to ambient temperature. After complete consumption of starting material, solvents evaporated from the reaction mixture under reduced pressure and the crude obtained was triturated with diethyl ether to obtain corresponding 14b.

| ID | Structure | 1H NMR | Mass | Yield | Purity |
|---|---|---|---|---|---|
| 14b_9 | 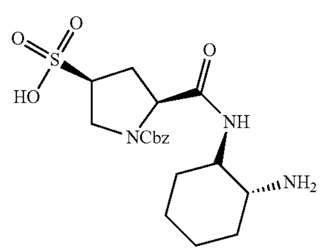 | — | — | — | — |
| 14b_10 | 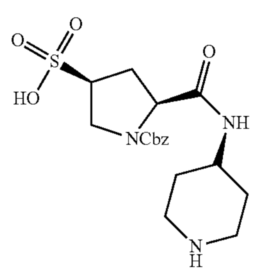 | — | — | — | — |
| 14b_11 | 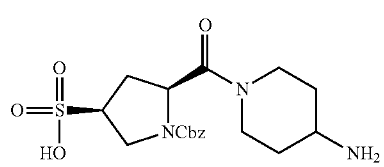 [SMILES: NC1CCN(C(=O)[C@@H]2C[C@H](S(=O)(=O)O)CN2C(=O)OCc2ccccc2)CC1] | — | — | — | — |

| ID | Structure | 1H NMR | Mass | Yield | Purity |
|---|---|---|---|---|---|
| 14b_12 | 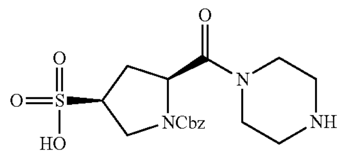 [SMILES: O=C([C@@H]1C[C@H](S(=O)(=O)O)CN1C(=O)OCc1ccccc1)N1CCNCC1] | — | — | — | — |
| 14b_13 | 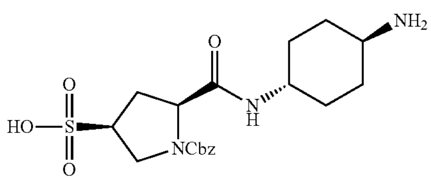 [SMILES: N[C@H]1CC[C@H](NC(=O)[C@@H]2C[C@H](S(=O)(=O)O)CN2C(=O)OCc2ccccc2)CC1] | — | — | — | — |

General Experimental Procedure for Step-13:

13b, or 14b (1.0 eq) was dissolved in the mixture of ethyl acetate, THF and water (1:1:0.5) under nitrogen atmosphere. Pd/C (10% w/w, 50% moisture, w/w) was added and the mixture was stirred under hydrogen atmosphere (hydrogen balloon) at room temperature for 16 h. After complete consumption of starting material, reaction mixture was diluted with water and filtered through a celite bed. Then celite bed was thoroughly washed with water (3×). Mixture of filtrate and washings was concentrated under reduced pressure and the crude compound was purified by prep HPLC to obtain corresponding compounds in the following table, also listed in FIG. 2 with NMR and MS data.

| ID | Structure |
|---|---|
| 2076 | |
| 2077 | |
| 2078 | 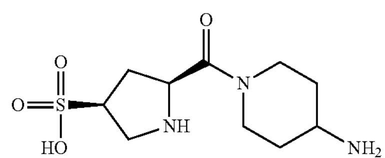 [SMILES: NC1CCN(C(=O)[C@@H]2C[C@H](S(=O)(=O)O)CN2)CC1] |
| 2079 | 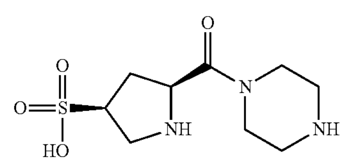 [SMILES: O=C([C@@H]1C[C@H](S(=O)(=O)O)CN1)N1CCNCC1] |
| 2080 | 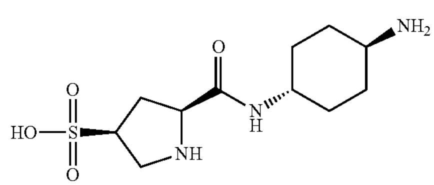 [SMILES: N[C@H]1CC[C@H](NC(=O)[C@@H]2C[C@H](S(=O)(=O)O)CN2)CC1] |
| 2081 | 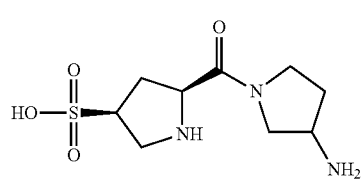 [SMILES: NC1CCN(C(=O)[C@@H]2C[C@H](S(=O)(=O)O)CN2)C1] |

Example 28. Syntheses of Trans-Proline Based Compounds
Scheme-1: General Scheme for the syntheses of trans-proline based compounds
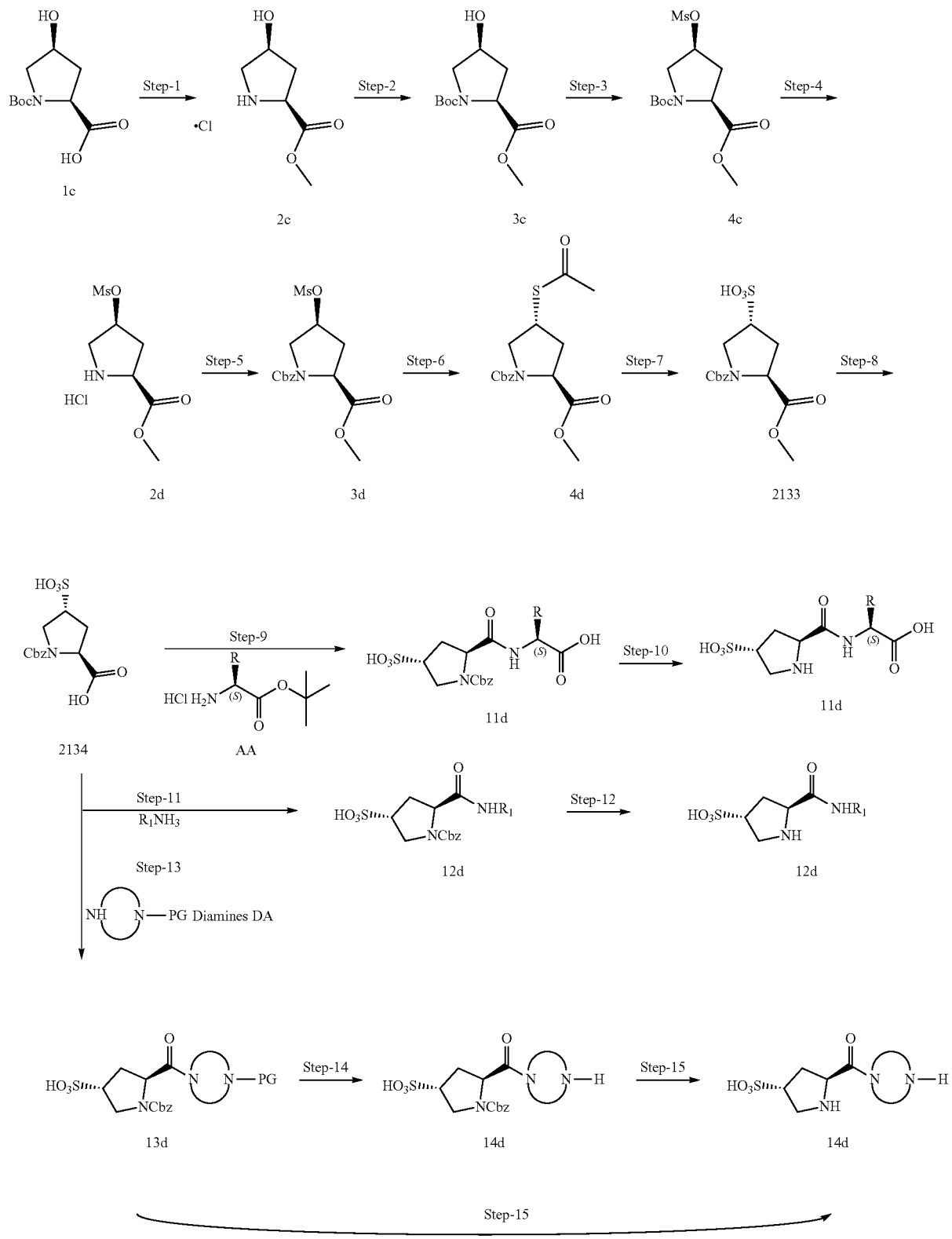

Scheme-2: Preparation of scaffold 2134 (used for library synthesis)

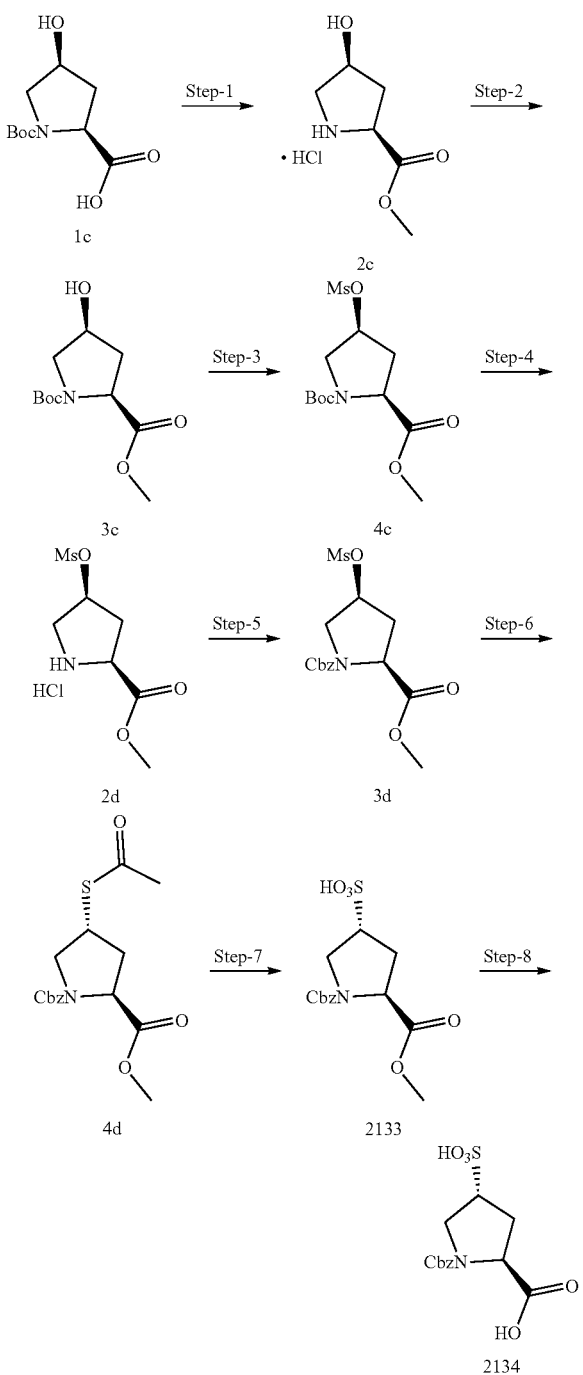

Experimental

Step-1: Synthesis of methyl (2S,4S)-4-hydroxypyrrolidine-2-carboxylate hydrochloride (2c)

(2S,4S)-1-(tert-butoxycarbonyl)-4-hydroxypyrrolidine-2-carboxylicacid, 1c (4.0 gm, 17.3 mmol, 1.0 eq) was dissolved in methanol (40 mL) and the solution was cooled to 0° C. Then thionyl chloride (1.9 mL, 26.0 mmol, 1.5 eq) was added and the mixture was stirred for 6 h, during which, the temperature was allowed to rise from 0° C. to ambient temperature. After complete consumption of starting material, solvents evaporated from the reaction mixture under reduced pressure and the crude obtained was triturated diethyl ether and pentane. The precipitated solid was filtered and dried under vacuum to obtain 2c as white solid (3.07 gm, 98.0%). $^1$H NMR (400 MHz, DMSO-d6): δ 10.58 (bs, 1H), 8.98 (bs, 1H), 5.48-5.44 (bs, 1H), 4.49-4.47 (d, J=8.0 Hz, 1H), 4.36 (s, 1H), 3.74 (s, 3H), 3.19-3.13 (m, 2H), 2.33-2.28 (m, 1H), 2.15-2.12 (d, J=12 Hz, 1H).

Step-2: Synthesis of 1-(tert-butyl) 2-methyl (2S,4S)-4-hydroxypyrrolidine-1,2-dicarboxylate (3c)

(2S,4S)-4-hydroxypyrrolidine-2-carboxylate hydrochloride, 2c (4.0 gm, 22.09 mmol, 1.0 eq) was dissolved in DCM (40 mL) and the solution was cooled to 0° C. Then triethyl amine (9.25 mL, 66.27 mmol, 3.0 eq), dimethylamino pyridine (0.27 gm, 2.21 mmol, 0.1 eq) and Boc$_2$O (6.1 mL, 25.50 mmol, 1.2 eq) were added and the mixture was stirred for 16 h, during which, the temperature was allowed to rise from 0° C. to ambient temperature. After complete consumption of starting material, reaction mixture was diluted with water (40 mL) and separated the DCM layer. The organic layer was then washed with water (2×40 mL) followed by brine (1×40 mL), dried over anhydrous Na$_2$SO$_4$, filtered and solvents evaporated from the filtrate under reduced pressure. The crude residue obtained was purified by column chromatography on silica gel, 100-200 mesh, using 0-30% gradient of EtOAc in hexanes as eluent. The fractions containing the desired product were concentrated to obtain 3c as white solid (4.0 gm, 74.0%). LC-MS: Purity 98.57%. MS calculated for [M] 245.13 and found [M+H]$^+$ 246.05. $^1$H NMR (400 MHz, CDCl$_3$): δ 4.38-4.34 (m, 2H), 3.80-3.78 (d, J=8.0 Hz, 3H), 3.72-3.62 (m, 1H), 3.59-3.49 (m, 1H), 2.38-2.26 (m, 1H), 2.11-2.04 (m, 1H), 1.46-1.42 (d, J=16.0 Hz, 9H).

Step-3: Synthesis of 1-(tert-butyl) 2-methyl (2S,4S)-4-((methylsulfonyl)oxy)pyrrolidine-1,2-dicarboxylate (4c)

1-(tert-butyl) 2-methyl (2S,4S)-4-hydroxypyrrolidine-1,2-dicarboxylate, 3c (50.0 gm, 204.1 mmol, 1.0 eq) was dissolved in pyridine (250 mL) and the solution was cooled to 0° C. Then methanesulfonyl chloride (37.0 mL, 489.8 mmol, 2.4 eq) was added and the mixture was stirred for 6 h, during which, the temperature was allowed to rise from 0° C. to ambient temperature. After complete consumption of starting material, reaction mixture was diluted with DCM (500 mL). The mixture was then washed with 0.1N HCl (1×500 mL), water (2×500 mL) and brine (1×500 mL), dried over anhydrous Na$_2$SO$_4$, filtered and solvents evaporated from the filtrate under reduced pressure. The crude residue obtained was purified by column chromatography on silica gel, 100-200 mesh, using 0-30% gradient of EtOAc in hexanes as eluent. The fractions containing the desired product were concentrated to obtain 4c as off-white solid (37.0 gm, 93.6%). $^1$H NMR (400 MHz, CDCl$_3$): δ 5.23 (bs, 1H), 4.40-4.35 (m, 1H), 3.72-3.63 (m, 4H), 3.54-3.49 (m, 1H), 3.19 (s, 3H), 2.67-2.55 (m, 1H), 2.25-2.22 (m, 1H), 1.41-1.35 (d, J=24.0 Hz, 9H).

Step-4: Synthesis of methyl (2S,4S)-4-((methylsulfonyl)oxy)pyrrolidine-2-carboxylate hydrochloride (2d)

1-(tert-Butyl) 2-methyl (2S,4S)-4-((methylsulfonyl)oxy)pyrrolidine-1,2-dicarboxylate 4c (30.0 gm, 92.9 mmol, 1.0 eq) was dissolved in 1, 4-Dioxane (150 mL) and the solution was cooled to 0° C. Then 4N HCl in 1,4-dioxane (150 mL) was added and the mixture was stirred for 16 h, during which, the temperature was allowed to rise from 0° C. to ambient temperature. After complete consumption of starting material solvents evaporated from the reaction mixture under reduced pressure and the crude obtained was triturated with 10% ethanol in diethyl ether. The precipitated solid was filtered and dried under vacuum to obtain 2d as white solid (18.6 gm, 77.5%). $^1$H NMR (400 MHz, DMSO-d6): δ 10.21-10.17 (bs, 2H), 5.39 (s, 1H), 4.65-4.61 (m, 1H), 3.77 (s, 3H), 3.54 (s, 2H), 3.25 (s, 3H), 2.71-2.64 (m, 1H), 2.50 (merged with solvent peak, 1H).

Step-5: Synthesis of 1-benzyl 2-methyl (2S, 4S)-4-((methylsulfonyl)oxy)pyrrolidine-1,2-dicarboxylate (3d)

Methyl (2S, 4S)-4-((methylsulfonyl) oxy) pyrrolidine-2-carboxylate hydrochloride 2d (18.0 gm, 69.5 mmol, 1.0 eq) was suspended in DCM (180 mL) and the mixture was cooled to 0° C. Then triethylamine (97.0 mL, 695.0 mmol, 10.0 eq) and CbzCl (50% solution in Toluene, 26.0 mL, 76.5 mmol, 1.1 eq) were added and the mixture was stirred for 16 h. During stirring, temperature of the system gradually allowed to increase to ambient temperature. After completion consumption of the starting material, the mixture was diluted with chilled water (180 mL), the organic extract was separated and washed with chilled water (2×180 mL). The organic extract was then dried over anhydrous $Na_2SO_4$, filtered and solvents evaporated from the filtrate to obtain a crude residue, which was purified by flash chromatography on silica gel, 230-400 mesh, using 10-40% gradient of ethyl acetate in hexanes as eluent. The fractions with the desired product were concentrated to obtain 3d as a colourless viscous liquid (22.0 g, 88.7%). LCMS: Purity 83.38%. MS calculated for [M] 357.09 and found [M+H]$^+$ 358.07. $^1$H NMR (400 MHz, CDCl$_3$): δ 7.36-7.32 (m, 5H), 5.25-5.08 (m, 3H), 4.60-4.51 (dd, J=8.0 Hz, 28.0 Hz, 1H), 3.87-3.85 (d, J=10.4 Hz, 2H), 3.77 (s, 1.5H), 3.66 (s, 1.5H), 3.00 (s, 3H), 2.62-2.46 (m, 2H).

Step-6: Synthesis of 1-benzyl 2-methyl (2S, 4R)-4-(acetylthio) pyrrolidine-1, 2-dicarboxylate (4d)

1-Benzyl 2-methyl (2S, 4S)-4-((methylsulfonyl) oxy) pyrrolidine-1, 2-dicarboxylate 3d (22.0 gm, 61.6 mmol, 1.0 eq) was dissolved in DMF (220 mL). Potassium thioacetate (10.5 gm, 92.4 mmol, 1.5 eq) was added and the mixture was heated at 80° C. for 24 h. After complete consumption of starting material, reaction mixture was cooled to ambient temperature and diluted with chilled water (220 mL). The mixture was then extracted with diethyl ether (2×440 mL). The organic extract was again washed with water (1×440 mL) followed by brine (1×440 mL), dried over anhydrous $Na_2SO_4$, filtered and solvents evaporated from the filtrate under reduced pressure. The crude residue obtained was purified by flash chromatography on silica gel, 230-400 mesh, using 0-15% gradient of EtOAc in hexanes as eluent. The fractions containing the desired product were concentrated to obtain 4d as brown viscous liquid (14.1 gm, 68.0%). LCMS: Purity 98.01%. MS calculated for [M] 337.10 and found [M+H]$^+$ 338.03. $^1$H NMR (400 MHz, CDCl$_3$): δ 7.36-7.28 (m, 5H), 5.21-5.02 (m, 2H), 4.49-4.40 (m, 1H), 4.06-4.02 (m, 2H), 3.76 (s, 1.5H), 3.59 (s, 1.5H), 3.51-3.41 (dd, J=5.0 Hz, 36.4 Hz, 1H), 2.43-2.41 (m, 1H), 2.33 (s, 3H), 2.27-2.23 (m, 1H).

Step-7: Synthesis of (3R, 5S)-1-((benzyloxy)carbonyl)-5-(methoxycarbonyl)pyrrolidine-3-sulfonic (2133)

1-Benzyl 2-methyl (2S, 4R)-4-(acetylthio) pyrrolidine-1, 2-dicarboxylate 4d (1.5 gm, 4.45 mmol, 1.0 eq) was dissolved in AcOH (15 mL). Sodium acetate trihydrate (0.6 gm, 4.45 mmol, 1.0 eq) and 33% $H_2O_2$ (4.6 ml, 44.5 mmol, 10.0 eq) were added and the mixture was heated at 60° C. for 16 h. After complete consumption of starting material, reaction mixture was cooled to ambient temperature and solvents evaporated under reduced pressure. The resulting residue was dissolved in water (15 mL) and washed with EtOAc (2×15 mL). The aqueous layer was concentrated under vacuum to get 1.5 gm of crude compound. 0.25 gm of crude compound was purified by reverse phase flash chromatography on Agela Cheetah purification system, using AQ C18 column (20-35 µm, 12 gm) and 0-17% gradient of water in MeCN as eluent. The fractions with desired product were concentrated and lyophilized to obtain 2133 as white solid (0.06 gm, 23.5%). LCMS: Purity 90.93%. MS calculated for [M] 343.07 and found [M+H]$^+$ 344.00. $^1$H NMR (400 MHz, D$_2$O): δ 7.45-7.36 (m, 5H), 5.24-5.04 (m, 2H), 4.67-4.58 (m, 1H), 3.92-3.85 (dd, J=6.8 Hz, 24.0 Hz, 2H), 3.77 (s, 1.5H), 3.62 (s, 1.5H), 3.75-3.72 (m, 1H), 2.73-2.64 (m, 1H), 2.47-2.40 (m, 1H).

Step-8: Synthesis of (2S, 4R)-1-((benzyloxy)carbonyl)-4-sulfopyrrolidine-2-carboxylic acid (2134)

(3R,5S)-1-((Benzyloxy)carbonyl)-5-(methoxycarbonyl) pyrrolidine-3-sulfonic acid, 2133 (0.3 gm, 0.87 mmol, 1.0 eq) was dissolved in a mixture of THF and water (1:1, 6.0 mL) and the mixture was cooled to 0° C. Lithium hydroxide monohydrate (0.11 gm, 2.61 mmol, 3.0 eq) was added and the reaction mixture was stirred for 16 h, allowing temperature to gradually rise to ambient temperature. After complete consumption of starting material, reaction mixture was diluted with water (6 mL) and washed with DCM (2×12 mL). The resulting aqueous layer was acidified with amberlite IR 120 (H$^+$) resin up to pH=2 and filtered. The aqueous layer was concentrated under reduced pressure and the crude obtained was purified by prep HPLC on Atlantis HILIC column. The fractions with desired product were concentrated and lyophilized to obtain 2134 as white solid (0.045 gm, 15.7%). LCMS: Purity 99.23%. MS calculated for [M] 329.06 and found [M+H]$^+$ 329.92. $^1$H NMR (400 MHz, D$_2$O): δ 7.48-7.40 (m, 5H), 5.20-5.16 (m, 2H), 4.44-4.35 (m, 1H), 3.91-3.84 (m, 2H), 3.73-3.69 (m, 1H), 2.69-2.64 (m, 1H), 2.37-2.30 (m, 1H).

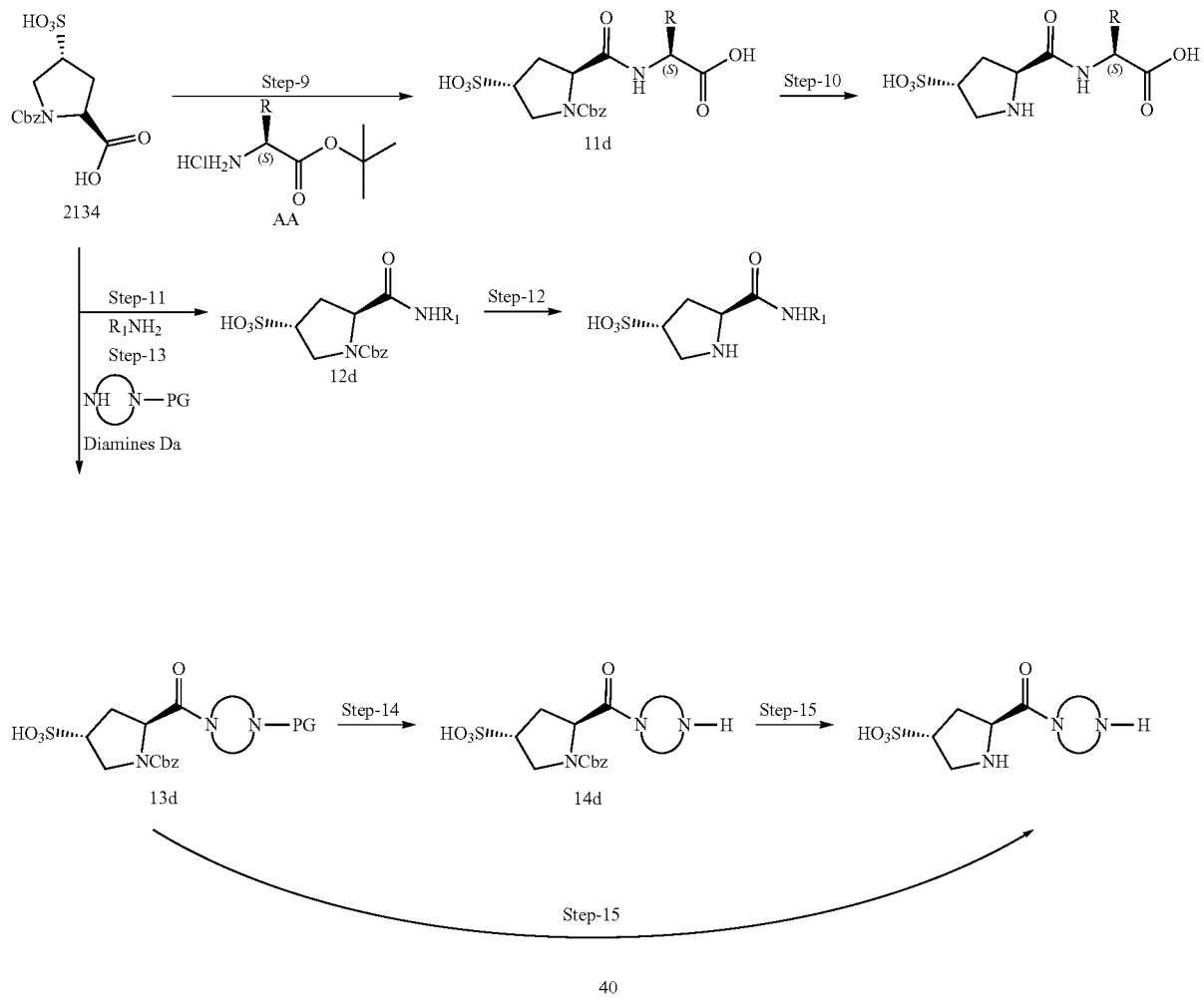

Scheme-3: General Scheme for Library syntheses

General Experimental Procedure for Step-9:

Scaffold 2134 (1.0 eq) was dissolved in DMF and the mixture was cooled to 0° C. DIPEA (3.0 eq) and HATU (1.5 eq) were added and the reaction mixture was stirred at 0° C. for 0.5 h. Then amino acids AA (1.5 eq) was added and the reaction mixture was stirred for 16 h, allowing temperature to gradually rise to ambient temperature. After complete consumption of starting material, reaction mixture was poured in diethyl ether. The precipitate obtained was triturated with the mixture of ethyl acetate and DCM, filtered the solid residue and washed it thoroughly with ethyl acetate (3×). Mixture of filtrate and washings was concentrated under reduced pressure. The resulting crude was dissolved in water, acidified the aqueous layer with amberlite IR 120 ($H^+$) resin up to pH=1 and filtered the resin. The aqueous layer was concentrated under reduced pressure to obtain corresponding 11d.

-continued
| ID | Amino acid | Structure |
|---|---|---|
| 11d_2 | 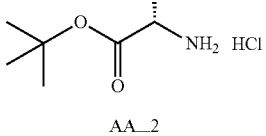<br>AA_2 | 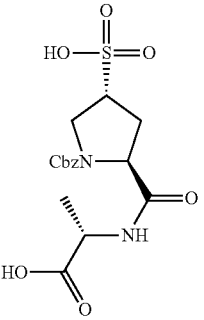 [SMILES: C[C@H](NC(=O)[C@@H]1C[C@@H](S(=O)(=O)O)CN1C(=O)OCc1ccccc1)C(=O)O] |
| 11d_3 | 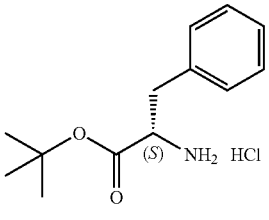<br>AA_3 | 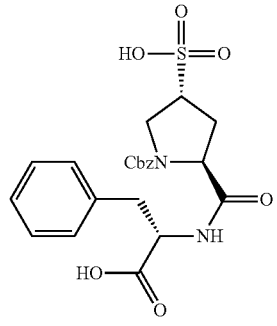 [SMILES: O=C(O)[C@H](Cc1ccccc1)NC(=O)[C@@H]1C[C@@H](S(=O)(=O)O)CN1C(=O)OCc1ccccc1] |
| 11d_4 | 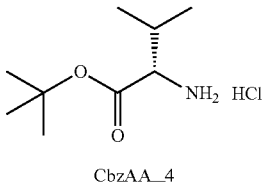<br>CbzAA_4 | 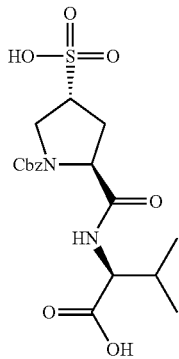 |
| 11d_5 | 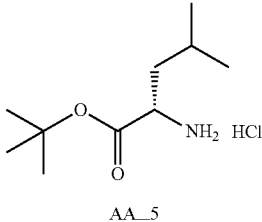<br>AA_5 | 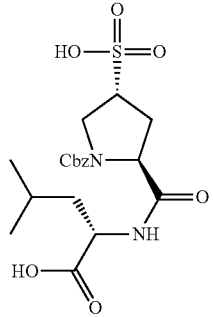 [SMILES: CC(C)C[C@H](NC(=O)[C@@H]1C[C@@H](S(=O)(=O)O)CN1C(=O)OCc1ccccc1)C(=O)O] |

-continued

| ID | Amino acid | Structure |
|---|---|---|
| 11d_6 | AA_6 | 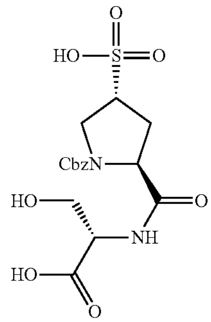 [SMILES: O=C(O)[C@H](CO)NC(=O)[C@@H]1C[C@@H](S(=O)(=O)O)CN1C(=O)OCc1ccccc1] |
| 11d_7 | AA_7 | 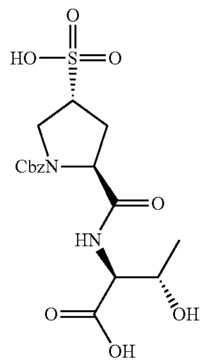 [SMILES: C[C@H](O)[C@H](NC(=O)[C@@H]1C[C@@H](S(=O)(=O)O)CN1C(=O)OCc1ccccc1)C(=O)O] |
| 11d_8 | AA_8 | 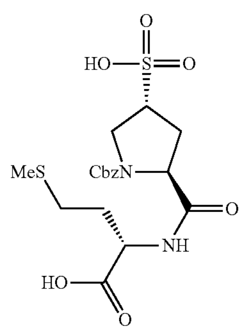 [SMILES: CSCC[C@H](NC(=O)[C@@H]1C[C@@H](S(=O)(=O)O)CN1C(=O)OCc1ccccc1)C(=O)O] |
| 11d_9 | AA_9 | 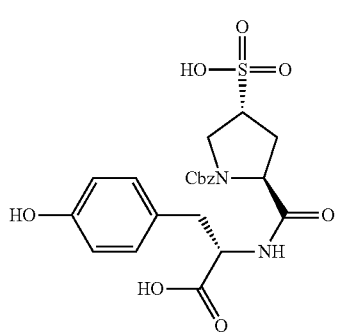 [SMILES: O=C(O)[C@H](Cc1ccc(O)cc1)NC(=O)[C@@H]1C[C@@H](S(=O)(=O)O)CN1C(=O)OCc1ccccc1] |

-continued
| ID | Amino acid | Structure |
|---|---|---|
| 11d_10 | 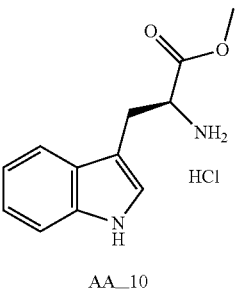 [SMILES: COC(=O)[C@@H](N)Cc1c[nH]c2ccccc12 ; Cl] AA_10 | 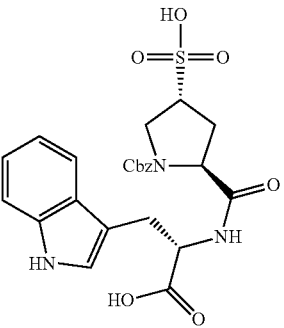 [SMILES: O=C(O)[C@H](Cc1c[nH]c2ccccc12)NC(=O)[C@@H]1C[C@@H](S(=O)(=O)O)CN1C(=O)OCc1ccccc1] |
| 11d_11 | 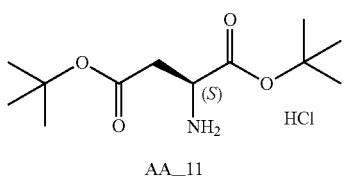 AA_11 | 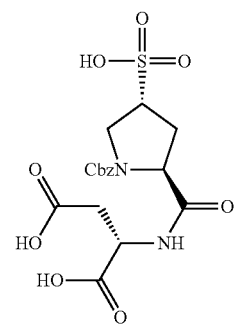 |
| 11d_12 | 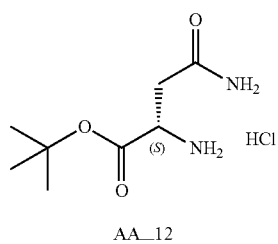 AA_12 | 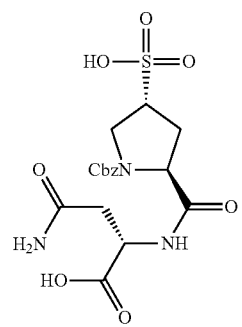 [SMILES: NC(=O)C[C@H](NC(=O)[C@@H]1C[C@@H](S(=O)(=O)O)CN1C(=O)OCc1ccccc1)C(=O)O] |
| 11d_13 | 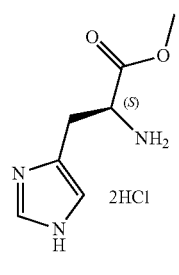 AA_13 | 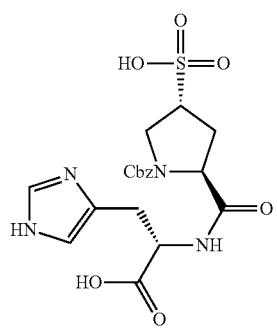 |

-continued

| ID | Amino acid | Structure |
|---|---|---|
| 11d_14 | AA_14: BocHN-(CH2)4-CH(NH2)-C(=O)-O-tBu · HCl, (S) | H2N-(CH2)4-CH(NH-C(=O)-[pyrrolidine-CbzN, 4-SO3H])-COOH |

General Experimental Procedure for Step-10:

11d (1.0 eq) was dissolved in the mixture of ethyl acetate, THF and water (1:1:0.5) under nitrogen atmosphere. Pd/C (10% w/w, 50% moisture, w/w) was added and the mixture was stirred under hydrogen atmosphere (hydrogen balloon) at room temperature for 16 h. After complete consumption of starting material, reaction mixture was diluted with water and filtered through a celite bed. Then celite bed was thoroughly washed with water (3×). Mixture of filtrate and washings was concentrated under reduced pressure and the crude compound was purified by prep HPLC to obtain corresponding compounds in the following table, also listed in FIG. 2 with NMR and MS data.

| ID | Structure |
|---|---|
| 2088 | 4-sulfo-pyrrolidine-2-carboxamide coupled with glycine |
| 2089 | 4-sulfo-pyrrolidine-2-carboxamide coupled with alanine |
| 2090 | 4-sulfo-pyrrolidine-2-carboxamide coupled with phenylalanine |
| 2091 | 4-sulfo-pyrrolidine-2-carboxamide coupled with valine |
| 2092 | 4-sulfo-pyrrolidine-2-carboxamide coupled with leucine |

-continued
| ID | Structure |
|---|---|
| 2093 | 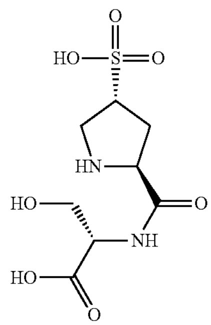 [SMILES: O=C(O)[C@H](CO)NC(=O)[C@@H]1C[C@@H](S(=O)(=O)O)CN1] |
| 2094 | 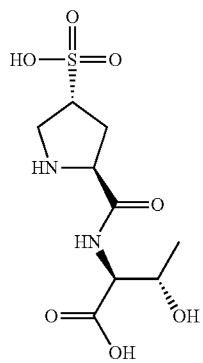 [SMILES: C[C@H](O)[C@H](NC(=O)[C@@H]1C[C@@H](S(=O)(=O)O)CN1)C(=O)O] |
| 2095 | 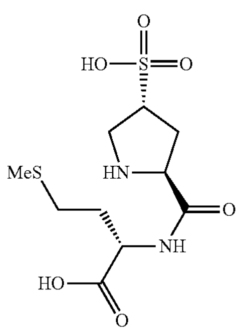 [SMILES: CSCC[C@H](NC(=O)[C@@H]1C[C@@H](S(=O)(=O)O)CN1)C(=O)O] |
| 2096 | 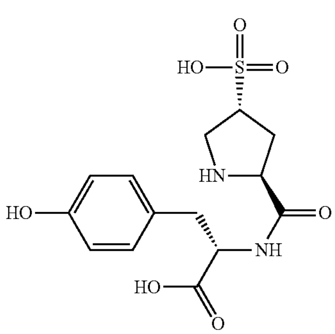 [SMILES: O=C(O)[C@H](Cc1ccc(O)cc1)NC(=O)[C@@H]1C[C@@H](S(=O)(=O)O)CN1] |
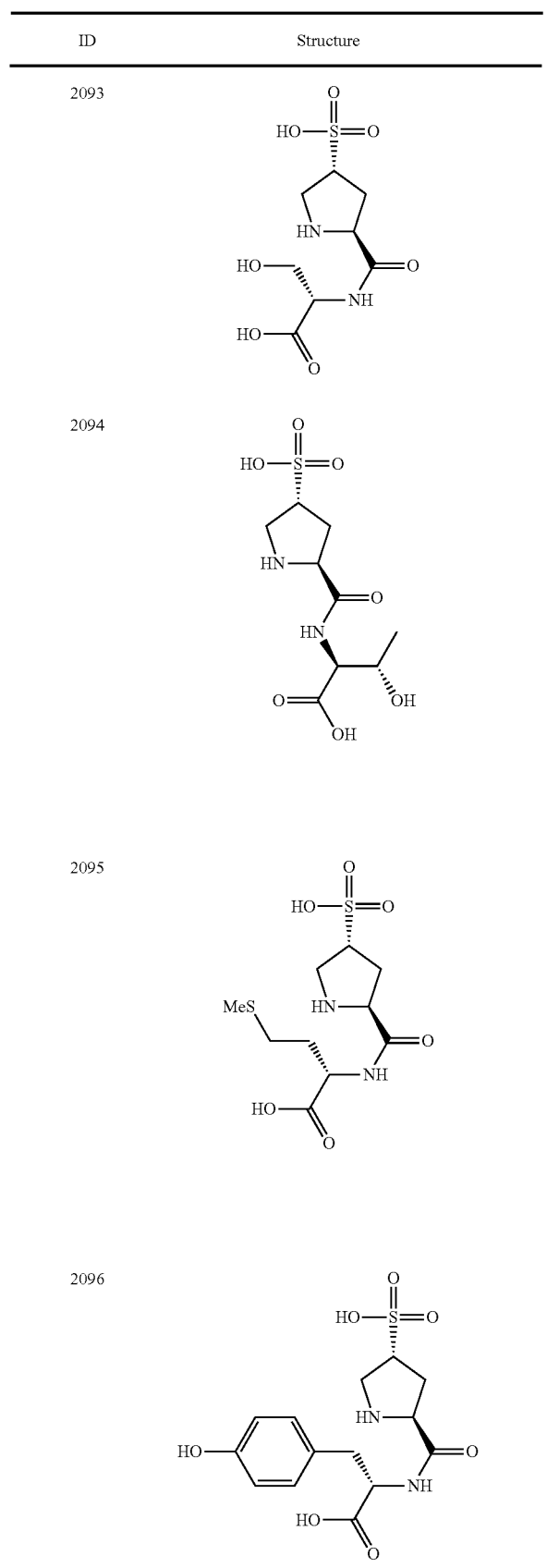
-continued
| ID | Structure |
|---|---|
| 2097 | 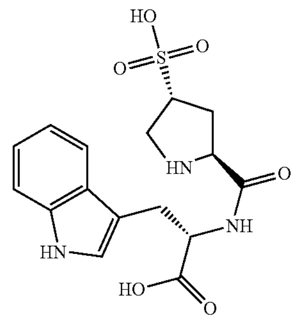 [SMILES: O=C(O)[C@H](Cc1c[nH]c2ccccc12)NC(=O)[C@@H]1C[C@@H](S(=O)(=O)O)CN1] |
| 2098 | 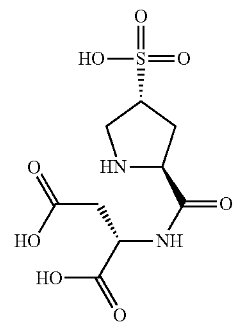 [SMILES: O=C(O)C[C@H](NC(=O)[C@@H]1C[C@@H](S(=O)(=O)O)CN1)C(=O)O] |
| 2099 | 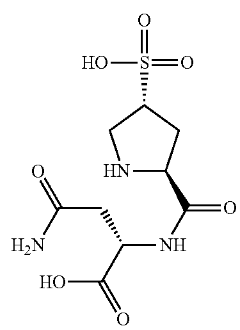 [SMILES: NC(=O)C[C@H](NC(=O)[C@@H]1C[C@@H](S(=O)(=O)O)CN1)C(=O)O] |
| 2100 | 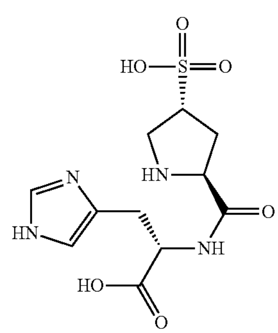 [SMILES: O=C(O)[C@H](Cc1c[nH]cn1)NC(=O)[C@@H]1C[C@@H](S(=O)(=O)O)CN1] |
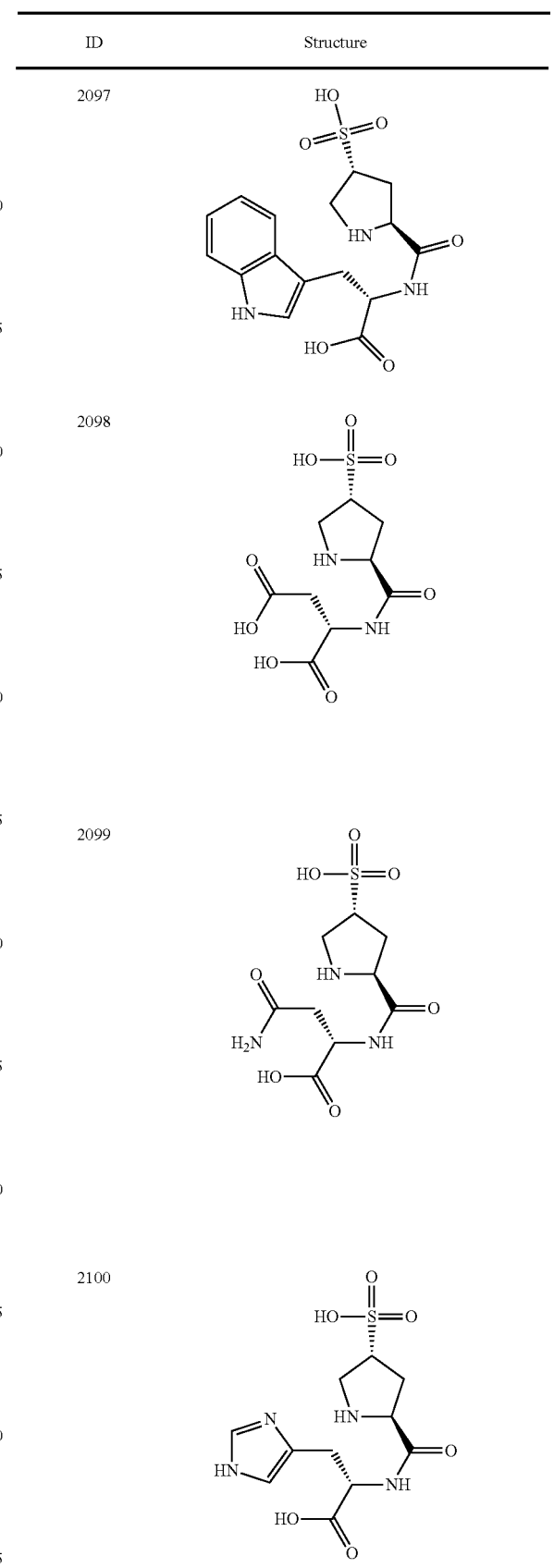

| ID | Structure |
|---|---|
| 2101 | (structure: pyrrolidine with sulfonic acid, attached to lysine-like side chain with H₂N, HN, NH, COOH, C=O) |

General Experimental Procedure for Step-11:

Scaffold 2134 (1.0 eq) was dissolved in DMF and the mixture was cooled to 0° C. DIPEA (3.0 eq) and HATU (1.5 eq) were added and the reaction mixture was stirred at 0° C. for 0.5 h. Then amines A_1 to A_6, DA_1 and DA_2 (1.5 eq) was added and the reaction mixture was stirred for 16 h, allowing temperature to gradually rise to ambient temperature. After complete consumption of starting material, reaction mixture was poured in diethyl ether. The precipitate obtained was triturated with the mixture of ethyl acetate and DCM, filtered the solid residue and washed it thoroughly with ethyl acetate (3×). Mixture of filtrate and washings was concentrated under reduced pressure. The resulting crude was dissolved in water, acidified the aqueous layer with amberlite IR 120 (H⁺) resin up to pH=1 and filtered the resin. The aqueous layer was concentrated under reduced pressure to obtain corresponding 12d.

| ID | Amines/Diamines | Structure |
|---|---|---|
| 12d_1 | benzylamine (A_1) | CbzN-pyrrolidine-SO₃H with benzylamide |
| 12d_2 | diethanolamine (A_2) | CbzN-pyrrolidine-SO₃H with bis(2-hydroxyethyl)amide |
| 12d_3 | diethylamine (A_3) | CbzN-pyrrolidine-SO₃H with diethylamide |
| 12d_4 | morpholine (A_4) | CbzN-pyrrolidine-SO₃H with morpholine amide |
| 12d_5 | ethylamine (A_5) | CbzN-pyrrolidine-SO₃H with ethylamide |
| 12d_6 | NH₃ (A_6) | CbzN-pyrrolidine-SO₃H with primary amide (H₂N) |
| 12d_7 | N,N,2,2-tetramethyl-1,3-propanediamine (DA_1) | CbzN-pyrrolidine-SO₃H (OH) with neopentyl-type diamide linker to N(CH₃)₂ |

| ID | Amines/Diamines | Structure |
|---|---|---|
| 12d_8 | 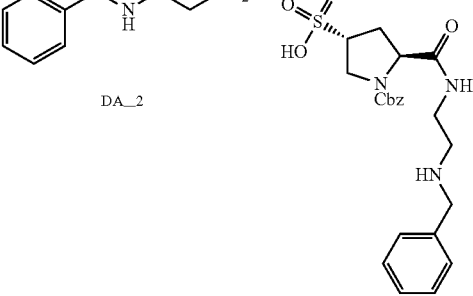 DA_2 | 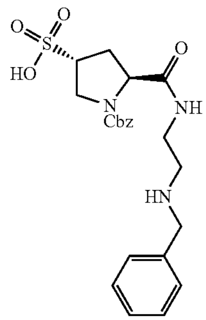 [SMILES: O=C(NCCNCc1ccccc1)[C@@H]1C[C@@H](S(=O)(=O)O)CN1C(=O)OCc1ccccc1] |

General Experimental Procedure for Step-12:

12d (1.0 eq) was dissolved in the mixture of ethyl acetate, THF and water (1:1:0.5) under nitrogen atmosphere. Pd/C (10% w/w, 50% moisture, w/w) was added and the mixture was stirred under hydrogen atmosphere (hydrogen balloon) at room temperature for 16 h. After complete consumption of starting material, reaction mixture was diluted with water and filtered through a celite bed. Then celite bed was thoroughly washed with water (3×). Mixture of filtrate and washings was concentrated under reduced pressure and the crude compound was purified by prep HPLC to obtain corresponding compounds in the following table, also listed in FIG. 2 with NMR and MS data.

| ID | Structure |
|---|---|
| 2083 | 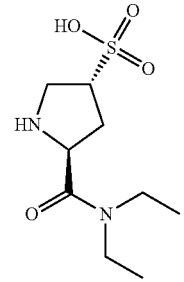 [SMILES: CCN(CC)C(=O)[C@@H]1C[C@@H](S(=O)(=O)O)CN1] |
| 2087 | 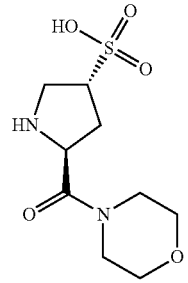 [SMILES: O=C([C@@H]1C[C@@H](S(=O)(=O)O)CN1)N1CCOCC1] |
| 2085 | 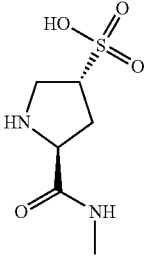 |
| 2086 | 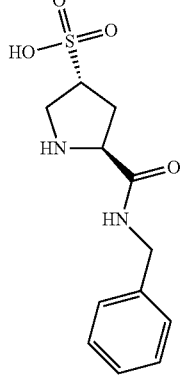 |
| 2084 | 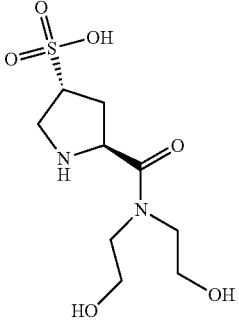 |
| 2082 | 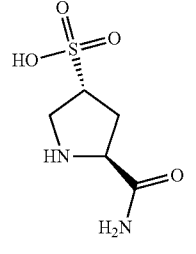 |
| 2102 | 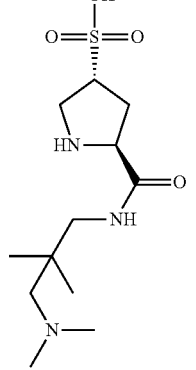 |

| ID | Structure |
|---|---|
| 2103 | 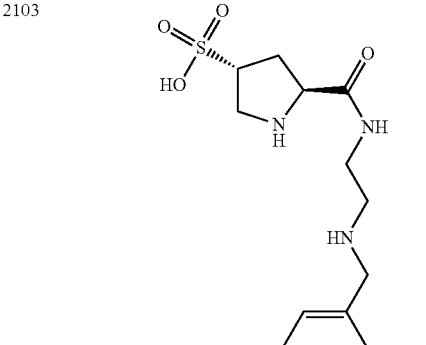 |

General Experimental Procedure for Step-13:

Scaffold 2134 (1.0 eq) was dissolved in DMF and the mixture was cooled to 0° C. DIPEA (3.0 eq) and HATU (1.5 eq) were added and the reaction mixture was stirred at 0° C. for 0.5 h. Then DA_3 to 8 (1.5 eq) was added and the reaction mixture was stirred for 16 h, allowing temperature to gradually rise to ambient temperature. After complete consumption of starting material, reaction mixture was poured in diethyl ether. The precipitate obtained was triturated with the mixture of ethyl acetate and DCM, filtered the solid residue and washed it thoroughly with ethyl acetate (3×). Mixture of filtrate and washings was concentrated under reduced pressure. The resulting crude was dissolved in water, acidified the aqueous layer with amberlite IR 120 (H⁺) resin up to pH=1 and filtered the resin. The aqueous layer was concentrated under reduced pressure to obtain corresponding 13d.

| ID | Diamines | Structure |
|---|---|---|
| 13d_14 | DA_8 (pyrrolidine with NHCbz) | (sulfonic acid pyrrolidine-NCbz-carbonyl-pyrrolidine-NCbz with NHCbz) |

General Experimental Procedure for Step-14:

13d (1.0 eq) was dissolved in dioxane and the solution was cooled to 0° C. Then 4M HCl in dioxane (50%, v/v) was added and the mixture was stirred for 3 h, during which, the temperature was allowed to rise from 0° C. to ambient temperature. After complete consumption of starting material, solvents evaporated from the reaction mixture under reduced pressure and the crude obtained was triturated with diethyl ether to obtain corresponding 14d.

| ID | Structure |
|---|---|
| 14d_9 | 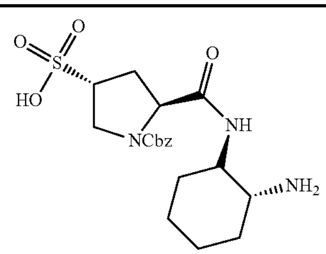 |
| 14d_10 | 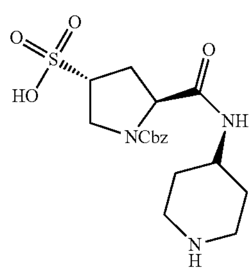 |
| 14d_11 | 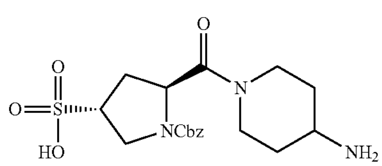 [SMILES: NC1CCN(C(=O)[C@@H]2C[C@@H](S(=O)(=O)O)CN2C(=O)OCc2ccccc2)CC1] |
| 14d_12 | 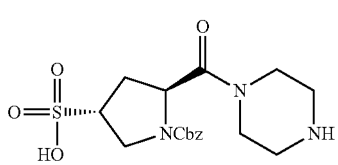 [SMILES: O=C([C@@H]1C[C@@H](S(=O)(=O)O)CN1C(=O)OCc1ccccc1)N1CCNCC1] |
| 14d_13 | 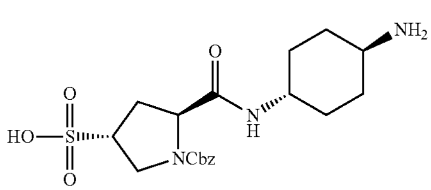 [SMILES: N[C@H]1CC[C@H](NC(=O)[C@@H]2C[C@@H](S(=O)(=O)O)CN2C(=O)OCc2ccccc2)CC1] |

General Experimental Procedure for Step-15:

13d, or 14d (1.0 eq) was dissolved in the mixture of ethyl acetate, THF and water (1:1:0.5) under nitrogen atmosphere. Pd/C (10% w/w, 50% moisture, w/w) was added and the mixture was stirred under hydrogen atmosphere (hydrogen balloon) at room temperature for 16 h. After complete consumption of starting material, reaction mixture was diluted with water and filtered through a celite bed. Then celite bed was thoroughly washed with water (3×). Mixture of filtrate and washings was concentrated under reduced pressure and the crude compound was purified by prep HPLC to obtain corresponding compounds in the following table, also listed in FIG. 2 with NMR and MS data.

| ID | Structure |
|---|---|
| 2104 | 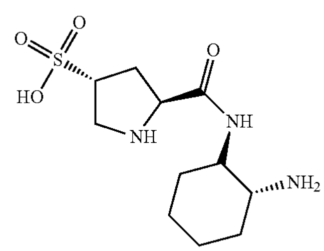 |
| 2105 | 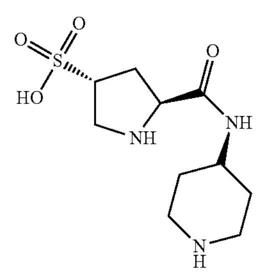 |
| 2106 | 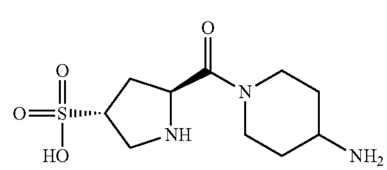 [SMILES: NC1CCN(C(=O)[C@@H]2C[C@@H](S(=O)(=O)O)CN2)CC1] |
| 2107 | 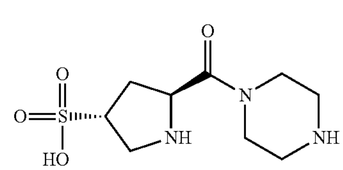 [SMILES: O=C([C@@H]1C[C@@H](S(=O)(=O)O)CN1)N1CCNCC1] |

-continued

| ID | Structure |
|---|---|
| 2108 | 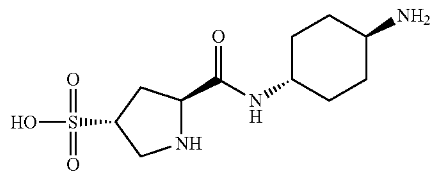 [SMILES: N[C@H]1CC[C@H](NC(=O)[C@@H]2C[C@@H](S(=O)(=O)O)CN2)CC1] |
| 2109 | 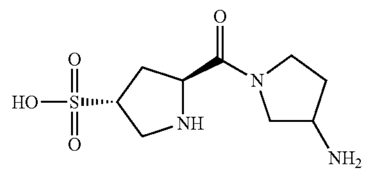 [SMILES: NC1CCN(C(=O)[C@@H]2C[C@@H](S(=O)(=O)O)CN2)C1] |

The foregoing detailed description has been given for clearness of understanding only and no unnecessary limitations should be understood there from as modifications will be obvious to those skilled in the art.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

The disclosures, including the claims, figures and/or drawings, of each and every patent, patent application, and publication cited herein are hereby incorporated herein by reference in their entireties.

What is claimed is:

1. A compound selected from any one of the following formula:

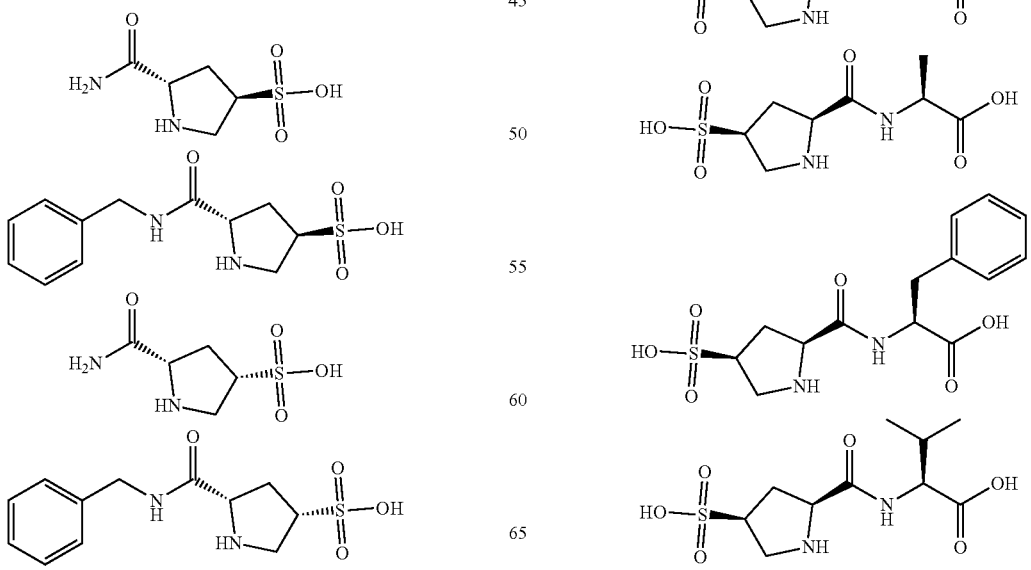

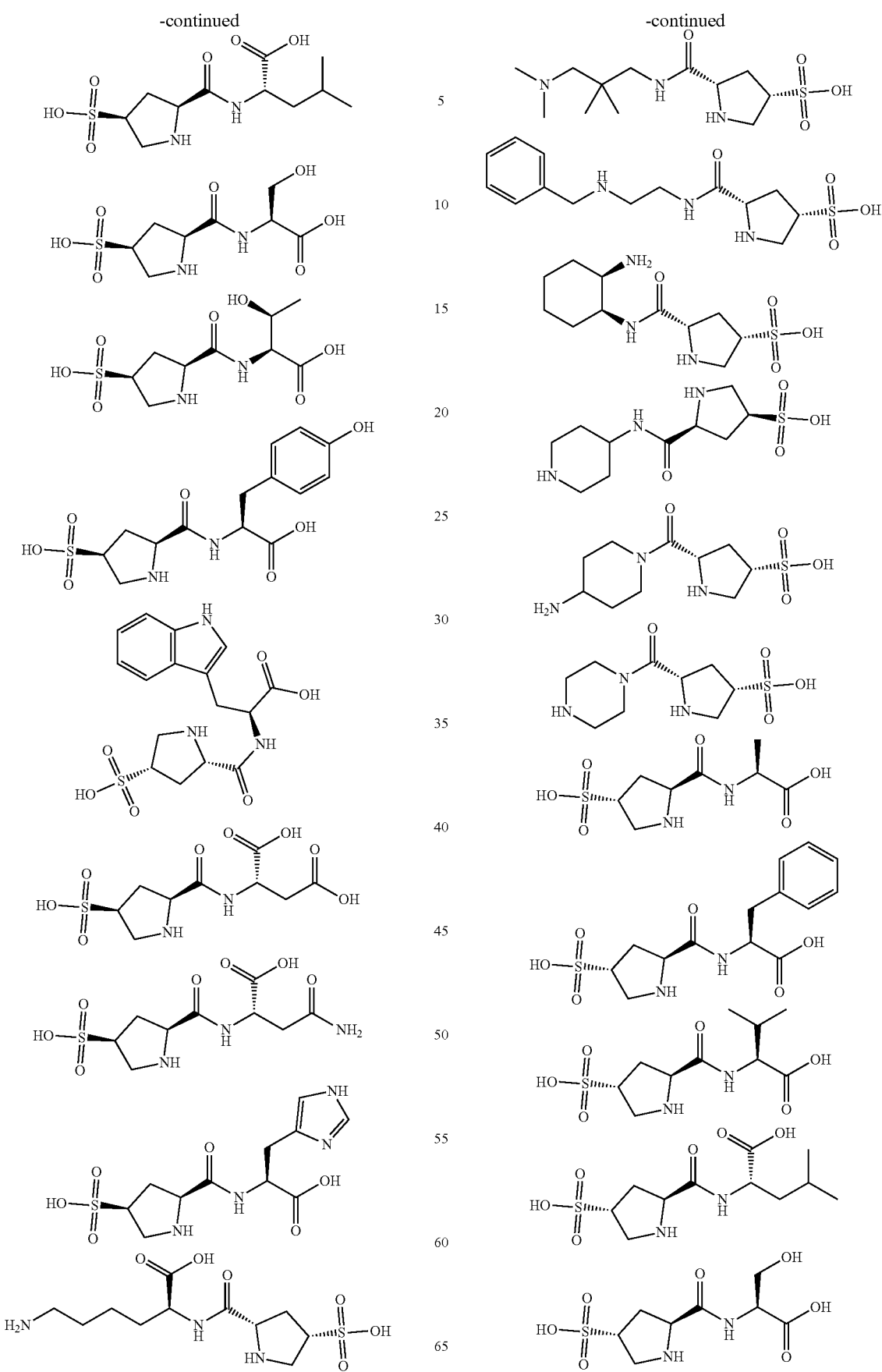

-continued
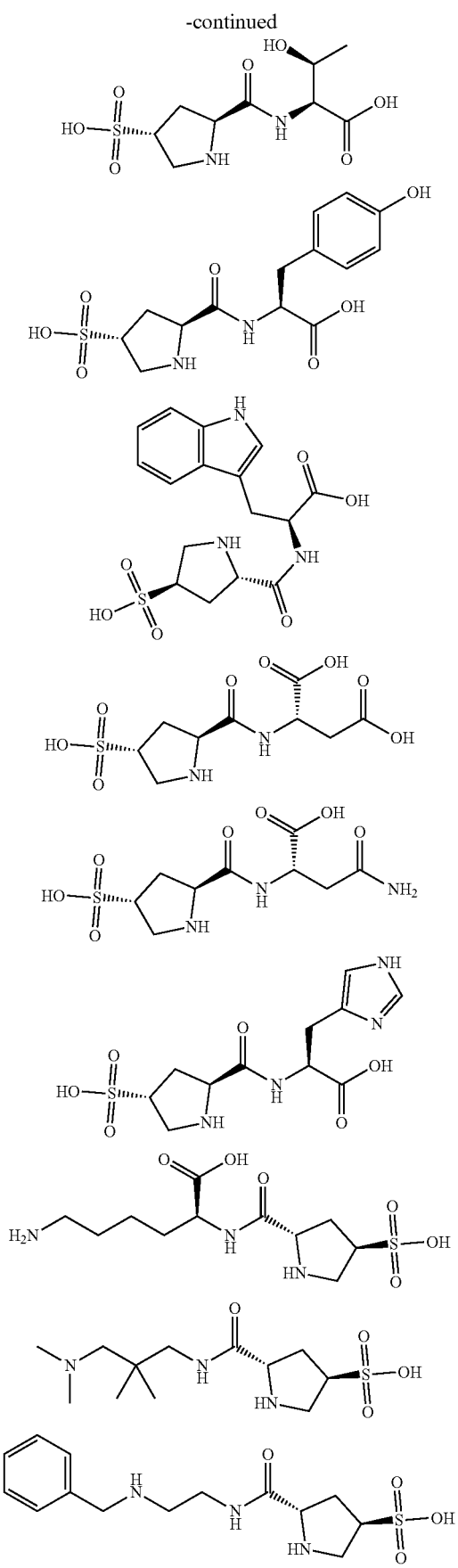
-continued
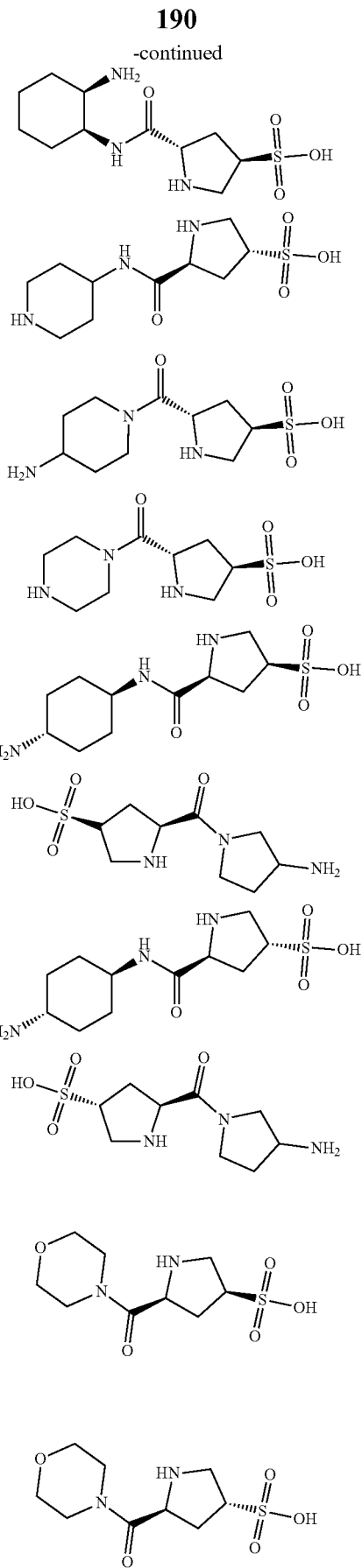

-continued

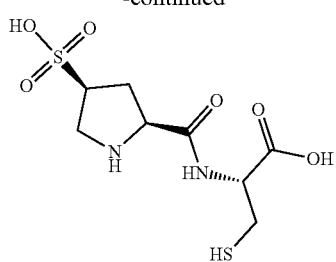

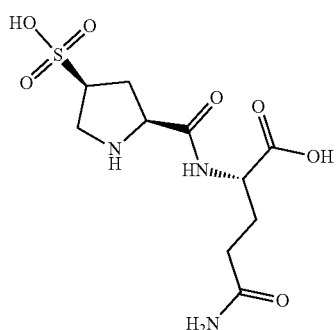

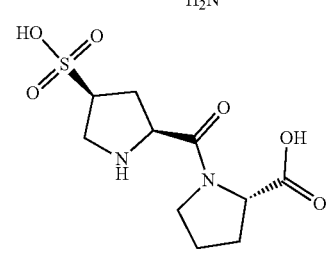

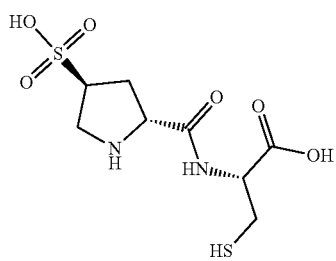

-continued

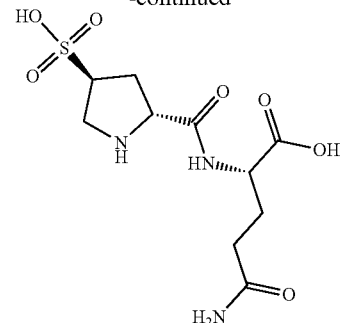

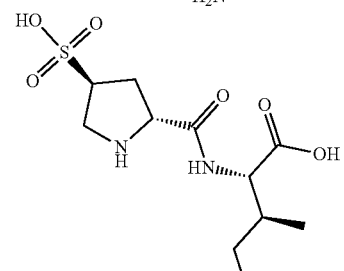

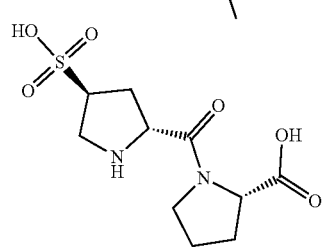

or a pharmaceutically acceptable salt of any of the foregoing.

2. A pharmaceutical composition comprising a compound of claim 1, or a pharmaceutically acceptable salt thereof and a pharmaceutically acceptable carrier.

3. A method of treating Alzheimer's disease comprising the step of administering to a patient in need thereof a compound of claim 1, or a pharmaceutically acceptable salt thereof.

4. The method of claim 3, wherein the patient is ApoE4-positive.

5. The method of claim 4, wherein the patient is homozygous for ApoE4.

* * * * *